US010870683B2

(12) United States Patent
Dubrovskaya et al.

(10) Patent No.: US 10,870,683 B2
(45) Date of Patent: *Dec. 22, 2020

(54) N-GLYCAN DELETED HIV-1 ENVELOPE GLYCOPROTEIN TRIMERS

(71) Applicants: International AIDS Vaccine Initiative, New York, NY (US); The Scripps Research Institute, La Jolla, CA (US)

(72) Inventors: Viktoriya Dubrovskaya, La Jolla, CA (US); Francisco Javier Guenaga, New York, NY (US); Richard Wyatt, La Jolla, CA (US)

(73) Assignees: INTERNATIONAL AIDS VACCINE INITIATIVE, New York, NY (US); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/130,531

(22) Filed: Sep. 13, 2018

(65) Prior Publication Data

US 2019/0135872 A1 May 9, 2019

Related U.S. Application Data

(60) Provisional application No. 62/558,262, filed on Sep. 13, 2017, provisional application No. 62/621,682, filed on Jan. 25, 2018.

(51) Int. Cl.

| | |
|---|---|
| ***A61K 39/21*** | (2006.01) |
| ***C12N 7/00*** | (2006.01) |

(Continued)

(52) U.S. Cl.

CPC ............ *C07K 14/005* (2013.01); *A61K 39/12* (2013.01); *A61K 2039/545* (2013.01); *A61K 2039/55555* (2013.01); *A61K 2039/58* (2013.01); *C12N 2740/16122* (2013.01); *C12N 2740/16134* (2013.01)

(58) Field of Classification Search

None

See application file for complete search history.

(56) References Cited

U.S. PATENT DOCUMENTS

| | | | | |
|---|---|---|---|---|
| 10,058,604 B2 * | 8/2018 | Wyatt | .................... | A61K 39/21 |
| 2016/0272948 A1 * | 9/2016 | Dubrovskaya | ......... | A61K 39/39 |

(Continued)

OTHER PUBLICATIONS

Li et al., "Removal of a Single N-Linked Glycan in human Immunodeficiency Virus Type 1 gp120 Results in an Enhanced Ability to Induce Neutralizing Antibody Responses," Journal of Virology, vol. 82, No. 2: 638-651 (Year: 2008).*

(Continued)

*Primary Examiner* — M Franco G Salvoza

(74) *Attorney, Agent, or Firm* — Duane Morris LLP; Thomas J. Kowalski; Deborah L. Lu

(57) ABSTRACT

The present application relates to novel HIV-1 envelope glycoproteins which may be utilized as an HIV-1 vaccine immunogens, antigens for crystallization and for the identification of broad neutralizing antibodies. The present invention encompasses the preparation and purification of immunogenic compositions which are formulated into the vaccines of the present invention.

14 Claims, 83 Drawing Sheets
(50 of 83 Drawing Sheet(s) Filed in Color)
Specification includes a Sequence Listing.

(51) Int. Cl.
*C07K 14/005* (2006.01)
*A61K 39/12* (2006.01)
*A61K 39/00* (2006.01)

(56) References Cited

U.S. PATENT DOCUMENTS

| | | | | |
|---|---|---|---|---|
| 2016/0279230 | A1* | 9/2016 | Sharma | A61K 39/21 |
| 2019/0085032 | A1* | 3/2019 | Lusso | A61K 39/12 |

OTHER PUBLICATIONS

Binley et al., "Role of Complex Carbohydrates in Human Immunodeficiency Virus Type 1 Infection and Resistance to Antibody Neutralization," Journal of Virology, vol. 84, No. 11: 5637-5655 (Year: 2010).*

Wang et al., "N564 Glycosylation Site on V5 Loop of a Mutant gp120 Regulates the Sensitivity of HIV-1 to Neutralizing Monoclonal Antibodies VRC01/03", J Acquir Immune Defic Syndr. 69(3): 27-277 (Year: 2015).*

Sharma et al., "Cleavage-independent HIV-1 Env trimers engineered as soluble native spike mimetics for vaccine design," Cell Rep. 11(4): 539-550 (Year: 2015).*

Liang et al., "Changes in Structure and Antigenicity of HIV-1 Env Trimers Resulting from Removal of a Conserved CD4 Binding Site-Proximal Glycan", Journal of Virology, vol. 90, No. 20: 9224-9236 (Year: 2016).*

* cited by examiner

| Trimer | KD(nM) | kon(1/Ms) | kdis(1/s) |
|---|---|---|---|
| PT | 241 | 1.08E+04 | 2.60E-03 |
| N276Q/N463Q | 8.6 | 5.87E+04 | 5.05E-04 |
| | | | |
| +*N332*PT | 131 | 1.56E+04 | 2.04E-03 |
| +*N332*N301Q | 270 | 1.37E+04 | 3.70E-03 |
| +*N332*N276Q/N360Q/N463Q | 12.9 | 5.71E+04 | 7.39E-04 |
| +*N332*N276Q/N360Q/N463Q/N301Q | 16.4 | 7.54E+04 | 1.24E-03 |

Figure 5:
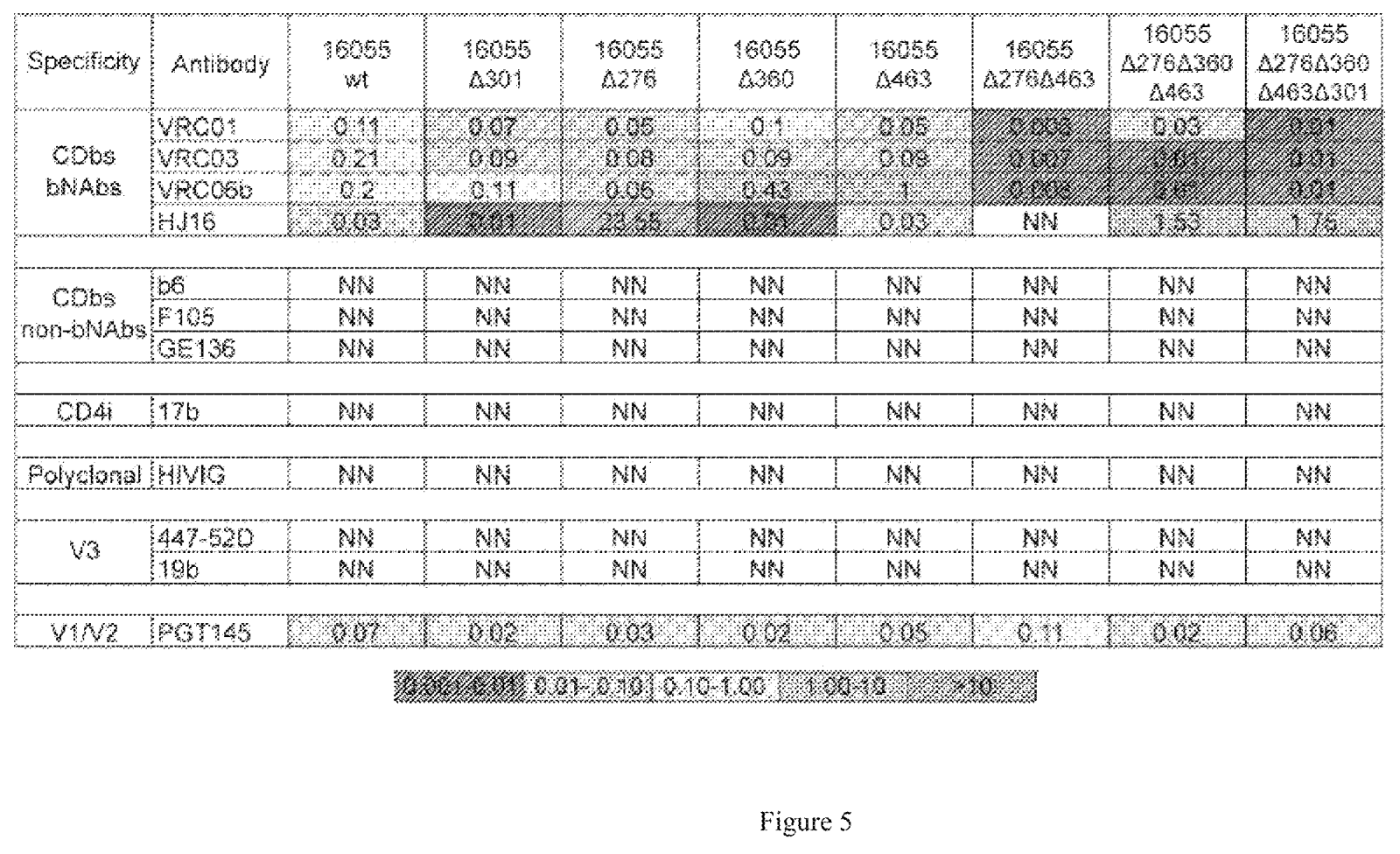

| Specificity | Antibody | 16055 wt | 16055 Δ301 | 16055 Δ276 | 16055 Δ360 | 16055 Δ463 | 16055 Δ276Δ463 | 16055 Δ276Δ360 Δ463 | 16055 Δ276Δ360 Δ463Δ301 |
|---|---|---|---|---|---|---|---|---|---|
| CDbs bNAbs | VRC01 | 0.11 | 0.07 | 0.05 | 0.1 | 0.05 | 0.003 | 0.03 | 0.01 |
| | VRC03 | 0.21 | 0.09 | 0.08 | 0.09 | 0.08 | 0.007 | [illegible] | 0.01 |
| | VRC06b | 0.2 | 0.11 | 0.06 | 0.43 | 1 | 0.008 | [illegible] | 0.01 |
| | HJ16 | 0.03 | [illegible] | 23.55 | [illegible] | 0.03 | NN | 1.53 | 1.75 |
| | | | | | | | | | |
| CDbs non-bNAbs | b6 | NN | NN | NN | NN | NN | NN | NN | NN |
| | F105 | NN | NN | NN | NN | NN | NN | NN | NN |
| | GE136 | NN | NN | NN | NN | NN | NN | NN | NN |
| | | | | | | | | | |
| CD4i | 17b | NN | NN | NN | NN | NN | NN | NN | NN |
| | | | | | | | | | |
| Polyclonal | HIVIG | NN | NN | NN | NN | NN | NN | NN | NN |
| | | | | | | | | | |
| V3 | 447-52D | NN | NN | NN | NN | NN | NN | NN | NN |
| | 19b | NN | NN | NN | NN | NN | NN | NN | NN |
| | | | | | | | | | |
| V1/V2 | PGT145 | 0.07 | 0.02 | 0.03 | 0.02 | 0.05 | 0.11 | 0.02 | 0.06 |

| | | | | |
|---|---|---|---|---|
| [illegible] | 0.01-0.10 | 0.10-1.00 | 1.00-10 | >10 |

Figure 5 a

| virus | animal index | post 2 Group 1 wt | post 2 Group 2 ΔGly4 | post 2 Group 3 ΔGly2 | post 3 Group 1 wt | post 3 Group 2 wt | post 3 Group 3 ΔGly1 | post 4 Group 1 wt | post 4 Group 2 wt | post 4 Group 3 wt |
|---|---|---|---|---|---|---|---|---|---|---|
| 16055 | 1 | <5 | 6 | <5 | <5 | 9 | <5 | <5 | 668 | 36 |
| | 2 | <5 | <5 | <5 | <5 | 10 | 130 | <5 | 209 | 242 |
| | 3 | <5 | <5 | <5 | 83 | <5 | 5 | 1058 | 14 | 1575 |
| | 4 | <5 | <5 | <5 | <5 | 6 | 48 | 48 | 312 | 359 |
| | 5 | <5 | 16 | <5 | <5 | 113 | 5 | 37 | 481 | 10 |
| | 6 | <5 | <5 | 11 | 10 | <5 | 53 | 136 | <5 | 531 |
| 16055 Δ276Δ360 Δ463Δ301 | 1 | <5 | 506 | 131 | <5 | 234 | 98 | <5 | 1797 | 148 |
| | 2 | <5 | 774 | 553 | <5 | 533 | 2100 | <5 | 2859 | 1791 |
| | 3 | <5 | 995 | <5 | 41 | 657 | 103 | 3232 | 2427 | 3708 |
| | 4 | <5 | 123 | 2745 | <5 | 161 | 38580 | 90 | 1569 | 12623 |
| | 5 | <5 | 94 | 6221 | <5 | 401 | 885 | 77 | 1052 | 719 |
| | 6 | <5 | 2242 | 98 | 16 | 154 | 155 | 540 | 474 | 834 |
| 16055 Δ276Δ463 | 1 | <5 | 203 | 86 | <5 | 180 | 76 | <5 | 1218 | 121 |
| | 2 | <5 | 585 | 388 | <5 | 860 | 1512 | <5 | 1364 | 1382 |
| | 3 | 30 | 23 | <5 | 177 | 173 | 42 | 1385 | 2393 | 1802 |
| | 4 | <5 | 162 | 3771 | <5 | 252 | 13753 | 66 | 988 | 16013 |
| | 5 | <5 | 232 | 1384 | <5 | 509 | 645 | 54 | 1142 | 16 |
| | 6 | <5 | 1242 | 73 | 13 | 321 | 159 | 202 | 150 | 431 |

5-100 | 100-1000 | 1000-10,000 | 10,000-100,000 b

Figure 8:
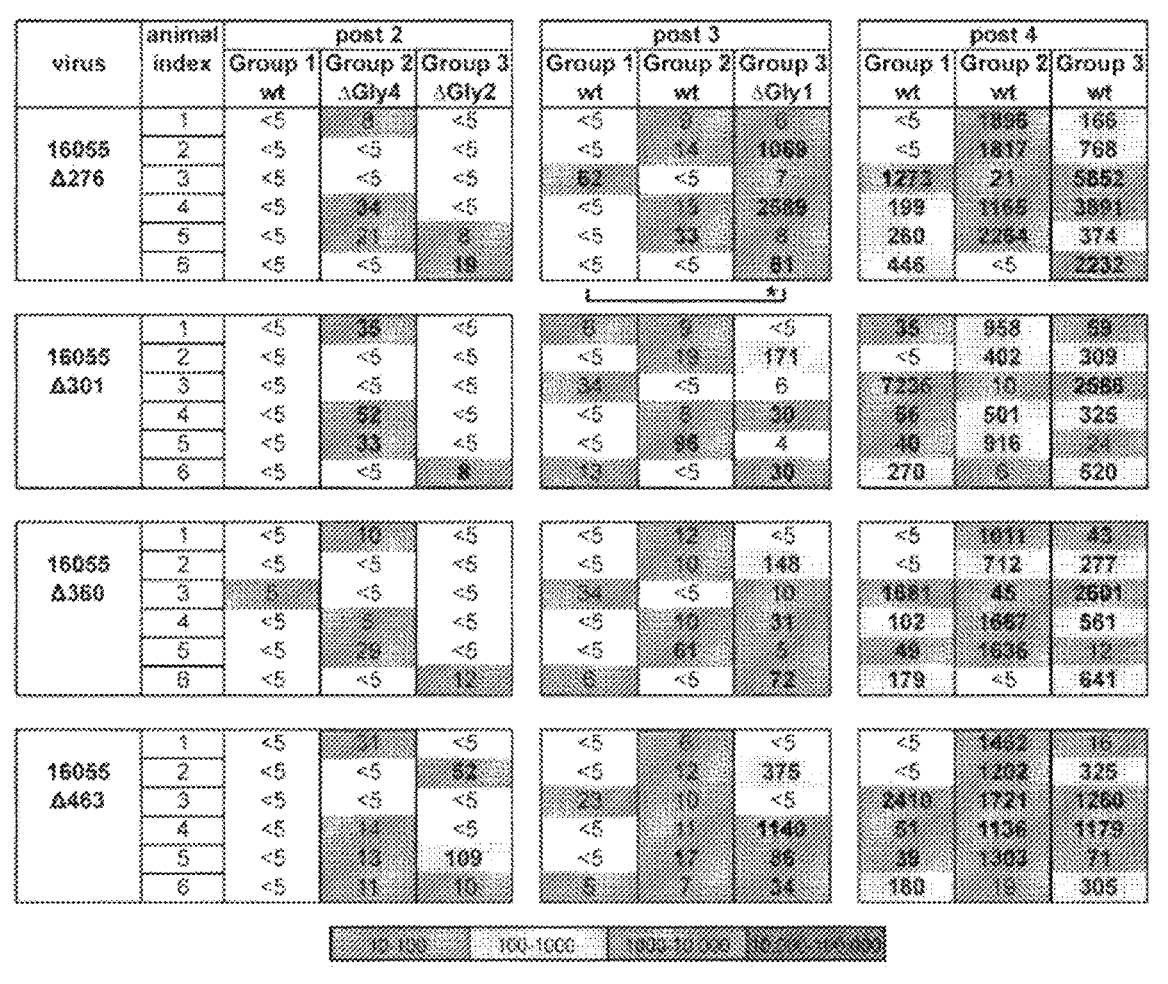

| virus | animal index | post 2 | | | post 3 | | | post 4 | | |
|---|---|---|---|---|---|---|---|---|---|---|
| | | Group 1 wt | Group 2 ΔGly4 | Group 3 ΔGly2 | Group 1 wt | Group 2 wt | Group 3 ΔGly1 | Group 1 wt | Group 2 wt | Group 3 wt |
| 16055 Δ276 | 1 | <5 | 8 | <5 | <5 | 8 | 6 | <5 | 1896 | 166 |
| | 2 | <5 | <5 | <5 | <5 | 14 | 1069 | <5 | 1817 | 768 |
| | 3 | <5 | <5 | <5 | 62 | <5 | 7 | 1273 | 21 | 5852 |
| | 4 | <5 | 34 | <5 | <5 | 15 | 2589 | 199 | 1165 | 3891 |
| | 5 | <5 | 21 | 8 | <5 | 33 | 8 | 260 | 2264 | 374 |
| | 6 | <5 | <5 | 19 | <5 | <5 | 81 | 446 | <5 | 2232 |
| 16055 Δ301 | 1 | <5 | 35 | <5 | 8 | 8 | <5 | 35 | 958 | 59 |
| | 2 | <5 | <5 | <5 | <5 | 19 | 171 | <5 | 402 | 309 |
| | 3 | <5 | <5 | <5 | 34 | <5 | 6 | 7226 | 10 | 2568 |
| | 4 | <5 | 52 | <5 | <5 | 8 | 30 | 56 | 501 | 326 |
| | 5 | <5 | 33 | <5 | <5 | 95 | 4 | 40 | 916 | 24 |
| | 6 | <5 | <5 | 8 | 13 | <5 | 30 | 278 | 5 | 520 |
| 16055 Δ360 | 1 | <5 | 10 | <5 | <5 | 12 | <5 | <5 | 1011 | 43 |
| | 2 | <5 | <5 | <5 | <5 | 10 | 148 | <5 | 712 | 277 |
| | 3 | 5 | <5 | <5 | 34 | <5 | 10 | 1881 | 45 | 2601 |
| | 4 | <5 | 8 | <5 | <5 | 10 | 31 | 102 | 1667 | 561 |
| | 5 | <5 | 29 | <5 | <5 | 61 | 5 | 49 | 1636 | 12 |
| | 6 | <5 | <5 | 13 | 5 | <5 | 72 | 179 | <5 | 641 |
| 16055 Δ463 | 1 | <5 | 27 | <5 | <5 | 6 | <5 | <5 | 1462 | 16 |
| | 2 | <5 | <5 | 62 | <5 | 12 | 375 | <5 | 1282 | 325 |
| | 3 | <5 | <5 | <5 | 23 | 10 | <5 | 2410 | 1721 | 1260 |
| | 4 | <5 | 14 | <5 | <5 | 11 | 1140 | 61 | 1136 | 1179 |
| | 5 | <5 | 13 | 109 | <5 | 17 | 85 | 39 | 1303 | 71 |
| | 6 | <5 | 11 | 10 | 5 | 7 | 34 | 180 | 15 | 305 |

*

| 10-100 | 100-1000 | 1000-10,000 | 10,000-[illegible] |
|---|---|---|---|

Figure 8 a
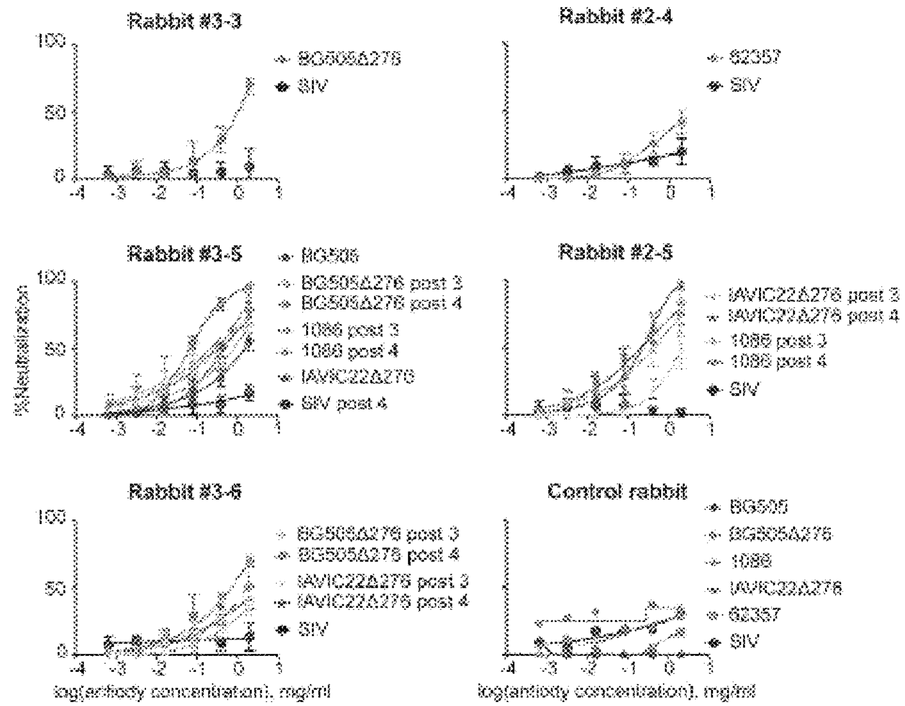
b
| virus | #2-4 | #2-5 | #3-3 | #3-5 | #3-6 | control |
|---|---|---|---|---|---|---|
| 62357 | 4.685 | >2 | >2 | >2 | >2 | >2 |
| AVIC22Δ276 post 3 | >2 | 0.244 | >2 | >2 | 0.464 | >2 |
| AVIC22Δ276 post 4 | >2 | 0.208 | >2 | 0.473 | 3.651 | >2 |
| 1086 post 3 | >2 | 0.372 | >2 | 0.230 | >2 | >2 |
| 1086 post 4 | >2 | 0.327 | >2 | 0.355 | >2 | >2 |
| BG505Δ276 post 3 | >2 | >2 | >2 | 0.813 | [illegible] | >2 |
| BG505Δ276 post 4 | >2 | >2 | 0.922 | 0.964 | 0.780 | >2 |
| BG505 | >2 | >2 | >2 | [illegible] | >2 | >2 |
| SIV | >2 | >2 | >2 | >2 | >2 | >2 |
c
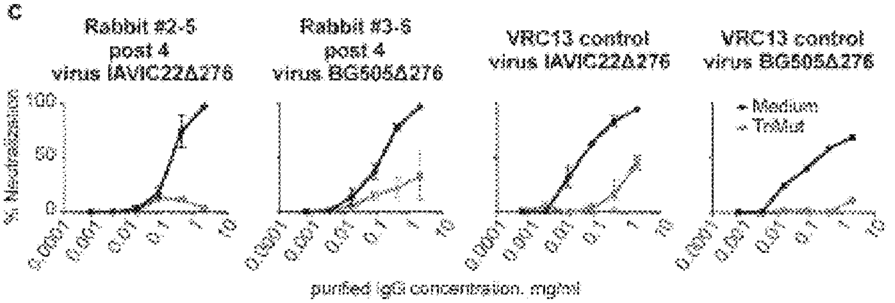
Figure 9A-9C

Figure 15:
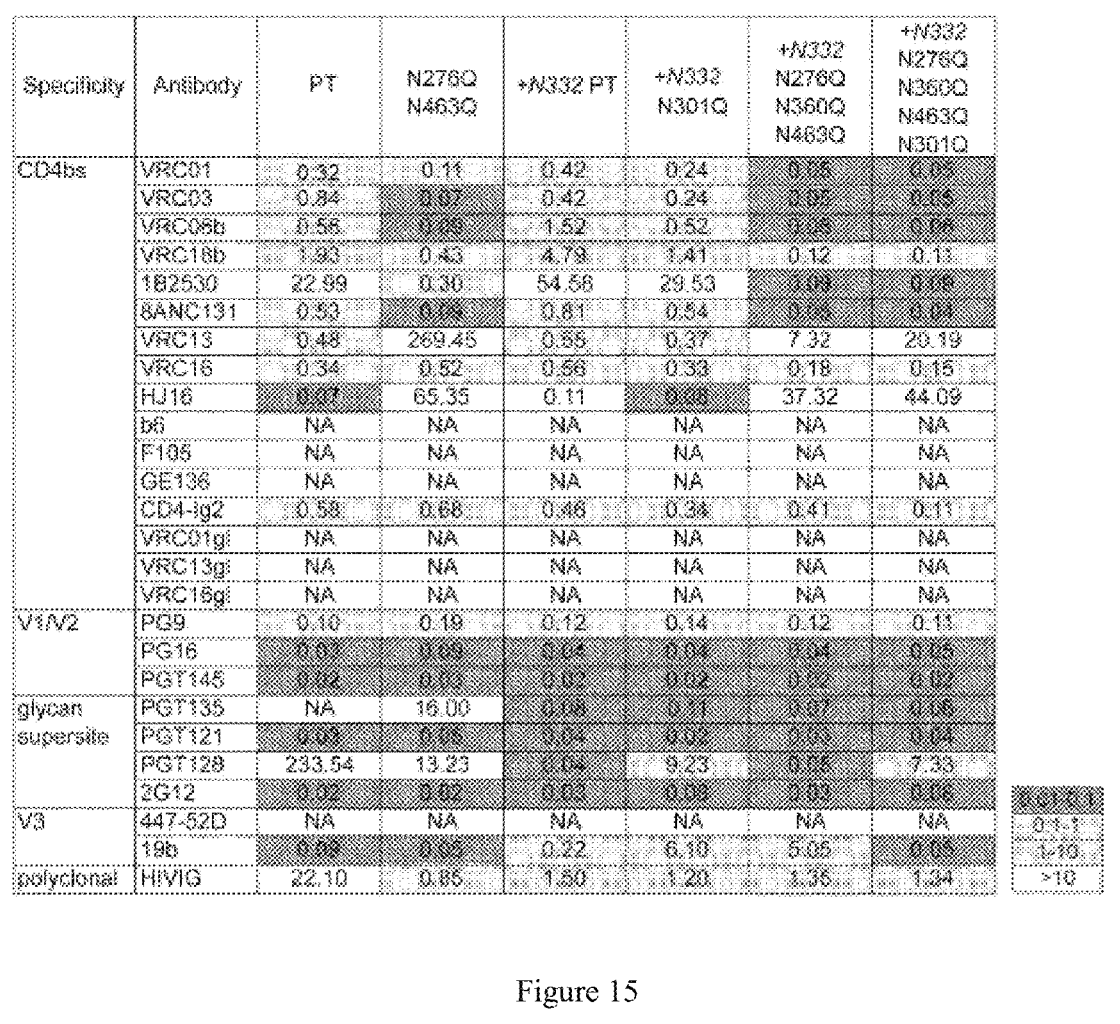

| Specificity | Antibody | PT | N276Q N463Q | +*N332* PT | +*N332* N301Q | +*N332* N276Q N360Q N463Q | +*N332* N276Q N360Q N463Q N301Q |
|---|---|---|---|---|---|---|---|
| CD4bs | VRC01 | 0.32 | 0.11 | 0.42 | 0.24 | [illegible] | [illegible] |
| | VRC03 | 0.84 | 0.07 | 0.42 | 0.24 | [illegible] | [illegible] |
| | VRC06b | 0.56 | [illegible] | 1.52 | 0.52 | [illegible] | 0.06 |
| | VRC18b | 1.93 | 0.43 | 4.79 | 1.41 | 0.12 | 0.11 |
| | 1B2530 | 22.99 | 0.30 | 54.56 | 29.53 | [illegible] | [illegible] |
| | 8ANC131 | 0.53 | [illegible] | 0.81 | 0.54 | [illegible] | [illegible] |
| | VRC13 | 0.48 | 269.45 | 0.55 | 0.37 | 7.32 | 20.19 |
| | VRC16 | 0.34 | 0.52 | 0.56 | 0.33 | 0.18 | 0.15 |
| | HJ16 | 0.07 | 65.35 | 0.11 | [illegible] | 37.32 | 44.09 |
| | b6 | NA | NA | NA | NA | NA | NA |
| | F105 | NA | NA | NA | NA | NA | NA |
| | GE136 | NA | NA | NA | NA | NA | NA |
| | CD4-Ig2 | 0.58 | 0.68 | 0.46 | 0.34 | 0.41 | 0.11 |
| | VRC01gl | NA | NA | NA | NA | NA | NA |
| | VRC13gl | NA | NA | NA | NA | NA | NA |
| | VRC16gl | NA | NA | NA | NA | NA | NA |
| V1/V2 | PG9 | 0.10 | 0.19 | 0.12 | 0.14 | 0.12 | 0.11 |
| | PG16 | 0.07 | [illegible] | 0.04 | 0.04 | 0.04 | [illegible] |
| | PGT145 | 0.02 | [illegible] | 0.02 | 0.02 | [illegible] | 0.02 |
| glycan supersite | PGT135 | NA | 16.00 | 0.08 | [illegible] | 0.07 | [illegible] |
| | PGT121 | 0.03 | 0.05 | 0.04 | 0.02 | [illegible] | 0.04 |
| | PGT128 | 233.54 | 13.23 | 0.04 | 9.23 | [illegible] | 7.33 |
| | 2G12 | 0.02 | 0.02 | 0.03 | [illegible] | 0.03 | 0.06 |
| V3 | 447-52D | NA | NA | NA | NA | NA | NA |
| | 19b | [illegible] | [illegible] | 0.22 | 6.10 | 5.05 | [illegible] |
| polyclonal | HIVIG | 22.10 | 0.85 | 1.50 | 1.20 | 1.35 | 1.24 |

| |
|---|
| [illegible] |
| 0.1-1 |
| 1-10 |
| >10 |

Figure 15 a
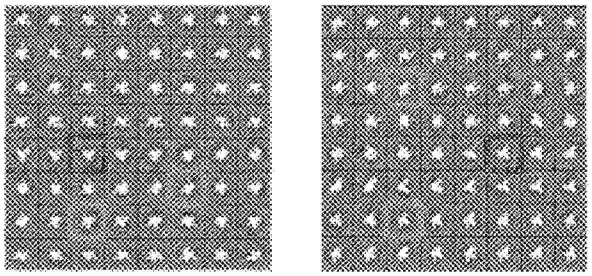
b
| Trimer Complex | Unliganded | 1 Fab | 2 Fabs | 3 Fabs |
|---|---|---|---|---|
| +*N332* PT | 19% | 20% | 34% | 27% |
| +*N332* **N276Q/N360Q/N463Q/N301Q** | 22% | 23% | 30% | 25% |
c
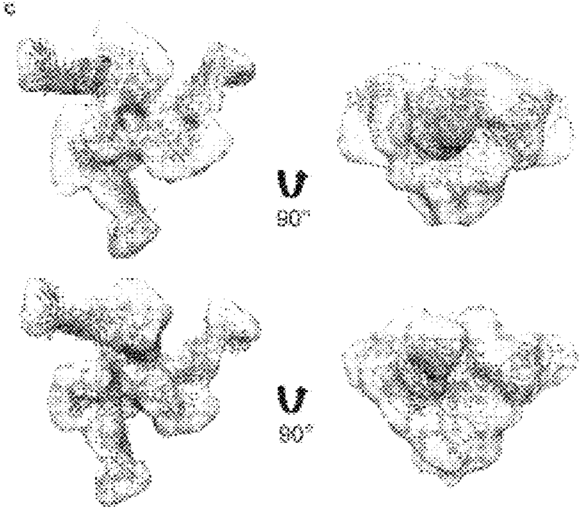
Figure 16A-16C

| Group # | Imm1 | Imm2 | Imm3 | Imm4 | Imm5 | Imm6 |
|---|---|---|---|---|---|---|
| 1<br>wt control | 16055wt | 16055wt | 16055wt | 16055wt | 16055wt | 16055wt |
| 2 | 16055del4 | 16055del4 | 16055wt | 16055wt | 1120wt | ZM197wt |
| 3 | 16055del4 | 16055del2 | 16055del1 | 16055wt | 1120wt | ZM197wt |
| 4 | 16055del4 | JRFLdel1 | BG505del1 | 16055wt<br>BG505wt<br>JRFLwt | 1120wt | ZM197wt |
| 5 | 16055del4 | 16055del2<br>BG505del2<br>JRFLdel2 | BG505del1<br>JRFLdel1 | BG505wt<br>JRFLwt | 1120wt | ZM197wt |

Post 5 Post 6

Figure 20

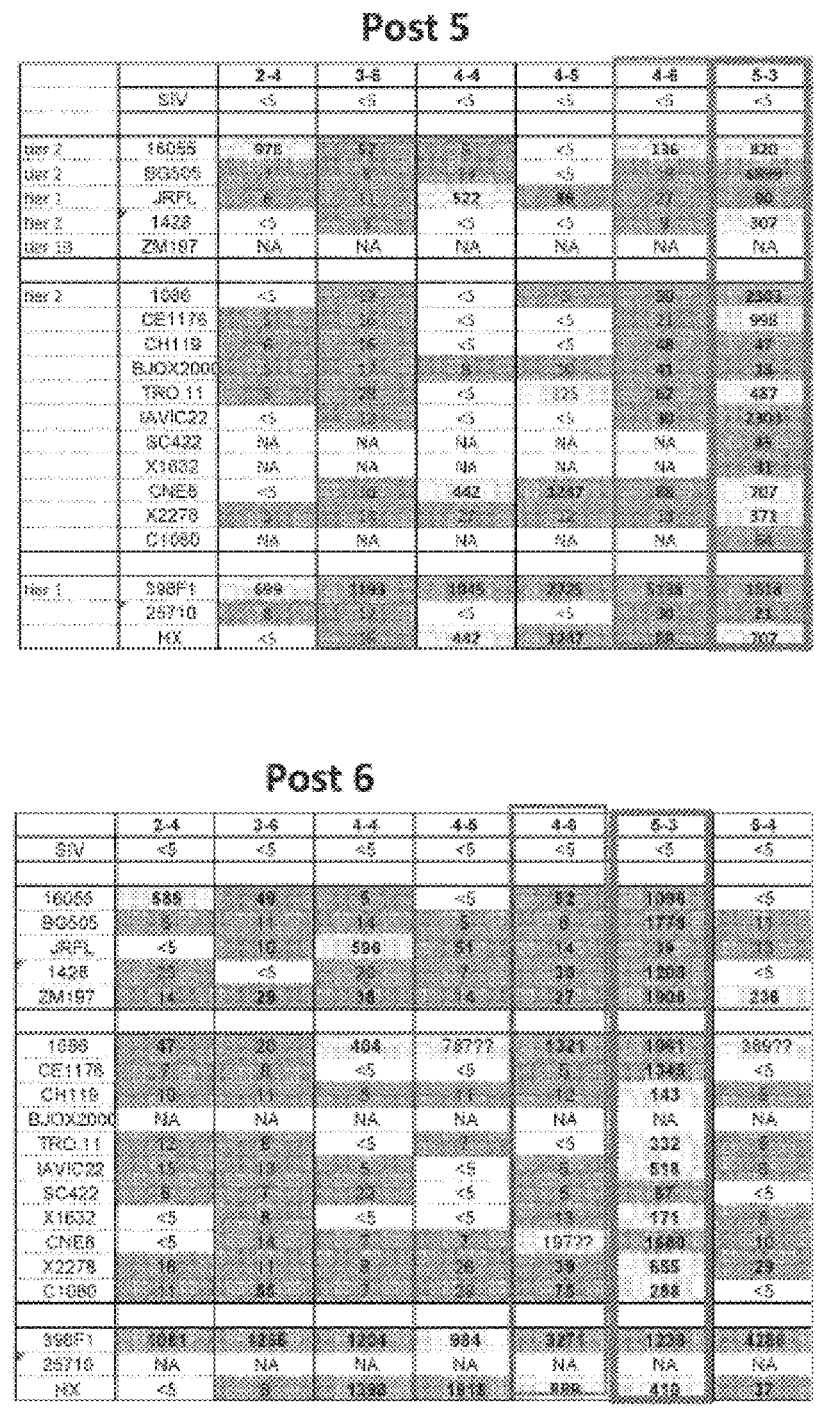

Post 5

| | | 2-4 | 3-6 | 4-4 | 4-5 | 4-6 | 5-3 |
|---|---|---|---|---|---|---|---|
| | SIV | <5 | <5 | <5 | <5 | <5 | <5 |
| | | | | | | | |
| tier 2 | 16055 | 978 | 57 | 5 | <5 | 136 | 820 |
| tier 2 | BG505 | [illegible] | [illegible] | 14 | <5 | [illegible] | [illegible] |
| tier 1 | JRFL | 6 | [illegible] | 522 | 88 | [illegible] | 90 |
| tier 2 | 1428 | <5 | [illegible] | <5 | <5 | 9 | 307 |
| tier 1B | ZM197 | NA | NA | NA | NA | NA | NA |
| | | | | | | | |
| tier 2 | 1086 | <5 | [illegible] | <5 | [illegible] | 30 | [illegible] |
| | CE1176 | [illegible] | [illegible] | <5 | <5 | [illegible] | 998 |
| | CH119 | 6 | 15 | <5 | <5 | 48 | 47 |
| | BJOX2000 | [illegible] | [illegible] | 5 | [illegible] | 41 | 36 |
| | TRO.11 | [illegible] | 24 | <5 | 125 | 62 | 487 |
| | IAVIC22 | <5 | [illegible] | <5 | <5 | 80 | [illegible] |
| | SC422 | NA | NA | NA | NA | NA | [illegible] |
| | X1632 | NA | NA | NA | NA | NA | [illegible] |
| | CNE8 | <5 | [illegible] | 442 | 2247 | 66 | 707 |
| | X2278 | [illegible] | [illegible] | [illegible] | [illegible] | [illegible] | 371 |
| | C1080 | NA | NA | NA | NA | NA | [illegible] |
| | | | | | | | |
| tier 1 | 398F1 | 688 | [illegible] | [illegible] | [illegible] | [illegible] | [illegible] |
| | 25710 | 8 | [illegible] | <5 | <5 | 30 | 21 |
| | HX | <5 | [illegible] | 442 | 2247 | 66 | 707 |

Post 6

| | 2-4 | 3-6 | 4-4 | 4-5 | 4-6 | 5-3 | 5-4 |
|---|---|---|---|---|---|---|---|
| SIV | <5 | <5 | <5 | <5 | <5 | <5 | <5 |
| | | | | | | | |
| 16055 | 588 | 49 | 5 | <5 | 52 | [illegible] | <5 |
| BG505 | 8 | 11 | 14 | 5 | 8 | 1779 | 11 |
| JRFL | <5 | 18 | 596 | 51 | 4 | 39 | 13 |
| 1428 | [illegible] | <5 | [illegible] | 7 | 33 | [illegible] | <5 |
| ZM197 | 14 | 28 | 18 | 14 | 27 | [illegible] | 238 |
| | | | | | | | |
| 1086 | 47 | 26 | 404 | 78777 | 1321 | [illegible] | 38977 |
| CE1176 | 7 | 8 | <5 | <5 | 5 | 1348 | <5 |
| CH119 | 10 | 11 | 8 | 11 | 12 | 143 | [illegible] |
| BJOX2000 | NA | NA | NA | NA | NA | NA | NA |
| TRO.11 | 12 | 6 | <5 | 7 | <5 | 332 | 8 |
| IAVIC22 | 15 | 13 | 5 | <5 | 8 | 518 | 8 |
| SC422 | 6 | 7 | 22 | <5 | 6 | 87 | <5 |
| X1632 | <5 | 8 | <5 | <5 | 13 | 171 | 8 |
| CNE8 | <5 | 14 | 7 | 7 | 19777 | 1680 | 10 |
| X2278 | 16 | 11 | 9 | 26 | 39 | 655 | 29 |
| C1080 | 11 | 44 | 7 | 24 | 75 | 288 | <5 |
| | | | | | | | |
| 398F1 | [illegible] | [illegible] | 1204 | 984 | 3271 | [illegible] | [illegible] |
| 25710 | NA | NA | NA | NA | NA | NA | NA |
| HX | <5 | 9 | 1398 | 1918 | 888 | 418 | 37 |

Figure 21

| | | prebleed | post 4 | post 5 |
|---|---|---|---|---|
| JRCSF.JB.SG3 | B | <20 | <20 | 95 |
| JRFL.JB.SG3 | B | <20 | 1,437 | 276 |
| RHPA.7.SG3 | B | <20 | <20 | 3,311 |
| TRO.11.SG3 | B | <20 | <20 | 326 |
| QH0515.01.SG3 | B | <20 | <20 | 54 |
| 45_01dG5.SG3 | B | <20 | 17,770 | 105,801 |
| ZM249.1.SG3 | C | <20 | <20 | 65 |
| 3301.V1.C24.SG3 | AC | <20 | <20 | 57 |
| RW020.2.SG3 | A | <20 | <20 | 772 |
| NKU3006.ec1.SG3 | D | <20 | 23 | 936 |
| MW965.26.SG3 | C (tier 1A) | <20 | 5,197 | 22,646 |
| SIV | Non HIV control | <20 | <20 | <20 |

Figure 22

Purified IgG CROSS-NEUTRALIZATION of clinical tier 2 isolates NOT in the "vaccine"

Post 5

| IC50 post 5 | | 2-4 | 3-6 | 4-4 | 4-5 | 4-6 | 5-3 |
|---|---|---|---|---|---|---|---|
| | SIV | ND | ND | ND | ND | ND | ND |
| | | | | | | | |
| tier 2 | 16055 | [illegible] | 0.168 | [illegible] | >2 | 0.037 | [illegible] |
| tier 2 | 1086 | >2 | >2 | >2 | 2.534 | 0.320 | [illegible] |
| | CE1176 | >2 | >2 | >2 | >2 | [illegible] | [illegible] |
| | CH119 | >2 | >2 | >2 | >2 | 0.166 | 0.053 |
| | BJOX2000 | >2 | >2 | >2 | 3.500 | 0.101 | 0.139 |
| | TRO.11 | >2 | >2 | >2 | 3.442 | 0.301 | 0.013 |
| | IAVIC22 | 0.861 | 0.305 | 0.322 | 0.315 | 0.060 | 0.051 |
| | SC422 | >2 | >2 | 0.147 | 0.263 | 0.389 | 0.050 |
| | CNE8 | >2 | >2 | >2 | >2 | [illegible] | [illegible] |
| | C1080 | 3.532 | >2 | 0.374 | 0.201 | 0.251 | 0.041 |
| | X2278 | [illegible] | 0.756 | 0.469 | 0.215 | 0.068 | [illegible] |
| tier 1 | HX | >2 | >2 | 0.016 | [illegible] | 0.034 | 0.014 |

Rabbit 5-3 has the most potent IgG tier 2 cross neutralizing titers (Group 5 animal)

Rabbit 4-6 has lower titers, but detectable cross neutralization as well (Group 4 animal)

Note: two different regimens

Figure 23

Serum and IgG Neutralization for rabbit #5-3

| | | Post 5 | Post 6 |
|---|---|---|---|
| | | 5-3 | 5-3 |
| | SIV | <5 | <5 |
| | | | |
| tier 2 | 16055 | 830 | [illegible] |
| tier 2 | BG505 | [illegible] | [illegible] |
| tier 1 | JRFL | [illegible] | 38 |
| tier 2 | 1428 | 307 | [illegible] |
| tier 1B | ZM197 | NA | [illegible] |
| | | | |
| tier 2 | 1086 | [illegible] | [illegible] |
| | CE1176 | [illegible] | [illegible] |
| | CH119 | [illegible] | 143 |
| | BJOX2000 | [illegible] | NA |
| | TRO.11 | 467 | 332 |
| | IAVIC22 | [illegible] | 518 |
| | SC422 | [illegible] | [illegible] |
| | X1632 | [illegible] | 171 |
| | CNE8 | 707 | [illegible] |
| | X2278 | 371 | 656 |
| | C1080 | [illegible] | 258 |
| | | | |
| tier 1 | 398F1 | [illegible] | [illegible] |
| | 25710 | [illegible] | NA |
| | HX | 707 | 410 |

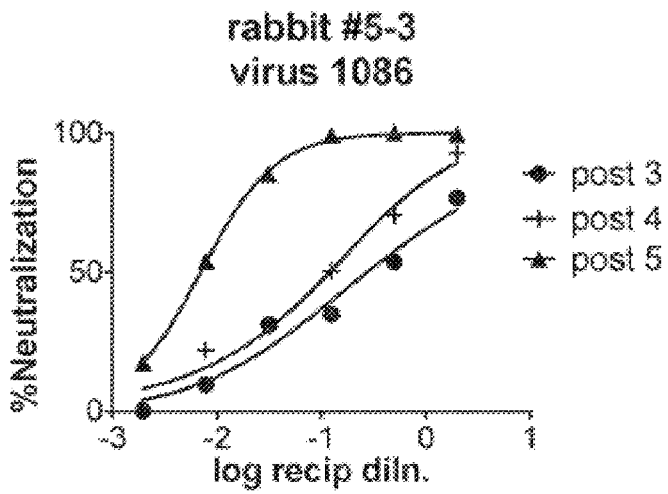

Figure 24

Autologous Prime:Boost Regimen

| | | Group A-3 | | | | | |
|---|---|---|---|---|---|---|---|
| | | Pre | P2 | P3 | P4 | P5 | P6 |
| RW020 | A | <20 | <20 | <20 | <20 | 33 | <20 |
| 3301.V1.C24 | AC | <20 | <20 | <20 | <20 | <20 | <20 |
| 45_01dG5 | B | <20 | <20 | <20 | <20 | <20 | 22 |
| JRFL | B | <20 | <20 | <20 | <20 | <20 | <20 |
| JRCSF | B | <20 | <20 | <20 | <20 | <20 | <20 |
| RHPA | B | <20 | <20 | <20 | <20 | <20 | <20 |
| TRO.11 | B | <20 | <20 | <20 | <20 | <20 | <20 |
| QH0515 | B | <20 | <20 | <20 | <20 | <20 | <20 |
| ZM249 | C | <20 | <20 | <20 | <20 | <20 | <20 |
| NKU3006.ec1 | D | <20 | <20 | <20 | <20 | <20 | <20 |
| MW965 | C | <20 | <20 | 504 | 2130 | 2391 | 1442 |

Figure 27A

Heterologous Prime:Boost Regimens

| Group B-6 | | | | ↓ | | Group C-3 | | | | ↓ | |
|---|---|---|---|---|---|---|---|---|---|---|---|
| Pre | P2 | P3 | P4 | P5 | P6 | Pre | P2 | P3 | P4 | P5 | P6 |
| <20 | <20 | <20 | <20 | 54 | <20 | <20 | <20 | <20 | <20 | 772 | 2391 |
| <20 | <20 | <20 | <20 | 194 | 29 | <20 | <20 | <20 | <20 | 57 | <20 |
| <20 | <20 | <20 | 29 | 148 | 27 | <20 | <20 | 78 | 17,278 | 105,501 | 24,619 |
| <20 | <20 | 25 | 175 | 192 | 64 | <20 | <20 | 21 | 1437 | 276 | 151 |
| <20 | <20 | 25 | <20 | 200 | 80 | <20 | <20 | <20 | <20 | 95 | 29 |
| <20 | <20 | <20 | <20 | <20 | <20 | <20 | <20 | <20 | <20 | 3311 | 17,494 |
| <20 | <20 | <20 | <20 | 68 | <20 | <20 | <20 | <20 | <20 | 328 | 366 |
| <20 | <20 | <20 | <20 | 25 | <20 | <20 | <20 | <20 | <20 | 54 | <20 |
| <20 | <20 | <20 | <20 | 28 | <20 | <20 | <20 | <20 | <20 | 65 | 258 |
| <20 | <20 | <20 | <20 | 49 | <20 | <20 | <20 | <20 | 23 | 936 | 1120 |
| <20 | 763 | 12,026 | 4622 | 98,153 | 132,879 | <20 | 4036 | 7063 | 5197 | 22,840 | 13,916 |

Figure 27B

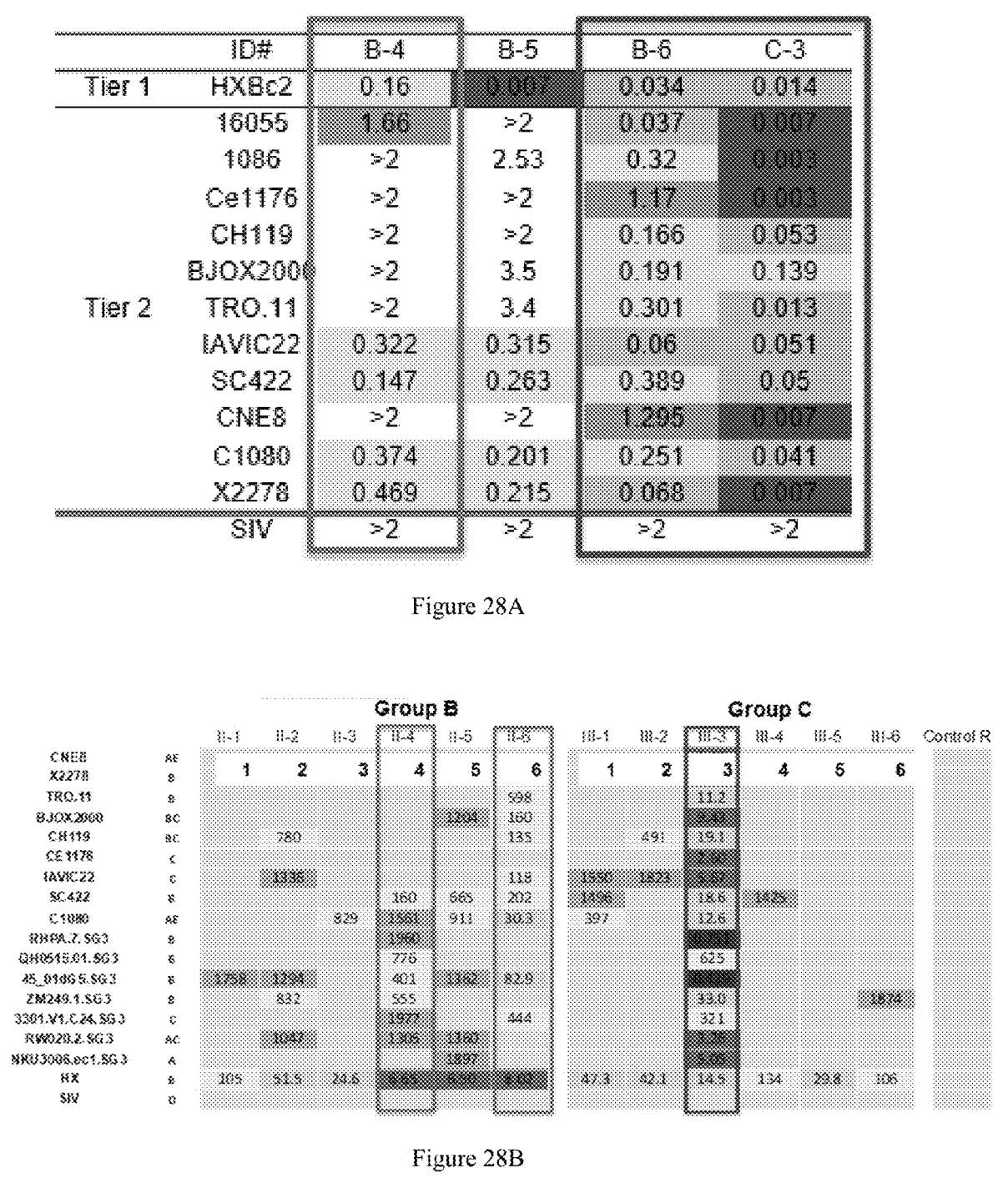

| | ID# | B-4 | B-5 | B-6 | C-3 |
|---|---|---|---|---|---|
| Tier 1 | HXBc2 | 0.16 | 0.007 | 0.034 | 0.014 |
| Tier 2 | 16055 | 1.66 | >2 | 0.037 | 0.007 |
| | 1086 | >2 | 2.53 | 0.32 | 0.003 |
| | Ce1176 | >2 | >2 | 1.17 | 0.003 |
| | CH119 | >2 | >2 | 0.166 | 0.053 |
| | BJOX2000 | >2 | 3.5 | 0.191 | 0.139 |
| | TRO.11 | >2 | 3.4 | 0.301 | 0.013 |
| | IAVIC22 | 0.322 | 0.315 | 0.06 | 0.051 |
| | SC422 | 0.147 | 0.263 | 0.389 | 0.05 |
| | CNE8 | >2 | >2 | 1.295 | 0.007 |
| | C1080 | 0.374 | 0.201 | 0.251 | 0.041 |
| | X2278 | 0.469 | 0.215 | 0.068 | 0.007 |
| | SIV | >2 | >2 | >2 | >2 |

Figure 28A

| | | Group B | | | | | | Group C | | | | | | |
|---|---|---|---|---|---|---|---|---|---|---|---|---|---|---|
| | | II-1 | II-2 | II-3 | II-4 | II-5 | II-6 | III-1 | III-2 | III-3 | III-4 | III-5 | III-6 | Control R |
| CNE8 | AE | 1 | 2 | 3 | 4 | 5 | 6 | 1 | 2 | 3 | 4 | 5 | 6 | |
| X2278 | B | | | | | | | | | | | | | |
| TRO.11 | B | | | | | | 598 | | | 11.2 | | | | |
| BJOX2000 | BC | | | | | 1304 | 160 | | | [illegible] | | | | |
| CH119 | BC | | 780 | | | | 135 | | 491 | 19.1 | | | | |
| CE1176 | C | | | | | | | | | [illegible] | | | | |
| IAVIC22 | C | | 1335 | | | | 118 | 1590 | 1623 | [illegible] | | | | |
| SC422 | B | | | | 160 | 665 | 202 | 1496 | | 18.6 | 1425 | | | |
| C1080 | AE | | | 829 | 1561 | 911 | 30.3 | 397 | | 12.6 | | | | |
| RHPA.7.SG3 | B | | | | 1960 | | | | | [illegible] | | | | |
| QH0515.01.SG3 | B | | | | 776 | | | | | 625 | | | | |
| 45_01dG5.SG3 | B | 1758 | 1294 | | 401 | 1362 | 82.9 | | | [illegible] | | | | |
| ZM249.1.SG3 | B | | 832 | | 555 | | | | | 33.0 | | | 1874 | |
| 3301.V1.C24.SG3 | C | | | | 1977 | | 444 | | | 321 | | | | |
| RW020.2.SG3 | AC | | 1047 | | 1305 | 1160 | | | | [illegible] | | | | |
| NKU3006.ec1.SG3 | A | | | | | 1897 | | | | [illegible] | | | | |
| HX | B | 105 | 51.5 | 24.6 | [illegible] | [illegible] | [illegible] | 47.3 | 42.1 | 14.5 | 134 | 29.8 | 106 | |
| SIV | O | | | | | | | | | | | | | |

Figure 28B

| | | IC50 (µg/ml) | | | IC80 (µg/ml) | |
|---|---|---|---|---|---|---|
| | | IC2 | | VRC01 | IC2 | VRC01 |
| Clade | Virus | 50µg/ml | 200µg/ml | | 200µg/ml | |
| A | KER2008.12.SG3 | 14.00 | 8.11 | 0.49 | 70.10 | 2.13 |
| A | Q259.17.SG3 | 46.30 | 47.40 | 0.17 | 164 | 0.37 |
| A | RW020.2.SG3 | >50 | 32.60 | 0.25 | 58 | 0.85 |
| AC | 3301.V1.C24.SG3 | 32.90 | 20.30 | 0.19 | 67.50 | 0.58 |
| AD | Q461.e2.SG3 | >50 | >200 | 0.95 | >200 | 2.66 |
| AE | 620345.c1.SG3 | >50 | 50.60 | >50 | >200 | >50 |
| AE | CNE5.SG3 | >50 | 68.40 | 0.46 | >200 | 1.32 |
| AE | CNE55.SG3 | 9.01 | 8.46 | 0.45 | 49.20 | 1.22 |
| AE | M02138.SG3 | 1.00 | 1.00 | 1.10 | 10.50 | 3.75 |
| AE | TH976.17.SG3 | 7.70 | 13.40 | 0.29 | 37.30 | 0.66 |
| AG | 242-14.SG3 | 8.88 | 11.00 | >50 | 32.20 | >50 |
| B | 45_01dG5.SG3 | 11.70 | 15.60 | 0.04 | 60.50 | 0.13 |
| B | 7165.18.SG3 | 14.30 | 16.60 | 34.40 | 41.40 | >50 |
| B | QH0515.01.SG3 | >50 | 77.60 | 1.13 | 168 | 4.10 |
| B | RHPA.7.SG3 | 9.00 | 9.00 | 0.056 | 34.20 | 0.21 |
| B | YU2.DG.SG3 | 27.60 | 19.80 | 0.24 | 57.00 | 0.39 |
| BC | CH038.12.SG3 | >50 | >200 | 0.65 | >200 | 2.14 |
| BC | CH070.1.SG3 | >50 | >200 | 5.26 | >200 | >50 |
| C | 0013095-2.11.SG3 | 14.00 | 11.60 | 0.15 | 37.10 | 0.40 |
| C | 001428-2.42.SG3 | 15.10 | 11.90 | 0.044 | 32.10 | 0.11 |
| C | 26191-2.48.SG3 | >50 | 52.10 | 0.27 | >200 | 0.98 |
| C | 3168.V4.C10.SG3 | 12.50 | 9.57 | 0.35 | 20.90 | 0.72 |
| C | ZM135.10a.SG3 | 6.52 | 6.52 | 1.05 | 34.40 | 3.74 |
| C | ZM249.1.SG3 | 7.93 | 7.93 | 0.14 | 31.20 | 0.47 |
| D | 231965.c1.SG3 | >50 | 75 | 0.78 | >200 | 1.76 |
| D | 247-23.SG3 | >50 | 30.70 | 1.73 | 136 | 14.80 |
| D | NKU3006.ec1.SG3 | 30.00 | 24.40 | 1.06 | 79.40 | 2.93 |
| nonHIV | SIVmac251.30.SG3 | >50 | nd | nd | nd | nd |

Figure 30B.

| Sequence | V-Gene | J-gene | D-Gene | CDR3 | CDR3 length |
|---|---|---|---|---|---|
| 1C2 HC | IGHV1S40*01 | IGHJ4*01 | IGHD8-1*01 | ARGAVTYGLGGAYLKHFNL | 20 |
| E70 HC | 1GHV1S40*01 | IGHJ4*01 | IGHD3-1*01 | RFAGYRYSVWSYPDL | 15 |
| 1C2 KC | IGKV1S47*01 | IGKJ1-4*03 | | LYGYISSDRID | 11 |
| E70 KC | IGKV1S36*01 | IGKJ1-2*01 | | QSAYNGDGDNA | 11 |

| Alignment | % HC Identity (aa) | % LC Identity (aa) |
|---|---|---|
| 1C2 and E70 | 69.3% | 64.9% |
| 1C2 and 3BC315 | 45.0% | 40.9% |

| Virus | Clade | E70 | Virus | Clade | E70 |
|---|---|---|---|---|---|
| BG505 | A | 0.03 | 45_01dG5 | B | 0.04 |
| MG505 | A | 8.04 | RHPA.7 | B | >50 |
| Q769 | A | 0.21 | YU2 | B | >50 |
| KER2008.12 | A | >50 | 92TH021 | B | 2.13 |
| Q259.17 | A | >50 | BJOX002000 | BC | >50 |
| RW020.2 | A | >50 | CH119 | BC | >50 |
| Q461.e2 | AD | >50 | CH038.12 | BC | >50 |
| 620345.c1 | AE | >50 | CH070.1 | BC | >50 |
| CNE5 | AE | 2.54 | 13095 | C | >50 |
| CNE55 | AE | >50 | Du156 | C | >50 |
| CNE8 | AE | >50 | 1086.B2 | C | 0.05 |
| M02138 | AE | >50 | 16055 | C | 0.45 |
| TH976.17 | AE | >50 | 1428 | C | >50 |
| 242-14 | AG | >50 | Ce1176 | C | 0.11 |
| TRO.11 | B | 2.67 | Ce0217 | C | >50 |
| SC422 | B | >50 | 3168.V4.C10 | C | >50 |
| X2278 | B | >50 | 231965.c1 | D | >50 |
| 7165.18 | B | >50 | 247-23 | D | >50 |
| QH0515.01 | B | >50 | NKU3006.ec1 | D | >50 |
| SIV | | >50 | | | |

N234 dependence

| 16055 | |
|---|---|
| WT | 0.96 |
| N234Q | >50 |

| 1086.B2 | |
|---|---|
| WT | 0.05 |
| N234A | >50 |

| BG505 | |
|---|---|
| WT | 0.05 |
| N234S | >50 |

Deletion of N276 enhances breadth

| 92TH021 | |
|---|---|
| WT | 2.13 |
| N276A | 0.018 |

| IAVIC22 | |
|---|---|
| WT | >50 |
| N276A | 0.46 |

But not on BG505

| BG505 | |
|---|---|
| WT | 0.05 |
| N276A | 0.03 |

Figure 32A

Group B-3

| E70-resistant | Pre | P2 | P3 | P4 | P5 | P6 |
|---|---|---|---|---|---|---|
| RHPA | <20 | <20 | <20 | <20 | 3311 | 17,484 |
| NKU3006 | <20 | <20 | <20 | 23 | 936 | 1120 |

| | BG505 NFL | 1086 NFL TD |
|---|---|---|
| PGT145 | - | - |
| 2G12 | - | - |
| VRC01 | ++ | ++ |
| VRC03 | ++ | +++ |
| VRC13 | +++ | ++ |
| 8ANC195 | +++ | ++ |
| 35O22 | - | |

Design 1 PaxVax1: Env150 KN-6R-SOSIP
Design 2 PaxVax2: Env150 KN
Design 3 SOSIP
Design 4 SOSIP

| | Man5 | Man6 | Man7 | Man8 | Man9 | Sum |
|---|---|---|---|---|---|---|
| BG505 NFL S553P | 5.9 | 3.9 | 6.0 | 19.8 | 33.4 | 69.1 |
| BG505 NFL N554P | 4.9 | 3.6 | 6.7 | 22.7 | 38.9 | 76.7 |
| BG505 NFL L555P | 5.9 | 3.4 | 6.6 | 21.5 | 40.4 | 77.9 |
| BG505 NFL Q562P | 8.2 | 4.5 | 6.6 | 19.0 | 32.8 | 71.1 |
| BG505 NFL Q563P | 5.2 | 3.5 | 6.6 | 19.7 | 43.4 | 78.4 |

16055 NFL L555P aa sequence

MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTAAKRRVVEGGGGSGGGGSAV
GLGAVIFGFLGAAGSTMGAASITLTVQARQLLSGIVQQQSNPLKAIEAQQHLLQLTVWGIKQLQTRVLAIERY
LKDQQLLGIWGCSGKLICTTAVPWNSSWSNKSHDEIWGNMTWMQWDREISNYTNTIYRLLEDSQNQQEQ
NEKDLLALDGGGGSHHHHHHHH
L555P

Figure 48

16055 NFL S553P aa sequence

MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTAAKRRVVEGGGGSGGGGSAV
GLGAVIFGFLGAAGSTMGAASITLTVQARQLLSGIVQQQPNLLKAIEAQQHLLQLTVWGIKQLQTRVLAIERY
LKDQQLLGIWGCSGKLICTTAVPWNSSWSNKSHDEIWGNMTWMQWDREISNYTNTIYRLLEDSQNQQEQ
NEKDLLALDGGGGSHHHHHHHH
S553P

Figure 49

16055 NFL N554P aa sequence

MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTAAKRRVVEGGGGSGGGGSAV
GLGAVIFGFLGAAGSTMGAASITLTVQARQLLSGIVQQQSPLLKAIEAQQHLLQLTVWGIKQLQTRVLAIERY
LKDQQLLGIWGCSGKLICTTAVPWNSSWSNKSHDEIWGNMTWMQWDREISNYTNTIYRLLEDSQNQQEQ
NEKDLLALDGGGGSHHHHHHHH
N554P

Figure 50

16055 NFL Q562P aa sequence
MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTAAKRRVVEGGGGSGGGGSAV
GLGAVIFGFLGAAGSTMGAASITLTVQARQLLSGIVQQQSNLLKAIEAPQHLLQLTVWGIKQLQTRVLAIERYL
KDQQLLGIWGCSGKLICTTAVPWNSSWSNKSHDEIWGNMTWMQWDREISNYTNTIYRLLEDSQNQQEQ
NEKDLLALDGGGGSHHHHHHHH
Q562P

Figure 51

16055 NFL Q563P aa sequence

MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTAAKRRVVEGGGGSGGGGSAV
GLGAVIFGFLGAAGSTMGAASITLTVQARQLLSGIVQQQSNLLKAIEAQPHLLQLTVWGIKQLQTRVLAIERYL
KDQQLLGIWGCSGKLICTTAVPWNSSWSNKSHDEIWGNMTWMQWDREISNYTNTIYRLLEDSQNQQEQ
NEKDLLALDGGGGSHHHHHHHH
Q563P

Figure 52

16055 NFL CC2 aa sequence

MPMGSLQPLATLYLLGMLVASVLAGNLWVTVYYGVPVWKEAKTTLFCASDAKAYEKEVHNVWATHACVP
TDPNPQEMVLENVTENFNMWKNDMVEQMHEDVISLWDQSLKPCVKLTPLCVTLECRQVNTTNATSSVN
VTNGEEIKNCSFNATTEIRDKKQKVYALFYRLDIVPLEEERKGNSSKYRLINCNTSAITQACPKVTFDPIPIHYCA
PAGYAILKCNNKTFNGTGPCNNVSTVQCTHGIKPVVSTQLLLNGSLAEGEIIIRSENLTNNVKTIIVHLNESVEIV
CTRPNNNTRKSIRIGPGQTFYATGDIIGNIRQAYCNIKKDDWIRTLQRVGKKLAEHFPRRIINFTSPAGGDLEIT
THSFNCRGEFFYCNTSSLFNSTYNPNDTNSNSSSSNSSLDITIPCRIKQIINMWQEVGRAMYAPPIEGNITCKS
NITGLLLVRDGGVESNETEIFRPGGGDMRNNWRSELYKYKVVEIKPLGIAPTACKRRVVEGGGGSGGGGSAV
GLGAVIFGFLGAAGSTMGAASITLTVQARQLLSGIVQQQSNLLKAPEAQQHLLQLTVWGIKQLQTRVLAIERY
LKDQQLLGIWGCSGKLICTTAVPWNSSWSNKSHDEIWGNMTWMQWDREISNYTNTIYRLLEDSQNQQEQ
NEKDLLACDGGGGSHHHHHHHH

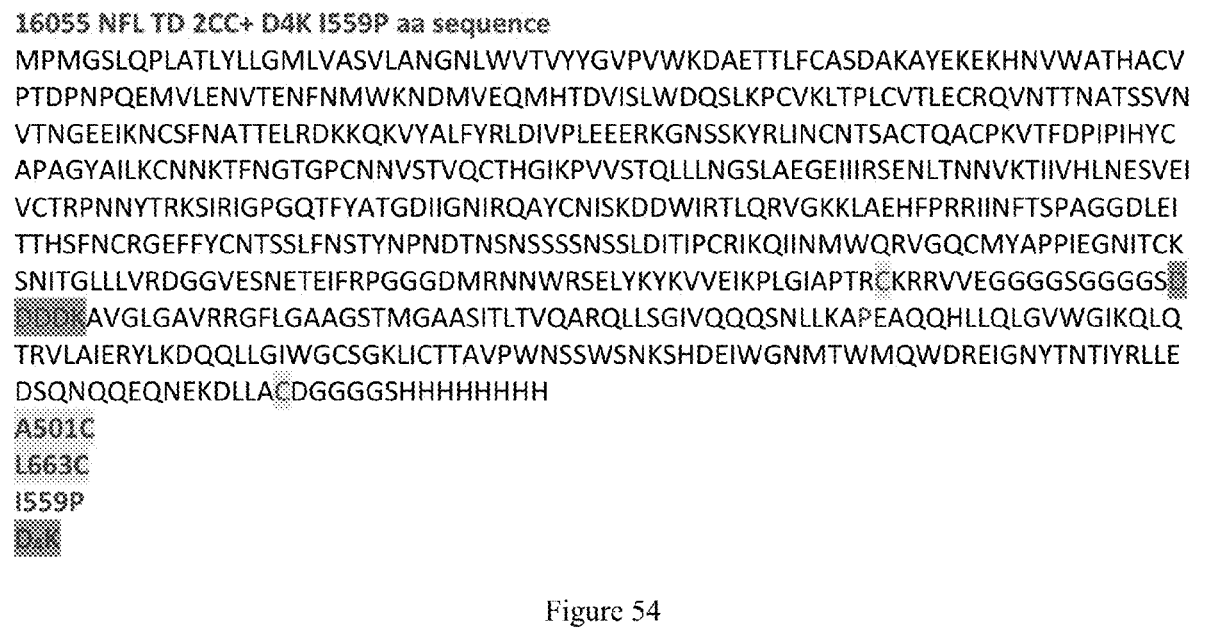

16055 NFL TD 2CC+ D4K I559P aa sequence

MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSENLTNNVKTIIVHLNESVEI
VCTRPNNYTRKSIRIGPGQTFYATGDIIGNIRQAYCNISKDDWIRTLQRVGKKLAEHFPRRIINFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESNETEIFRPGGGDMRNNWRSELYKYKVVEIKPLGIAPTRCKRRVVEGGGGSGGGGS[illegible]
[illegible]AVGLGAVRRGFLGAAGSTMGAASITLTVQARQLLSGIVQQQSNLLKAPEAQQHLLQLGVWGIKQLQ
TRVLAIERYLKDQQLLGIWGCSGKLICTTAVPWNSSWSNKSHDEIWGNMTWMQWDREIGNYTNTIYRLLE
DSQNQQEQNEKDLLACDGGGGSHHHHHHHH A501C
L663C
I559P
[illegible]

Figure 54

Figure 55:
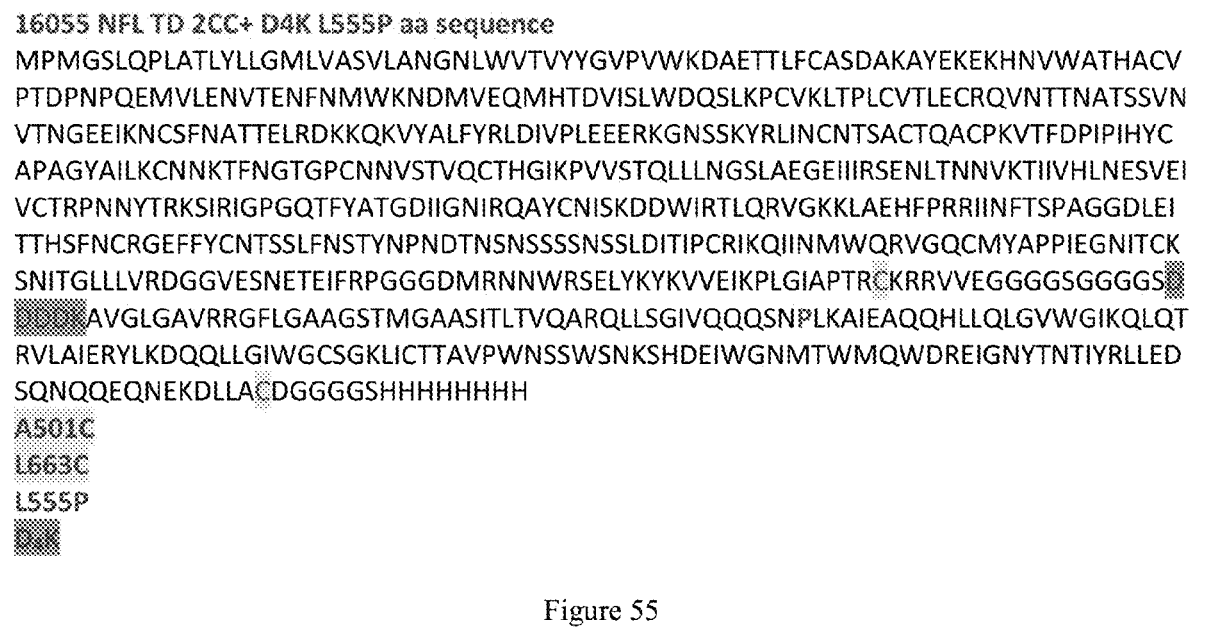

16055 NFL TD 2CC+ D4K L555P aa sequence

MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSENLTNNVKTIIVHLNESVEI
VCTRPNNYTRKSIRIGPGQTFYATGDIIGNIRQAYCNISKDDWIRTLQRVGKKLAEHFPRRIINFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESNETEIFRPGGGDMRNNWRSELYKYKVVEIKPLGIAPTRCKRRVVEGGGGSGGGGS[illegible]AVGLGAVRRGFLGAAGSTMGAASITLTVQARQLLSGIVQQQSNPLKAIEAQQHLLQLGVWGIKQLQT
RVLAIERYLKDQQLLGIWGCSGKLICTTAVPWNSSWSNKSHDEIWGNMTWMQWDREIGNYTNTIYRLLED
SQNQQEQNEKDLLACDGGGGSHHHHHHHH

BG505 NFL L555P aa sequence

MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRAKRRVVGGGGGS
GGGGSAVGIGAVFLGFLGAAGSTMGAASMTLTVQARNLLSGIVQQQSNPLRAIEAQQHLLKLTVWGIKQL
QARVLAVERYLRDQQLLGIWGCSGKLICTTNVPWNSSWSNRNLSEIWDNMTWLQWDKEISNYTQIIYGLLE
ESQNQQEKNEQDLLALDGGGGSHHHHHHHH

BG505 NFL S553P aa sequence
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRAKRRVVGGGGGS
GGGGSAVGIGAVFLGFLGAAGSTMGAASMTLTVQARNLLSGIVQQQPNLLRAIEAQQHLLKLTVWGIKQLQ
ARVLAVERYLRDQQLLGIWGCSGKLICTTNVPWNSSWSNRNLSEIWDNMTWLQWDKEISNYTQIIYGLLEE
SQNQQEKNEQDLLALDGGGGSHHHHHHHH
S553P

Figure 57

BG505 NFL N554P aa sequence
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRAKRRVVGGGGGS
GGGGSAVGIGAVFLGFLGAAGSTMGAASMTLTVQARNLLSGIVQQQSPLLRAIEAQQHLLKLTVWGIKQLQ
ARVLAVERYLRDQQLLGIWGCSGKLICTTNVPWNSSWSNRNLSEIWDNMTWLQWDKEISNYTQIIYGLLEE
SQNQQEKNEQDLLALDGGGGSHHHHHHHH
 N554P

Figure 58

BG505 NFL Q562P aa sequence
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRAKRRVVGGGGGS
GGGGSAVGIGAVFLGFLGAAGSTMGAASMTLTVQARNLLSGIVQQQSNLLRAIEAPQHLLKLTVWGIKQLQ
ARVLAVERYLRDQQLLGIWGCSGKLICTTNVPWNSSWSNRNLSEIWDNMTWLQWDKEISNYTQIIYGLLEE
SQNQQEKNEQDLLALDGGGGSHHHHHHHH
　　　Q562P

Figure 59

BG505 NFL Q563P aa sequence
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRAKRRVVGGGGGS
GGGGSAVGIGAVFLGFLGAAGSTMGAASMTLTVQARNLLSGIVQQQSNLLRAIEAQPHLLKLTVWGIKQLQ
ARVLAVERYLRDQQLLGIWGCSGKLICTTNVPWNSSWSNRNLSEIWDNMTWLQWDKEISNYTQIIYGLLEE
SQNQQEKNEQDLLALDGGGGSHHHHHHHH
    Q563P

Figure 60

BG505 NFL CC2 aa sequence
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSAITQACPKVSFEPIPIHYCA
PAGFAILKCKDKKFNGTGPCPSVSTVQCTHGIKPVVSTQLLLNGSLAEEEVMIRSENITNNAKNILVQFNTPVQ
INCTRPNNNTRKSIRIGPGQAFYATGDIIGDIRQAHCNVSKATWNETLGKVVKQLRKHFGNNTIIRFANSSGG
DLEVTTHSFNCGGEFFYCNTSGLFNSTWISNTSVQGSNSTGSNDSITLPCRIKQIINMWQRIGQAMYAPPIQ
GVIRCVSNITGLILTRDGGSTNSTTETFRPGGGDMRDNWRSELYKYKVVKIEPLGVAPTRCKRRVVGGGGGS
GGGGSAVGIGAVFLGFLGAAGSTMGAASMTLTVQARNLLSGIVQQQSNLLRAPEAQQHLLKLTVWGIKQL
QARVLAVERYLRDQQLLGIWGCSGKLICTTNVPWNSSWSNRNLSEIWDNMTWLQWDKEISNYTQIIYGLLE
ESQNQQEKNEQDLLACDGGGGSHHHHHHHH
    A501C
    L663C

Figure 61

BG505 NFL TD 2CC+ D4K I559P aa sequence

MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSACTQACPKVSFEPIPIHYC
APAGFAILKCKDKKFNGTGPCPSVSTVQCTHGIKPVVSTQLLLNGSLAEEEVMIRSENITNNAKNILVQFNTPV
QINCTRPNNYTRKSIRIGPGQAFYATGDIIGDIRQAHCNVSKATWNETLGKVVKQLRKHFGNNTIIRFANSSG
GDLEVTTHSFNCGGEFFYCNTSGLFNSTWISNTSVQGSNSTGSNDSITLPCRIKQIINMWQRIGQCMYAPPI
QGVIRCVSNITGLILTRDGGSTNSTTETFRPGGGDMRDNWRSELYKYKVVKIEPLGVAPTRCKRRVVGGGGG
SGGGGS[redacted]AVGIGAVRRGFLGAAGSTMGAASMTLTVQARNLLSGIVQQQSNLLRAPEAQQHLLKLTV
WGIKQLQARVLAVERYLRDQQLLGIWGCSGKLICTTNVPWNSSWSNRNLSEIWDNMTWLQWDKEISNYT
QIIYGLLEESQNQQEKNEQDLLACDGGGGSHHHHHHHH A501C
L663C
I559P
[redacted]

Figure 62

BG505 NFL TD 2CC+ D4K L555P aa sequence

MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSACTQACPKVSFEPIPIHYC
APAGFAILKCKDKKFNGTGPCPSVSTVQCTHGIKPVVSTQLLLNGSLAEEEVMIRSENITNNAKNILVQFNTPV
QINCTRPNNYTRKSIRIGPGQAFYATGDIIGDIRQAHCNVSKATWNETLGKVVKQLRKHFGNNTIIRFANSSG
GDLEVTTHSFNCGGEFFYCNTSGLFNSTWISNTSVQGSNSTGSNDSITLPCRIKQIINMWQRIGQCMYAPPI
QGVIRCVSNITGLILTRDGGSTNSTTETFRPGGGDMRDNWRSELYKYKVVKIEPLGVAPTRCKRRVVGGGGG
SGGGGSDDDDKAVGIGAVRRGFLGAAGSTMGAASMTLTVQARNLLSGIVQQQSNPLRAIEAQQHLLKLTV
WGIKQLQARVLAVERYLRDQQLLGIWGCSGKLICTTNVPWNSSWSNRNLSEIWDNMTWLQWDKEISNYT
QIIYGLLEESQNQQEKNEQDLLACDGGGGSHHHHHHH

A501C
L663C
L555P
[illegible]

Figure 63

JRFL NFL CC2 aa sequence
MPMGSLQPLATLYLLGMLVASVLAVEKLWVTVYYGVPVWKEATTTLFCASDAKAYDTEVHNVWATHACVP
TDPNPQEVVLENVTEHFNMWKNNMVEQMQEDIISLWDQSLKPCVKLTPLCVTLNCKDVNATNTTNDSEG
TMERGEIKNCSFNITTSIRDKVQKEYALFYKLDVVPIDNNNTSYRLISCDTSVITQACPKISFEPIPIHYCAPAGFA
ILKCNDKTFNGKGPCKNVSTVQCTHGIRPVVSTQLLLNGSLAEEEVVIRSDNFTNNAKTIIVQLKESVEINCTRP
NNNTRKSIHIGPGRAFYTTGEIIGDIRQAHCNISRAKWNDTLKQIVIKLREQFENKTIVFNHSSGGDPEIVMHS
FNCGGEFFYCNSTQLFNSTWNNNTEGSNNTEGNTITLPCRIKQIINMWQEVGKAMYAPPIRGQIRCSSNITG
LLLTRDGGINENGTEIFRPGGGDMRDNWRSELYKYKVVKIEPLGVAPTKCKRRVVQGGGGSGGGGSAVGIG
AVFLGFLGAAGSTMGAASMTLTVQARLLLSGIVQQQNNLLRAPEAQQRMLQLTVWGIKQLQARVLAVERY
LGDQQLLGIWGCSGKLICTTAVPWNASWSNKSLDRIWNNMTWMEWEREIDNYTSEIYTLIEESQNQQEKN
EQELLECDGGGGSHHHHHHHH
   A501C
   L663C

Figure 64

JRFL NFL TD CC+ C3d L60 aa sequence

MPMGSLQPLATLYLLGMLVASVLAVEKLWVTVYYGVPVWKDAETTLFCASDAKAYDTEKHNVWATHACV
PTDPNPQEVVLENVTEHFNMWKNNMVEQMQTDIISLWDQSLKPCVKLTPLCVTLNCKDVNATNTTNDSE
GTMERGEIKNCSFNITTELRDKVQKVYALFYKLDVVPIDNNNTSYRLISCDTSVCTQACPKISFEPIPIHYCAPAG
FAILKCNDKTFNGKGPCKNVSTVQCTHGIRPVVSTQLLLNGSLAEEEVVIRSDNFTNNAKTIIVQLKESVEINCT
RPNNYTRKSIRIGPGRAFYTTGEIIGDIRQAHCNISRAKWNDTLKQIVIKLREQFENKTIVFNHSSGGDPEIVMH
SFNCGGEFFYCNSTQLFNSTWNNNTEGSNNTEGNTITLPCRIKQIINMWQRVGQCMYAPPIRGQIRCSSNIT
GLLLTRDGGINENGTEIFRPGGGDMRDNWRSELYKYKVVKIEPLGVAPTRAKRRVVQGGGGSGGGGSAVGI
GAVRRGFLGAAGSTMGAASMTLTVQARNLLSGIVQQQSNLLRAPEAQQRMLQLGVWGIKQLQARVLAVE
RYLRDQQLLGIWGCSGKLICTTAVPWNASWSNKSLDRIWNNMTWMEWEREIDNYTSEIYTLIEESQNQQE
KNEQELLALDGSGGGGSGGGGSGSGGSGGGGSGGSGGSGSGGGGSGGGGSGSGGGGGGGSGGGGSGG
GGSTPAGSGEQHMIGMTPTVIAVHYLDQTEQWGKFGIEKRQEALELIKKGYTQQLAFKQPSSAYAAFNNRP
PSTWLTAYVVKVFSLAANLIAIDSHVLCGAVKWLILEKQKPDGVFQEDGPVIHQEMIGGFRNAKEADVSLTAF
VLIALQEARDICEGQVNSLPGSINKAGEYIEASYMNLQRPYTVAIAGYALALMNKLEEPYLGKFLNTAKDRNR
WEEPDQQLYNVEATSYALLALLLLKDFDSVPPVVRWLNEQRYYGGGYGSTQATFMVFQALAQYQTDVPDH
KDLNMDVSFHLPS

L60

Mouse C3d

Figure 65

JRFL NFL TD CC+ C3d L30 aa sequence

MPMGSLQPLATLYLLGMLVASVLAVEKLWVTVYYGVPVWKDAETTLFCASDAKAYDTEKHNVWATHACV
PTDPNPQEVVLENVTEHFNMWKNNMVEQMQTDIISLWDQSLKPCVKLTPLCVTLNCKDVNATNTTNDSE
GTMERGEIKNCSFNITTELRDKVQKVYALFYKLDVVPIDNNNTSYRLISCDTSVCTQACPKISFEPIPIHYCAPAG
FAILKCNDKTFNGKGPCKNVSTVQCTHGIRPVVSTQLLLNGSLAEEEVVIRSDNFTNNAKTIIVQLKESVEINCT
RPNNYTRKSIRIGPGRAFYTTGEIIGDIRQAHCNISRAKWNDTLKQIVIKLREQFENKTIVFNHSSGGDPEIVMH
SFNCGGEFFYCNSTQLFNSTWNNNTEGSNNTEGNTITLPCRIKQIINMWQRVGQCMYAPPIRGQIRCSSNIT
GLLLTRDGGINENGTEIFRPGGGDMRDNWRSELYKYKVVKIEPLGVAPTRAKRRVVQGGGGSGGGGSAVGI
GAVRRGFLGAAGSTMGAASMTLTVQARNLLSGIVQQQSNLLRAPEAQQRMLQLGVWGIKQLQARVLAVE
RYLRDQQLLGIWGCSGKLICTTAVPWNASWSNKSLDRIWNNMTWMEWEREIDNYTSEIYTLIEESQNQQE
KNEQELLALDGSGGGGSGGGGSGSGGSGGGGSGGSGGSGSTPAGSGEQHMIGMTPTVIAVHYLDQTEQ
WGKFGIEKRQEALELIKKGYTQQLAFKQPSSAYAAFNNRPPSTWLTAYVVKVFSLAANLIAIDSHVLCGAVKW
LILEKQKPDGVFQEDGPVIHQEMIGGFRNAKEADVSLTAFVLIALQEARDICEGQVNSLPGSINKAGEYIEASY
MNLQRPYTVAIAGYALALMNKLEEPYLGKFLNTAKDRNRWEEPDQQLYNVEATSYALLALLLLKDFDSVPPV
VRWLNEQRYYGGGYGSTQATFMVFQALAQYQTDVPDHKDLNMDVSFHLPS

L30
Mouse C3d

Figure 66

426c del3 NFL TD CC+ C3d L60 aa sequence

MPMGSLQPLATLYLLGMLVASVLAVGNLWVTVYYGVPVWKDAETTLFCASDAKAYEKEKHNVWATHACV
PTDPNPQEVVLENVTENFNMWKNDMVDQMQTDVISIWDQSLKPCVKLTPLCVTLNCTNVNVTSNSTNVN
SSSTDNTTLGEIKNCSFNITTELRDKTRKVYALFYRLDIVPLDNSSNPNSSNTYRLINCNTSTLTQACPKVTFDPIP
IHYCAPAGYAILKCNNKTFNGKGPCNNVSTVQCTHGIKPVVSTQLLLNGSLAEEEIVIRSKNLRDNAKIIIVQLN
KSVEIVCTRPNNYTRRSIRIGPGQTFYATDIIGDIRQAYCNISGRNWSEAVNQVKKKLKEHFPHKNISFQSSSG
GDLEITTHSFNCGGEFFYCNTSGLFNDTISNATIMLPCRIKQIINMWQRVGQAIYAPPIKGNITCKSDITGLLLL
RDGGNTANNAEIFRPGGGDMRDNWRSELYKYKVVEIKPLGVAPTRAKRRVVEGGGGSGGGGSAVGIGAV
RRGFLGAAGSTMGAASITLTVQARQGLSGIVQQQSNLLRAPEAQQHMLQLGVWGIKQLQTRVLAIERYLKD
QQLLGLWGCSGKLICTTAVPWNISWSNKSKEEIWENMTWMQWDREIGNYTNTIYRLLEESQNQQENNEK
DLLALDGSGGGGSGGGGSGSGGSGGGGSGGSGGSGSGGGGSGGGGSGSGGGGGGGSGGGGSGGGGST
PAGSGEQHMIGMTPTVIAVHYLDQTEQWGKFGIEKRQEALELIKKGYTQQLAFKQPSSAYAAFNNRPPSTW
LTAYVVKVFSLAANLIAIDSHVLCGAVKWLILEKQKPDGVFQEDGPVIHQEMIGGFRNAKEADVSLTAFVLIAL
QEARDICEGQVNSLPGSINKAGEYIEASYMNLQRPYTVAIAGYALALMNKLEEPYLGKFLNTAKDRNRWEEP
DQQLYNVEATSYALLALLLLKDFDSVPPVVRWLNEQRYYGGGYGSTQATFMVFQALAQYQTDVPDHKDLN
MDVSFHLPS

L60
Mouse C3d

Figure 67

426c del3 NFL TD CC+ C3d L30 aa sequence

MPMGSLQPLATLYLLGMLVASVLAVGNLWVTVYYGVPVWKDAETTLFCASDAKAYEKEKHNVWATHACV
PTDPNPQEVVLENVTENFNMWKNDMVDQMQTDVISIWDQSLKPCVKLTPLCVTLNCTNVNVTSNSTNVN
SSSTDNTTLGEIKNCSFNITTELRDKTRKVYALFYRLDIVPLDNSSNPNSSNTYRLINCNTSTLTQACPKVTFDPIP
IHYCAPAGYAILKCNNKTFNGKGPCNNVSTVQCTHGIKPVVSTQLLLNGSLAEEEIVIRSKNLRDNAKIIIVQLN
KSVEIVCTRPNNYTRRSIRIGPGQTFYATDIIGDIRQAYCNISGRNWSEAVNQVKKKLKEHFPHKNISFQSSSG
GDLEITTHSFNCGGEFFYCNTSGLFNDTISNATIMLPCRIKQIINMWQRVGQAIYAPPIKGNITCKSDITGLLLL
RDGGNTANNAEIFRPGGGDMRDNWRSELYKYKVVEIKPLGVAPTRAKRRVVEGGGGSGGGGSAVGIGAV
RRGFLGAAGSTMGAASITLTVQARQGLSGIVQQQSNLLRAPEAQQHMLQLGVWGIKQLQTRVLAIERYLKD
QQLLGLWGCSGKLICTTAVPWNISWSNKSKEEIWENMTWMQWDREIGNYTNTIYRLLEESQNQQENNEK
DLLALDGSGGGGSGGGGSGSGGSGGGGSGGSGGSGSTPAGSGEQHMIGMTPTVIAVHYLDQTEQWGKF
GIEKRQEALELIKKGYTQQLAFKQPSSAYAAFNNRPPSTWLTAYVVKVFSLAANLIAIDSHVLCGAVKWLILEK
QKPDGVFQEDGPVIHQEMIGGFRNAKEADVSLTAFVLIALQEARDICEGQVNSLPGSINKAGEYIEASYMNL
QRPYTVAIAGYALALMNKLEEPYLGKFLNTAKDRNRWEEPDQQLYNVEATSYALLALLLLKDFDSVPPVVRW
LNEQRYYGGGYGSTQATFMVFQALAQYQTDVPDHKDLNMDVSFHLPS

L30

Mouse C3d

Figure 68

16055 NFL TD CC+
MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSENLTNNVKTIIVHLNESVEI
VCTRPNNYTRKSIRIGPGQTFYATGDIIGNIRQAYCNISKDDWIRTLQRVGKKLAEHFPRRIINFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESNETEIFRPGGGDMRNNWRSELYKYKVVEIKPLGIAPTRAKRRVVEGGGGSGGGGSA
VGLGAVRRGFLGAAGSTMGAASITLTVQARQLLSGIVQQQSNLLKAPEAQQHLLQLGVWGIKQLQTRVLAI
ERYLKDQQLLGIWGCSGKLICTTAVPWNSSWSNKSHDEIWGNMTWMQWDREIGNYTNTIYRLLEDSQNQ
QEQNEKDLLALDGGGGSHHHHHHHH

Figure 69

16055 NFL TD CC+ΔGly276
MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSEQLTNNVKTIIVHLNESVEI
VCTRPNNYTRKSIRIGPGQTFYATGDIIGNIRQAYCNISKDDWIRTLQRVGKKLAEHFPRRIINFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESNETEIFRPGGGDMRNNWRSELYKYKVVEIKPLGIAPTRAKRRVVEGGGGSGGGGSA
VGLGAVRRGFLGAAGSTMGAASITLTVQARQLLSGIVQQQSNLLKAPEAQQHLLQLGVWGIKQLQTRVLAI
ERYLKDQQLLGIWGCSGKLICTTAVPWNSSWSNKSHDEIWGNMTWMQWDREIGNYTNTIYRLLEDSQNQ
QEQNEKDLLALDGGGGSHHHHHHHH

16055 NFL TD CC+ΔGly276/463
MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSEQLTNNVKTIIVHLNESVEI
VCTRPNNYTRKSIRIGPGQTFYATGDIIGNIRQAYCNISKDDWIRTLQRVGKKLAEHFPRRIINFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESQETEIFRPGGGDMRNNWRSELYKYKVVEIKPLGIAPTRAKRRVVEGGGGSGGGGSA
VGLGAVRRGFLGAAGSTMGAASITLTVQARQLLSGIVQQQSNLLKAPEAQQHLLQLGVWGIKQLQTRVLAI
ERYLKDQQLLGIWGCSGKLICTTAVPWNSSWSNKSHDEIWGNMTWMQWDREIGNYTNTIYRLLEDSQNQ
QEQNEKDLLALDGGGGSHHHHHHHH

16055 NFL TD CC+ΔGly276/301/360/463
MPMGSLQPLATLYLLGMLVASVLANGNLWVTVYYGVPVWKDAETTLFCASDAKAYEKEKHNVWATHACV
PTDPNPQEMVLENVTENFNMWKNDMVEQMHTDVISLWDQSLKPCVKLTPLCVTLECRQVNTTNATSSVN
VTNGEEIKNCSFNATTELRDKKQKVYALFYRLDIVPLEEERKGNSSKYRLINCNTSACTQACPKVTFDPIPIHYC
APAGYAILKCNNKTFNGTGPCNNVSTVQCTHGIKPVVSTQLLLNGSLAEGEIIIRSEQLTNNVKTIIVHLNESVEI
VCTRPNQYTRKSIRIGPGQTFYATGDIIGNIRQAYCNISKDDWIRTLQRVGKKLAEHFPRRIIQFTSPAGGDLEI
TTHSFNCRGEFFYCNTSSLFNSTYNPNDTNSNSSSSNSSLDITIPCRIKQIINMWQRVGQCMYAPPIEGNITCK
SNITGLLLVRDGGVESQETEIFRPGGGDMRNNWRSELYKYKVVEIKPLGIAPTRAKRRVVEGGGGSGGGGSA
VGLGAVRRGFLGAAGSTMGAASITLTVQARQLLSGIVQQQSNLLKAPEAQQHLLQLGVWGIKQLQTRVLAI
ERYLKDQQLLGIWGCSGKLICTTAVPWNSSWSNKSHDEIWGNMTWMQWDREIGNYTNTIYRLLEDSQNQ
QEQNEKDLLALDGGGGSHHHHHHHH

Figure 70

BG505 NFL CC+
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSACTQACPKVSFEPIPIHYC
APAGFAILKCKDKKFNGTGPCPSVSTVQCTHGIKPVVSTQLLLNGSLAEEEVMIRSENITNNAKNILVQFNTPV
QINCTRPNNYTRKSIRIGPGQAFYATGDIIGDIRQAHCNVSKATWNETLGKVVKQLRKHFGNNTIIRFANSSG
GDLEVTTHSFNCGGEFFYCNTSGLFNSTWISNTSVQGSNSTGSNDSITLPCRIKQIINMWQRIGQCMYAPPI
QGVIRCVSNITGLILTRDGGSTNSTTETFRPGGGDMRDNWRSELYKYKVVKIEPLGVAPTRAKRRVVGGGGG
SGGGGSAVGIGAVRRGFLGAAGSTMGAASMTLTVQARNLLSGIVQQQSNLLRAPEAQQHLLKLTVWGIKQ
LQARVLAVERYLRDQQLLGIWGCSGKLICTTNVPWNSSWSNRNLSEIWDNMTWLQWDKEISNYTQIIYGLL
EESQNQQEKNEQDLLALDGGGGSHHHHHHHH

Figure 71

BG505 NFL CC+ΔGly276
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSACTQACPKVSFEPIPIHYC
APAGFAILKCKDKKFNGTGPCPSVSTVQCTHGIKPVVSTQLLLNGSLAEEEVMIRSEQITNNAKNILVQFNTPV
QINCTRPNNYTRKSIRIGPGQAFYATGDIIGDIRQAHCNVSKATWNETLGKVVKQLRKHFGNNTIIRFANSSG
GDLEVTTHSFNCGGEFFYCNTSGLFNSTWISNTSVQGSNSTGSNDSITLPCRIKQIINMWQRIGQCMYAPPI
QGVIRCVSNITGLILTRDGGSTNSTTETFRPGGGDMRDNWRSELYKYKVVKIEPLGVAPTRAKRRVVGGGGG
SGGGGSAVGIGAVRRGFLGAAGSTMGAASMTLTVQARNLLSGIVQQQSNLLRAPEAQQHLLKLTVWGIKQ
LQARVLAVERYLRDQQLLGIWGCSGKLICTTNVPWNSSWSNRNLSEIWDNMTWLQWDKEISNYTQIIYGLL
EESQNQQEKNEQDLLALDGGGGSHHHHHHHH

BG505 NFL CC+ΔGly276/463
MPMGSLQPLATLYLLGMLVASVLAAENLWVTVYYGVPVWKDAETTLFCASDAKAYETEKHNVWATHACV
PTDPNPQEIHLENVTEEFNMWKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLINCNTSACTQACPKVSFEPIPIHYC
APAGFAILKCKDKKFNGTGPCPSVSTVQCTHGIKPVVSTQLLLNGSLAEEEVMIRSEQITNNAKNILVQFNTPV
QINCTRPNNYTRKSIRIGPGQAFYATGDIIGDIRQAHCNVSKATWNETLGKVVKQLRKHFGNNTIIRFANSSG
GDLEVTTHSFNCGGEFFYCNTSGLFNSTWISNTSVQGSNSTGSNDSITLPCRIKQIINMWQRIGQCMYAPPI
QGVIRCVSNITGLILTRDGGSTQSTTETFRPGGGDMRDNWRSELYKYKVVKIEPLGVAPTRAKRRVVGGGGG
SGGGGSAVGIGAVRRGFLGAAGSTMGAASMTLTVQARNLLSGIVQQQSNLLRAPEAQQHLLKLTVWGIKQ
LQARVLAVERYLRDQQLLGIWGCSGKLICTTNVPWNSSWSNRNLSEIWDNMTWLQWDKEISNYTQIIYGLL
EESQNQQEKNEQDLLALDGGGGSHHHHHHHH

Figure 72

JRFL NFL TD CC+
MPMGSLQPLATLYLLGMLVASVLAVEKLWVTVYYGVPVWKDAETTLFCASDAKAYDTEKHNVWATHACV
PTDPNPQEVVLENVTEHFNMWKNNMVEQMQTDIISLWDQSLKPCVKLTPLCVTLNCKDVNATNTTNDSE
GTMERGEIKNCSFNITTELRDKVQKVYALFYKLDVVPIDNNNTSYRLISCDTSVCTQACPKISFEPIPIHYCAPAG
FAILKCNDKTFNGKGPCKNVSTVQCTHGIRPVVSTQLLLNGSLAEEEVVIRSDNFTNNAKTIIVQLKESVEINCT
RPNNYTRKSIRIGPGRAFYTTGEIIGDIRQAHCNISRAKWNDTLKQIVIKLREQFENKTIVFNHSSGGDPEIVMH
SFNCGGEFFYCNSTQLFNSTWNNNTEGSNNTEGNTITLPCRIKQIINMWQRVGQCMYAPPIRGQIRCSSNIT
GLLLTRDGGINENGTEIFRPGGGDMRDNWRSELYKYKVVKIEPLGVAPTRAKRRVVQGGGGSGGGGSAVGI
GAVRRGFLGAAGSTMGAASMTLTVQARNLLSGIVQQQSNLLRAPEAQQRMLQLGVWGIKQLQARVLAVE
RYLRDQQLLGIWGCSGKLICTTAVPWNASWSNKSLDRIWNNMTWMEWEREIDNYTSEIYTLIEESQNQQE
KNEQELLALDGGGGSHHHHHHH

JRFL NFL TD CC+ΔGly276
MPMGSLQPLATLYLLGMLVASVLAVEKLWVTVYYGVPVWKDAETTLFCASDAKAYDTEKHNVWATHACV
PTDPNPQEVVLENVTEHFNMWKNNMVEQMQTDIISLWDQSLKPCVKLTPLCVTLNCKDVNATNTTNDSE
GTMERGEIKNCSFNITTELRDKVQKVYALFYKLDVVPIDNNNTSYRLISCDTSVCTQACPKISFEPIPIHYCAPAG
FAILKCNDKTFNGKGPCKNVSTVQCTHGIRPVVSTQLLLNGSLAEEEVVIRSDQFTNNAKTIIVQLKESVEINCT
RPNNYTRKSIRIGPGRAFYTTGEIIGDIRQAHCNISRAKWNDTLKQIVIKLREQFENKTIVFNHSSGGDPEIVMH
SFNCGGEFFYCNSTQLFNSTWNNNTEGSNNTEGNTITLPCRIKQIINMWQRVGQCMYAPPIRGQIRCSSNIT
GLLLTRDGGINENGTEIFRPGGGDMRDNWRSELYKYKVVKIEPLGVAPTRAKRRVVQGGGGSGGGGSAVGI
GAVRRGFLGAAGSTMGAASMTLTVQARNLLSGIVQQQSNLLRAPEAQQRMLQLGVWGIKQLQARVLAVE
RYLRDQQLLGIWGCSGKLICTTAVPWNASWSNKSLDRIWNNMTWMEWEREIDNYTSEIYTLIEESQNQQE
KNEQELLALDGGGGSHHHHHHH

JRFL NFL TD CC+ΔGly276/463
MPMGSLQPLATLYLLGMLVASVLAVEKLWVTVYYGVPVWKDAETTLFCASDAKAYDTEKHNVWATHACV
PTDPNPQEVVLENVTEHFNMWKNNMVEQMQTDIISLWDQSLKPCVKLTPLCVTLNCKDVNATNTTNDSE
GTMERGEIKNCSFNITTELRDKVQKVYALFYKLDVVPIDNNNTSYRLISCDTSVCTQACPKISFEPIPIHYCAPAG
FAILKCNDKTFNGKGPCKNVSTVQCTHGIRPVVSTQLLLNGSLAEEEVVIRSDQFTNNAKTIIVQLKESVEINCT
RPNNYTRKSIRIGPGRAFYTTGEIIGDIRQAHCNISRAKWNDTLKQIVIKLREQFENKTIVFNHSSGGDPEIVMH
SFNCGGEFFYCNSTQLFNSTWNNNTEGSNNTEGNTITLPCRIKQIINMWQRVGQCMYAPPIRGQIRCSSNIT
GLLLTRDGGINEQGTEIFRPGGGDMRDNWRSELYKYKVVKIEPLGVAPTRAKRRVVQGGGGSGGGGSAVGI
GAVRRGFLGAAGSTMGAASMTLTVQARNLLSGIVQQQSNLLRAPEAQQRMLQLGVWGIKQLQARVLAVE
RYLRDQQLLGIWGCSGKLICTTAVPWNASWSNKSLDRIWNNMTWMEWEREIDNYTSEIYTLIEESQNQQE
KNEQELLALDGGGGSHHHHHHH

Figure 73

001428 NFL TD CC+
MPMGSLQPLATLYLLGMLVASVLAAENLWVTVYYGVPVWKDAETTLFCASDAKAYETEKHNVWATHACV
PTDPNPQEMVLGNVTENFNMWKNDMVDQMHTDVISLWAQSLKPCVKLTPLCVTLECTQVNATQGNTTQ
VNVTQVNGDEMKNCSFNTTTELRDKKQKVYALFYRLDLVPLERENRGDSNSASKYILINCNTSAITQACPKVN
FDPIPIHYCTPAGYAILKCNNKTFNGTGSCNNVSTVQCTHGIKPVVSTQLLLNGSLAEEEIIIRSENLTDNVKTIIV
HLDQSVEIVCTRPNNYTRKSIRIGPGQTFYATGDIIGNIREAHCNISEKKWHEMLRRVSEKLAEHFPNKTIKFTS
SSGGDLEITTHSFNCRGEFFYCNTSGLFNSTYMPNGTYMPNGTNNSNSTIILPCRIKQIINMWQRVGQCMYA
PPIAGNITCNSNITGLLLVRDGGKNNNTEIFRPGGGDMRDNWRSELYKYKVVEIKPLGVAPTRAKRRVVEGG
GGSGGGGSAVGLGAVRRGFLGAAGSTMGAASITLTVQARQLLSGIVQQQSNLLQAPEAQQHLLQGTVWGI
KQLQTRVLAIERYLKDQQLLGIWGCSGKLICTTAVPWNSSWSNKSLTDIWDNMTWMQWDREVGNYTGIIY
RLLEDSQNQQERNEQDLLALDGGGGSHHHHHHHH

Figure 74

ZM197M NFL TD CC+
MPMGSLQPLATLYLLGMLVASVLAMEQLWVTVYYGVPVWKDAEATLFCASDAKAYEKEKHNVWATHACV
PTDPNPQEIPLGNVTENFNMWKNDMADQMHTDIISLWDQSLKPCVKLTPLCVTLNCSDATSNTTKNATNT
NTTSTDNRNATSNDTEMKGEIKNCTFNITTELRDRKTKVRALFYKLDVVPLEEEKNSSSKNSSYKEYRLISCNTS
TCTQACPKVSFDPIPIHYCAPAGYAILKCNNKTFNGTGPCHNVSTVQCTHGIKPVVSTQLLLNGSLAEEEIIIRSE
NLTDNTKTIIVHLNESVEINCTRPNNYTRKSVRIGPGQTFFATGEIIGDIRQAHCNLSKSNWTTTLKRIEKKLKE
HFNNATIKFESSAGGDLEITTHSFNCRGEFFYCNTSGLFNSSLLNDTDGTSNSTSNATITLPCRIKQIINMWQR
VGQCMYASPIAGIITCKSNITGLLLTRDGGNKSAGIETFRPGGGNMKDNWRSELYKYKVVEIKPLGIAPTRAKR
RVVEGGGGSGGGGSAAGIGAVRRGFLGAAGSTMGAASVMLTVQARQLLSGIVQQQSNLLRAPEAQQHM
LQGTVWGIKQLQTRVLAIERYLKDQQLLGLWGCSGKLICTTAVPWNTSWSNKSKDEIWDNMTWMQWDR
EIGNYTQVIYQLLEVSQNQQEKNENDLLALDGGGGHHHHHH

Figure 75

N-GLYCAN DELETED HIV-1 ENVELOPE GLYCOPROTEIN TRIMERS

RELATED APPLICATIONS AND INCORPORATION BY REFERENCE

This application claims priority to US provisional patent application Ser. Nos. 62/558,262 filed Sep. 13, 2017 and 62/621,682 filed Jan. 25, 2018.

Reference is made to U.S. application Ser. No. 15/075,329 filed Mar. 21, 2016 which published as U.S. patent publication US-2016-0272948-A1 on Sep. 22, 2016, which claims benefit of and priority to U.S. provisional patent application Ser. No. 62/136,365 filed Mar. 20, 2015, U.S. provisional patent application Ser. No. 62/145,855 filed Apr. 10, 2015, U.S. provisional patent application Ser. No. 62/164,459 filed May 20, 2015, U.S. provisional patent application Ser. No. 62/234,782 filed Sep. 30, 2015 and U.S. provisional patent application Ser. No. 62/251,872 filed Nov. 6, 2015. Reference is made to U.S. patent application Ser. No. 14/508,369 filed Oct. 7, 2014 which claims priority to U.S. provisional patent application Ser. Nos. 62/054,727 filed Sep. 24, 2014, 62/032,507 filed Aug. 1, 2014, 61/941,101 filed Feb. 18, 2014 and 61/887,618 filed Oct. 7, 2013.

Reference is also made to international patent application Serial No. PCT/US11/26862 filed Mar. 2, 2011 which published as international patent publication WO 2011/109511 on Sep. 9, 2011 and claims priority to U.S. provisional patent application Ser. No. 61/309,685 filed Mar. 2, 2010. Reference is also made to U.S. provisional patent application Ser. Nos. 61/664,990 and 61/722,739 filed Jun. 27, 2012 and Nov. 5, 2012, respectively.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been filed electronically in ASCII format and is hereby incorporated by reference in its entirety. Said ASCII copy, created on Jan. 9, 2019, is named Y7969-03049_SL.txt and is 211,385 bytes in size.

FIELD OF THE INVENTION

This application relates to a novel HIV-I envelope glycoprotein which may be utilized as an HIV-I vaccine immunogen, as a native Env trimer mimic, for identification of small molecules for use as immunogen that bind specific HIV-I broad neutralizing antibodies, for identification of small molecules for use as anti-viral compound that bind specific HIV-I envelope glycoprotein monomer and/or trimer, as antigens for crystallization and electron microscopy (EM) structural analysis and for the identification of broad neutralizing antibodies from HIV-I infected individuals or vaccinated subjects or antibody or ligand libraries.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-I and HIV-2, have been identified thus far, of which HIV-I is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+ T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 1 9; 280(5371):1884-8). For fusion with its target cells, HIV-I uses a trimeric Env complex containing gp120 and gp41 subunits (Burton et al., Nat Immunol. 2004 March; 5(3): 233-6). The fusion potential of the Env complex is triggered by engagement of the CD4 receptor and a coreceptor, usually CCR5 or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 200 I; 77:195-262). In the latter case, neutralizing antibodies may bind to epitopes whose exposure is enhanced or triggered by receptor binding. However, given the potential antiviral effects of neutralizing antibodies, it is not unexpected that HIV-I has evolved multiple mechanisms to protect it from antibody binding (Johnson & Desrosiers, Annu Rev Med. 2002; 53:499-518).

Most experimental HIV-I vaccines tested in human and/or non-human primate suggests that a successful vaccine incorporate immunogens that elicit broad neutralizing antibodies (bNabs) and robust cell-mediated immunity. HIV-I envelope glycoprotein (Env) is the main viral protein involved in the entry of the virus and is also the primary target for neutralizing antibodies, but due to immune evasion strategies and extreme sequence variability of Envs, generation of bNabs has been a daunting task (Phogat S, Wyatt R. Curr Pharm Des. 2007; 13:213-27, Phogat S, et al. J Intern Med. 2007 262:26-43, Karlsson Hedestam G B, et al Nat Rev Microbial. 2008 6:143-55).

The ability to elicit broad and potent neutralizing antibodies is a major challenge in the development of an HIV-I vaccine. Namely, HIV-I has evolved an impressive array of strategies to evade antibody-mediated neutralization, bNAbs develop over time in a proportion of HIV-I infected individuals, and a handful of broad neutralizing monoclonal antibodies have been isolated from clade B infected donors. These antibodies tend to display less breadth and potency against non-clade B viruses, and they recognize epitopes on the virus that so far have failed to elicit broad neutralizing responses when incorporated into a diverse range of immunogens. Presumably, due to the ability of these bNabs to recognize conserved recessed targets on HIV Env which are either inaccessible by elicited antibodies or difficult to precisely redesign and present to the immune system. Recently using a sensitive high-throughput micro-neutralization screening of supenatants from approximately 30,000 IgG+memory B cells from a HIV-I clade A-infected African donor, Applicants identified two new bNabs PG9 and PG16 that are broad and exceptionally potent neutralizing antibodies (Walker L, Phogat S, et al. Science. 2009; 326:285-Epub 2009 Sep. 3). These antibodies recognize a new conserved, yet accessible, vaccine target (consisting of conserved elements on the variable loops 2 and 3) on the Env and show preferential binding to HIV Env trimer (Model of PG9 and 16 epitopes on HIV-I trimer.). When tested for binding, these antibodies did not show binding to many empirically designed soluble (Env gp140) HIV Env trimer thought to be mimics of the native HIV-I Env spike, suggesting that either these Env designs are either incorrect or they are fixed in a form not recognized by PG9 and PG16.

SUMMARY OF THE INVENTION

A first embodiment of the present invention relates to an engineered or non-naturally occurring trimeric Env trimer, advantageously a flexibly linked NFL2P trimer having one or more BG505 Trimer-Derived mutations ("TD mutations") relative to BG505 positions and numbering. Said, wherein said TD mutations may comprise one or more mutations at residue 569. In particular, the mutations may include G at residue 569. The trimer may be derived from an Indian subtype C HIV-I Env sequence. The trimer may further comprise a disulfide linkage, which may be an engineered intra-protomer disulfide I201C-A433C (CC).

The trimer may further comprise a 10 residue (G4S) flexible linker (SEQ ID NO: 34) between a REKR-deleted Env gp120 C-terminus ("REKR" disclosed as SEQ ID NO: 35) and the unmodified gp41 N-terminus. The trimer may further comprise substitutions E47D, K49E, V65K, EI06T, 1165L, E429R, R432Q and/or A500R and may further comprise a T569G substitution.

The trimer may further comprise substitutions at residues 197, 276, N234, 262, 276, 301, 360, 463 or any combination thereof. The trimer may comprise substitutions N197Q, N276Q, N234Q, N262Q, N276Q, N301Q, N360Q, N463Q or any combination thereof. The trimer may comprise substitutions at residues 276, 301, 360, 463 or any combination thereof. The trimer may comprise substitutions N276Q, N301Q, N360Q, N463Q or any combination thereof.

The trimer may further comprise a potential N-linked glycans (PNGS) introduced at residue 332 by a K334S mutation ("+N332 PT"), wherein the italicized N refers to an N-glycan, not an asparagine residue.

The invention also encompasses an engineered or non-naturally occurring trimer, wherein the trimer may be a flexibly linked NFL2P trimer, wherein the trimer may comprise a N276Q/N463Q glycan-deleted variant with or without N332 restored, a +N332 N276Q/N360Q/N463Q triple N-glycan-deleted variant or a +N332 N276Q/N360Q/N463Q/N301Q quadruple N-glycan-deleted variant.

Another embodiment of the invention relates to an engineered or non-naturally occurring HIV Env trimer, advantageously a flexibly linked NFL2P trimer, wherein the trimer may comprise one or more trimer-derived mutations ("TD mutations"). In a preferred embodiment, the trimer comprises one or more mutations at residue position 555. In a preferred embodiment, the trimer comprises amino acid substitution L555P.

The trimer may further comprise one or more mutations that form one or more inter-protomer disulfide bonds. In particular embodiments, the trimer comprises amino acid substitutions A501C and/or L663C that form the inter-protomer disulfide bond. In particular embodiments, the trimer further comprises an enterokinase cleavage site. In a preferred embodiment, the trimer comprises an enterokinase cleavage site upstream of the fusion peptide (FP) N-terminus.

Another embodiment of the present invention encompasses methods of eliciting an immune response which may comprise administering to a mammal the any of the trimers disclosed herein. The method may further comprise adding an adjuvant. The adjuvant may be a lecithin and may optionally be combined with an acrylic polymer, a lecithin coated oil droplet in an oil-in-water emulsion or a lecithin and an acrylic polymer in an oil-in-water emulsion. The adjuvant may be ISCOMATRIX or Adjuplex. In another embodiment, the adjuvant may comprise alum.

In another embodiment, the trimer may be administered on the surface of a liposome or a nanoparticle. In another embodiment, the trimer may be fixed, for example, in glutaraldehyde. Advantageously, the trimers may be fixed in about 5 mM glutaraldehyde, which may be for about five minutes. In another embodiment, the chemically fixed trimers are quenched with glycine. Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 5. Antibody sensitivity of glycan-deleted variants of 16055 pseudovirus. Neutralization IC50 values of the panel of bNAbs and mAbs are shown and color-coded for concentrations (μg/ml) regarding potency as indicated. NN=No Neutralization. These experiments were performed two independent times for the bNAbs and most antibodies shown.

FIG. 8. Neutralizing ID50 values for the singly N-glycan-deleted viruses. ID50 values are indicated in bold; those derived by extrapolation are shown in non-bolded text. Statistical differences were evaluated by Mann-Whitney test and, when detected, were indicated under each data set with * P<0.05.

FIG. 9A-9C. Purified serum IgG cross-neutralization. (a) IgG neutralization curves derived from mean values for each data point of three independent TZM-bl-based neutralization assays. Error bars represent the standard deviation. The rabbits are designated by the Group number first (1, 2 or 3) followed by a dash and the animal index number as indicated in FIG. 7 (i.e., #5-3). If specified otherwise, the serum was analyzed following the fourth immunization. The "control rabbit" was immunized four times with blank liposomes in adjuvant and IgG was purified similarly to the experimental rabbit IgGs; the mean values of two experimental replicates are shown for this negative specificity control (b) ID50 values were derived from the curves described above and are color-coded as indicated. Weak neutralizing values were extrapolated based on the two highest IgG dilution data points and are indicated in italics. (c) Cross-neutralization of IAVIC22Δ276 and BG505Δ276 viruses analyzed by depletion with the 16055 gp120 TriMut protein. Purified IgG from the serum of rabbit #2-5 and rabbit #3-5 were titrated at the concentrations indicated (horizontal axis) in the absence or presence of the 16055 gp120 TriMut (two left panels). The 16055 gp120 TriMut protein was used at fixed concentration of 100 mg/ml. The mean values of two independent TZM-bl-based neutralization assays are shown with the bars at each dilution indicating the individual values. VRC13 IgG was used as a CD4bs directed antibody positive control (two right panels) and in case of BG505Δ276 virus representative control experiment is shown.

FIG. 15. EC50 values of antibody binding to the N-glycan-deleted trimers.

FIG. 16A-16C. EM analysis of the trimer—VRC03 Fab complexes. (a) Reference free 2D classes of +N332 PT in complex with VRC03 (left panel) and +N332 N276Q/N360Q/N463Q/N301Q in complex with VRC03 (right panel). Red: 3 Fabs bound, orange: 2 Fabs bound, green: 1 Fab bound, and blue: unbound trimers. (b) Table listing the occupancy of VRC03 Fab relative to the trimers. (c) EM 3D reconstructions of +N332 PT in complex with VRC03 (top panel; symmetry C3 applied) and +N332 N276Q/N360Q/N463Q/N301Q in complex with VRC03 (lower panel; symmetry C3 applied). The crystal structure of the BG505 soluble trimer in complex with PGV04 (PDB:3J5M) was fitted inside the EM volumes. The contour levels used for the symmetric volumes (C3) were ~19.

FIG. 20. Immunization scheme for all groups in rabbit experiment. Group 1: rabbits immunized with parental trimer 16055 NFL TD CC. Group 2: rabbits immunized with N-glycan deleted 16055 trimer. Group 3: rabbits were immunized sequentially with N-glycan deleted 16055 variants followed by glycosylated graduate restoration. Group 4: rabbits were immunized following heterologous sequential boosting scheme. Group 5: rabbits were immunized following heterologous cocktail boosting scheme, where the trimers were arrayed as mixtures on the same liposome to enhance B cell/BCR cross-recognition of conserved determinants.

FIG. 21. Serum neutralization titers with two time points. Cross-neutralization responses on the serum level was demonstrated for several animals from Groups 2-5. Rabbit 5-3 has the strongest serum titers and tier 2 cross-neutralization (orange box); Rabbit 4-6 has lower titers, but detectable cross neutralization as well.

FIG. 22. Serum cross-neutralization confirmed at the using isolated total serum IgG. 29/29 viruses were neutralized.

FIG. 23. Purified IgG CROSS-NEUTRALIZATION of clinical tier 2 isolates. Neutralization titers increase against 1086 virus overtime. Rabbit 5-3 (Group 5) has the most potent IgG tier 2 cross neutralizing titers. Rabbit 4-6 (Group 4) has lower titers, but detectable cross neutralization as well.

FIG. 24. Serum and IgG Neutralization for rabbit #5-3. Tested animal maintains the broadly neutralizing responses in the serum after the 5th and 6th immunizations.

FIG. 27A-27B. Increased neutralization serum breadth using heterologous prime:boost regimens (ID50). Trimer binding was assessed by antiserum from all animals following trimer-liposome inoculations. Boosting of trimer-specific IgG following each inoculation was detected. A: Autologous prime:boost tegimen. B: Heterologous prime: boost regimens.

FIG. 28A-28C. IgG-mediated tier 2 cross-neutralization elicited by ΔGly NFL:liposome heterologous cross-boosting in multiple animals. A: tier-2 IgG cross neutralization (IC50, mg/ml) following the 5th immunization. B: IgG cross neutralization (IC50, μg/ml—VRC.Mascola) following the 6th immunization. C: Longitudinal analysis using C3 IgG demonstrated clear boosting of 1086 virus neutralization following the 3rd, 4th and 5th trimer-liposome immunization.

FIG. 30A-30B. NFL:liposome elicited bNAb, gp41-directed bNAb 1C2. A: nsEM 3D reconstructions and of 1C2:16055 NFL CC2 complexes. 1C2 rabbit bNAb is interface Ab similar to 3BC315 with greater breadth. 1C2 fab appears to make contact with Glycan N88 (pink) and gp41 HR1 and HR2. B: The NFL-liposome-elicited 1C2 gp41 mAb is a bona fide broadly neutralizing antibody. 1C2 neutralized greater than 80% of viruses tested with modest potency.

FIG. 31 discloses SEQ ID NOS 37-40, 42-43, 42 and 44, respectively, in order of appearance.

FIG. 32A-32E. E70 is a CD4 binding site-directed antibody with a VRC01-like approach. A: deletion of the N-glycan at N276 enabled E70 to neutralize selected viruses, increasing both neutralization breadth and potency. B: E70 epitope significantly overlaps other CD4bs epitopes. in the BG505 context, E70 is biased toward and binds a conserved glycan at N234. C: Epitope Mapping by Cross-Competition ELISA. VRC33 is patient derived and ~50% breadth; VRC40 is patient derived and 3% breadth; 090 is derived from VelocImmune mice immunized with JR-FL NFL trimer. D: Aminal Sera after immunization neutralizes E70 resistant viruses at CD4bs with greater breadth. E: nsEM analysis revealed that the E70 epitope overlapped with VRC01 and other CD4bs nAbs of varying breadth Top: top view. Middle and bottom: side view.

FIG. 33B discloses "$(GGGGS)_2$" as SEQ ID NO: 34 and "(GGGGS)" as SEQ ID NO: 41. C: TZM-bI Nautralization with 1086 cell-surface tethered NFL compared to cleaved trimers (SOSIP).

FIG. 34A discloses "(D4K)" as SEQ ID NO: 36 and "$2\times(G_4S)$" as SEQ ID NO: 34. (B) Linear schematic diagram of the 16055

NFL with I559P or L555P, A501C-L663C, TD+ substitutions. FIG. 34B discloses "2×($G_4$S)" as SEQ ID NO: 34. (C) Linear schematic diagram of the 16055 NFL with all favorable modifications and an engineered EK cleavage site. FIG. 34C discloses "D4K" as SEQ ID NO: 36.

FIG. 48. 16055 NFL L555P amino acid sequence (SEQ ID NO: 1). L555P mutation is highlighted.

FIG. 49. 16055 NFL S553P amino acid sequence (SEQ ID NO: 2). S553P mutation is highlighted.

FIG. 50. 16055 NFL N554P amino acid sequence (SEQ ID NO: 3). N554P mutation is highlighted.

FIG. 51. 16055 NFL Q562P amino acid sequence (SEQ ID NO: 4). Q562P mutation is highlighted.

FIG. 52. 16055 NFL Q563P amino acid sequence (SEQ ID NO: 5). Q563P mutation is highlighted.

FIG. 53. 16055 NFL A501C/L663C amino acid sequence (SEQ ID NO: 6). A501C/L663C mutations are highlighted.

FIG. 54. 16055 NFL TD 2CC+D4K_I559P amino acid sequence (SEQ ID NO: 7). Yellow highlight: A501C/L663C mutations. Green highlight: D4K (SEQ ID NO: 36) cleavage site. Red text only: I559P mutation.

FIG. 55. 16055 NFL TD 2CC+D4K L555P amino acid sequence (SEQ ID NO: 8). Yellow highlight: A501C/L663C mutations. Green highlight: D4K (SEQ ID NO: 36) cleavage site. Red text only: L555P mutation.

FIG. 56. BG505 NFL L555P amino acid sequence (SEQ ID NO: 9). L555P mutation is highlighted.

FIG. 57. BG505 NFL S553P amino acid sequence (SEQ ID NO: 10). S553P mutation is highlighted.

FIG. 58. BG505 NFL N554P amino acid sequence (SEQ ID NO: 11). N554P mutation is highlighted.

FIG. 59. BG505 NFL Q562P amino acid sequence (SEQ ID NO: 12). Q562P mutation is highlighted.

FIG. 60. BG505 NFL Q563P amino acid sequence (SEQ ID NO: 13). Q563P mutation is highlighted.

FIG. 61. BG505 NFL CC2 amino acid sequence (SEQ ID NO: 14). A501C/L663C mutations are highlighted.

FIG. 62. BG505 NFL TD 2CC+D4K I559P amino acid sequence (SEQ ID NO: 15). Yellow highlight: A501C/L663C mutations. Green highlight: D4K (SEQ ID NO: 36) cleavage site. Red text only: I559P mutation.

FIG. 63. BG505 NFL TD 2CC+D4K L555P amino acid sequence (SEQ ID NO: 16). Yellow highlight: A501C/L663C mutations. Green highlight: D4K (SEQ ID NO: 36) cleavage site. Red text only: L555P mutation.

FIG. 64. JRFL NFL CC2 amino acid sequence (SEQ ID NO: 17). A501C/L663C mutations are highlighted.

FIG. 65. JRFL NFL TD CC+C3d L60 amino acid sequence (SEQ ID NO: 18). Yellow highlight: L60 linker. Green highlight: Mouse C3d.

FIG. 66. JRFL NFL TD CC+C3d L30 amino acid sequence (SEQ ID NO: 19). Yellow highlight: L30 linker. Green highlight: Mouse C3d.

FIG. 67. 426c del3 NFL TD CC+C3d L60 amino acid sequence (SEQ ID NO: 20). Yellow highlight: L60 linker. Green highlight: Mouse C3d.

FIG. 68. 426c del3 NFL TD CC+C3d L30 amino acid sequence (SEQ ID NO: 21). Yellow highlight: L30 linker. Green highlight: Mouse C3d.

FIG. 69. Amino acid sequence of 16055 NFL TD CC+ (SEQ ID NO: 22).

FIG. 70. Amino acid sequences of 16055 NFL TD CC+ΔGly276, 16055 NFL TD CC+ΔGly276/463, and 16055 NFL TD CC+ΔGly276/301/360/463 (SEQ ID NOs: 23-25).

FIG. 71. Amino acid sequence of BG505 NFL CC+ (SEQ ID NO: 26).

FIG. 72. Amino acid sequences of BG505 NFL CC+ΔGly276 and BG505 NFL CC+ΔGly276/463 (SEQ ID NOs 27-28).

FIG. 73. Amino acid sequences of JRFL NFL TD CC+, JRFL NFL TD CC+ΔGly276, JRFL NFL TD CC+ΔGly276/463 (SEQ ID NOs: 29-31).

FIG. 74. Amino acid sequence of 001428 NFL TD CC+ (SEQ ID NO: 32).

FIG. 75. Amino acid sequence of ZM197M NFL TD CC+ (SEQ ID NO: 33).

DETAILED DESCRIPTION OF THE INVENTION

Figures 1A, 1B, 1C:
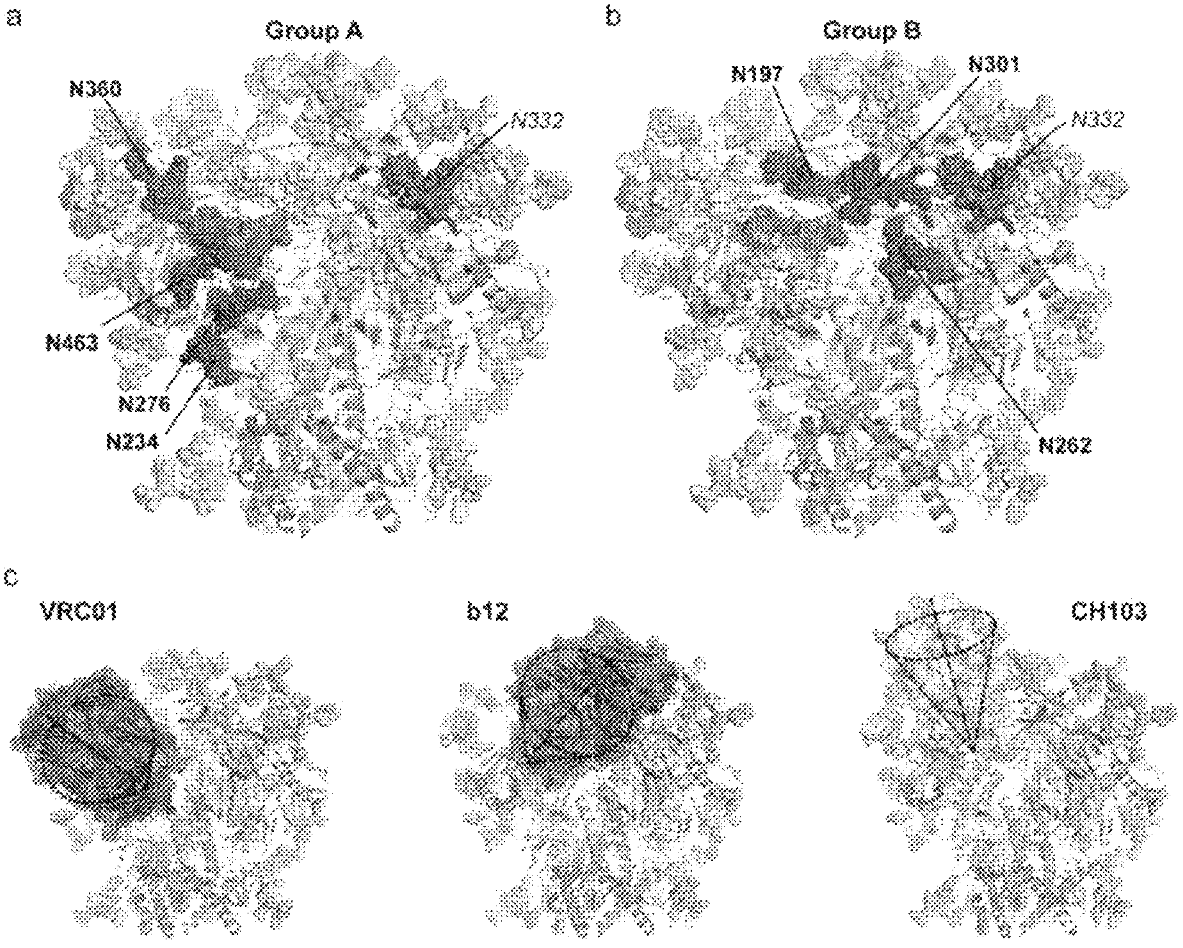
FIG. 1A-1C. HIV Env trimer N-glycans and the CD4bs. Structure of soluble BG505 SOSIP.664 HIV trimer (PDB accession number 5FYL) with gp120 in gray, gp41 in brown and the CD4bs shown as a magenta surface. N-glycans are shown in shades of blue. (a) The Group A N-glycans proximal to the CD4bs are shown in dark blue as indicated in bold and the N332 N-glycan is shown in dark turquoise. (b) The Group B N-glycans proximal to the CD4bs are shown in dark blue and are indicated in bold. N332 N-glycan is shown indark turquoise. (c) Trimer docking models of VRC01 (purple), b12 (red) and CH103(yellow) Fabs, each approaching the CD4bs with different angles of access.

The envelope glycoproteins show significantly better binding to newly identified broad neutralizing antibodies PG9 and/or PG16 and are well recognized by all known broadly neutralizing antibodies (bNAbs). The JRFL HPTMs and gp120 MIFs may be recognized by trimer-specific bNabs and likely recognized by bNAbs of other specificities. The envelope glycoproteins Envs have value (a) as reagents for screening of broad neutralizing antibodies (bNAbs), such as but not limited to, PG9 and PG16, the PGT145 family, the PGT128 family and for the SOSIPs the VRCOI-like mabs including VRC06, (b) as reagents for screening of small molecules that compete binding of broad neutralizing antibodies, such as but not limited to, PG9 and PG16, (c) as monomer and native envelope trimer mimic for crystallization studies and (d) as immunogens in different forms to use as HIV-I vaccine components, for example, to elicit broadly neutralizing antibodies.

In an advantageous embodiment, the soluble envelope glycoproteins of the present invention may be isolated from HIV-I Clade A virus, HIV-I Clade B virus, HIV-I Clade C virus, a HIV-I Clade A pseudo-virus, HIV-I Clade B pseudo-virus or a HIV-I Clade C pseudo-virus, such as an Indian subtype C HIV-I Env sequence. In an advantageous embodiment, the soluble envelope glycoproteins of the present invention may be isolated from the 6535 virus, the 13095 virus, the 16055 virus, the 25710 virus, the 25925 virus, the CAAN virus, the BG505 virus or the Zm109F virus.

In a particularly advantageous embodiment, the trimer protein, is prepared, purified and formulated for immunization in a human.

In another particularly advantageous embodiment, the trimer protein, is formulated for immunization in a human to contain an adjuvant. A number of adjuvants are well known to those investigating vaccines but could include but are not limited to those containing alum.

In another particularly advantageous embodiment, the trimer protein is further attached to a particle such that multiple copies of the trimer are attached and this material is prepared and formulated for immunization in a human.

In a particularly advantageous embodiment, the soluble envelope glycoproteins of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or the specification.

Another advantageous embodiment encompasses a stable soluble HIV-I envelope glycoprotein trimer mimic.

Immunogens in different forms are used to use as HIV-I vaccine components to elicit bNabs. The different forms of the HIV-I envelope are used in a prime, as DNA/vector expressing the protein/protein and as a boost as protein. The envelopes could also be used as particulate immunogen by cross linking to virus particles like Qbeta, cow pea mosaic virus, CRM, HPV, HBsAg etc.

In an advantageous embodiment, the soluble envelope glycoproteins of the present invention may be isolated from HIV-I Clade A virus, HIV-I Clade B virus, HIV-I Clade C virus, a HIV-I Clade A pseudo-virus, HIV-I Clade B pseudo-virus or a HIV-I Clade C pseudo-virus In an advantageous embodiment, the soluble envelope glycoproteins of the present invention may be isolated from the 6535 virus, the 13095 virus, the 16055 virus, the 25710 virus, the 25925 virus, the CAAN virus or the Zm 109F virus.

HIV type I (HIV-I) envelope is a noncovalent trimer of gp120-gp41 heterodimers, and its lability has hindered structural studies. SOSIP gp140 is a soluble, proteolytically mature form of the HIV-I envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140.

Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-I envelope trimers. These proteins may be useful as vaccine immunogens and for studying structure-function relationships within the HIV-I envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-I strain KNHI 144 form particularly homogenous trimers compared to a prototypic strain (JR-FL, subtype B). Described in U.S. Pat. No. 7,939,083 are the determinants of this enhanced stability which are located in the N-terminal region of KNHI 1144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The HIV-I envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371):1884-1888). HIV-I gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbial 6(2):143-155). The surface-exposed HIV-I Env trimer is the sole target for antibodies capable of neutralizing the virus (Burton D R, et al. (2004) Nat Immunol 5(3):233-236). Recently, a myriad of Env-directed broadly neutralizing antibodies (bNAbs) were isolated from numerous HIV-I-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-I envelope spike. Cell reports 7(3):785-795; Klein F, et al. (2012) J Exp Med 209(8):1469-1479). Infection of macaques by a chimeric model virus, SHIV, can be prevented by prior passive immunization of all bNAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci US A 109(46):18921-18925; Barouch D H, et al. (2013) Therapeutic efficacy of potent neutralizing HIV-I-specific monoclonal antibodies in SHIV-infected rhesus monkeys. Nature 503 (7475):224-228).

Along with virus-specific T cells, an efficacious HIV-I vaccine therefore would likely need to generate bNAbs targeting Env. Although the premise is simple, in actuality, it is a tremendous challenge without precedent in the history of vaccinology. The difficulty to vaccinate against HIV arises from the extensive variability of Env present on the large number of HIV-I isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci US A 108(27):11181-11186; Sundling C, et al. (2012) Science translational medicine 4(142):142ra196; Tran K, et al. (2014) Vaccine-elicited primate antibodies use a distinct approach to the HIV-I primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to VIV2 regions of multiple HIV-I subtypes correlate with decreased risk of HIV-I infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-I infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci US All 1(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-I primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci USA 109(30):12111-12116; Nkolola J P, et al. (2014) Comparison of multiple adjuvants on the stability and immunogenicity of a clade C HIV-I gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bNAbs, (GE148 and GE136) generated following immunization of uncleaved gp140 trimers (YU2 gp140-foldon) in non-human primates (NHP). Non-bNAbs, represented by GE136 and 148, can only neutralize the sensitive so-called "tier I viruses" that are not representative of the more neutralization resistant tier 2-like primary isolates circulating in the human population. Using crystallography, EM reconstructions, paratope scanning and molecular modeling, Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-I spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNHI 144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNH1144 SOSIP trimers are derived from the Env sequences of the subtype A BG505 and KNHI 144 strains. These soluble trimers possess an engineered disulfide linkage between the gp120 and gp41 (at residues 501C and 605C, respectively) and an additional mutation in the heptad repeat I (HRI) of gp41 (1559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-I primary strains were attempted over the past decade, the BG505- and KNHI 144-derived SOSIP trimers are the two limited examples of SOSIPs that yield homogeneous trimers suitable for high resolution biophysical and structural analysis. The structural explanation for the difficulty to readily transfer the SOSIP design to other HIV-I strain-derived sequences is not yet fully understood and would be valuable information to broaden the trimer design horizon.

Since the initial soluble native-like BG505 SOPIP.664 Env trimer was confirmed to adopt a near-native conformation by high-resolution structural analysis, multiple efforts to produce stable, soluble Env mimetics derived from multiple HIV-1 strains were pursued [Javiers, sanders]. Multiple solutions to this objective include the improved cleavage-independent NFL trimers, UFOs and modified SOSIPs. Both the SOSIP and NFL well-ordered trimers are efficiently recognized by broadly neutralizing antibodies (bNAbs) which arise sporadically during the course of natural infection. In some cases, including the important advances described here, have been used to isolate such bNAbs. One approach to elicit tier 2 neutralizing Abs has been to immunize the existing well-ordered trimers using prime:boosting in selected animal models. For BG505 and 16055 native-like trimers this approach does elicit tier 2 neutralizing antibodies, but of limited cross-reactive breadth (REFS).

Most cross-conserved sites on the HIV Env spike are occluded by evolved, incorporated self-N-glycans, limiting naïve B cell recognition of the underlying polypeptide surface. The exceptions are the protein surfaces of the primary receptor CD4 binding site (CD4bs) and the furin cleavage site (proximal to the gp120:41 interface). Infrequently, during the course of the natural HIV infection process, bNAbs are elicited to these aforementioned sites of vulnerability. In addition, other bNAbs directed to the V2 apex, the 332N-glycan supersite and to the fusion peptide or the high-mannose patch are elicited during the course of chronic HIV infection (REFS). However, prior to the present invention, rarely, if ever, have such bNAbs been elicited by vaccination of Env formulated with adjuvant.

Without being bound by limitation, Applicants believe that TD mutations may strengthen the interaction between gp120 and gp41, increasing trimer formation.

To re-elicit such bNAbs, Applicants integrated heterologous trimer prime boosting with liposomal multi-valent particulate array, to drive B cell responses directed at cross-conserved sites of vulnerability. In addition, Applicants preferentially exposed the gp120 CD4bs by eliminating proximal N-glycans, while maintaining the native-like state of highly homogeneous, cleavage-independent (NFL) trimers as recently reported. High-density trimer array on synthetic liposomes enhances B cell activation and the elicitation of neutralizing antibodies (REFS). Following N-glycan-deleted trimer priming, heterologous boosting was used to promote B cell recognition at cross-conserved sites, coupled with gradual N-glycan restoration proximal to the CD4bs to drive site-specific B cells. Remarkably, in a subset of animals this multi-faceted approach elicited cross-neutralizing serum IgG antibodies. Differential depletion demonstrated that much of the response, but not all, was directed to the CD4bs. Applicants isolated cross-neutralizing antibodies with one directed to the gp41-gp120 interface region and another to the CD4bs as confirmed by mapping and EM structural analysis. Therefore, N-glycan deletion and heterologous boosting, coupled with particulate array, is an effective proof-of-principle means to elicit Env-specific antibodies capable of cross-neutralizing multiple HIV-1 clinical isolates.

Two distinct approaches were taken to improve trimer formation in JRFL SOSIP and 16055 NFL. Firstly, Applicants compared the reference BG505 gp120 sequence with those of JRFL and 16055 gp120s and Applicants annotated all dissimilar residues in the context of the high-resolution BG505 SOSIP structure. A few trimer-axis proximal gp120 residues were selected and reverted in JRFL SOSIP and 16055 NFL. Secondly, Applicants introduced a disulfide linkage at residues 201 and 433 that covalently links the -sheet 3 to -sheet 21 to prevent CD4-induced conformational changes to lock gp120 in the native-trimer state.

After decades of development, advances in soluble HIV-1 Env mimics design permits the generation of a diverse array of native-like trimers (Ward and Wilson, 2017. The HIV-1 envelope glycoprotein structure: nailing down a moving target. Immunol Rev 275:21-32; Karlssonet al., 2017. Evolution of B cell analysis and Env trimer redesign. Immunol Rev 275:183-202). The successful development of the soluble SOSIP trimers provided proof-of-principle (Sanders et al, 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618) forming a prefusion native-like conformation (Lyumkis et al., 2013. Cryo-EM structure of a fully glycosylated soluble cleaved HIV-1 envelope trimer. Science 342:1484-1490; Julien et al, 2013. Crystal structure of a soluble cleaved HIV-1 envelope trimer. Science 342:1477-1483; Garces et al., 2015. Affinity Maturation of a Potent Family of HIV Antibodies Is Primarily Focused on Accommodating or Avoiding Glycans. Immunity 43:1053-1063; Pancera et al., 2014. Structure and immune recognition of trimeric pre-fusion HIV-1 Env. Nature 514:455-461). The SOSIP gp140 trimer is proteolytically cleaved by cellular furins to gp120 and gp41 subunits and covalently linked by an engineered intra-protomer disulfide bond A501C-T605C (SOS). These trimers also require mutation (I559P) in the gp41 heptad repeat 1 (HR1) to maintain well-ordered oligomers, as well as expression of exogenous furin for full conformational integrity (Sanders et al., 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618; Guenaga et al., 2015. Well-Ordered Trimeric HIV-1 Subtype B and C Soluble Spike Mimetics Generated by Negative Selection Display Native-like Properties. PLoS Pathog 11:e1004570; Julien et al., 2015. Design and structure of two HIV-1 clade C SOSIP.664 trimers that increase the arsenal of native-like Env immunogens. Proc Natl Acad Sci USA 112:11947-11952; de Taeye et al. 2015. Immunogenicity of Stabilized HIV-1 Envelope Trimers with Reduced Exposure of Non-neutralizing Epitopes. Cell 163:1702-1715; Pugach et al. 2015. A native-like SOSIP.664 trimer based on an HIV-1 subtype B env gene. J Virol 89:3380-3395; Ringe et al. 2013. Cleavage strongly influences whether soluble HIV-1 envelope glycoprotein trimers adopt a native-like conformation. Proc Natl Acad Sci USA 110:18256-18261; Ringe et al. 2015. Influences on the Design and Purification of Soluble, Recombinant Native-Like HIV-1 Envelope Glycoprotein Trimers. J Virol 89:12189-12210; Ringe et al. 2017. Reducing V3 Antigenicity and Immunogenicity on Soluble, Native-Like HIV-1 Env SOSIP Trimers. J Virol 91; Ahmedet al. 2017. Stabilization of a soluble, native-like trimeric form of an efficiently cleaved Indian HIV-1 clade C envelope glycoprotein. J Biol Chem 292:8236-8243; Sanders et al. 2002. Stabilization of the soluble, cleaved, trimeric form of the envelope glycoprotein complex of human immunodeficiency virus type 1. J Virol 76:8875-8889; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643). In the past years, Applicants developed an improved native-like trimer design, generating well-ordered soluble Env mimics that are fully cleavage-independent, termed native flexibly linked (NFL) trimers. This design uses a flexible linker (two copies of Gly4-Ser (SEQ ID NO: 34), "G45" (SEQ ID NO: 41)) to replace the natural cleavage site and sequence (Sharma et al. 2015. Cleavage-independent HIV-1 Env trimers engineered as soluble native spike mimetics for vaccine design. Cell Rep 11:539-550). The flexible linker between the natural C-terminus of gp120 and N-terminus of gp41, allows the un-cleaved trimers to achieve a native-like conformation without the need of furin for precursor processing. However, the original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. In the original NFL design, it is relatively inefficient in generating high yields of trimers derived from clade C strains, such as 16055 (Guenaga et al. 2015. Structure-Guided Redesign Increases the Propensity of HIV Env To Generate Highly Stable Soluble Trimers. J Virol 90:2806-2817). To improve trimer design, Applicants incorporated residues from BG505 (called trimer-derived (TD) residues) into 16055 NFLs, substantially improving the propensity to form native-like trimers (Guenaga et al. 2015. Structure-Guided Redesign Increases the Propensity of HIV Env To Generate Highly Stable Soluble Trimers. J Virol 90:2806-2817) and the elicitation of tier 2 clade C neutralizing antibodies (Martinez-Murillo et al., GB. 2017. Particulate Array of Well-Ordered HIV Clade C Env Trimers Elicits Neutralizing Antibodies that Display a Unique V2 Cap Approach. Immunity 46:804-817 e807; Dubrovskaya et al. 2017. Targeted N-glycan deletion at the receptor-binding site retains HIV Env NFL trimer integrity and accelerates the elicited antibody response. PLoS Pathog 13:e1006614). Further improvements on the TD design by targeted glycine substitutions at helix-to-coil transitions that disfavor the post-fusion state of Env (TD CC+, namely “TD+”), significantly improve trimer homogeneity, yield, stability and antigenicity, resulting in the first high-resolution clade C Env structure (Guenaga et al. 2017. Glycine Substitution at Helix-to-Coil Transitions Facilitates the Structural Determination of a Stabilized Subtype C HIV Envelope Glycoprotein. Immunity 46:792-803 e793).

Applicants believe that the glycine changes may lower the activation potential of the gp41 (and Env) to change conformation, and therefore results in better behaved trimers in a lower energy well from the “activation state” to spring to the next conformation. In a simple model, gp41 is essentially spring-loaded and constrained by gp120 until receptor binding. These mutations may contribute to reducing the springiness.

In a particularly advantageous embodiment, the soluble envelope glycoproteins of the present invention have about 75%, about 76%, about 77%, about 78%, about 79%, about 80%, bout 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to any of the sequences depicted in the figures and/or specification.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J Viral. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supematants containing pseudotyped virus may be co-incubated overnight with B cell supematants derived from activation of an infected donor’s primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in the combination with PG9 or PG16 or with any other neutralizing antibodies, including those identified by the above methods, to determine the exact molecular surface where the soluble envelope glycoprotein binds with the neutralizing antibody to design HIV-I immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry. 1982 Sep. 28; 21(20):4839-43; Brayer & McPherson, J Biol Chem. 1982 Apr. 10; 257(7):3359-61; McPherson & Weickmann, J Biomol Struct Dyn. 1990 April; 7(5): 1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody, such as PG9 or PG16, and soluble envelope glycoprotein in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to a neutralizing antibody, such as PG9 or PG16, and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures of a synthetic or mutated neutralizing antibody, such as PG9 or PG16, domains, as well as the structures of co-crystals of such domains with ligands.

The provision of the crystal structure of a neutralizing antibody, such as PG9 or PG16, complexed with a soluble envelope glycoprotein provide the skilled artisan with a detailed insight into the mechanisms of action of a neutralizing antibody, such as PG9 or PG16. This insight provides a means to design compounds that bind to a neutralizing antibody, such as PG9 or PG16, and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody, such as PG9 or PG16, complexed with a soluble envelope glycoprotein allows a novel approach for drug or compound discovery, identification, and design for compounds that bind to a neutralizing antibody, such as PG9 or PG16, and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody, such as PG9 or PG16, complex as defined by the co-ordinates or the identifying co-ordinates, providing a structure of a candidate compound; and fitting the structure of the candidate to the structure of a neutralizing antibody, such as PG9 or PG16.

In an alternative aspect, the method may use the co-ordinates of atoms of interest of a neutralizing antibody, such as PG9 or PG16, which are in the vicinity of the active site or binding region in order to model the pocket in which the substrate or ligand binds. These co-ordinates may be used to define a space which is then screened "in silica" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody, such as PG9 or PG16, as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody, such as PG9 or PG16, which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody, such as PG9 or PG16; and fitting the structure of the candidate to the co-ordinates of the sub-domain provided.

The invention further provides a method for determining the structure of a binder of a neutralizing antibody, such as PG9 or PG16, bound to a neutralizing antibody, such as PG9 or PG16, comprising: providing a crystal of a neutralizing antibody, such as PG9 or PG16, e.g., according to the invention, soaking the crystal with the binder, and determining the structure of the neutralizing antibody-binder complex. Alternatively or additionally the neutralizing antibody, such as PG9 or PG16, and the binder may be co-crystallized.

The invention also provides a method of analyzing a complex of a neutralizing antibody, such as PG9 or PG16, and a potential binder comprising: employing X-ray crystallographic diffraction data from the complex and a three-dimensional structure of a neutralizing antibody, such as PG9 or PG16, or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, such as PG9 or PG16, and the solved structure of an uncomplexed neutralizing antibody, such as PG9 or PG16. These maps can then be used to determine whether and where a particular potential binder binds to a neutralizing antibody, such as PG9 or PG 16, and/or changes the conformation of a neutralizing antibody, such as PG9 or PG16. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody, such as PG9 or PG16, provides important information about the likely active/binding site(s) of a neutralizing antibody, such as PG9 or PG16. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

In yet another embodiment, the present invention also encompassed the use of the soluble envelope glycoproteins described herein as immunogens, advantageously as HIV-I vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab') 2, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')2, the fragment of the antibody that can be obtained by treating whole antibody with the enzyme pepsin without subsequent reduction; F(ab')2 is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-I virus F with a neutralization index >1.5 or >2.0. Broad and potent neutralizing antibodies may neutralize greater than about 50% of HIV-I viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions may generally be conservative in nature, i.e., those substitutions that take place within a family of amino acids. For example, amino acids are generally divided into four families: (1) acidic-aspartate and glutamate; (2) basic-lysine, arginine, histidine; (3) non-polar-alanine, valine, leucine, isoleucine, praline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Genart. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 9'7%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use according to the present invention is the WU-BLAST (Washington University BLAST) version 2.0 software. WU-BLAST version 2.0 executable programs for several UNIX platforms can be downloaded from the Washington University BLAST website. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, intrans, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986;

6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707; 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-I antigen and/or protective immunity against HIV-I, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-I566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-I antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.). (PEG).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., A1K(SO4)2, AlNa (SO4)2, AlNH(SO4)2, silica, alum, Al(OH)3, Ca3(PO4)2, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), cationic liposome DNA complexes (known in the art as JuvaVax™) (U.S. Pat. No. 6,693,086), certain natural substances (e.g., wax D from *Mycobacterium tuberculosis*, substances found in Cornyebacterium *parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-0-acylated monophosphoryl lipid A (3D-MPL), imiquimod (also known in the art as IQM and commercially available as Aldara®; U.S. Pat. Nos. 4,689,338; 5,238,944; Zuber, A K. et al (2004) 22(13-14): 1791-8), and the CCR5 inhibitor CMPD167 (see Veazey, R S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-a, IFN-, and IFN-y (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fe fragment of immunoglobulins (Barouch et al., Science 290:486-492, 2000) and co-stimulatory molecules B7. 1 and B7.2 (Boyer), all of which can be administered either as proteins or in the form of DNA, on the same expression vectors as those encoding the antigens of the invention or on separate ex In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)). pression vectors.

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethyl enevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-y ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.RIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Although the present invention and its advantages have been described in detail, it should be understood that various changes, substitutions and alterations can be made herein without departing from the spirit and scope of the invention as defined in the appended claims.

EXAMPLES

Example 1: Materials and Methods

Site-directed mutagenesis. The described Env DNA substitutions were introduced via site-directed mutagenesis PCR using a QuikChange Lightning Multi Site-Directed Mutagenesis kit (Agilent Technologies) into NFL expressing plasmids (CMV-R, where CMV is cytomegalovirus) (Guenaga J, Dubrovskaya V, de Val N, Sharma S K, Carrette B, Ward A B, et al. Structure-guided redesign increases the propensity of HIV Env to generate highly stable soluble trimers. J Virol. 2015; 90(December):JVI.02652-15) or into the pcDNA plasmid, containing codon-optimized 16055 env sequences. In brief, single primers were designed for each mutation. Applicants used up to three primers per reaction mixture to introduce multiple substitutions simultaneously. Reaction products were transformed into competent bacteria and plated onto Luria broth agar plates for colony selection, subsequent plasmid DNA isolation, and sequencing. To map serum neutralizing activity directed toward the CD4bs, TriMut and TriMut 368R/474A proteins were generated as described previously (Feng Y, McKee K, Tran K, O'Dell S, Schmidt S D, Phogat A, et al. Biochemically defined HIV-1 envelope glycoprotein variant immunogens display differential binding and neutralizing specificities to the CD4-binding site. J Biol Chem. 2012; 287(8):5673-86. pmid: 22167180). Briefly, three mutations, I423M, N425K and G431E, were introduced to make a triple mutant 16055 gp120 protein (TriMut) that eliminates CD4 binding but does not affect recognition by CD4bs-directed mAbs. For the receptor-binding-defective protein, TriMut 368R/474A, two additional mutations, D368R and M474A, were introduced to eliminate CD4 binding.

Expression and purification of HIV Env. The Env NFL trimeric proteins and TriMut proteins were produced as previously described (Sharma S K, De Val N, Ward A B, Wyatt R T, Sharma S K, De Val N, et al. Engineered as Soluble Native Spike Mimetics for Cleavage-Independent HIV-1 Env Trimers Engineered as Soluble Native Spike Mimetics for Vaccine Design. CellReports. 2015; 11(4):539-50; Guenaga J, De Val N, Tran K, Feng Y, Satchwell K, Ward A B, et al. Well-Ordered Trimeric HIV-1 Subtype B and C Soluble Spike Mimetics Generated by Negative Selection Display Native-like Properties. 2015; 11(1). Briefly, the 16055 Env proteins were transiently expressed as soluble glycoproteins in 293F (Free-style 293-F Cells, Thermo Fisher Scientific) cells from codon-optimized sequences under the control of the CMV promoter/enhancer (Guenaga J, Dubrovskaya V, de Val N, Sharma S K, Carrette B, Ward A B, et al. Structure-guided redesign increases the propensity of HIV Env to generate highly stable soluble trimers. J Virol. 2015; 90(December):JVI.02652-15). Cell culture supernatants were harvested at day 5 post-transfection, and the Env-derived glycoproteins were purified by affinity chromatography using a *Galanthus nivalis* lectin-agarose column (Vector Laboratories). Bound glycoproteins were eluted with phosphate buffered saline (PBS) containing 500 mM NaCl and 500 mM methyl-α-D-mannopyranoside and then concentrated with an Amicon filter (30-kDa) to 1 ml. The lectin-purified proteins were subsequently purified by size-exclusion chromatography (SEC) using a HiLoad Superdex 200 16/60 column to separate the trimer and gp120 monomer fractions.

Differential scanning calorimetry (DSC) studies. Thermal stability of the soluble 16055 trimer and its N-glycan-deleted variants were evaluated using MicroCal VP-Capillary differential scanning calorimetry instrument (General Electric). Protein samples were dialyzed in PBS, pH 7.4, and the concentrations were adjusted to 0.125 mg/ml. Scans were collected at a rate of 1° C. per min over a temperature range of 20-100° C., while pressure was maintained at 3.0 atm throughout the scan period. DSC data were analyzed after buffer correction, normalization, and baseline subtraction using CpCalc software provided by the manufacturer.

Electron microscopy (EM) sample preparation. The purified NFL trimers were analyzed by negative-stain electron microscopy (EM) following the same protocol previously described (Guenaga J, Dubrovskaya V, de Val N, Sharma S K, Carrette B, Ward A B, et al. Structure-guided redesign increases the propensity of HIV Env to generate highly stable soluble trimers. J Virol. 2015; 90(December): JVI.02652-15). Data were collected using an electron dose of ~30e−/Å2. All the data were processed as previously published. Briefly, particles were picked and assembled into a stack using the Appion software package (Lander G C, Stagg S M, Voss N R, Cheng A, Fellmann D, Pulokas J, et al. Appion: an integrated, database-driven pipeline to facilitate EM image processing. J Struct Biol. 2009 166(1):95-102.) Iterative multivariate statistical analysis (MSA)/multireference alignment (MRA)) was used to obtain 2D classes. Using EMAN2 (Tang G, Peng L, Baldwin P R, Mann D S, Jiang W, Rees I, et al. EMAN2: An extensible image processing suite for electron microscopy. J Struct Biol. 2007; 157(1):38-46) EM volumes were obtained of the trimers in complex with the VRC03 Fab. 2475 particles to were used to obtain the 3D volume of the +N332 PT in complex with 3 VRC03 Fabs and 3250 particles for the asymmetric volume bound to 2 VRC03. For the 3D reconstruction of the +N332 N276Q/N360Q/N463Q/N301Q trimer bound to 3 VRC03 Fabs, 2448 particles were used.

Enzyme-linked immunosorbent assay (ELISA). His-capture ELISA was performed as previously described. In brief, MaxiSorp plates (Thermo) were coated overnight at 4° C. with 1.5 μg/ml of a mouse anti-His tag monoclonal antibody (mAb) (R&D Systems) in PBS, pH 7.5. The next day the plates were incubated at 4° C. in blocking buffer (2% BSA in PBS, pH 7.5) for 2 h and the Env-derived soluble trimers was added to the plate at a concentration of 3 μg/ml in PBS and incubated at RT for 40 min. Serially diluted mAbs at a maximum concentration of 10 μg/ml or sera from vaccinated animals were added into wells, and following incubation and washing, the secondary antibodies of peroxidase-conjugated goat anti-human IgG or goat anti-rabbit IgG were added to all wells. Following incubation and washing, the signals were developed by addition of the 3,3',5,5;-tetramethylbenzidine chromogenic substrate solution (Life Technologies) and detected at 450 nm. For direct-coat ELISA, trimers were added directly to the wells at 3 μg/ml and analyzed for antibody binding as described above.

Bio-layer interferometry (BLI) binding analysis and kinetics. The kinetics of VRC03 Fab binding to glycan-deleted trimer varians were performed with an Octet RED96 system (ForteBio Inc, Menlo Park, Calif.) by BLI in a 96-well format. The trimers were subjected to SEC to remove undesired oligomeric forms where applicable. Then trimers were captured by anti-His biosensors (HIS2; ForteBio) at concentration 10 μg/ml and VRC03 Fab were used as analytes in solution (1000 nM-15.6 nM). Ab-Env associations (on-rate, Kon) were measured over a 2 min interval, followed by immersion of the sensors into wells containing buffer to measure dissociation (off-rate, Kdis). KD values (in nanomolar units) were calculated as off-rate/on-rate (Kdis/Kon). The sensograms were corrected with the blank reference and fit with the software ForteBio Data Analysis 7 using a 1:1 binding model with the global fitting function (grouped by color, Rmax).

Ethics statement. The rabbit immunogenicity study was performed at The Scripps Research Institute (TSRI), a site approved by the Association for Assessment and Accreditation of Laboratory Animal Care (AAALAC). The animal inoculation protocols were approved by TSRI's Institutional Animal Care and Use Committee (IACUC). protocol #10-0002, which was designed and conducted in strict accordance with the recommendations of the NIH Guide for the Care and Use of Laboratory Animals, the Animal Welfare Act and under the principles of the 3Rs. All efforts were made to minimize discomfort related to the inoculations and blood collection.

Animal immunization. For the immunogenicity experiment New Zealand White female rabbits (six per group) were immunized at weeks 0, 4, 12 and 24 with 30 μg of each trimer arrayed on the liposomes as described in (Ingale J, Stano A, Guenaga J, Sharma S K, Nemazee D, Zwick M B, et al. High-Density Array of Well-Ordered HIV-1 Spikes on Synthetic Liposomal Nanoparticles Efficiently Activate B Cells. Cell Rep 2016 May 15(9):1986-99). Briefly liposomes were prepared using mixture of DSPC (1,2-distearoyl-sn-glycero-3-phosphocholine), cholesterol, DGS-NTA(Ni2) in molar ratio 60:36:4, respectively. The components were dissolved in chloroform, mixed and placed overnight in a desiccator under vacuum to yield a lipid film. The lipids were hydrated in PBS for 2 hr at 37° C., with constant shaking followed by vigorous sonication. The liposomes were extruded by sequentially passing across a series of membrane filters (Whatman Nuclepore Track-Etch membranes) with pore sizes of 1.0, 0.8, 0.2, and 0.1 m, respectively. The liposomes were incubated overnight with trimer proteins (900 μg protein to 300 μl liposomes) and passed over a 5200 size-exclusion column to separate the protein-coupled liposomes from unbound protein. Quality of each trimer-liposome preparation was confirmed by EM negative stain analysis prior to each immunization. Trimer-coupled liposomes were formulated with 75 units of ISCOMATRIX adjuvant (CSL, Australia) and used for rabbits immunization via the subcutaneous route. Serum was collected on the day of inoculation and 2 weeks after each immunization to assess binding and neutralization titers.

Neutralization assays. Standard TZM-bl-based neutralization assays were performed as previously described (Landais E, Huang X, Havenar-Daughton C, Murrell B, Price M A, Wickramasinghe L, et al. Broadly Neutralizing Antibody Responses in a Large Longitudinal Sub-Saharan HIV Primary Infection Cohort. PLoS Pathog. 2016 Jan. 14, 12; Seaman M S, Janes H, Hawkins N, Grandpre L E, Devoy C, Giri A, et al. Tiered categorization of a diverse panel of HIV-1 Env pseudoviruses for assessment of neutralizing antibodies. J Virol 84(3):1439-52) using 16055 full-length Env natural sequence to complement the Env-deleted plasmid to generate clade C pseudovirus and its deglycosylated variants. Titrated 16055 pseudovirus was used to evaluate sensitivity and inhibition of entry (neutralization, IC50s) to a panel of mAbs (VRC01, VC03, VRC06b, HJ16, F105, b6, GE136, 17b, PGT145, 447-52D, 19b) and HIV Immunoglobulin (HIVIG, lot #140406), derived from a pool of HIV-infected individuals. Once characterized, the 16055 pseudoviruses were pre-incubated with serum samples derived from the vaccinated rabbits to determine anti-serum neutralization capacity. Neutralization titers were expressed as antibody concentrations sufficient to inhibit virus infection by 50% (EC50) or as the serum dilution factor sufficient to inhibit virus infection by 50% (ID50). Spearman's Rank Correlation analysis of neutralizing titers and DSC-determined Tm was performed using Prism 6 software (GraphPad).

To examine the contribution of potential CD4bs-directed antibodies to the serum neutralizing activity, neutralization assays were performed using the isogenic TriMut and TriMut D368R/D474A 16055 gp120 pair as Env-specific antibody-adsorbing probes as described previously. The D368R mutation eliminates gp120 (or trimer) binding to CD4 on the TZM-bI target cells in the neutralization assay so that the proteins can be added to serum for pre-incubation and then remain in the assay during assessment of viral entry. This assay is a modified version of the standard neutralization assay described above. To perform this analysis, total IgG was purified from the serum samples obtained after the third and fourth immunization, using 2 ml of serum and 600 μl of equal parts of Sepharose A and G (GE Healthcare Life Sciences) equilibrated in PBS. After overnight incubation at 4° C., the resin was washed with 15 ml of PBS and eluted with 4 ml of IgG elution buffer (Thermo Fisher Scientific). The eluates were neutralized with 400 μl of 1M Tris HCl pH 8.0 and dialyzed against PBS. Each serum IgG sample was titrated against 16055 virus in TZM-bl-based neutralization assay as described above. Before addition of pseudovirus, 100 μl of each total serum IgG sample at IC80 was pre-incubated with serial dilutions of TriMut, TriMut 368/474, or cell culture medium (12.5 μl), respectively, for 1 hour at 37° C. For each purified IgG, two neutralization assays were performed.

Statistical analysis. Applicants used the unpaired two-tailed Mann Whitney test when comparing neutralization values from Group 1 animals to samples derived from either Group 2 or Group 3 subjects. This nonparametric test that does not assume Gaussian distribution of values with 6 subjects per group.

Design of new NFL trimer constructs. The BG505 NFL and 16055 NFL Env sequences (Sharma et al. 2015. Cleavage-independent HIV-1 Env trimers engineered as soluble native spike mimetics for vaccine design. Cell Rep 11:539-550) (16055 accession numbers EF117268 and BG505 DQ208458) were used as parental templates to generate gp140 trimer mutants. The parental NFL contains a proline substitution at residue 559 (I559P) to facilitate trimer formation (Sanders et al. 2002. Stabilization of the soluble, cleaved, trimeric form of the envelope glycoprotein complex of human immunodeficiency virus type 1. J Virol 76:8875-8889. For the proline screening, a panel of 36 residues spanning the NFL HR1 region (from residue 548 to 585)

were individually substituted by prolines. For the disulfide bond linkage screening, a panel of 15 cysteine pairs were generated. To increase the exposure of epitopes in the fusion peptide, we engineered an EK cleavage site (DDDDK (SEQ ID NO: 36), namely D4K (SEQ ID NO: 36)) upstream of the fusion peptide for controlled post-expression cleavage. Finally, Applicants built promising proline (555 P), inter-protomer cysteine linkage (C501-C663) and enterokinase cleavage site into our recently reported NFL TD CC+ (namely TD+) trimer construct (Guenaga et al. 2017. Glycine Substitution at Helix-to-Coil Transitions Facilitates the Structural Determination of a Stabilized Subtype C HIV Envelope Glycoprotein. Immunity 46:792-803 e793), namely NFL TD+CC2-D4K (schematic representing the NFL trimer design is shown in FIG. 1A). Substitutions in the Env-derived NFL glycoproteins were introduced via site-directed mutagenesis PCR (AGILENT TECHNOLOGIES) into expression plasmids and confirmed by sequencing (GENEWIZ). The final constructs are shown as schematic representations in FIGS. 1B and 1C.

Expression and purification of soluble proteins. The constructs expressing 16055 and BG505 NFL trimeric Env glycoproteins were transiently transfected into suspension 293F cells as previously described (Sharma et al. 2015. Cleavage-independent HIV-1 Env trimers engineered as soluble native spike mimetics for vaccine design. Cell Rep 11:539-550; Guenaga et al. 2015. Structure-Guided Redesign Increases the Propensity of HIV Env To Generate Highly Stable Soluble Trimers. J Virol 90:2806-2817; Guenaga et al. 2017. Glycine Substitution at Helix-to-Coil Transitions Facilitates the Structural Determination of a Stabilized Subtype C HIV Envelope Glycoprotein. Immunity 46:792-803 e793). Env trimer containing cell culture supernatants were harvested four days post transfection and purified by lectin affinity chromatography (GALANTHUS NIVALIS, VECTOR LABS) followed by size exclusion chromatography (SEC) on a Superdex 200 16/60 or Superdex 200 10/300 GL (GE HEALTHCARE). In most cases, the trimer peak was subjected to negative selection by non-neutralizing mAbs GE136 or F105 to remove disordered trimers on the column. The flow-through from the GE136 or F105 column, containing the well-ordered trimers, was resolved by a second SEC.

Immunoprecipitation. Immunoprecipitation (IP) of the expressed Env variants were done as described previously (Sharma et al. 2015. Cleavage-independent HIV-1 Env trimers engineered as soluble native spike mimetics for vaccine design. Cell Rep 11:539-550) with minor modifications. In brief, ~1 ml of cell culture supernatant was incubated with 5 μg of selected Abs (2G12, VRC01, VRC06, PGT145, PGT151 and F105) at 4° C. overnight on the rocker. 25 μl of fast-flow protein-A sepharose beads (GE HEALTHCARE) was added to each tube and incubated for 1 h at room temperature (RT) on the rocker. Protein-A sepharose beads with the Ab-Env complex was pelleted and washed 2 times with 1.5 ml of cold PBS with 500 mM NaCl, pH 7.4 and finally resuspended in 50 μl of 1×SDS-PAGE loading dye with reducing agent. The samples were boiled for 10 min, spun and the supernatant was loaded onto 4-12% SDS-PAGE gradient gel and run at 200V for 30 min. The gels were stained with 1% tangerine orange dye for 30 min and visualized in the BIORAD gel documentation instrument under UV exposure.

Post-expression cleavage of NFL-TD+CC2-D4K trimers by recombinant enterokinase (rEK). Purified NFL-TD+CC2-D4K trimers containing engineered EK cleavage site were used for rEK (Novagen) digestion following the manufacture's instruction. Briefly, 2 mg of NFL-TD+CC2-D4K trimers were cleaved by 50 U rEK at 37° C. for 30 h in a buffer containing 20 mM Tris-HCl pH 7.4, 50 mM NaCl, 2 mM $CaCl_2$. The cleavage efficiency was determined by running trimers on SDS-PAGE under reducing and non-reducing conditions (with or without DTT).

Differential Scanning calorimetry (DSC). The thermal transition points ($T_m$) of 16055 NFL and BG505 NFL variants were determined by Differential Scanning calorimetry (DSC) using a MicroCal VP capillary instrument (MALVERN) as described previously (Sharma et al. 2015. Cleavage-independent HIV-1 Env trimers engineered as soluble native spike mimetics for vaccine design. Cell Rep 11:539-550; Guenaga et al. 2017. Glycine Substitution at Helix-to-Coil Transitions Facilitates the Structural Determination of a Stabilized Subtype C HIV Envelope Glycoprotein. Immunity 46:792-803 e793).

Binding Analyses by ELISA and Biolayer Interferometry (BLI). ELISA and BLI analyses were performed as previously described (Sharma et al. 2015. Cleavage-independent HIV-1 Env trimers engineered as soluble native spike mimetics for vaccine design. Cell Rep 11:539-550; Yang et al. 2012. HIV-1 Virus-Like Particles Produced by Stably Transfected *Drosophila* S2 Cells: a Desirable Vaccine Component. J Virol 86:7662-7676; Hogan et al. 2017. Increased surface expression of HIV-1 envelope is associated with improved antibody response in vaccinia prime/protein boost immunization. Virology 514:106-117). Briefly, ELISA plates coated with 2 μg/ml anti-His mAb were used to capture NFL trimers (2 μg/ml) followed by primary mAbs (5-fold serially diluted, starting from 10 μg/ml) and a peroxidase-conjugated goat anti-human secondary Ab (1:10,000). Plates were developed using 3,3', 5,5;-tetramethylbenzidine chromagen solution. The data were plotted in GraphPad Prism version 7.

The BLI analyses were carried out on an Octet Red instrument (FORTEBIO) with IgGs immobilized on anti-human IgG Fc capture sensors (FORTEBIO). The NFL trimers were assessed as free analytes in solution (PBS pH 7.4). The analytes started from 800 nM and then 2-fold serially diluted to a final concentration of 12.5 nM. Association and dissociation times were 2 and 2 minutes or 3 and 3 minutes respectively. Data were analyzed using the FORTEBIO analysis software version 7.1 (FORTEBIO) and the kinetic parameters were calculated using a global fit 1:1 model.

Electron microscopy data collection and processing. The purified trimers were analyzed by negative stain electron microscopy (NS-EM) and data were processed as previously described (Guenaga et al. 2017. Glycine Substitution at Helix-to-Coil Transitions Facilitates the Structural Determination of a Stabilized Subtype C HIV Envelope Glycoprotein. Immunity 46:792-803 e793). A 3 μL aliquot containing ~0.03 mg/mL of the sample was applied for 15 s onto a carbon-coated 400 Cu-mesh grid that had been glow discharged at 20 mA for 30 s, then negatively stained with 2% uranyl formate for 45 s. Data were collected using a FEI Tecnai Spirit electron microscope operating at 120 kV, with an electron dose of ~30 $e^-/Å^2$ and a magnification of 52,000× that resulted in a pixel size of 2.05 Å at the specimen plane. Images were acquired with a Tietz 4k/4k TemCam-F416 CMOS camera using a nominal defocus of 1000 nm and the Leginon package.

Particles were picked automatically using DoG Picker and put into a particle stack using the Appion software package. Reference-free, two-dimensional (2D) class averages were calculated using particles binned by two via the iterative msa/mra Clustering 2D Alignment and IMAGIC software systems and sorted into classes. To analyze the quality of the trimers (closed, open or non-native like trimers) the reference free 2D class averages were examined by eye using the same metrics that previously described.

N-lined glycan profiling of Env variants with new HR1 proline substitutions. The five BG505 HR1 proline mutants were expressed in 293F cells and purified by the same methods as described above. The overall N-linked glycosylation profiles of these Env variants were explored by hydrophilic interaction liquid chromatography-ultraperformance liquid chromatography (HILIC-UPLC) (Behrens et al. 2016. Composition and Antigenic Effects of Individual Glycan Sites of a Trimeric HIV-1 Envelope Glycoprotein. Cell Rep 14:2695-2706). In brief, 10 μg of each of the Envs were resolved by SDS-PAGE under nonreducing and reducing conditions, and the coomassie blue stained bands corresponding to gp140 were excised and washed five times alternatively with acetonitrile and water. The total N-lined glycans were enzymatically released by treatment with PNGase F and the released glcyans were washed extensively in water and finally dried in SpeedVac concentrator as described earlier. The released glycans were fluorescently labeled with 2-AA (2-Aminobenzoic Acid) and resolved on a Acquity BEH Amide column (2.1 mm×10 mm, 1.7 um particle size) (Waters) by HILIC-UPLC method as described in detail elsewhere. The raw data was analyzed by Empower 3 software. The relevant peak-areas of different N-linked oligomannose before and after Endo-H digestion were integrated and normalized to calculate the percentage abundance of oligomannose-type glycans in all the Envs.

Example 2: NFL Trimers with Selected N-Glycan Deletions Retain a Native-Like Conformation To preferentially increase recognition of the gp120 CD4bs, while maintaining well-ordered trimeric native-like structure, Applicants selected a highly stable and homogeneous soluble trimer 16055 NFL TD CC (T569G), as the parental backbone for targeted N-glycan deletions, designated as "PT" for "Parental Trimer" for the remainder of this manuscript. This soluble trimeric protein is derived from an Indian subtype C HIV-1 Env sequence that was isolated from a patient following acute infection (Kulkarni S S, Lapedes A, Tang H, Gnanakaran S, Daniels M G, Zhang M, et al. Highly complex neutralization determinants on a monophyletic lineage of newly transmitted subtype C HIV-1 Env clones from India. Virology 385(2):505-20). The original NFL trimer design consists of a 10 residue (G4S) flexible linker (SEQ ID NO: 34) between the REKR-deleted Env gp120 C-terminus ("REKR" disclosed as SEQ ID NO: 35) and the unmodified gp41 N-terminus, contains a I559P mutation in gp41 and is truncated at residue 664. The NFL TD, for trimer-derived, possesses substitutions at residues E47D, K49E, V65K, E106T, I165L, E429R, R432Q, A500R to increase trimer formation and stability and a T569G substitution that increases homogeneity and yields. An engineered intra-protomer disulfide I201C-A433C (CC) prevents CD4-induced conformational rearrangements that expose non-neutralizing determinants.

Applicants deduced that several N-linked glycosylation sites occlude the gp120 CD4bs within the quaternary packing of trimer (FIGS. 1*a* and 1*b*). In addition, by inspecting the angles of access determined for several CD4bs-directed bNAbs, it was reasoned that deleting one set of PNGSs, by genetic alteration of this motif, would increase access for most bNAbs approaching the CD4bs with a VRC01-like lateral path (Group A, FIG. 1*a*) without allowing access by non-broadly neutralizing CD4bs-directed mAbs such as F105. Although the VRC01-like antibodies were included as design guides, the non-VH-gene-restricted class of CD4bs-directed bNAbs such as VRC13 or VRC18 were also included, with the objective to open access to the CD4bs unfettered by VH or VL gene-restricted requirements. The PNGSs revealed by this analysis include N234, N276, N360 and N463 amongst others (Group A, FIG. 1*a*). PNGSs were not altered at the V-cap trimer apex (i.e. N386) because it was shown previously that non-broadly neutralizing CD4bs-directed mAbs bind this region by a vertical angle that allows access to the CD4bs on some tier 1 viruses (HXBc2), that is occluded by N-glycans on tier 2 viruses. It was also determined that deletion of the additional N-glycans N197, N262 and N301 would potentially open access to the CD4bs for antibodies displaying a similar angle of approach as the bNAb, b12 (Group B; FIG. 1*b*).

Figure 10:
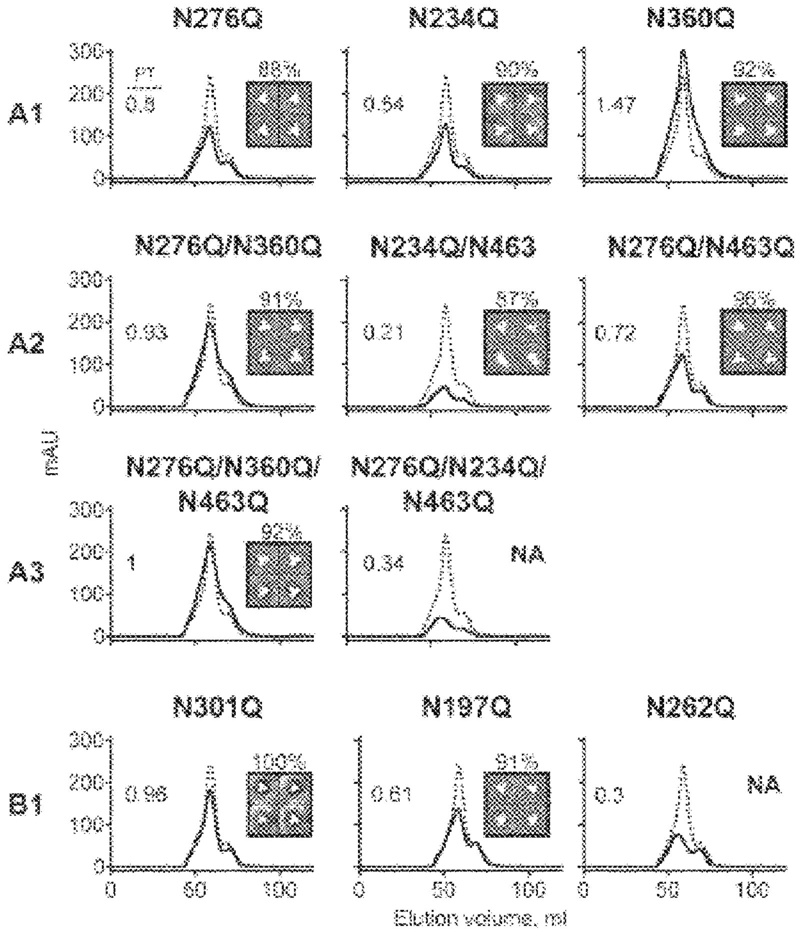
FIG. 10. SEC profiles and EM 2D class averages of lectin affinity-purified glycan deleted trimers lacking the 332 N-glycan. Panels A1, A2 and A3 indicate trimers with one, two or three Group A PNGS-mutations, respectively. Panel B1 indicates trimers with one PNGS mutated from Group B. SEC profiles of mutated trimers (solid line) are shown in comparison with the PT (parental trimer, dotted line) and the expression level relative to expression level of PT is shown on each SEC graph. The percentage of native-like trimers determined by negative stain EM (the sum of closed and open native-like trimers) for each mutant trimer protein is indicated above the 2D class averages. Four single-particle representative images shown for each variant.
Figure 11:
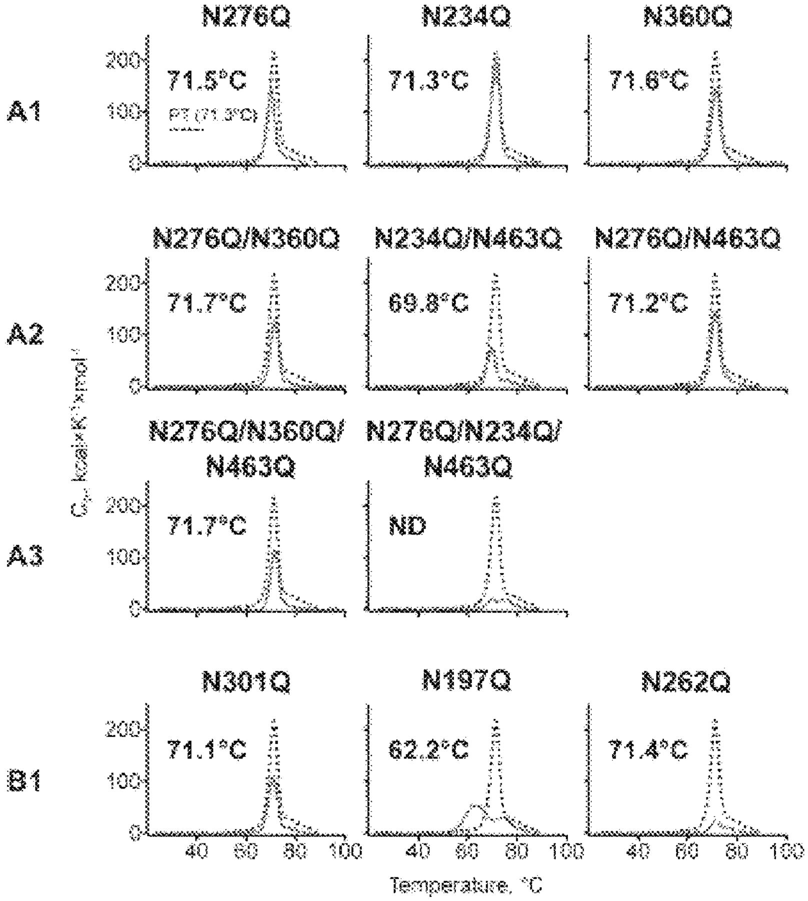
FIG. 11. DSC thermal transition (Tm) curves. The curves and derived Tms of glycan-deleted trimers (red solid line) compared to the backbone PT protein lacking N332 (black dotted line) are shown. Panels A1, A2 and A3 indicate trimers with one, two or three Group A PNGS-mutations, respectively. Panel B1 indicates trimers with one PNGS mutated from Group B.
Figures 12A, 12B, 12C:
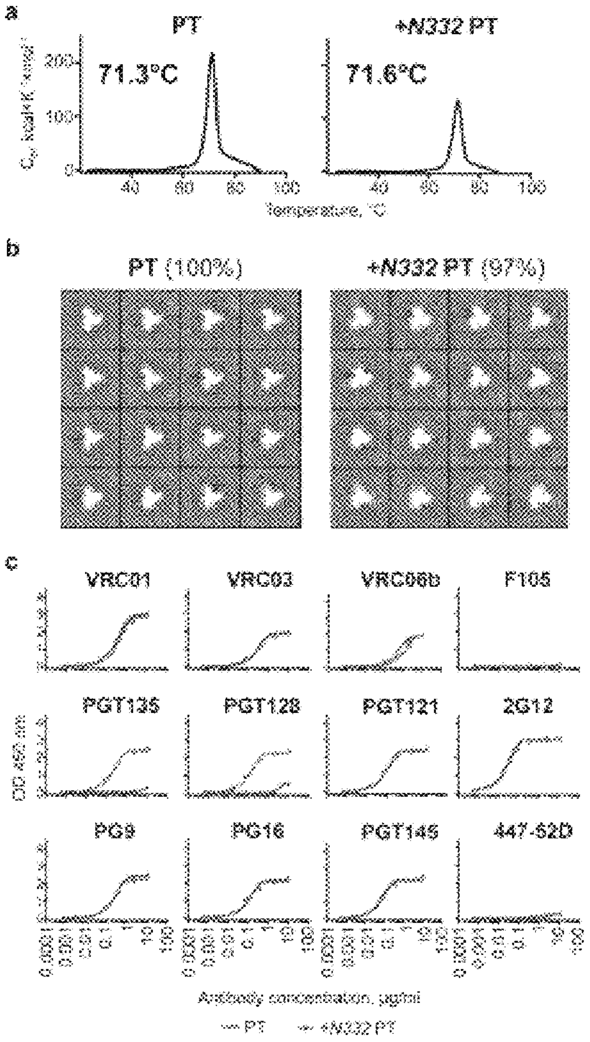
FIG. 12A-12C. Comparison of the 16055 NFL TD CC trimers without (PT) and with the 332 N-glycan (+N332 PT). (a) DSC thermal transition curves and derived Tms of PT and +N332 PT trimers. (b) EM 2D class averages. Percentage of native-like trimers determined by negative stain EM (the sum of closed and open native-like trimers) for each trimer is indicated above the 2D class averages; 16 representative single-particle images are shown for each variant. (c) ELISA binding curves of selected antibodies to the PT (blue) and +N332 PT (red) proteins. His-captured trimers were analyzed. Experimental duplicates were analyzed for each antibody dilution, mean values are shown.

Following lectin purification, Applicants analyzed trimer production by size-exclusion chromatography (SEC) relative to the PT as the first criterion to assess PNGS-deleted trimer integrity. Single (A1, B1), double (A2) and triple (A3) glycan-deleted trimer variants were analyzed (FIG. 10). In parallel, the conformational state of the selected glycan-deleted variants was investigated by negative stain EM as a second criterion to assess PNGS-deleted trimer integrity (FIG. 10). As a third criterion, Applicants analyzed trimer stability and homogeneity by DSC to assess trimer integrity harboring the targeted genetic PNGS deletions (FIG. 11). These biophysical analyses are detailed in the Supplementary materials and the findings can be summarized as follows. It was determined that mutations N276Q, N301Q and the combinations of mutations N276Q/N360Q, N276Q/N463Q and N276Q/N360Q/N463Q minimally affected the trimer yields and thermostability and allowed native-like trimer conformation (FIGS. 10 and 11). On the other hand, the PNGS mutations N197Q, N234Q and N262Q affected trimer integrity. Deletion of N262 PNGS resulted in extremely low trimer expression (FIG. 10). Similar effects were observed when N234Q was introduced in the combination with mutations N276Q and N463Q (FIG. 10). In the case of the N197Q substitution, it was observed that a substantial loss of both the propensity to form well-ordered trimers and protein thermostability (FIG. 11). Therefore, further analysis focused on PNGS modifications that did not affect trimer integrity, namely, N276Q, N301, N360Q, and N463Q.

As mentioned above, the 16055 Env naturally lacks a PNGS at residue N332, located in the gp120 outer domain. However, this N-glycan site is generally well-conserved across HIV Env strains and is central to the 332N-glycan "supersite" that is the target of many bNAbs such as 2G12, PGT128 and PGT135. It was reasoned that, in addition to restoring an important neutralizing determinant, that genetic restoration of this N-glycan might impact overall trimer stability, thereby allowing us to delete additional PNGS from Group A (FIG. 1*a*). Accordingly, PNGS were introduced at residue 332 in the 16055 PT by a K334S mutation. This N332-glycan-restored trimer was termed "+N332 PT", where the italicized N refers to the N-glycan, not the asparagine residue common to both trimer-types. To confirm conformational integrity, Applicants compared the thermal transition midpoints (Tms) and the EM 2D class averages for the two trimeric proteins with and without the PNGS at residue 332 (S3a and S3b Fig). The +N332 PT trimer was minimally more stable than the isogenic PT lacking the 332 N-glycan, displaying a Tm increase of +0.3° C. (S3a Fig).

Figures 2A, 2B:
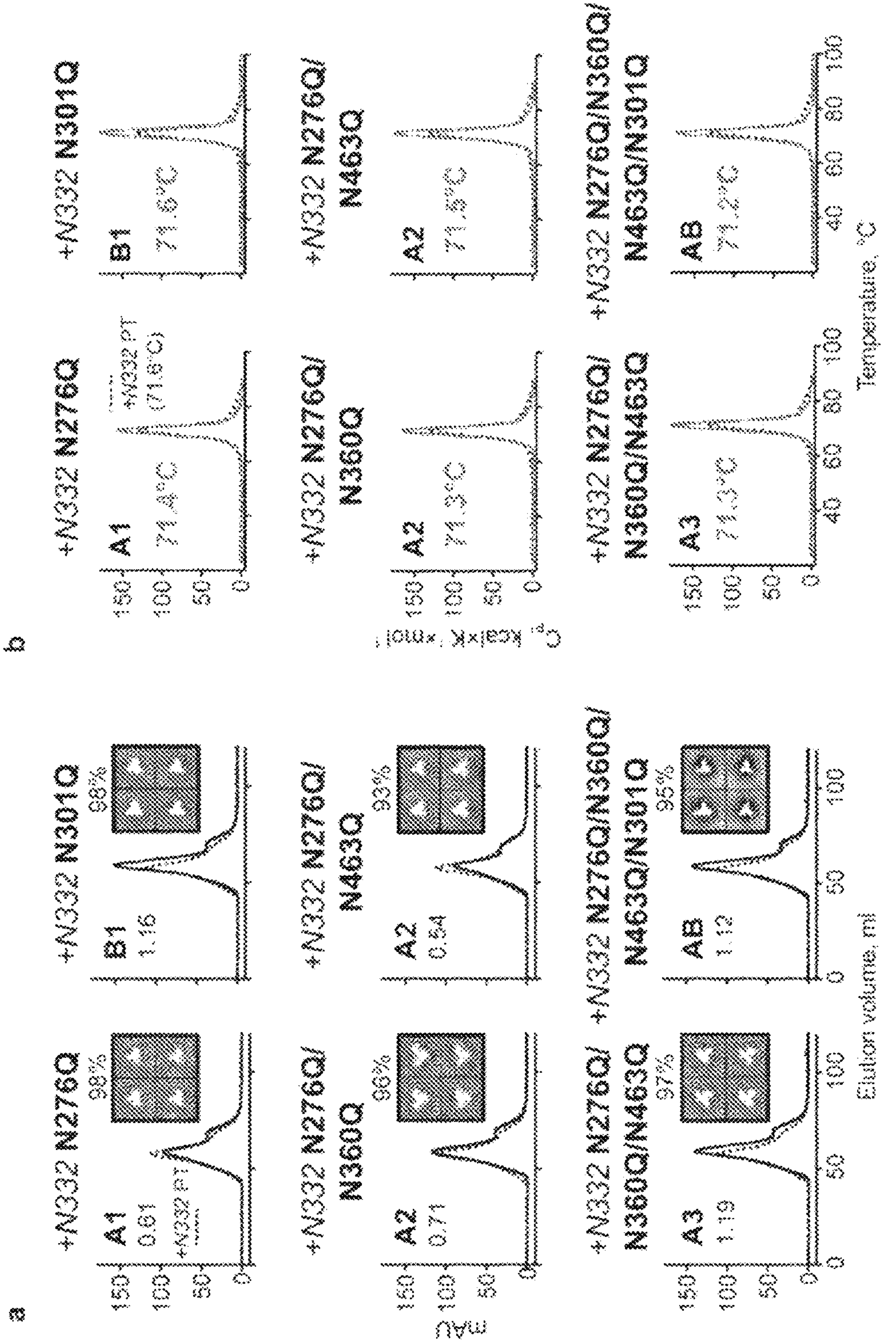
FIG. 2A-2B. Characterization of lectin affinity-purified 16055 glycan-deleted trimers with the 332 N-glycan restored. (a) SEC profiles and EM 2D class averages. A1 or B1, A2, A3 and AB indicate trimers with one, two, three and four N-glycan deletions, respectively. SEC profiles of N-glycan-deleted trimers (solid line) are shown in comparison with the +N332 PT trimer (dotted line). Percentage of native-like trimers is indicated above the 2D class averages representative images. (b) DSC thermal transition curves and derived Tms of glycan-deleted trimers (red solid line) compared to the backbone glycoprotein +N332 PT (black dotted line).

EM analysis showed nearly identical populations of native-like trimers for both proteins. It was demonstrated that there were no significant differences for the binding by a panel of CD4bs-directed mAbs (S3c Fig) and no difference in binding by the trimer-preferring bNAbs, PGT145, PG9 and PG16. Restoration of the N332 supersite was confirmed by efficient binding by the bNAbs, PGT135 and PGT128 (S3c Fig). Expression and yields of the PNGS-deleted NFL trimeric proteins for both Group A and B were not affected by the glycan alterations and EM analysis revealed that the trimeric glycoproteins retained a native-like conformation (FIG. 2). DSC analysis of both sets of N-glycan deleted trimers showed that their Tms remained practically identical suggesting that the N-glycan alterations did not affect stability of the proteins (FIG. 2B). These analyses allowed us to select the best combination of N-glycan deletions proximal to the CD4bs in the native-like NFL context.

Example 3: Deletion of N-Glycans Proximal to the CD4bs Enhances Env Recognition by Selected CD4bs-Directed bNAbs To examine the effects of N-glycan deletion on antibody accessibility at the CD4bs, Applicants analyzed binding of a set of CD4bs-directed bNAbs to specific N-glycan-deleted variants compared to their respective parental trimers. For this analysis, His-capture ELISA was used to maintain native-like trimer confirmation to assess bNAb recognition as previously described. Preservation of a native-like trimer conformation was confirmed by efficient recognition by the trimer-dependent bNAb, PGT145 (FIGS. 14 and 15), and by poor recognition by the non-broadly neutralizing, CD4bs-directed mAb, F105.

Figures 3A, 3B:
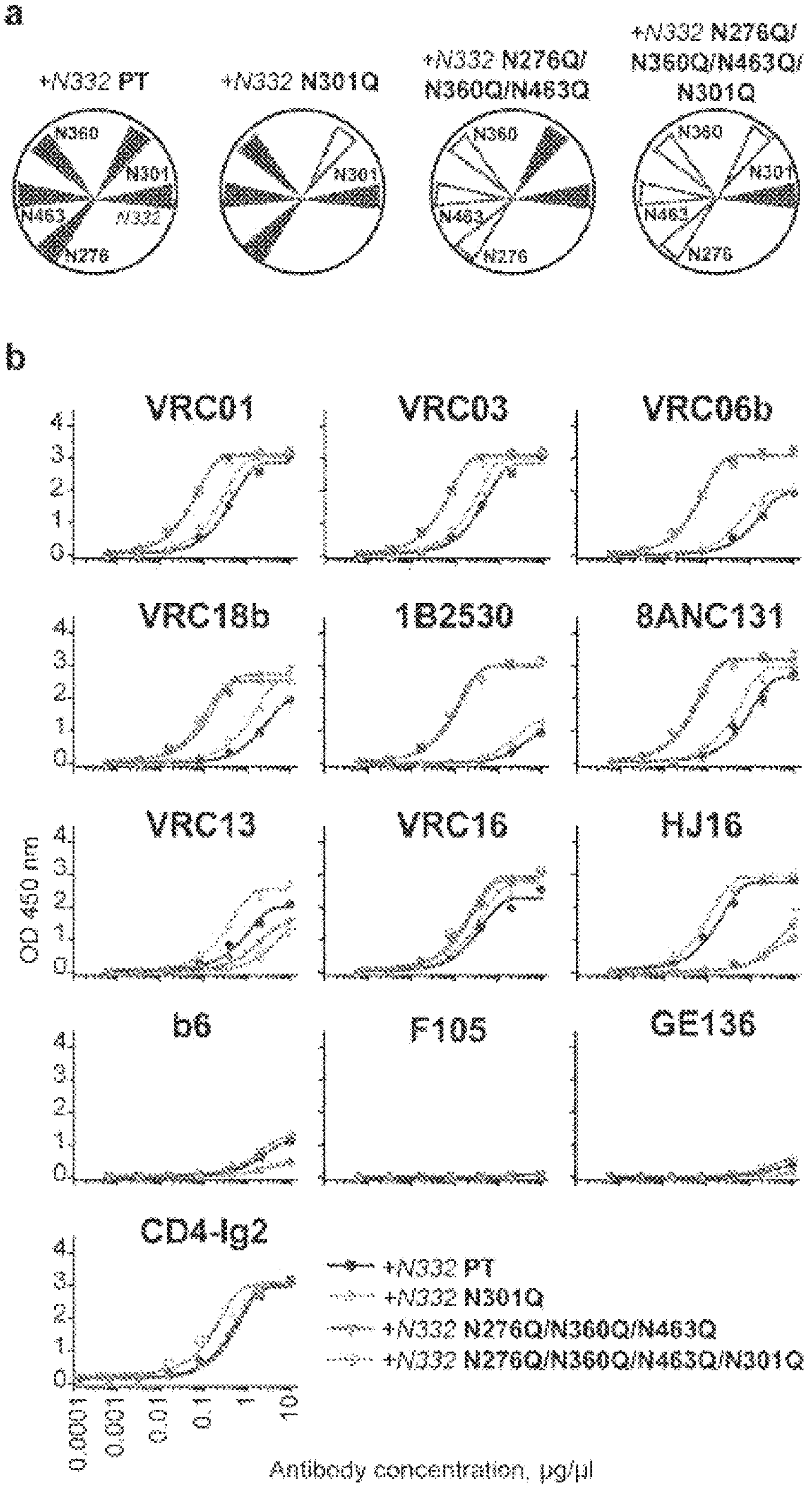
FIG. 3A-3B. CD4bs-specific antibody binding profiles to the N-glycan deleted trimers. (a) Schematic presentation of N-glycan composition around the trimer CD4bs in the selected N-glycan-deleted trimers. Filled blue triangle—the N-glycan is present; empty blue triangles—the N-glycan is genetically deleted. (b) Comparison of the +N332 PT (dark blue) with +N332 N301Q (yellow), +N332 N276Q/N360Q/N463 (red) and +N332 N276Q/N360Q/N463/N301Q (light blue) trimers. Recognition of His-captured trimers by the trimer-elicited rabbit serum were analyzed in duplicate at each antibody dilution. The error bars indicate variance of the mean binding values (OD450 nm) and a representative experiment of three independent repeats is shown.
Figures 13A, 13B:
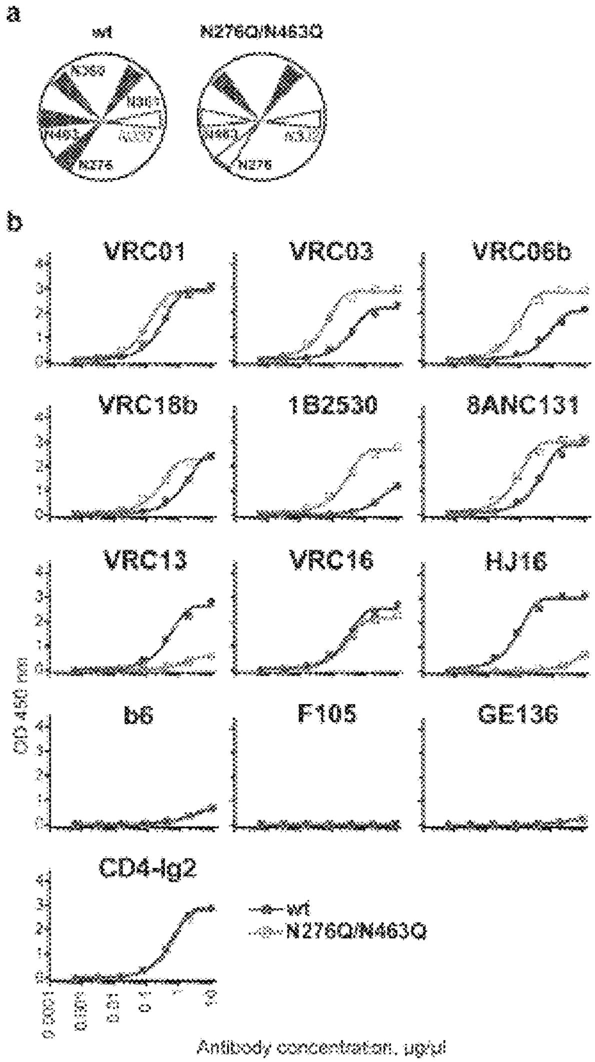
FIG. 13A-13B. CD4bs-specific antibody binding profiles of the glycan deleted trimer. (a) Schematic presentation of N-glycan composition proximal to the trimer CD4bs in the selected glycan-deleted trimers. Filled blue triangle—the N-glycan is present; empty blue triangles—the N-glycan is genetically deleted or naturally absent (residue 332). (b) Comparison of the PT (dark blue) and N276Q/N463 (green) trimers. His-captured trimers were analyzed. Experimental duplicates were analyzed for each antibody dilution, mean values are shown.

Applicants selected a panel of monoclonal antibodies based on their differential ability to neutralize 16055 pseudovirus and their different modes of Env recognition. Access to the CD4bs was assessed to determine whether specific targeted N-glycan deletions rendered this region more accessible for mAbs of different origin, angles of approach and neutralizing capacity. It was demonstrated that increased binding by the bNAbs VRC01, VRC03, VRC06b, VRC18b (VH1-2-derived;) and 1B2530 and 8ANC131 (VH1-46-derived) to the N276Q/N463Q glycan-deleted variants with or without N332 restored (FIGS. 3, 13 and 15). Increased binding by the bNAbs VRC01, VRC03, VRC06b, VRC18b, 1B2530 and 8ANC131 was also detected to the +N332 N276Q/N360Q/N463Q and +N332 N276Q/N360Q/N463Q/N301Q triple and quadruple N-glycan-deleted variants compared to the fully glycosylated +N332 PT backbone (FIGS. 3, 15). For the +N332 N301Q glycan-deleted variant, the difference in binding was less pronounced (FIGS. 3, 15).

Applicants next assessed recognition by the set of HCDR3-using CD4bs-directed mAbs, VRC13, VRC16 and HJ16. Binding to the +N332 N301Q glycan-deleted variant was enhanced in comparison with +N332 PT for all three antibodies (FIGS. 3, 15). As expected, HJ16 binding was impaired when the PNGS at residue 276 was altered, consistent with its known (FIGS. 3, 13 and 15) N276 glycan-dependence. VRC13 recognition was similarly impaired by deletion of the N463 PNGS and is likely dependent upon the presence of this N-glycan for efficient Env recognition (FIGS. 3,15). Both of these changes in recognition are consistent with deletion of the N-glycans at residues 276 and 463 by altering PNGS motif. With the four N-glycans eliminated in the 16055 trimers, binding was tested by the germline-reverted antibodies VRC01gl, VRC13gl, VRC16gl but as expected, did not detect binding (FIGS. 14, 15).

Figures 14A, 14B, 14C, 14D:
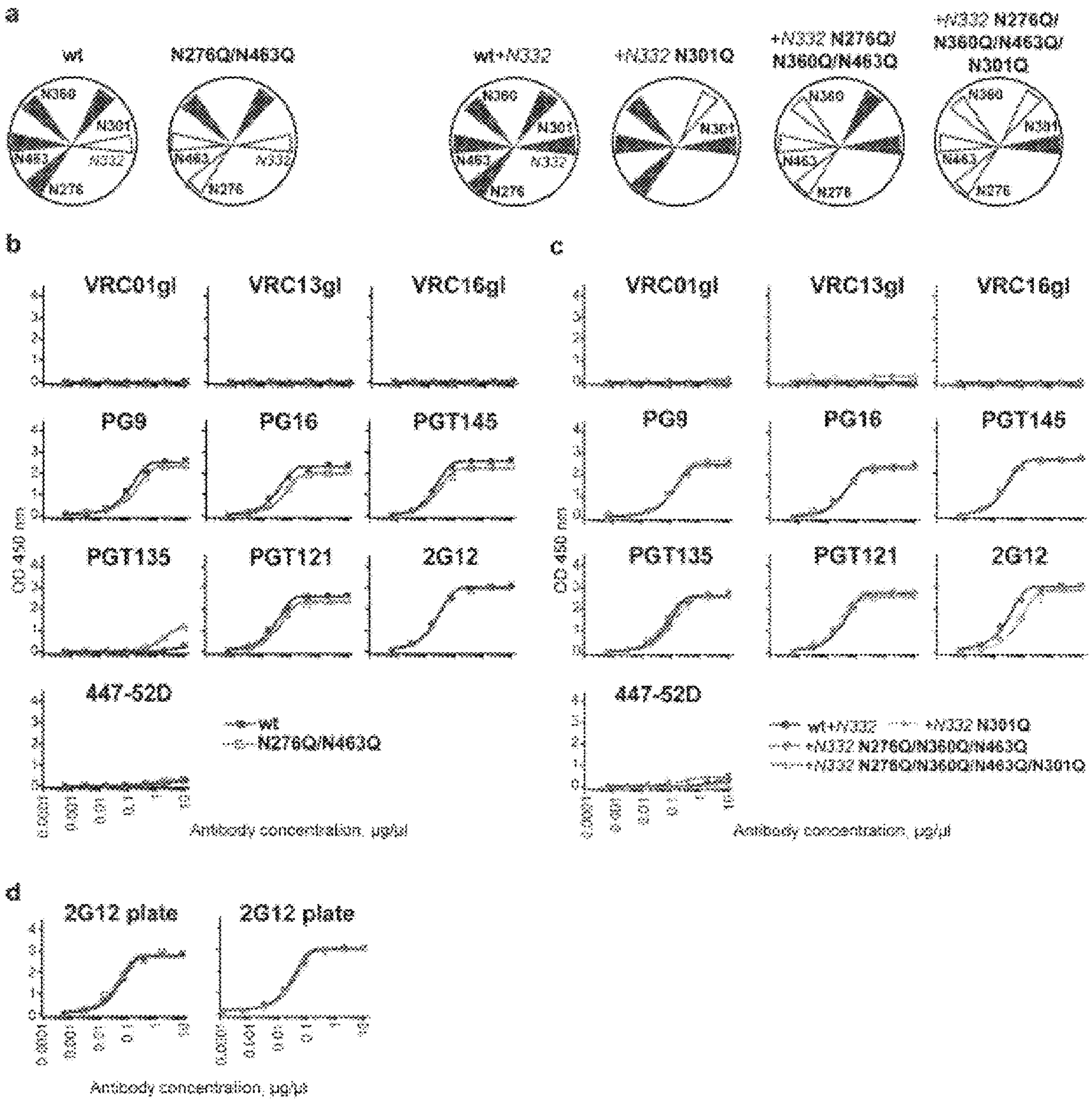
FIG. 14A-14D. Antibody binding profiles of the glycan-deleted trimers. (a) Comparison of the PT (dark blue) and N276Q/N463 (green) trimers. (b) Comparison of the PT (dark blue) and N276Q/N463 (green) trimers. His-captured trimers were analyzed. (c) Comparison of the +N332 PT (dark blue) with +N332 N301Q (yellow), +N332 N276Q/N360Q/N463 (red) and +N332 N276Q/N360Q/N463/N301Q (light blue) trimers. His-captured trimers were analyzed. (d) 2G12 binding of the trimers coated directly on the ELISA plate. Experimental duplicates were analyzed for each antibody dilution, mean values are shown.

To complete the antigenic analysis of the N-glycan-deleted trimer variants, efficient recognition was detected by the trimer-preferring V2-apex-directed bNAbs, PG9 and PG16, confirming that the trimer native-like conformation was not affected by the N-glycan deletions (FIGS. 14 and 15). No binding differences were observed for the N332-glycan "supersite" antibodies PGT121 and PGT135, whereas, 2G12 displayed slightly decreased recognition for the 301 N-glycan-deleted trimer variants (FIGS. 14*b* and 15).

In sum, targeted N-glycan deletions preferentially enhanced antibody recognition by the majority of CD4bs-directed antibodies without significantly altering bNAb recognition of other Env regions.

Example 4: Bio-Layer Interferometry (BLI) Confirms Enhanced Binding of the N-Glycan-Deleted Trimer by the CD4bs-Directed bNAb, VRC03

Figure 4:
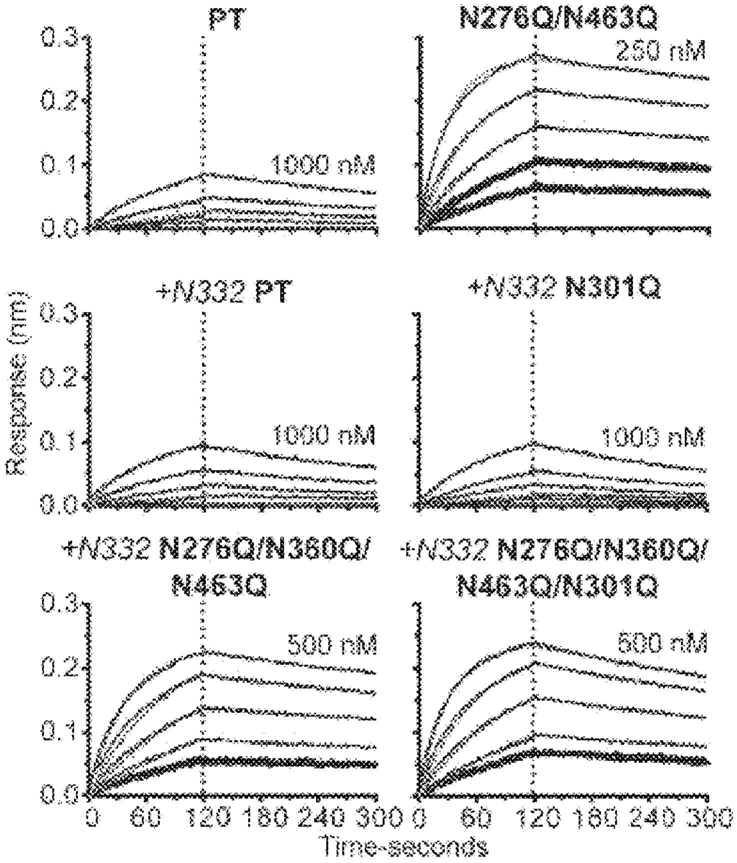
FIG. 4. Binding kinetics for glycan deleted trimers with the VRC03 Fab. Bio-layer interferometry (BLI) curves were generated with the PT and N276Q/N463 trimers (blue fitted curves) and +N332 PT with +N332 N301Q, +N332 N276Q/N360Q/N463 and +N332 N276Q/N360Q/N463/N301Q trimers (red fitted curves) immobilized on an anti-His sensor with serial dilutions of the VRC03 Fab at the concentrations indicated. A tabular summary of the Kd, kon and koff is shown.

Applicants used BLI (Octet) to assess the effect of N-glycan deletion on the binding efficiency of the CD4bs-directed bNAb, VRC03. Since the bivalent VRC03 IgG can potentially bind CD4bs epitopes on multiple trimers, creating avidity, VRC03 Fab was generated to permit precise determination of the affinity of this interaction with trimer. Using the Fab as the monomeric analyte in solution, it was observed that the N276Q/N463Q trimer, when captured in the sensor surface, was recognized by the VRC03 Fab approximately 30-times more efficiently compared to the PT "backbone" trimer (FIG. 4). In case of glycan-deleted variants of +N332 PT, there was a 10- and 8-fold difference, respectively, in affinity for the +N332 N276Q/N360Q/N463Q and +N332 N276Q/N360Q/N463Q/N301Q variants compared to the backbone protein. The binding of +N332 N301Q variant was two-fold lower in comparison with the +N332 PT backbone.

Following the detected increase in VRC03 Fab affinity for the four-position N-glycan-deleted trimer, Applicants assessed the effect of this N-glycan deletion on stoichiometry by negative-stain EM. Complexes were generated to obtain 2D class averages and 3D reconstructions of the +N332 N276Q/N360Q/N463Q/N301Q variant compared to the backbone +N332 PT trimer. It was observed that despite the large affinity increase of VRC03 Fab for the N-glycan-deleted trimer detected by BLI (and ELISA), the stoichiometry of the interaction was not altered relative to the +N332 PT backbone as determined by EM (FIG. 16).

Example 5: Full-Length 16055 Env Pseudoviruses with CD4bs Proximal PNGS Deletions Retain a "Tier 2-Like" Phenotype To evaluate Ab responses elicited by the PNGS-deleted trimer immunogens, Applicants generated full-length 16055 Env expression plasmids encoding matching CD4bs-proximal N-glycan deletions. Applicants generated 16055 HIV-1 pseudoviruses, termed "wt" for the fully glycosylated Env and "Δ followed by a numeral" to specify N-glycan deletions at the stated Env positions and assessed their properties of entry and neutralization sensitivity. For example, a pseudovirus with Env possessing two N-glycan deletions at positions 276 and 463 is designated 16055Δ276Δ463. Consistent with the observations made for the soluble Env trimers, pseudoviruses lacking two to four N-glycans were more sensitive to neutralization by VRC01, VRC03 and VRC06b and, as expected, less sensitive to the N276-glycan-dependent bNAb, HJ16 (FIG. 5). In the 16055 virus context, each of the glycan-deleted pseudoviruses displayed a tier 2-like phenotype as defined by selected mAbs and HIVIG (HIV Immunoglobulin, lot #140406). In particular, deletion of the N-glycan residue N301 often causes a "global opening" or tier 1 phenotype for other pseudoviruses with this same mutation (i.e., YU2, JRFL and SS1196), but it did not cause the same effect in the 16055 context. All 16055 pseudoviruses deleted of their Env CD4bs-proximal PNGS remained insensitive to the non-neutralizing mAbs, b6, F105, GE136, 17b, 447-52D and 19b (FIG. 5), as well as to polyclonal HIVIG derived from a pool of HIV-infected individuals. This analysis indicated that the same N-glycan deletions that were tolerated in the context of soluble PT and +N332 PT proteins also did not affect the native Env conformation on the pseudovirus, while increasing bNAb access to the CD4bs (FIG. 5). It was observed that the pseudovirus 16055Δ276Δ463 was the most sensitive to the CD4bs-directed bNAbs, and less sensitive to PGT145, in comparison with other N-glycan-deleted viruses, even those variants with additional N-glycan modifications.

This set of Env N-glycan-modified pseudoviruses recapitulated the trimer antigenic profiling of the N-glycan-deleted soluble trimers and represents a useful set of tools to characterize antibody responses generated by such trimers.

Figures 6A, 6B, 6C:
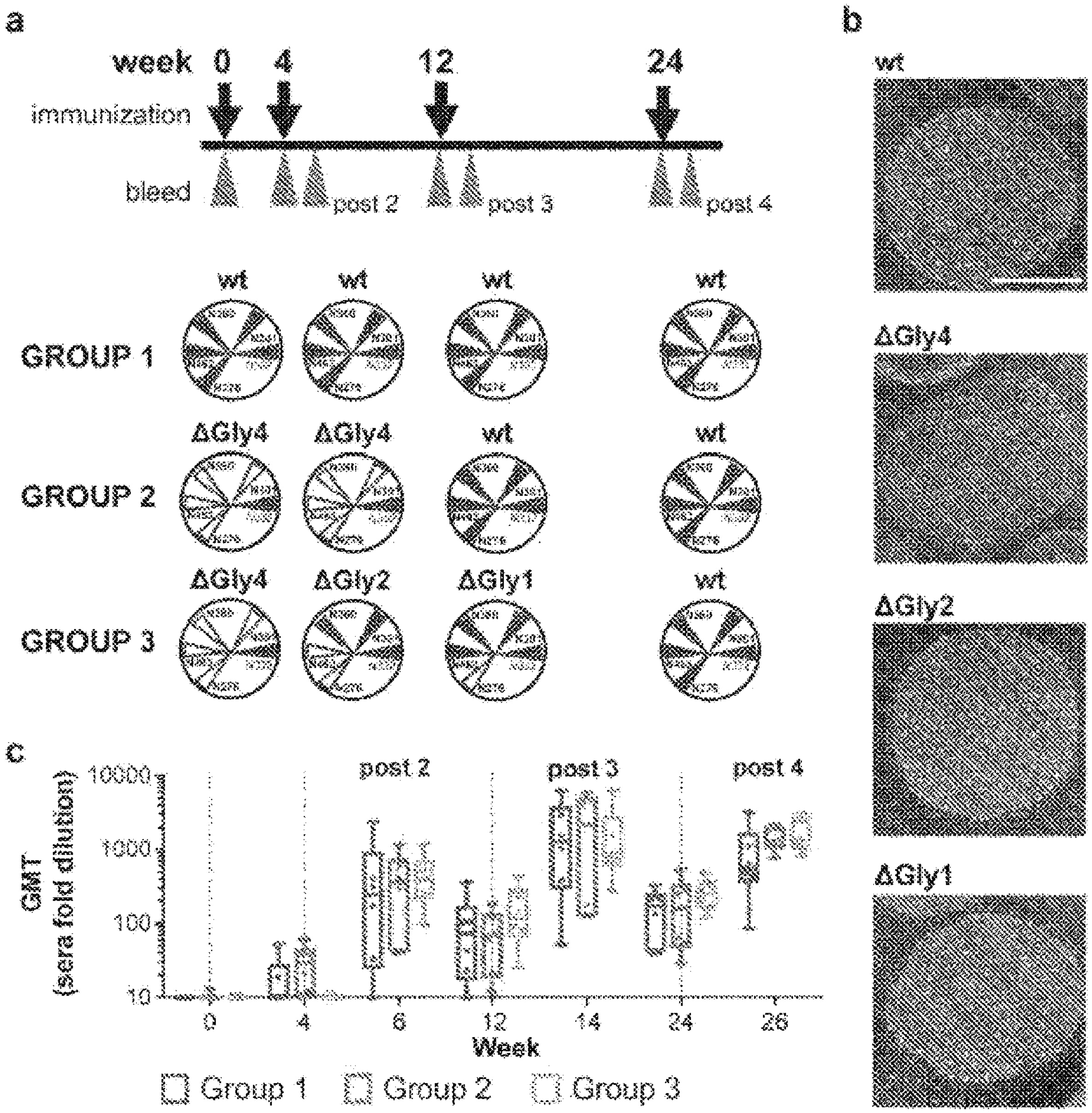
FIG. 6A-6C. Immunogenicity of glycan-deleted trimers. (a) The immunogenicity regimen and respective immunogens for Groups 1, 2 and 3 are shown. In brief, rabbits were immunized at weeks 0, 4, 12 and 24. Test bleeds are indicated by the red arrows following each immunization. (b) Representative negative stain EM images of the liposomes coupled with the respective trimers. The white scale bar on the top wt trimer-liposomes image is equivalent to 100 nm. (c) Geometric mean IgG titers (GMT) as measured by His-capture ELISA to the wt autologous trimer immunogen following each inoculation. Immunizations are indicated by the vertical dashed gray lines. Six data points per time point per group were determined. Two independent ELISA experiments were performed and a representative experiment is shown.

Example 6: Immunization with N-Glycan-Deleted Trimers Generates More Rapid and Consistent HIV-1 Neutralizing Antibody Responses Compared to Unmodified Trimers To assess if N-glycan-deletion at the CD4bs altered the elicited B cell response and serum antibodies compared to unmodified trimers following vaccination, Applicants performed an immunogenicity experiment in rabbits. Two different immunization regimens that involved priming animals with N-glycan-deleted trimers were tested, followed by comparing each of these regimens to the control immunization regimen, where all animals were immunized with fully glycosylated trimers (Group 1). The rabbits from this control Group 1 were immunized four times with the parental trimer 16055 NFL TD CC (T569G), to which the N332 glycan had been introduced as described above (FIG. 6*a*). For simplicity of the nomenclature this trimer will be referred to as the "wt" control immunogen for the remainder of the study. The rabbits in Group 2 were immunized twice with the N-glycan deleted +N332 N276Q/N360Q/N463Q/N301Q trimer (from now on, referred to as "ΔGly4") and boosted two times with the wt immunogen (FIG. 6*a*). The rabbits in Group 3 were immunized sequentially with the three N-glycan-deleted trimer variants: ΔGly4, then ΔGly2 (+N332N276Q/N463Q), then ΔGly1 (+N332 N276Q) and lastly with wt trimer (FIG. 6*a*). To enhance immune responses, all trimers were arrayed on liposomes at high-density as previously described. It has been demonstrated that this multivalent presentation of trimers on the surface of liposomes more effectively generates germinal centers B cells and serum neutralizing antibodies. Animals from each group were immunized via the subcutaneous route at weeks 0, 4, 12 and 24 with 30 μg of each trimer arrayed on the liposomes (FIG. 6*b*) and formulated in ISCOMATRIX adjuvant (CSL). Applicants confirmed the quality of each trimer-liposome preparation by EM negative stain analysis prior to each immunization (FIG. 6*b*).

Figures 7A, 7B:
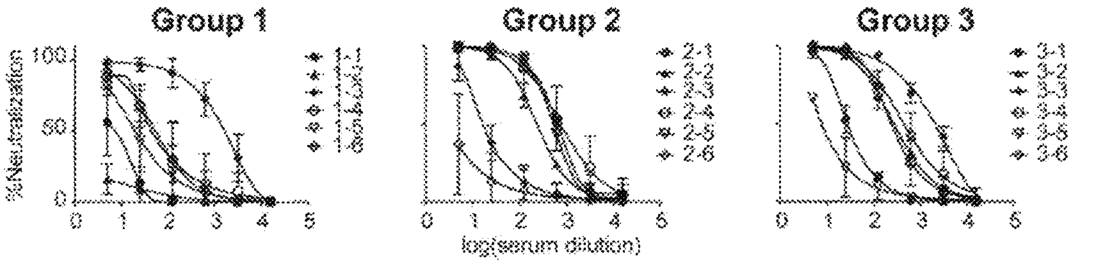
FIG. 7A-7B. Neutralizing ID50 titers (reciprocal serum, fold-dilution) against 16055 N1130 glycan-deleted viruses. ID50 values are indicated in bold. Those derived by extrapolation are shown in non-bolded text (a) ID50 values for the viruses with the same N-glycan deletions proximal to the CD4bs as those in the trimer immunogens. Statistical differences were evaluated by the non-parametric Mann-Whitney test and, when detected at a level significance, are indicated under the specific data set with * P<0.05 and ** P<0.01. (b) Serum neutralization curves for 16055 wt virus derived from mean values for each data point of three independent TZM-bl-based neutralization assays. Error bars represent the standard deviation of the values from three independently performed experiments.

Bleeds were obtained on the day of immunization and 2 weeks after each immunization, except following the first inoculation (FIG. 6*a*). After completion of the full regimen, serum IgG binding titers were tested against the +N332 PT trimer by anti-His capture ELISA (See Methods and FIG. 6*c*). There was no statistical difference in geometric mean binding titers (GMT) between Group 2 or Group 3 compared to Group 1, although the values obtained for the rabbits in Groups 2 and 3 displayed less variance following the fourth immunization (FIG. 6*c*). Applicants then analyzed the antibody neutralizing response of all animals in a longitudinal manner following the second, third and fourth immunization (post 2, post 3 and post 4, respectively). In terms of neutralizing capacity, the most striking difference for either Group 2 or Group 3 compared to Group 1 was observed with the N-glycan-deleted viruses. Specifically, the serum neutralizing capacity was first analyzed against the pseudoviruses with matching N-glycan deletions relative to the trimeric immunogens for Groups 2 and 3. Following two inoculations, all animals from Group 2 could neutralize the 16055Δ276Δ360Δ463Δ301 and the 16055Δ276Δ463 pseudoviruses and five of six animals from Group 3 neutralized these viruses. In contrast, only one animal in Group 1 weakly neutralized the 16055Δ276Δ463 virus after two immunizations. These differences were statistically significant (FIG. 7*a*). The differences in neutralization capacity of the 16055Δ276Δ360Δ463Δ301 and 16055Δ276Δ463 pseudoviruses between Groups 2 or 3 compared to Group 1 were also significant following the third immunization. After the fourth immunization, when the animals from Groups 2 and 3 were both inoculated with the fully glycosylated wt trimers, there was a trend to higher titers against 16055Δ276Δ360Δ463Δ301 and 16055Δ276Δ463 viruses for Group 2 compared to Group 1. The difference for Group 3 in comparison to Group 1 for the four-N-glycan deleted (16055Δ276Δ360Δ463Δ301) virus was statistically significant (FIG. 7*a*).

Because the pseudoviruses with multiple glycan deletions were better neutralized by the serum derived from Group 2 or 3 animals compared to those from Group 1, neutralization was assessed against each of the 16055 singly-N-glycan-deleted virus Δ276, Δ360, Δ463 and Δ301 to define clearly the neutralization specificity in the polyclonal serum. The experiment is designed to pinpoint if the elimination of single N-glycan would reflect the neutralization capacity detected against the multiple N-glycan deleted viruses (FIG. 8). Several animals from Group 2 or Group 3 elicited weak, but detectable, neutralizing activity against all four of the single N-glycan-deleted viruses after the second immunization (week 4/post 2), while only the highest responder in Group 1, showed weak neutralization against 16055Δ360 at that time point (FIG. 8). More animals in Group 2 or 3, compared to Group 1, exhibited neutralization serum activity against the singly glycan-deleted viruses after the third immunization (week 12/post 3). There was a statistically significant difference in titers between Groups 1 and 3 against the 16055Δ276 pseudovirus. After the fourth immunization (week 24/post 4), the neutralization titers against single glycan-deleted 16055 pseudoviruses increased substantially in all three groups although the tendency to display higher titers against single glycan-deleted viruses in either Groups 2 or 3, in comparison with Group 1, remained.

In terms of the specific viruses, titers against the 16055Δ301 pseudovirus did not increase more than two-fold in comparison with the titers against 16055 wt, indicating that this N-glycan had a minimal effect in regards to neutralizing activity (FIGS. 7 and 8). In terms of specific animals from Group 2, the 16055Δ463 pseudovirus was better neutralized by the rabbit #2-3 (that is, animal number 3, from Group 2). This might be due to the peripheral location of the N463 glycan relative to the CD4bs providing better accessibility to the underlying protein surface (FIG. 1*a*). Animals from Group 3 displayed high titers against the 16055Δ276 pseudovirus, and the difference in the responses between Group 1 and 3 was statistically significant after three immunizations. There was also a strong trend of more potent neutralization of the 16055Δ463 virus in this group after three immunizations, while the neutralization titer pattern for other single N-glycan-deleted viruses (16055Δ301 and 16055Δ360) was similar to the wt virus neutralization pattern at this time point. These results were consistent with a neutralizing antibody response focused toward the proximity of residue N276 by the ΔGly4, ΔGly2 and ΔGly1 sequential immunization, while responses proximal to residues 301 and 360 diminished, likely due to restoration of these N-glycans in the immunogens.

The trend of more potent and consistent neutralization elicited by the N-glycan deleted viruses was also detected when assessed against the autologous tier 2 fully-glycosylated 16055 wt virus. The differences in 16055 wt pseudovirus neutralization were detectable as well following the third immunization (post 3, FIG. 7*a*). Four animals from Group 2 and five animals from Group 3 displayed neutralizing activity against the 16055 wt, compared to only two animals from Group 1. After the final boost (post 4), five animals from Group 2 and six animals from Group 3 showed neutralization against 16055 wt virus (FIG. 7*a*). In terms of potency, four animals from each of these groups displayed autologous serum titers above 100, while only two animals displayed titers above 100 in Group 1 (FIG. 7*a*). In general, the responses in the animals from Group 1 were less potent than those in either Groups 2 or 3, with only one animal achieving 100% neutralization against the wt autologous virus after four immunizations (FIG. 7*b*), whereas, four animals in either Groups 2 or 3 achieved 100% wt virus neutralization (FIG. 7*b*).

These data suggest that genetic deletion of PNGS proximal to the CD4bs on the Env trimeric immunogens may eliminate steric barriers imposed by the presence of N-glycans that normally limit the B cells responding to this conserved epitope. In the present invention, the elimination of these barriers led to a more consistent and robust neutralizing antibody response when the N-glycan-deleted immunogens were used to prime the immune response.

Figure 17:
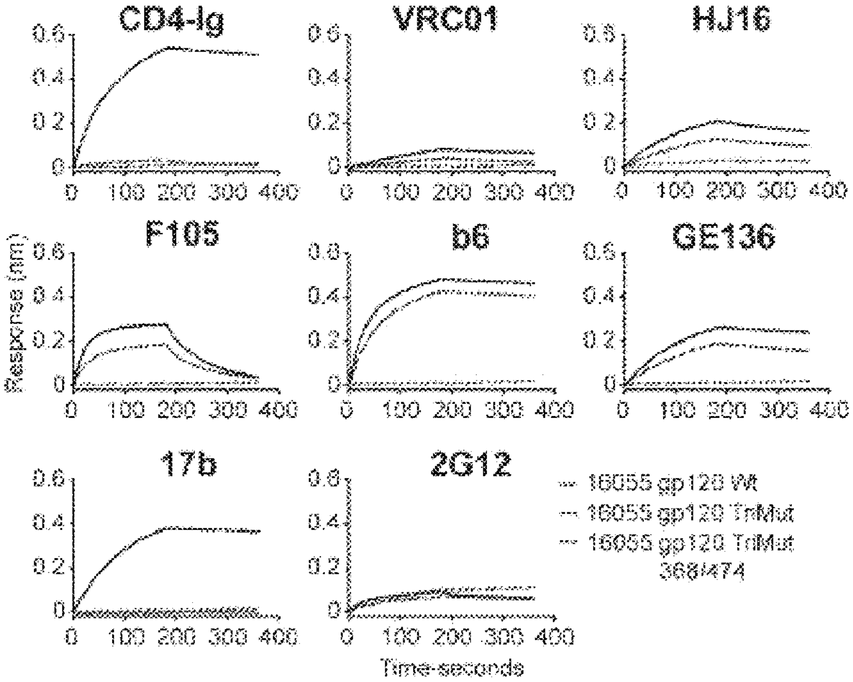
FIG. 17. Characterization of probes for the neutralization depletion assay. Based on 16055 gp120, two probes, TriMut with triple mutations (I423M, N425K and G431E) and TriMut 368/474 with two additional mutations (D368R and D474A), were designed to map the CD4bs neutralizing antibodies present in sera by neutralization depletion assay. To characterize the binding profile of the probes by Biolayer Interferometry (BLI), a panel of antibodies and CD4-Ig were captured by anti-human IgG Fc sensor and then dipped into 200 nM of probes in the well. The association and dissociation times are 3 min, respectively.
Figures 18A, 18B, 18C, 18D, 18E:
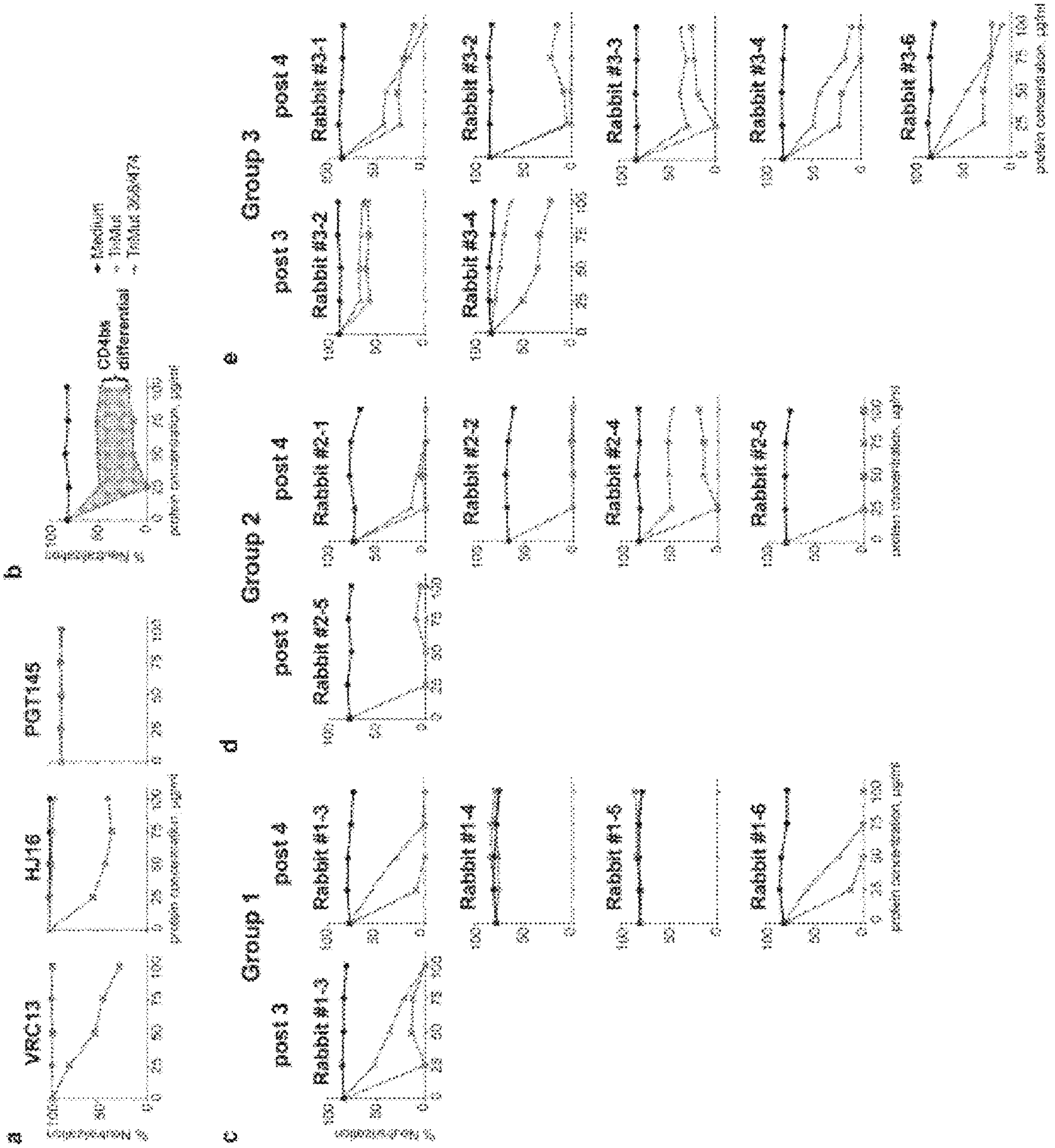
FIG. 18A-18E. Neutralization adsorption assay with the 16055 gp120 TriMut and TriMut 368/474 probes. Serum samples with neutralization titers above 100 were used to isolate total IgGs. The purified IgG samples were used in the assay at IC80 concentration. (a) panel confirms the differential depletion capacity of TriMut and TriMut 368/474 probes with CD4bs specific VRC13 and HJ16 bNAbs. PGT145 was used as a negative control. (b) A graphical depiction of the CD4bs differential is shown. Differential assays for Group 1 (c), Group 2 (d) and Group 3 (e) are shown. Two independent adsorption experiments were performed and a representative experiment is shown.
Figure 19:
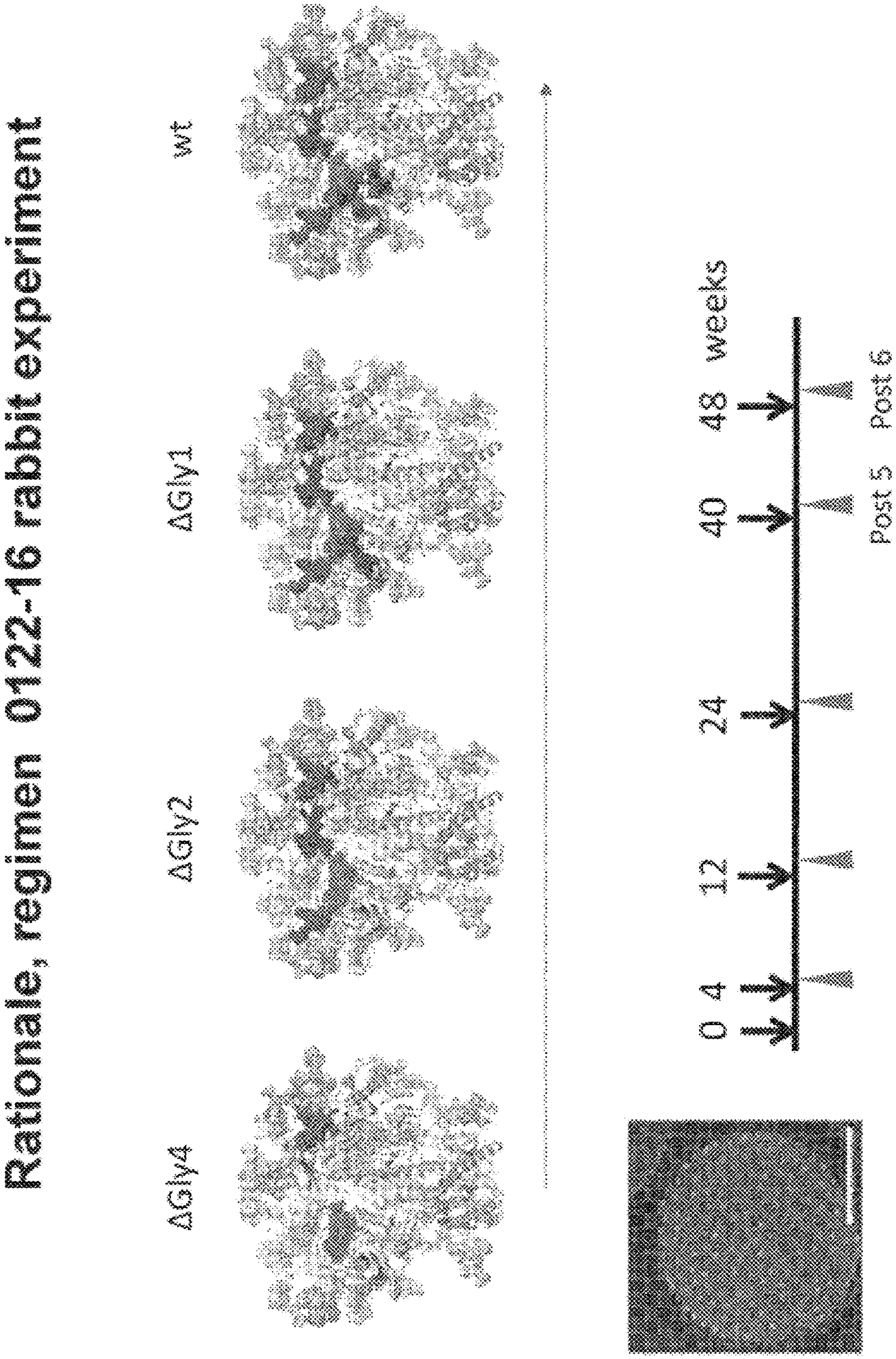
FIG. 19. CD4 binding site mutation and immunization experiment design. The rabbits were immunized sequentially with the three N-glycan-deleted trimer variants: ΔGly4, then ΔGly2 (+N332N276Q/N463Q), then ΔGly1 (+N332 N276Q) and lastly with wild type (wt) trimer, followed by glycan restoration.
Figure 25:
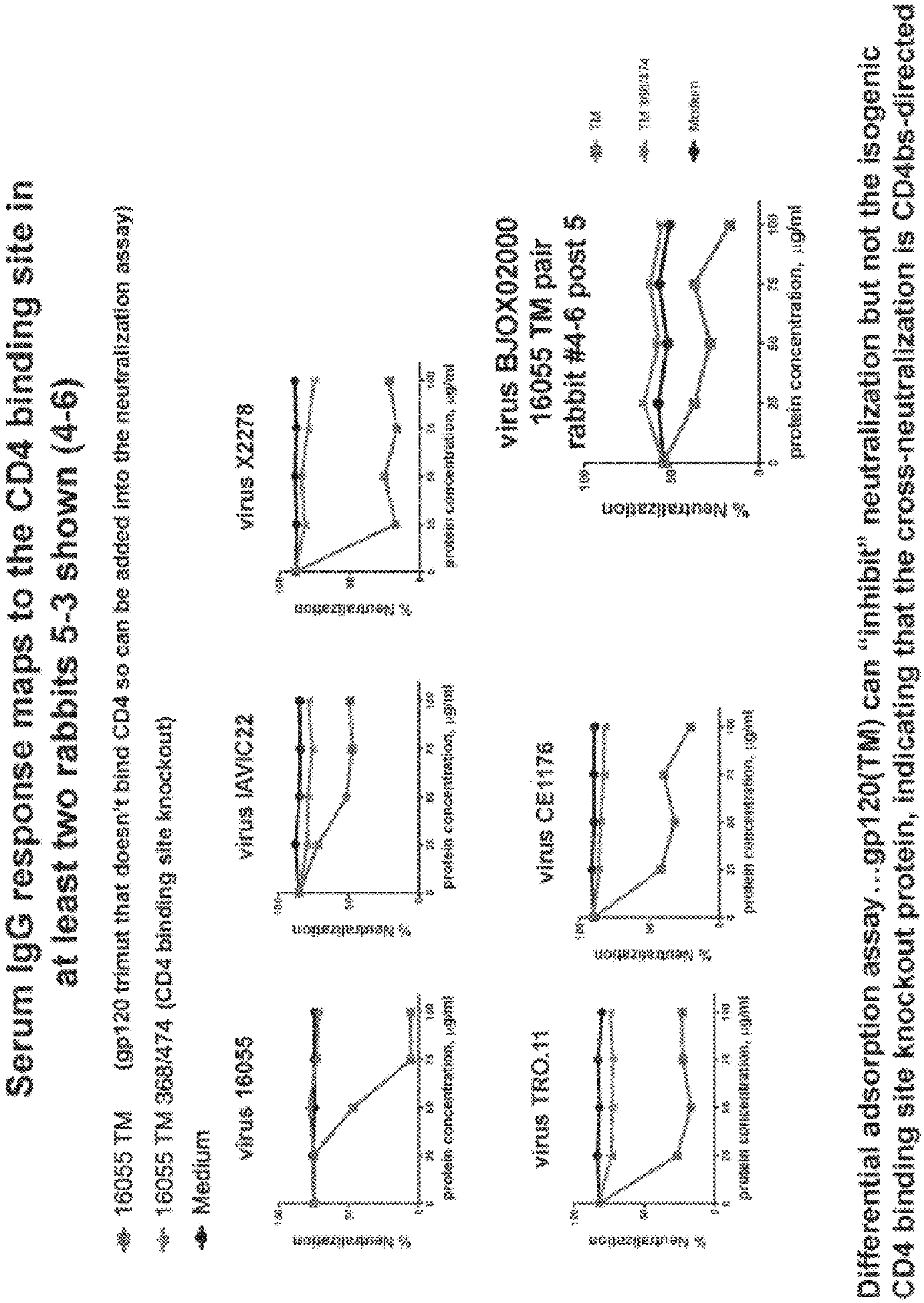
FIG. 25. Total serum IgG response mapping for rabbit #5-3. Serum IgG response maps to the CD4 binding site for CD4bs-directed responses. The CD4 binding site knockout protein (16055™) indicates that the cross-neutralization is CD4bs-directed.

Example 7: A Fraction of the Neutralizing Antibody Response Effectively Targets the CD4bs The analyses described in the previous section indicated that the neutralizing antibody responses were directed proximal to the CD4bs, especially in the sequential N-glycan-restored Group 3 animals. To determine by another means if the elicited neutralizing antibody response was in part directed to the CD4bs, a pair of 16055gp120-based TriMut probes were generated as previously described for the HXBc2 TriMut proteins. Both 16055 gp120 variants possess three mutations (I423M, N425K, and G431E) in the bridging sheet (hence, TriMut) that allow recognition by CD4bs-directed antibodies, but eliminates binding to the primary HIV receptor, CD4 (FIG. 17). These modification permit the addition of the TriMut gp120 glycoproteins directly into the neutralization assays ("dump-in") without affecting entry by the normal high-affinity binding of wt gp120 to CD4. The gp120 TriMut possesses an unmodified CD4bs, while the paired probe incorporates two additional mutations, D368R/M474A, which prevent binding by most CD4bs-directed antibodies (FIG. 17). These two isogenic proteins can be used to determine neutralization specificity directed toward the CD4bs by differential adsorption or depletion. The differential depletion assay was first validated using known bNAbs that can neutralize 16055, detecting a decrease in VRC13 and HJ16 neutralization upon the addition of the TriMut gp120, but not the isogenic 368R/474A variant (FIG. 18*a*). The differential between the two proteins confirmed their capacity to map neutralization specific for the CD4bs (FIG. 18*b*).

Applicants then analyzed total polyclonal IgG isolated from selected hyperimmune rabbit anti-sera using this assay. Following IgG isolation, it was established that the concentration for each sample that could neutralize 80% of virus entry. Using this concentration of IgG, adsorption assay was then performed. It was determined that increasing amounts of the TriMut gp120 could deplete neutralizing activity of the wt 16055 virus, while the 368R/474A TriMut gp120 depleted only a portion of this activity (FIG. 18). This differential indicated that some of the 16055-neutralizing activity was CD4bs-directed (FIG. 18). this differential neutralization was quantitated at the CD4bs as a difference between TM and TM368R/474A area under the curve (AUC) values, normalized by the control AUC value. CD4bs-directed activity was observed in rabbit #1-3, the highest responder from Group 1, after third and fourth immunizations (termed "post 3 and 4"; FIG. 18). Rabbit #1-6 from Group 1 also showed partial CD4bs-directed neutralization activity. Rabbit #2-1 from Group 2 displayed a small fraction of neutralization directed to the CD4bs after the fourth immunization (Table 1, FIG. 18*d*), while more than 50% of the total IgG neutralization in rabbit #2-4 was directed against the CD4bs at this time point (Table 1, FIG. 18*d*). In Group 3, however, two rabbits (#3-2 and #3-4) demonstrated partial CD4bs-directed neutralization following just the third immunization (post 3, FIG. 18*e*). Rabbit #3-4 displayed partial CD4bs-directed neutralization after fourth immunization, as well, whereas for rabbit #3-2 the CD4bs-directed differential was no longer detectable at this time point. In addition, following the fourth inoculation, three other rabbits from Group 3 displayed partial CD4bs-directed neutralizing activity (FIG. 18*e*).

In sum, Applicants observed CD4bs-directed activity in several animals from all three groups. Compared to animals from Group 1, animals from Group 3 showed more consistent CD4bs-directed neutralizing antibody responses following four immunizations.

Example 8: Purified Serum IgG Isolation and Analysis Reveals Cross-Neutralization With indications that there was some CD4bs-directed neutralizing activity proximal to the CD4bs (and the proximal N-glycan at residue), neutralization assays were performed using the purified polyclonal IgG purified from serum of the rabbits that demonstrated weak serum neutralization against a selected panel of heterologous viruses. neutralization was analyzed with a small set of pseudoviruses with PNGS N276 deleted, namely BG505Δ276, JRFLΔ276, IAVIC22Δ276, along with their respective wt pseudoviruses. IgG neutralization was also analyzed with several pseudoviruses naturally lacking the N276 PNGS, Q259 and 62357, another Indian clade C pseudovirus from the same cohort as 16055, 1428, and the pseudoviruses 1086 and CE1176. SIV pseudovirus was used as a negative control for neutralizing specificity as this virus is not recognized or neutralized by HIV Env-specific antibodies. For these experiments, the purified IgG was titrated starting at a relatively high initial concentration of 2 mg/ml because even in a hyper-immunized animal only a minor fraction of circulating IgG is antigen-specific (~5-10%), and, of that, only a subset is neutralizing. The negative control used was purified IgG isolated from a rabbit that was immunized similarly with blank liposomes in adjuvant, at the same concentrations, to rule out non-specific IgG effects in the cross-neutralization assay.

Applicants were able to detect weak cross-neutralization activity exclusively in IgG derived from animals in Group 2 or 3 that had been immunized with different variants of the N-glycan-deleted trimers (FIG. 9). Most cross-neutralization was detected in the IgG isolated from the animals in Group 3 with three animals displaying detectable activity. Rabbit #3-3 displayed neutralization of the BG505Δ276 pseudovirus (FIGS. 9*a* and 9*b*), while rabbits #3-5 and #3-6 were able to neutralize both the BG505Δ276 and IAVIC22Δ276 pseudoviruses. In addition, rabbit #3-5 showed neutralization even against both the wt, fully glycosylated BG505 and 1086 pseudoviruses (FIGS. 9*a* and 9*b*). Following three immunizations, rabbit #3-6 neutralized BG505Δ276 and this activity increased following four inoculations. Two animals from Group 2 displayed some detectable cross-neutralizing activity. Rabbit #2-5 was able to neutralize the IAVIC22Δ276 and 1086 pseudoviruses following three immunizations and this activity increased against the IAVIC22Δ276 pseudovirus following the fourth immunization (FIGS. 9*a* and 9*b*). Rabbit #2-4 very weakly neutralized the 62357 (NIH15) pseudovirus after the fourth immunization (FIGS. 9*a* and 9*b*), which naturally lacks the N-glycan at residue 276. None of the IgGs derived from the Env-trimer-immunized cross-neutralized the control SIV pseudovirus, confirming HIV cross-neutralization specificity.

To further confirm specificity of the cross-neutralization, a depletion assay was performed with the 16055 gp120 TriMut probe for the animals displaying the highest IgG IC50 values, i.e. rabbit #2-5 for the IAVIC22Δ276 pseudovirus and rabbit #3-5 for the BG505Δ276 pseudovirus (FIG. 9*c*). It was demonstrated that the cross-neutralizing activity was adsorbed substantially by pre-incubation of IgG with the 16055 gp120 TriMut protein, indicating that, in those animals, this activity was HIV Env-specific.

Overall, cross-neutralization was consistent with the CD4bs mapping for the animals from Group 2 and Group 3, thus, most animals with CD4bs-directed IgG neutralizing activity showed some level of cross-neutralization, except one rabbit from Group 3 (#3-5). This animal displayed generally low autologous neutralization and therefore the response could not be analyzed in the mapping experiment. Together, these data suggest that the sequential ΔGly4 to ΔGly2 to ΔGly1 immunization did better than the other two regimens at directing the neutralizing antibody response to the CD4bs.

Example 9: Immunogen Design and Characterization for Prime Boosting

Applicants focused at priming and driving B cells directed toward cross-conserved targets, especially those that expose protein surfaces required for viral entry and replication. The potentially most immunogenic regions are partially exposed protein surfaces proximal to that gp120:gp41 interface and the CD4bs. Accordingly, heterologous prime:boosting were used to preferentially drive B cells directed at cross-conserved determinants, including the CD4bs, while not boosting autologous strain-restricted B cells. Applicants targeted the CD4bs by a dual strategy of N-glycan deletion priming to expose the underlying protein surface, and then to selectively drive those that can penetrate the intact N-glycan shield by glycan restoration coupled with the heterologous Env trimer boosting to fold in cross-recognition at both the CD4bs and other conserved sites.

To generate the appropriate antigens to perform this line of investigation, well-ordered and homogeneous cleavage-independent NFL trimers were designed and characterized from diverse HIV Envs (16055, BG505, JR-FL and 1428). Selected trimers contained N-glycan deletions proximal to the CD4bs and step-wise restoration of these PNGS (16055, BG. Applicants selected Envs with cross-conserved sites at the V2 apex, the N332 supersite, the CD4bs and the gp120:gp41 interface region (FIG. 26) and generated "NFL TD+CC" trimers, as previously described (REF). For the targeted N-glycan deletion, both the non-VRC01 class and VRC01-class bNAbs to the CD4bs as described herewith were used as guides, genetically deleting potential N-glycan sites (PNGS) at residues N276, N301, N360, N463.

Figure 26:
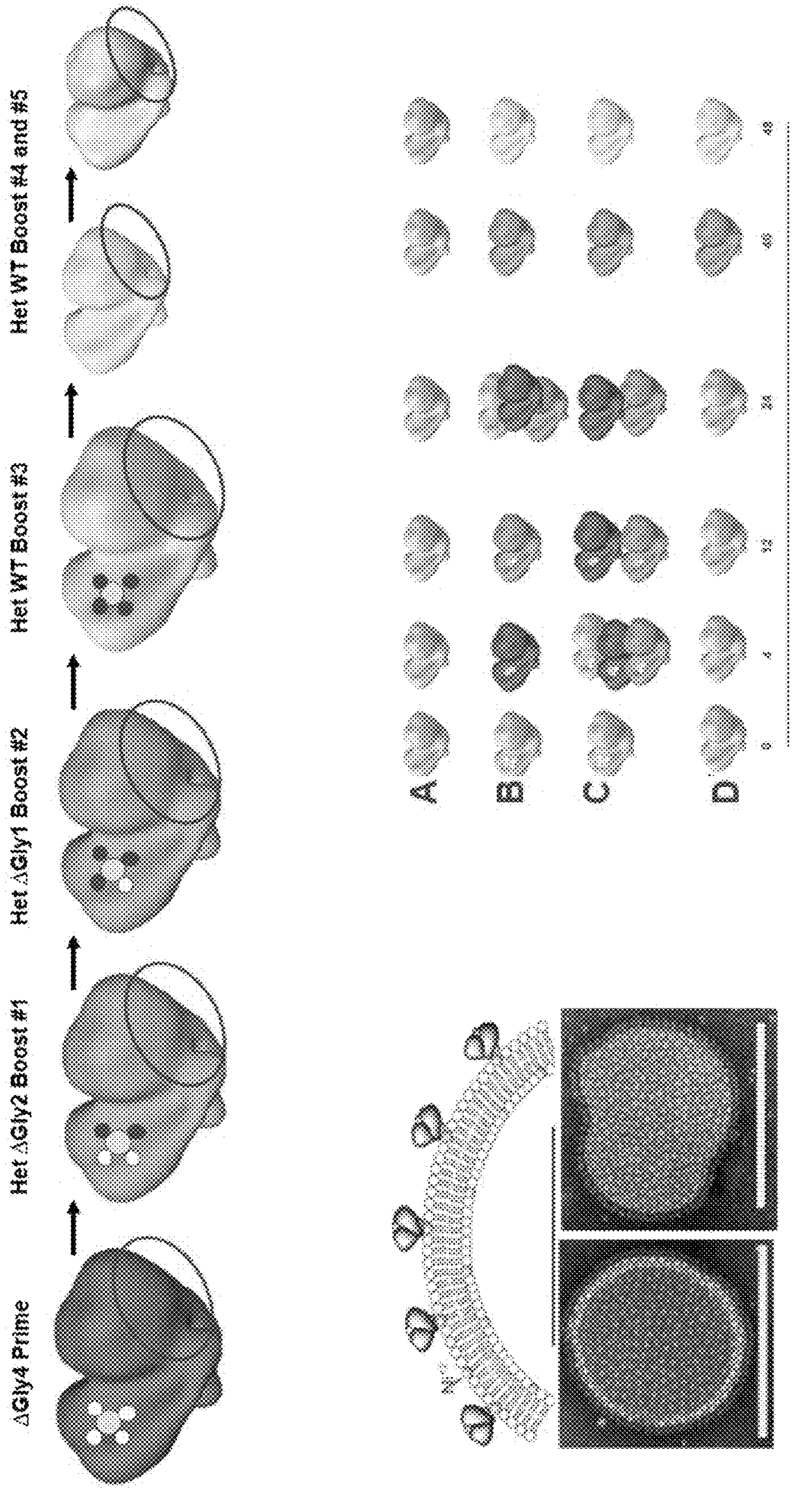
FIG. 26. NFL-liposome N-glycan deletion priming, heterologous boosting with restoration. Top: deleted N-glycans (white) ringing conserved CD4 binding site (yellow). Bottom: His-tagged trimers were coupled to nickel-bearing liposomes. Note that 332N, apex, interface and other cross-conserved sites can be boost-driven.

Following expression from transient transfection of 293F cells and purification, Applicants performed analysis of trimers stability, antigenicity and glycosylation. The PNGS genetic modifications were confirmed by mass spectrometry, site-specific N-glycan analysis (FIG. 26). Minimal but local effects on processing were detected at N-glycan sites proximal to those that were genetically deleted in their respective motifs. Detailed analysis of glycosylation was performed to detect changes in glycan-deleted trimers glycosylation in comparison with their wt originals. These data showed that removal of one glycan site generally results in slightly increased processing at nearby sites, which is exaggerated upon removal of two or more glycans. This is consistent with the hypothesis that glycan density can affect N-glycan processing and is similar to what is observed on glycan-depleted SOSIPs (Behrens et al., Integrity of Glycosylation Processing of a Glycan-Depleted Trimeric HIV-1 Immunogen Targeting Key B-Cell Lineages. J Proteome Res. 2018 Mar. 2; 17(3):987-999)

The BG505 NFL TD+ trimer seems to be the most sensitive to N-glycan deletion in that it displays the biggest percentage point differences, at the most sites. This is echoed in the UPLC analysis; it is the only strain to show a shift from predominantly man9 to man8 in the glycan mutants.

In parallel, the data indicated that the Tm of glycan-deleted versions of BG505 and JRFL trimers did not change significantly, similar to previous analysis of 16055 NFL trimers with and without targeted N-glycan deletions (Dubrovskaya et al, 2017. Targeted N-glycan deletion at the receptor-binding site retains HIV Env NFL trimer integrity and accelerates the elicited antibody response. PLoS Pathogens 13 (9): e1006614. Doi: 10.1371/journal.ppat.1006614). WT versions of the trimers used in the immunogenicity experiment bind VH-restricted bnAbs (VRC01, 1B2530) as well as bnAbs that are not VH-restricted and use their HCDR3s to contact the CD4bs (VRC13, VRC16). The trimers were confirmed to be well-folded by low recognition with the non-neutralizing CD4bs-directed mAb, GE136 (FIG. 26). The His-tagged trimers were coupled to nickel-bearing liposomes as previously described. Prior to each immunization, the quality of each trimer-liposome preparation was confirmed by EM negative stain analysis.

Example 10: Heterologous Prime: Boosting and N-Glycan Modification Elicits Cross-Neutralization of Clinical HIV-1 Isolates The overall immunization experiment is schematically shown in FIG. 27. Animals in Group A were immunized sequentially with the fully glycosylated, stabilized (TD+CC) 16055-strain-only NFL-His trimers arrayed at high-density on the nickel-containing liposomes (0, 4, 12, 24 and 40 weeks). Animals in Group B were inoculated with a priming dose of the delta glycan 4 (ΔN276.301.360.463) 16055 trimer:liposomes, followed by heterologous boosting and restoration of the N-glycans at N301.360.463 in first the JRFL, then the BG505, context (immunizations 2 and 3, respectively). Following the third inoculation, and a long rest interval, boosting was performed wt trimers derived from these three Env. Following another long interval to allow serum IgG titers to decrease, the stabilized 1428 NFL TD CC+ were selected based upon the highest recognition by bNAbs directed to the CD4bs (FIG. 27), while retaining recognition by most other bNAbs, to immunize these animals for the 5th time. For the animals in Group C, Applicants followed the 16055 del gly4 prime, with a boost of delgly2 trimers (16055, JRFL and BG505 lacking N276.463, arrayed as a cocktail on each liposome), followed by a del gly1 boost of JRFL and BG505 trimers, omitting 16055 trimers to potentially boost cross-conserved B cell responses. These animals were next boosted with wt JRFL and BG505 trimers (immunization #4), followed by fully glycosylated 1428 NFL trimer:liposomes for the 5th inoculation. Group D consisted of the autologous 16055 fully glycosylated trimers for the first 4 immunizations, followed by the 1428 NFL trimer:liposome:adjuvant for the 5th inoculation. All trimer:liposomes were formulated with ISCOMATRIX or the lab-grade similar ISCOMIT adjuvant.

Following 5 trimer:liposome inoculations, trimer binding was assessed by the antiserum from all animals and, as expected, boosting of trimer-specific IgG following each inoculation was detected (FIG. 27). Applicants next assessed serum neutralization against autologous N-glycan deleted viruses in selected animals using a rationale of neutralization capacity, progressing from autologous to heterologous viruses. Since all animals in Groups A-D, were initially immunized with 16055 NFLs of two types, Applicants first assessed neutralization of autologous 16055 delgly4, 3 and 2 and 1 pseudo-viruses to assess functional antibody responses proximal to the CD4bs site. As seen, several animals could neutralize the N-glycan deleted viruses after 2-3 immunizations. To determine if any of these responses could cross recognize another strain not included as an immunogen, delgly1 heterologous viruses were assessed. Only a few sera could cross-neutralize the N-glycan-deleted viruses. For the next level of cross-recognition, Applicants assessed neutralization of the tier 2, but CD4bs-sensitive. pt45G5 virus, which naturally lacks two N-glycans proximal to the CD4bs.

Figure 28C:
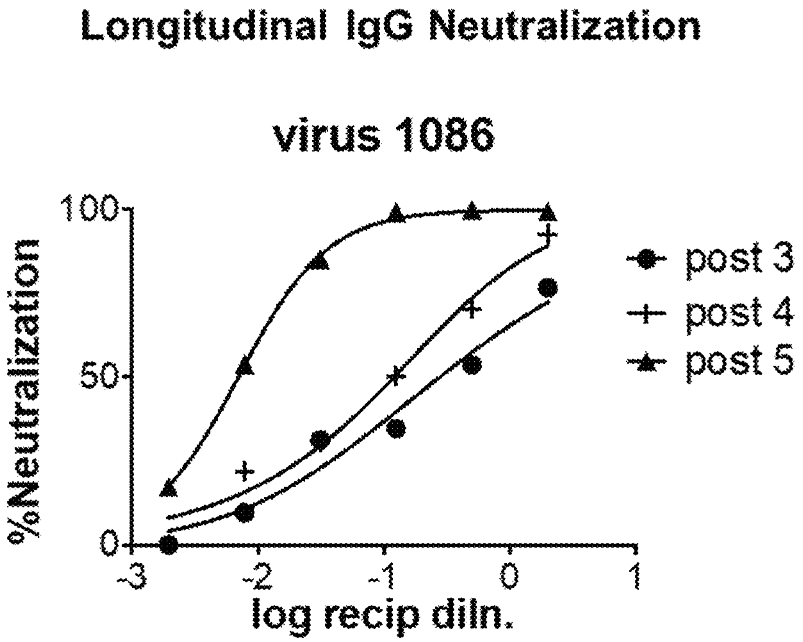

Next, Applicants assessed tier 2 virus neutralization against two heterologous isolates where cross-neutralization was detected in the serum from animal C3 and modest activity in animal B6. Cross-neutralization was confirmed with purified IgG from selected animal serum following the 5th immunization against a panel of Global isolates, mostly tier 2 in phenotype. Considerable cross-neutralization was detected in the serum derived from two animals, B6 and C3, with higher potency in the C3 IgG followed by IgG from animal B6. IgG derived from other animals could cross-neutralized some but not most tier 2 isolates from this panel and there was no neutralization of SIV, used to confirm HIV-1 Env specificity. Longitudinal analysis using C3 IgG demonstrated clear boosting of 1086 virus neutralization following the 3rd, 4th and 5th trimer-liposome immunization (FIG. 28).

Having detected cross-neutralization in selected animals, Applicants selected a 2nd heterologous well-ordered trimer derived from the ZM197 strain to potentially boost these responses. This trimer was selected as it was well-recognized by several CD4bs-directed bNAbs, where the activity for the most potent rabbit sera, C3, was previously mapped. This trimer is also well recognized by other bNAbs at the interface of 332N, so could potentially boost these responses as well. The 6th immunization was performed 6 weeks following the 5th and two weeks later the serum was analyzed for neutralizing activity. Following the 6th immunization, cross-neutralization was detected by serum of at least 6 of the 24 animals, with 5 of these from heterologous prime:boosted animals (FIG. 28).

Example 11: Neutralizing Specificity Confirmed by Solid-Phase Env Trimer Depletion To confirm the specificity, Applicants performed adsorptions using selected NFL trimers captured on *Galanthus* lectin sepharose beads as the solid phase. Applicants used the bNAb VRC01 as a positive neutralization control to confirm that the trimers could deplete neutralization. As expected the neutralizing activity of this mAb to to the viruses SC422 and TRO.11 was depleted by the NFL trimer-lectin beads, but not by the lectin beads alone. Similarly, the C3 post 5 (C3.5), C3.6, A1.6, B4.6, D1.5 and D1.6 sera were fully depleted by this process, confirming the Env-directed specificity of these sera. Similar results were obtained using purified IgG derived from the rabbit antisera.

Example 12: Mapping of the Most Potent Serum Neutralization

Figure 29:
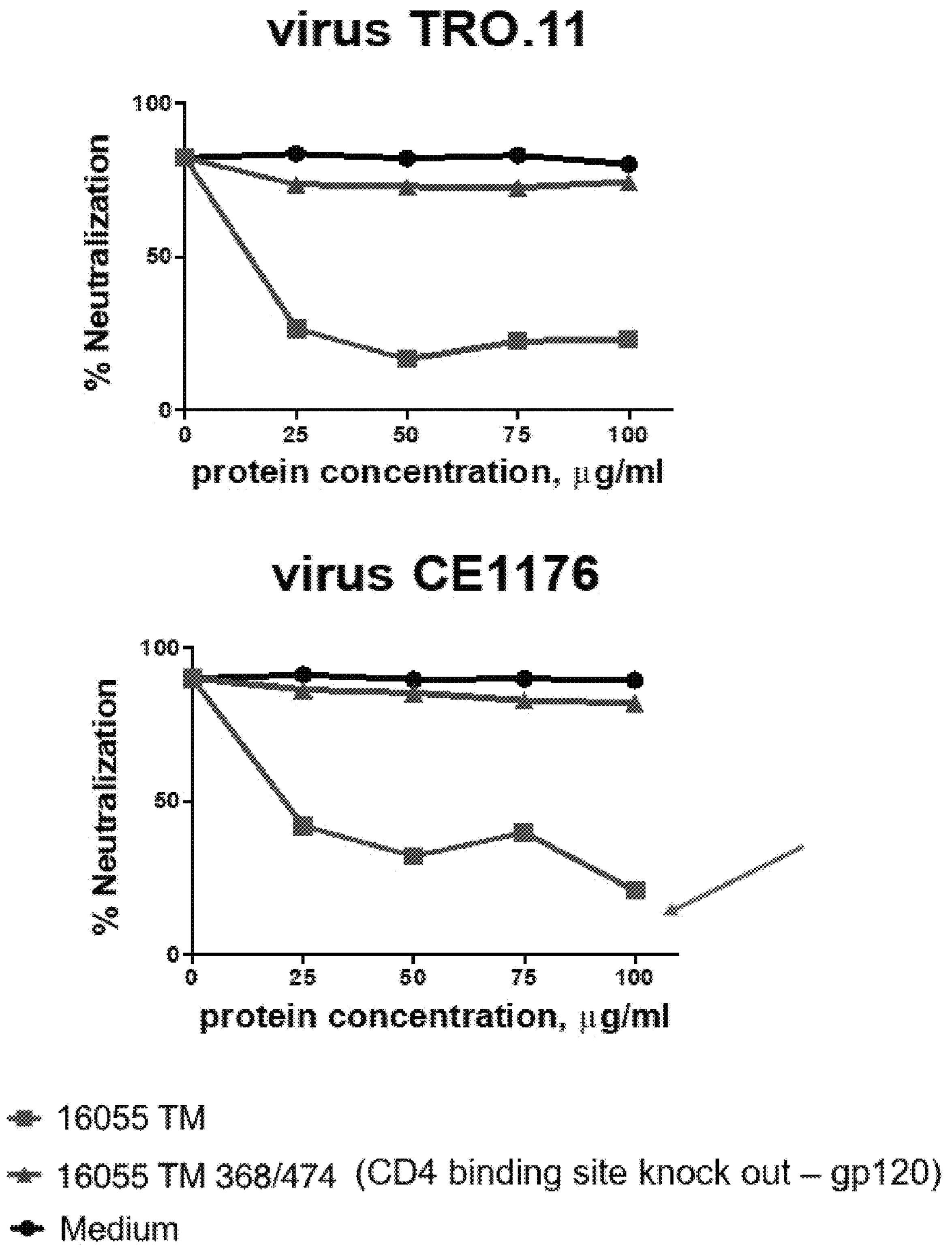
FIG. 29. Differential adsorption showing purified rabbit IgG cross-neutralization maps predominantly to the CD4bs. C3 IgG neutralizing activity was greatly reduced by preincubation with the Trimut but not by the CD4bs knockout D368R/M474A mutant Trimut.

Applicants performed differential depletions at the CD4bs on the most potent IgG from rabbit C3 using the Trimut proteins that do not bind CD4 due to bridging sheet mutations. These modifications do not affect recognition by all known and tested CD4bs-directed mAbs This isogenic pair lacks or possess CD4bs Ab knockout mutations in the CD4bs (D368R and M474A) as previously described. As seen in FIG. 29, C3 IgG neutralizing activity was greatly reduced by preincubation with the Trimut but not by the CD4bs KO mutant Trimut. Applicants were able to demonstrate CD4bs-directed heterologous tier 2 neutralization for rabbit C3 against the TRO.11, CE1176, IAVIC22, X2278 pseudo-viruses. Note that not all activity was inhibited by the gp120 Trimut "dump in", indicating that there is likely other neutralizing capacity that is not directed to epitopes on gp120.

In addition, to potentially enhance neutralization potency, serum IgG purification was performed using Env-specific Sepharose gp120 column. Flow-through that did not bind 16055 gp120 covalently linked to the solid phase was collected Next, IgG bound to the gp120 column sequentially was eluted using buffer as first pH 2.7 and then pH 1.7. Applicants assessed the neutralization capacity of the flow-through and the eluates in the Tzm-BL assay against autologous tier 2 16055 virus and heterologous tier 2 BJOX02000 and CH119 viruses. Lower neutralization potency for autologous 16055 virus was detected in flow-through for sample B6.5 B6.6, while both pH 2.7 and pH 1.7 eluates showed comparable or higher IC50s. For the tier 2 heterologous viruses, BJOX02000 and CH119, decreases in neutralization potency was not detected in the gp120 the flow-through fractions, suggesting that heterologous neutralization maps to gp41.

Example 13: Single B Cell Sorting and RT-PCR of Matched H/Ls Isolates Two Cross-Neutralizing mAb Because the C3 rabbit demonstrated the most potent and broad neutralization activity, Applicants performed Env-specific B cell sorting and cloning from different immune compartments of this rabbit to confirm cross-neutralization by isolating Abs derived from memory B cells of this animal. Initially, IgG+ rabbit splenocyte-derived B cells were sorted using Avi-tagged Trimut probes without and with the CD4bs KO mutations, but differentially recognized cells were not detected. Next, +IgG+NFLtrimer-gp120 B cells were sorted from the LN and IG+NFLtrimer++ B cells from the spleen by flow cytometry. Following single B cell lysis and RT-PCR, Applicants generated matched heavy and light chain expression plasmids. Following transient expression of the paired heavy and light chains to generate secreted mAbs, Applicants performed binding and neutralization analysis. From a mini-panel of viruses, Applicants detected a one cross-neutralizing mAb, 1C2, that was isolated from the LN and a 2nd, more potent mAb, E70, isolated from the spleen, confirming the neutralization activity against heterologous clinical isolates detected in the rabbit antiserum and purified IgG.

Example 14: Analysis of 1C2 Reveals a bNAb that Maps to the Gp41:Gp120 Interface Applicants assessed breadth of 1C2 neutralization on a 40 virus panel and determined that this antibody neutralized greater than 80% of viruses tested, although with modest potency, not always achieving 80% neutralization (IC80). To accomplish more complete neutralization, Applicants repeated the assay with higher starting mAb concentration of 200 ug/ml and could achieve IC80 values for most viruses (FIG. 30 B), In fact, the higher Ab concentration increased breadth of neutralization for an additional few viruses.

Figure 30A:
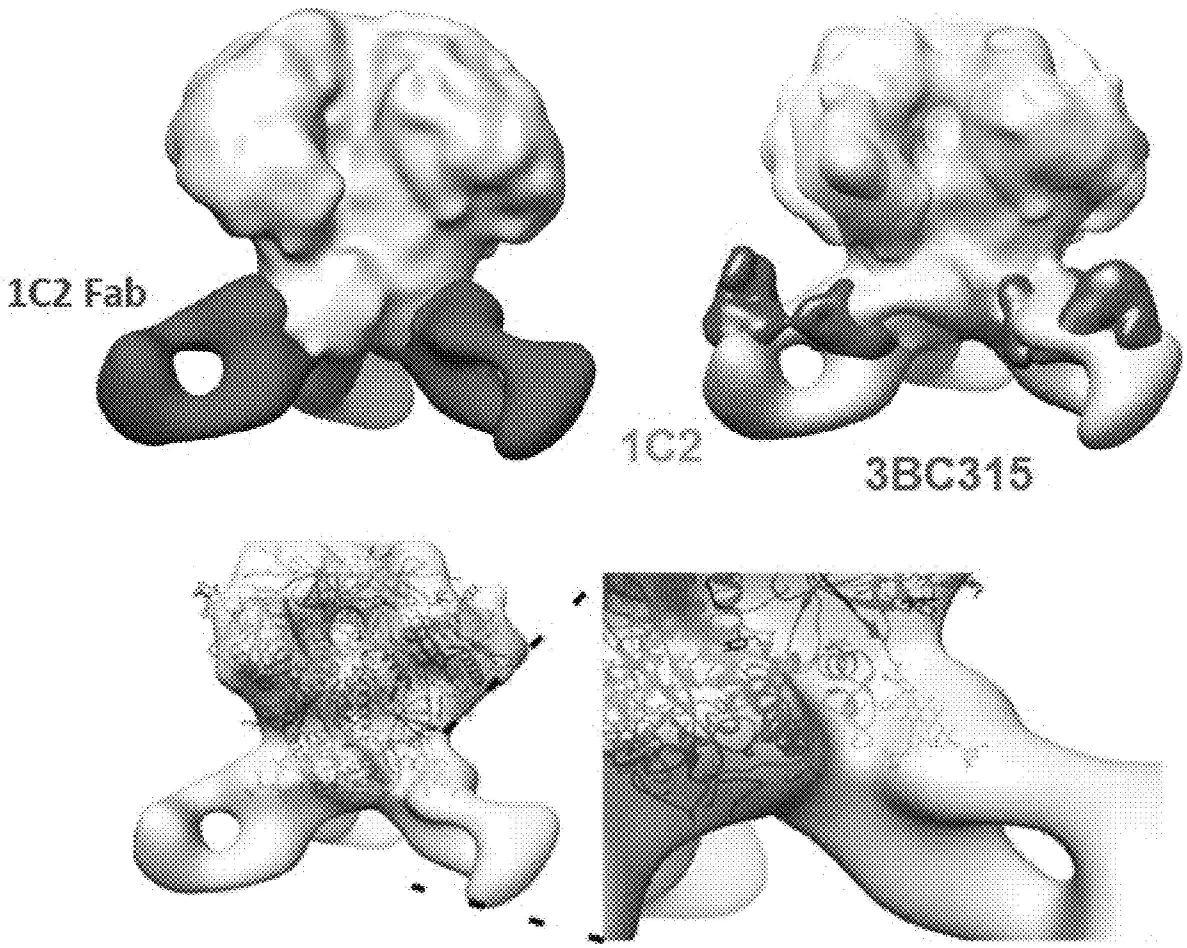

Applicants sought to determine the recognition specificity of this vaccine-elicited bNAb. Binding analysis of gp140 and gp120 revealed that the antibody did not bind to gp120, suggesting a trimer-specific or gp41-directed specificity. Applicants performed ELISA analysis to overlapplng gp41 peptides, one in HR2 and the other located in the fusion peptide. In parallel, Applicants attempted to form complexes to perform low resolution negative stain EM of the 1C2 Fab in complex with the trimer, but found that 1C2, appeared to dissociate that soluble NFL trimer, reminiscent of other gp41-directed human bNAbs. This was confirmed by BN PAGE. Fortuitously, Applicants had discovered a new inter-protomer cysteine disulfide linkage, in the NFL context, that was resistant to 1C2-mediated dissociation by BN PAGE. Use of this NFL variant facilitated trimer stability following 1C2 association, permitting nsEM 3D reconstructions and density of 1C2:16055 NFL CC2 complexes (FIG. 30 A). Comparison of the Fab density with other gp41-directed human bNAbs revealed similarities with some binding sites and angles of approach, especially with the interface-directed bNAb, 3BC315. (from HIVRAD) A low resolution reconstruction of the NFL trimer bound to 1C2 superimposed with known human bnAbs with similar epitopes (35O22, CAP248, VRC34, 3BC315), a rabbit-elicited nAb (11A), and a NHP-elicited non-nAb (1E6).

Figure 31:
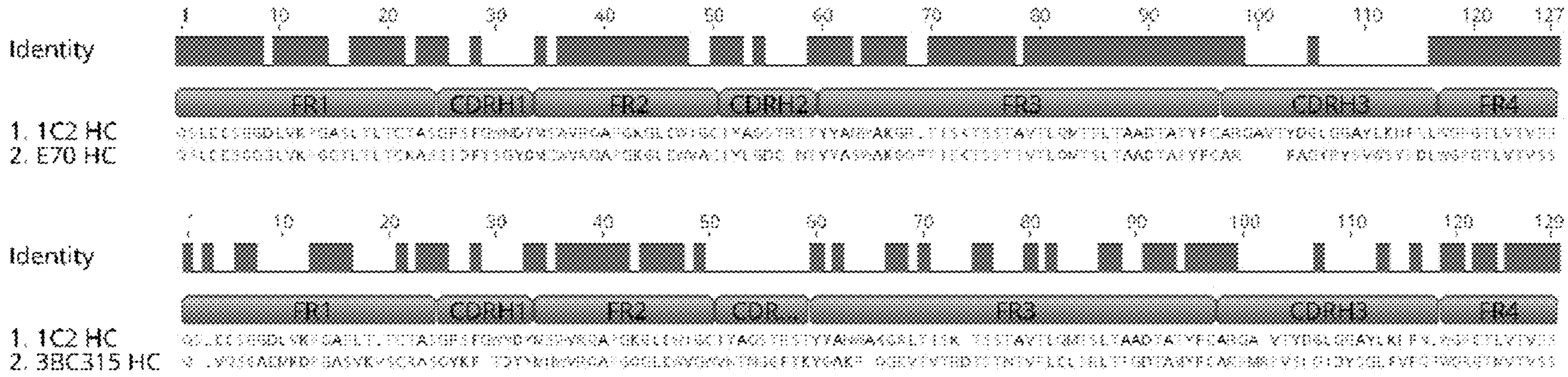
FIG. 31. Sequence analysis of 1C2 compared to the other rabbit mAbs: E70 and 3BC315.
Figure 32B:
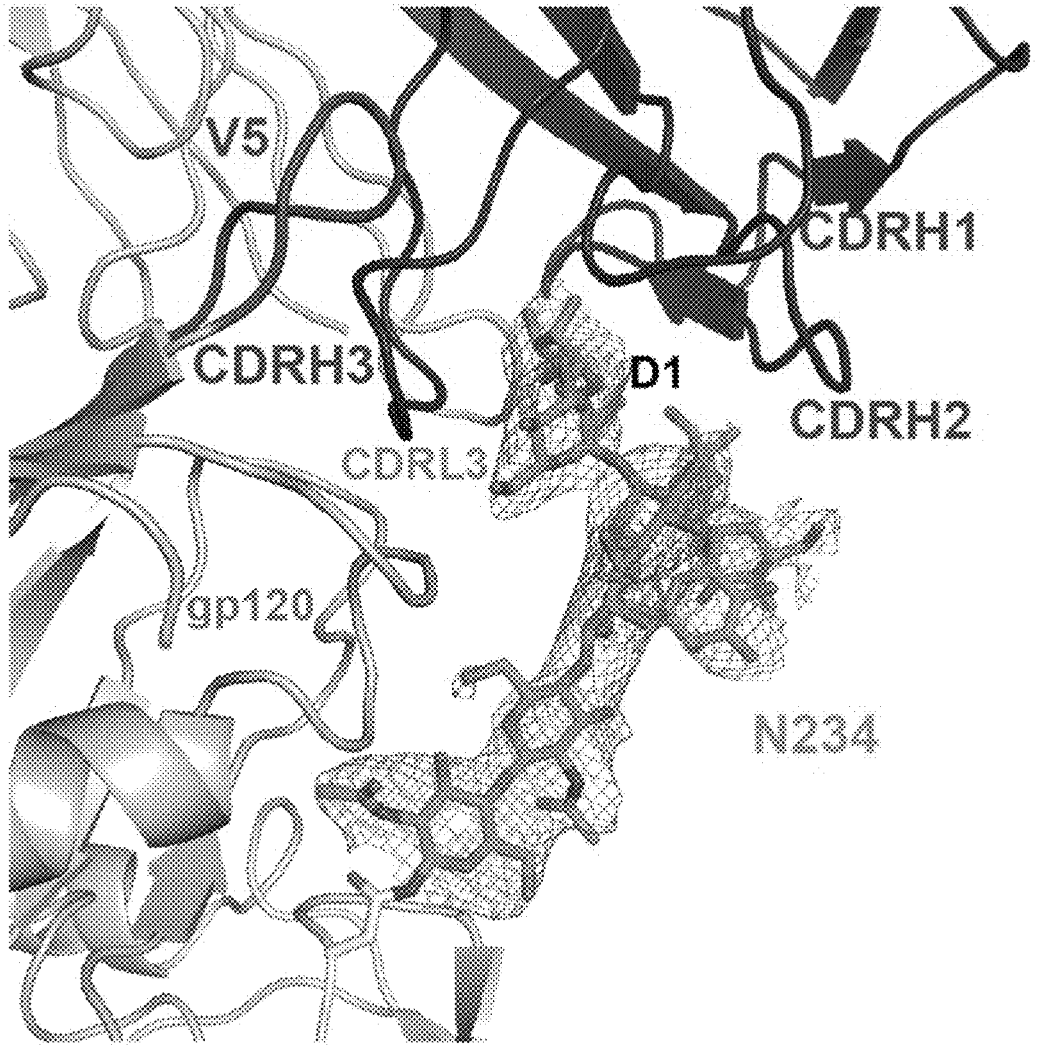
Figure 32C:
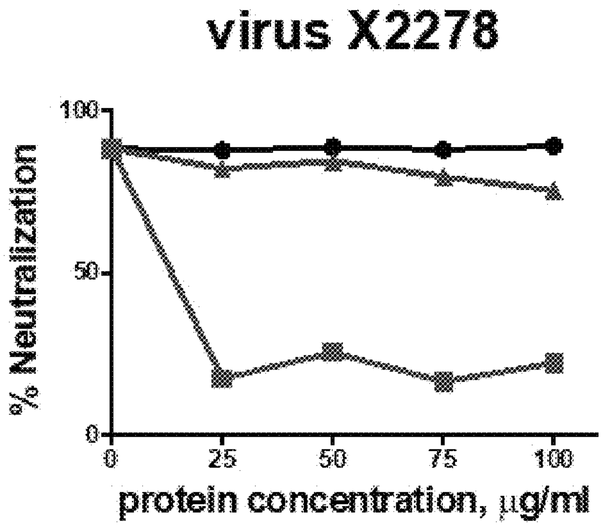
Figure 32D:
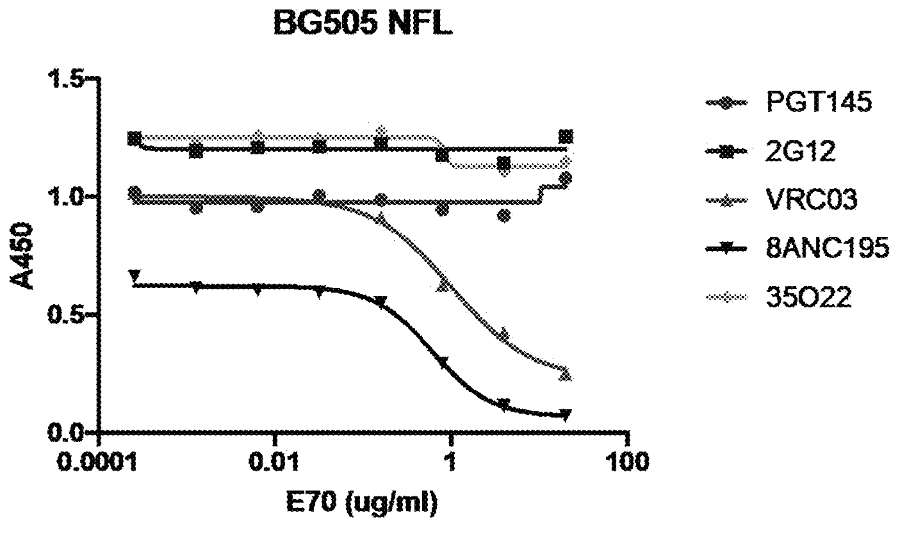
Figure 32E:
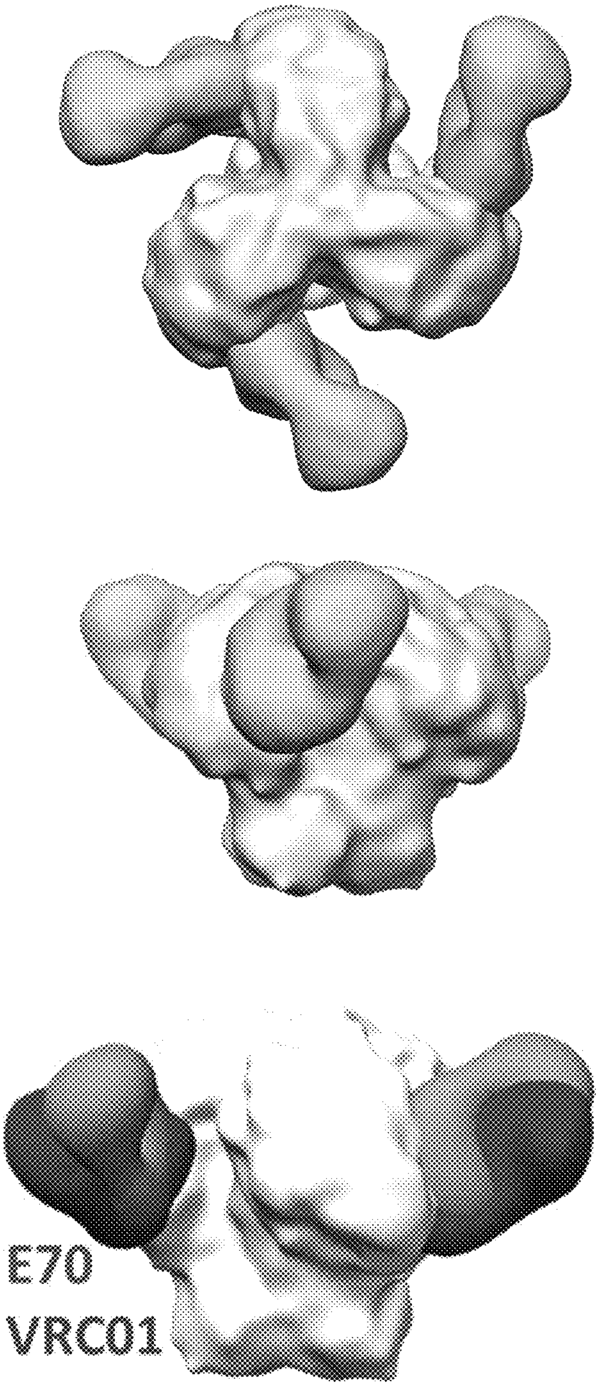
Figure 33A:
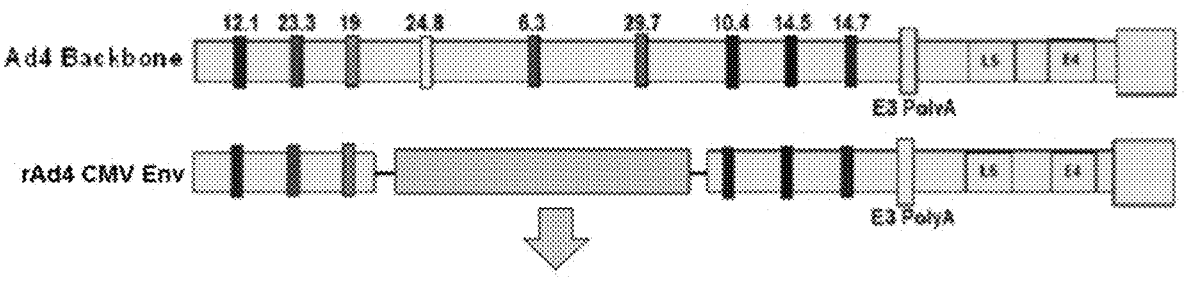
FIG. 33A-33C. Env150 NFL-TD "cell surface tethered" trimers. A: HIV-1 1086.0 Env designs. B: schematic drawing and assessment of cell-surface tethered 1086 NFL-MPER-linker-TM Trimer.
Figure 33B:
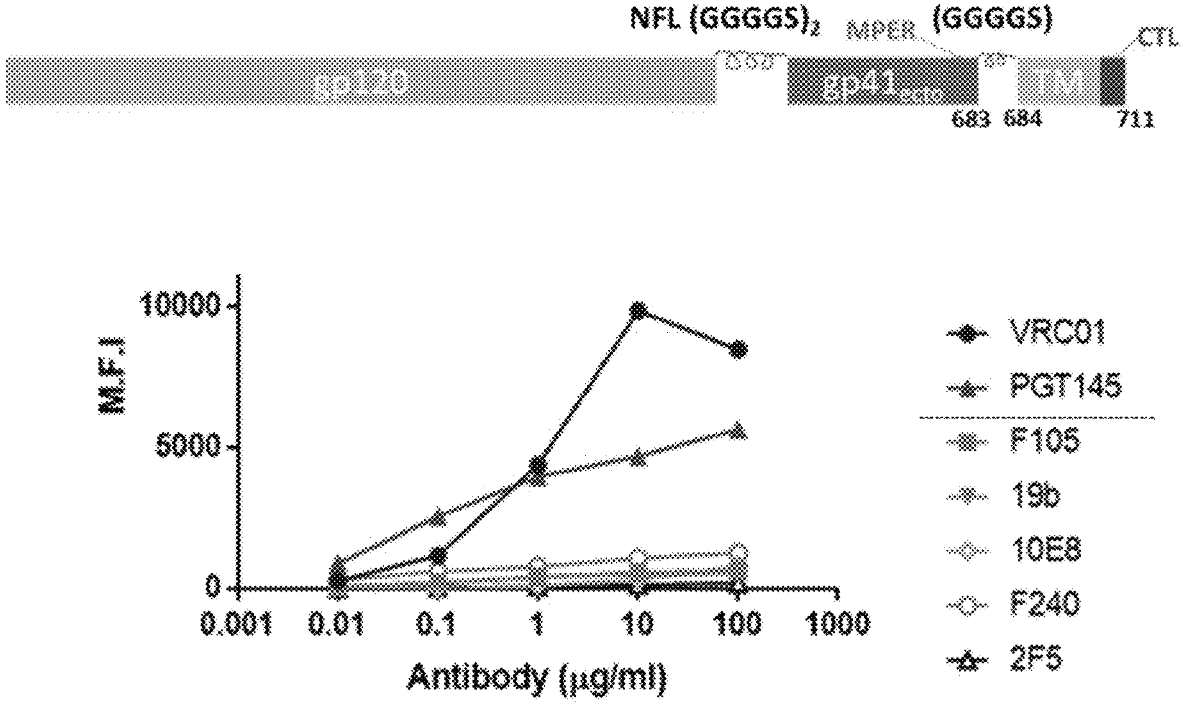
Figure 33C:
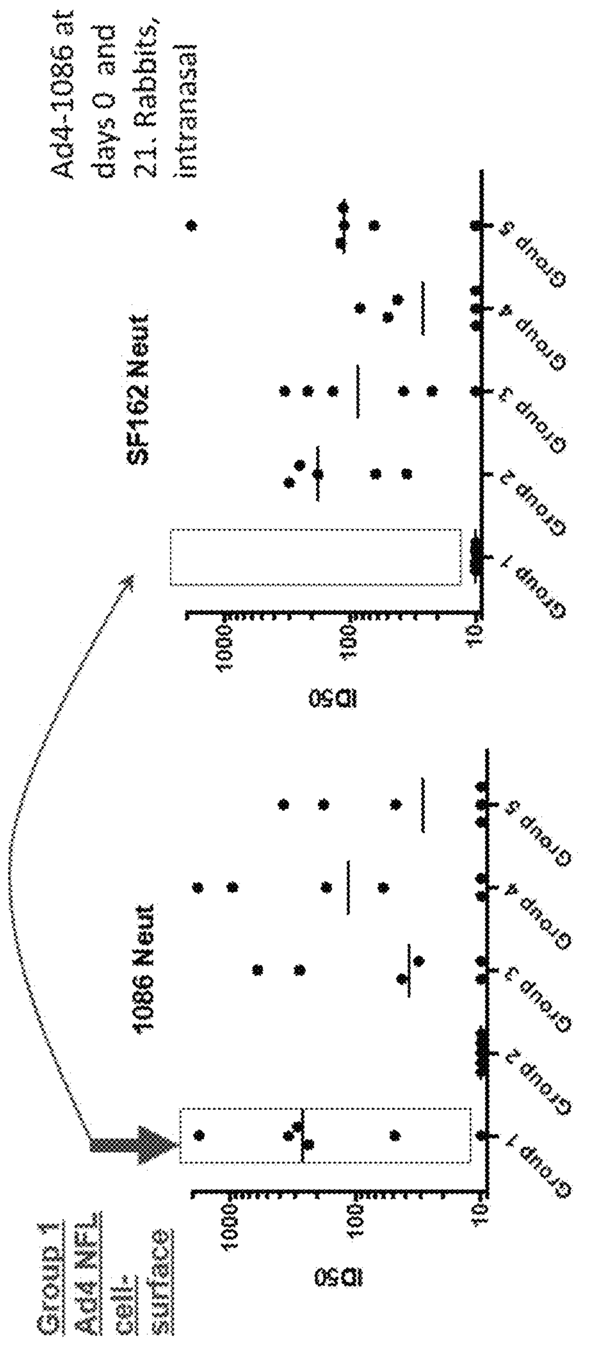

Following the EM analysis, Applicants examined the effect of deleting the N-glycans at N88 and N611, proximal to the gp120:41 interface and found that genetic removal enhanced 1C2 neutralizing potency on selected viruses. Binding to cell-surface Env by flow cytometry confirmed that 1C2 recognized the prefusion Env ectodomain and cell-surface Env shedding experiments following incubation with 1C2 again reflected similarity with the human 3BC315 bNAb. Due to this striking similarity, Applicants analyzed the sequence of 1C2 compared to the other rabbit mAb and to 3BC315 to ensure that this was indeed a rabbit IgG, which was confirmed by homology comparisons (FIG. 31). The rabbit antibodies shared about ~69% sequence homology, with most of the variability located in the CDRs and were 49% homologous to 3BC315.

In sum, the vaccine-elicited rabbit bNAb 1C2 is directed to the gp41:gp120 interface and displays properties similar to the human bNAb, 3BC315, derived by chronic, natural human infection by HIV-1.

Example 15: Analysis of the mAb, E70, Defines a New Cross-Neutralizing Determinant Proximal to the Conserved CD4bs The E70 cross-neutralizing mAb was analyzed for breadth on the same 40 virus panel. This more potent vaccine-elicited cross-mAb neutralized ~20% of the clinical isolates in this panel. To identify the binding specificity of E70, Applicants performed a cross-competition with bNAbs to discrete Env epitopes and found that the E70 cross-competed CD4bs-directed bNAbs, suggesting that E70 was directed to this region. Focusing on the CD4bs, Applicants analyzed viruses deleted of the N-glycan at residue N234 and found viruses deleted of conserved N234 glycan were completely resistant to neutralization by E70. In addition, deletion of the N-glycan at N276 enabled E70 to neutralize selected viruses, increasing both neutralization breadth and potency. Reexamination of neutralization breadth with viruses lacking N234, increases the breadth to 26% of viruses naturally possessing N234. These data indicate that lack of N234 alone is not the only restriction to greater neutralization breadth, and that the N276 glycan, either directly or indirectly can restrict E70 breadth (FIG. 32 A). Next, nsEM analysis revealed that the E70 epitope overlapped with VRC01 and other CD4bs nAbs of varying breadth isolated from infection or following Env trimer vaccination of small animals.

To resolve the E70 epitope at higher resolution, Applicants performed cryoEM of E70 Fab:trimer complexes. This analysis further defined the E70 epitope, revealing that it significantly overlaps other CD4bs epitopes (FIG. 32 B), providing insight for further design and boosting strategies. Interestingly, in the BG505 context, E70 is biased toward and binds a conserved glycan at N234, completely avoiding the N276 glycan, which has been shown to be a major impediment to accessing the CD4bs.

In sum, the cross-neutralizing, vaccine-elicited mAb E70 recognizes a new epitope that is composed of ~50% conserved N-glycan and 50% adjacent polypetide, proximal to the CD4bs. This Ab represents a new CD4bs-related prototype of recognition that provides utility for future vaccine designs attempting to target the N-glycan shield.

Example 16: Structure-Guided Redesign Improves NFL HIV Env Trimer Integrity

Figures 34A, 34B, 34C:
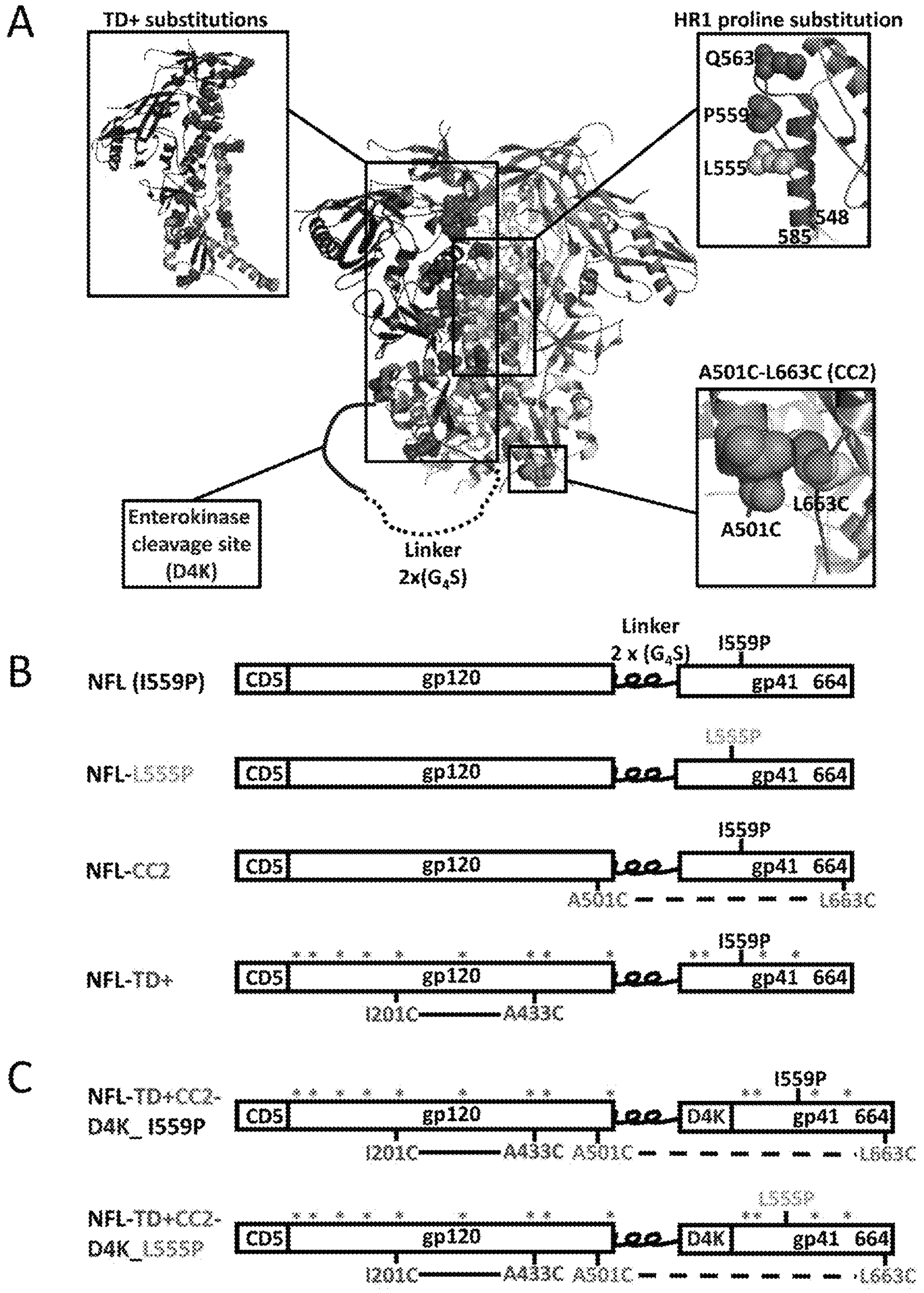
FIG. 34A-34C. Design and schematic representation of HIV-1 Env gp140 NFL Trimers. (A) Schematic depiction of the approaches used to redesign the NFL trimers using the available BG505 SOSIP.664 structure (PDB: 5CEZ). The trimer is shown in the ribbon representation with an inset of a closer view to indicate different approaches of NFL trimer redesign. The gp120 and gp41 in the 1st gp140 protomer are shown in blue and green, in the 2nd protomer in light blue and yellow, and in the 3rd protomer, in gray. Previously reported trimer-derived residues from BG505 (TD+) back-reverted in 16055 NFL are shown in the upper-left close-up view of the 1st protomer in red spheres. Proline substitutions screened in HR1 region (aa 548-585) are shown in the hot pink ribbon representation in the 2nd protomer in a close-up view (upper right). Favorable proline substitutions are shown in spheres, I559P in magenta, L555P in light pink and Q563P in hot pink. The cysteine pair (A501C-L663C) forming an inter-protomer disulfide bond between the 1st and 2nd protomers is shown in green and yellow spheres in the lower-right, close-up view. The engineered enterokinase (EK) cleavage site is shown as a in solid blue line, upstream of the FP for controlled post-expression cleavage.
Figures 39A, 39B, 39C, 39D, 39E, 39F:
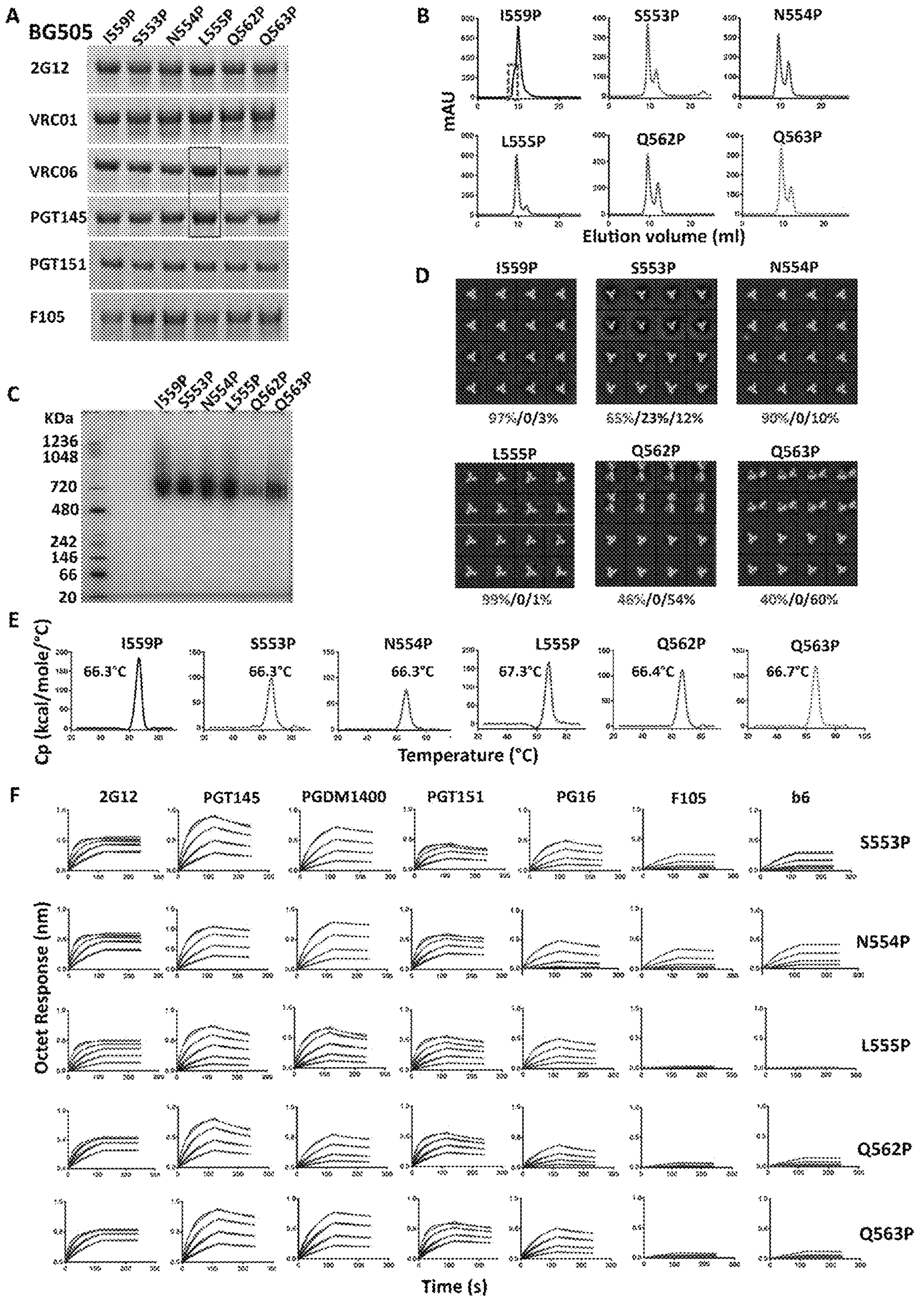
FIG. 39A-39F. Proline substitutions screening in BG0505 NFL HR1 region. (A) Representative IP data of BG505 NFL trimers variants with selected proline substitutions. (B) SEC profiles of BG505 NFL trimers with selected proline substitutions. Aggregates in the SEC of 160555NFL-I559P are shown in red dash box. Yields are summarized in Table 1. (C) Blue-native PAGE (BN-PAGE) analyses of proteins taken from SEC trimer peaks. (D) 2D averages from NS-EM of BG505 NFL trimer variants. The percentage of closed native-like and open native-like trimers are shown in red and black, as well as the percentage of non-native trimers in blue. The data are summarized in Table 1. (E) DSC measurements of BG505 NFL trimer variants. The $T_m$ values are shown on top of the peaks, and summarized in Table 1. (F) Bio-layer interferometry (BLI) measuring trimer interaction with selected mAbs. The kinetic parameters are summarized in Table 3.
Figures 40A, 40B:
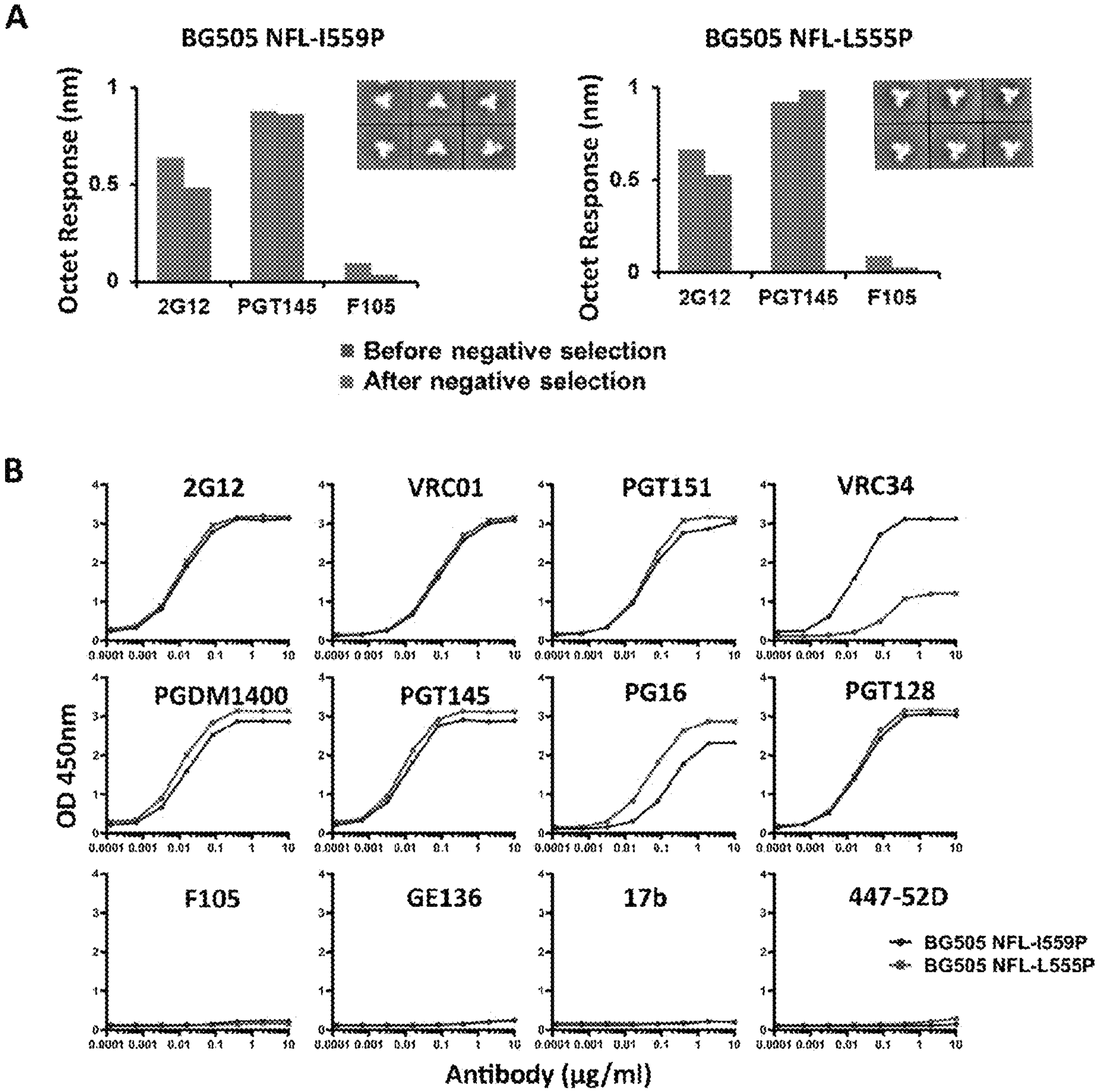
FIG. 40A-40B. Biophysical comparison of BG505 NFL-I559P and -L555P trimers. (A) BLI measurements and 2D averages from NS-EM for BG505 NFL (I559P) (left) and BG505 NFL-L555P (right) trimers before and after negative selection. As shown by the Octet binding data, there is no significant effect of negative selection on the binding reactivity of PGT145 and F105 to L555P and I559P, suggesting that the trimers without negative selection are native-like. 2D class averages from NS-EM show that >95% of the trimers without negative selection are in closed native-like conformation (as shown in the inset of the figures). (B) ELISA binding of selected mAbs to the BG505 NFL-I559P and -L555P trimers. The half-maximal binding concentrations (EC50) are summarized in Table 2.
Figure 41:
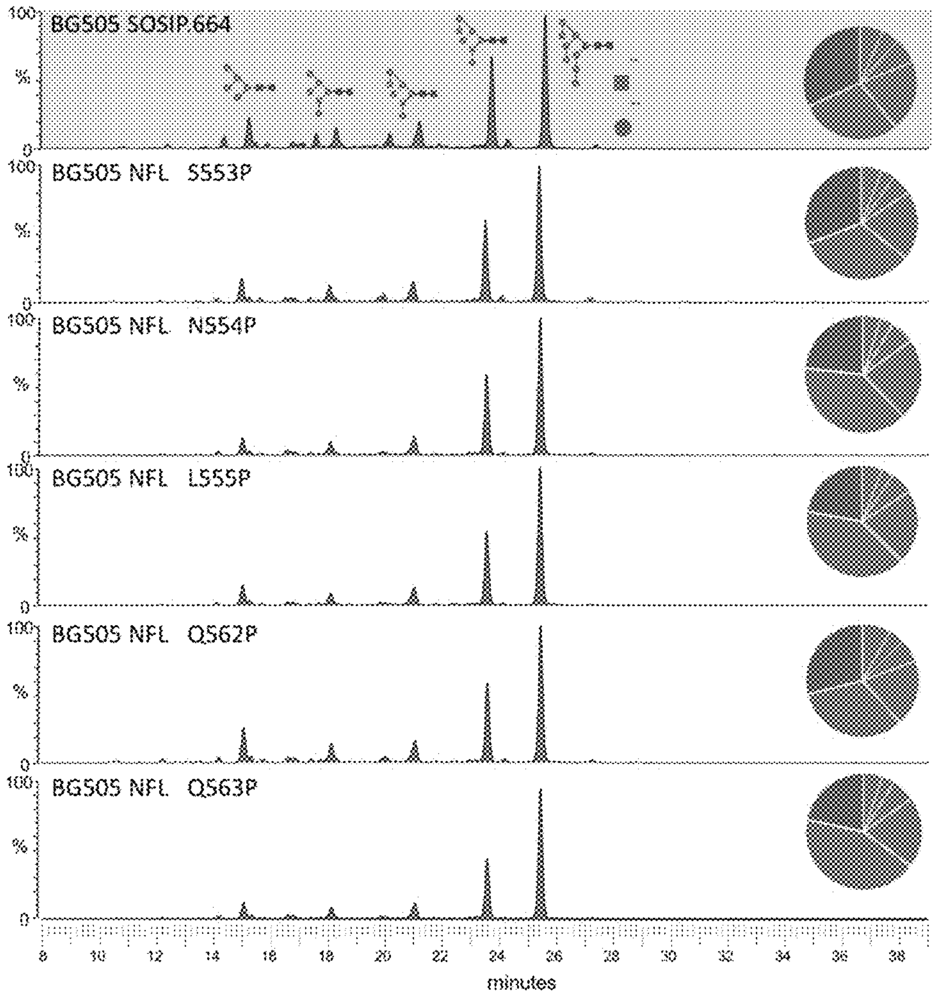
FIG. 41. Glycan profiles of BG505 NFL trimers with selected proline substitutions. The glycan profiles of trimer variants are determined by HILIC-UPLC. The peaks colored in green shades represent the oligomannose ($Man_{5-9}GlcNAc_2$) and hybrid type glycans, and peaks colored in pink represent the remaining complex glycans. The areas under the peaks converted into percentage occupancy of glycans are plotted correspondingly in the form of pie-chart and summarized in the table below. The BG505 NFL proline mutants have higher percentage of oligomannose (especially $Man_{8-9}GlcNAC_2$) than the -SOSIP counterpart.

Two strategies were designed to increase the propensity of clade A, C and B NFLs to form well-ordered, homogenous and stable trimers. Firstly, a proline substitution screening was performed across the gp41 HR1 region using immunoprecipitation analysis, which identified a new proline substitution (L555P) that improves the generation of stable trimers compared to I559P. Secondly, 15 cysteine pairs at different positions of the NFL were screened using structure-guided design. A new cysteine pair A501C-L663C (CC2) was identified, which forms a stabilizing inter-protomer disulfide bond that combines well with TD+ substitutions. In addition, to increase the exposure of the FP N-terminus, an EK cleavage site upstream of the FP was engineered for controlled post-expression cleavage (designated as NFL TD+CC2-D4K). Following cleavage by recombinant EK (rEK), the cleaved trimers were systematically compared to their uncleaved counterparts. These new designs provide insights regarding the critical elements and interactions in the soluble Env trimer, adding substantially to the plethora of native-like immunogens available for hypothesis-driven, but empirical, immunogenicity analysis. The original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. Accordingly, Applicants introduced single-site proline substitutions in HR1 (residues 548 to 585) to identify other positions in Env that could more efficiently form well-ordered trimers (Guenaga et al. 2015. Structure-Guided Redesign Increases the Propensity of HIV Env to Generate Highly Stable Soluble Trimers. J Virol 90:2806-2817). To begin, Applicants initiated a proline screen in the BG505 NFL context, and studied effects on NFL trimer formation by immunoprecipitation analysis (IP) (Sharma et al. 2015. Cleavage-independent HIV-1 Env trimers engineered as soluble native spike mimetics for vaccine design. Cell Rep 11:539-550). The substitutions that generated trimers recognized by the trimer-specific/quaternary-dependent bNAbs VRC06, PGT145 and PGT151, and with low-level of recognition by the non-neutralizing mAb F105, were selected for more comprehensive characterization. In total, Applicants interrogated 36 residues in HR1 (FIG. 34A). Applicants found that residues 548 to 569 can be individually substituted with proline to form a detectable fraction of native-like trimers based upon PGT145, VRC06 and PGT151 recognition. Of the 22 substitutions, five substitutions (S553P, N554P, L555P, Q562P, Q563P) displayed equivalent or more favorable features compared to the original I559P based upon trimer-specific bNAb recognition compared to that of F105 in the oligomeric mixture (FIG. 39A). Five substitutions were examined in regard to their effect on the trimer production, homogeneity, stability and antigenicity. Following lectin-affinity purification, five HR1 mutants displayed a SEC profile possessing distinct (putative) trimer peak, along with a small dimer/monomer peak. The oligomeric states were confirmed by BN-PAGE. In comparison, by SEC and BN-PAGE, the BG505 NFL-I559P trimers contained more aggregates (FIGS. 39B and 39C). All five P substitutions resulted in high yield of trimer production after lectin affinity purification, followed by negative selection (Table 2: The yields of purified trimers after negative selection are listed, together with the percentages of closed native-like conformation determined by NS-EM. The 2D class averages from NS-EM of the trimers are shown in related figures and supplementary figures). These selected P substitutions did not work efficiently in the BG505 SOS (A501C-T605C) backbone, resulting in a broad peak by SEC with no resolution of aggregates, trimers and dimers/monomers (data not shown). Negative stain-EM (NS-EM) analysis of the five trimer variants showed that BG505 NFL-L555P trimers are 99% in closed native-like conformation, slightly better than BG505 NFL-I559P trimers with 97% in closed native-like conformation (FIG. 39D). Even without negative selection, the BG505 NFL-L555P trimers are over 95% in closed native-like conformation, which is comparable to BG505 NFL-I559P (FIG. 40A, Table 2). Thermostability analysis by DSC of the five trimer variants revealed that the BG505 NFL-L555P trimer was slightly more stable than BG505 NFL-I559P trimer with 1° C. increase in Tm (FIG. 39E, Table 2). Antigenicity analysis of the trimer variants by ELISA and BLI showed that BG505 NFL-L555P trimers were well recognized, similarly to BG505 NFL-I559P, by the bNAbs 2G12, VRC01, PGT145, PGDM1400, PGT151 and PGT128 with no recognition by the non-NAbs F105, b6, GE136, 17b and 447-52D (FIGS. 39F and 40B; Tables 3 and 4). The glycosylation profiles of the five trimer variants were similar as that of BG505 SOSIP.664, but with a higher percentage of oligomannose glycoforms (69.1% to 78.4%) than previously described (FIG. 41). The high-density of unprocessed oligomannose glycans in the gp120 subunit of the trimer is consistent with a native-like, closed conformation of these trimers (Pritchard et al. 2015. Structural Constraints Determine the Glycosylation of HIV-1 Envelope Trimers. Cell Rep 11:1604-1613; Pritchard et al. 2015. Cell- and Protein-Directed Glycosylation of Native Cleaved HIV-1 Envelope. J Virol 89:8932-8944) that restrict N-glycan modification to more complex forms.

TABLE 2

Biophysical characterization of stabilized trimers from 16055, BG505 and JRFL isolates.

| New substitutions added to parental NFL | Yield (mg/L) | Morphology (NS-EM) Native-like (%) | Thermostability (DSC) Tm (° C.)[a] | ΔTm (° C.)[b] |
|---|---|---|---|---|
| | 16055 | | | |
| 16055 NFL (I559P) parental [c] | 0.2 | 90 | 58.8 | — |
| 16055 NFL-L555P | 1.8 | 98 | 57.7 | −1.1 |
| 16055 NFL-Q562P | 1.9 | 94 | 57.5 | −1.3 |
| 16055 NFL-Q563P | 2.0 | 95 | 59.3 | 0.5 |
| 16055 NFL-CC2 | 1.0 | 98 | 65.4 | 6.6 |
| 16055 NFL-TD+ | 2.5 | 98 | 77.0 | 18.2 |

TABLE 2-continued

Biophysical characterization of stabilized trimers from 16055, BG505 and JRFL isolates.

| New substitutions added to parental NFL | Yield (mg/L) | Morphology (NS-EM) Native-like (%) | Thermostability (DSC) Tm (° C.)[a] | ΔTm (° C.)[b] |
|---|---|---|---|---|
| 16056 NFL-TD+CC2-D4K_L555P | 4.4 | 97 | 80.2 | 21.4 |
| 16057 NFL-TD+CC2-D4K_L555P w/rEK | 3.8 | 94 | 82.8 | 24.0 |
| 16055 NFL-TD+CC2-D4K_I559P | 4.0 | 98 | 80.1 | 21.3 |
| 16056 NFL-TD+CC2-D4K_I559P w/rEK | 3.4 | 98 | 82.6 | 23.8 |
| | BG505 | | | |
| BG505 NFL (I559P) parental | 2.6 | 97 | 66.3 | — |
| BG505 NFL-S553P | 1.8 | 89 | 66.3 | 0.0 |
| BG505 NFL-N554P | 2.0 | 90 | 66.3 | 0.0 |
| BG505 NFL-L555P | 2.8 | 99 | 67.3 | 1.0 |
| BG505 NFL-Q562P | 1.7 | 46 | 66.4 | 0.1 |
| BG505 NFL-Q563P | 2.0 | 40 | 66.7 | 0.4 |
| BG505 NFL-CC2 | 1.2 | 94 | 70.4 | 4.1 |
| BG505 NFL-TD+ | 2.0 | 98 | 77.0 | 10.7 |
| BG505 NFL-TD+CC2-D4K_L555P | 3.2 | 93 | 80.9 | 14.6 |
| BG505 NFL-TD+CC2-D4K_L555P w/rEK | 2.7 | 98 | 81.6 | 15.3 |
| BG505 NFL-TD+CC2-D4K_I559P | 3.4 | 98 | 80.4 | 14.1 |
| BG505 NFL-TD+CC2-D4K_I559P w/rEK | 2.9 | 98 | 81.0 | 14.7 |
| | JRFL | | | |
| JRFL NFL (I559P) parental [c] | 1.0 | 15 | 54.3 | — |
| JRFL NFL-CC2 | 3.8 | 94 | 59.3 | 5.0 |

[a]The Tm values for each construct were obtained by DSC.

[b]ΔTm represents the change of melting temperature of the modified trimer compared to parental NFL (I559P) trimer.

[c] Data shown here are adapted from previously published studies.

Figures 35A, 35B, 35C, 35D:
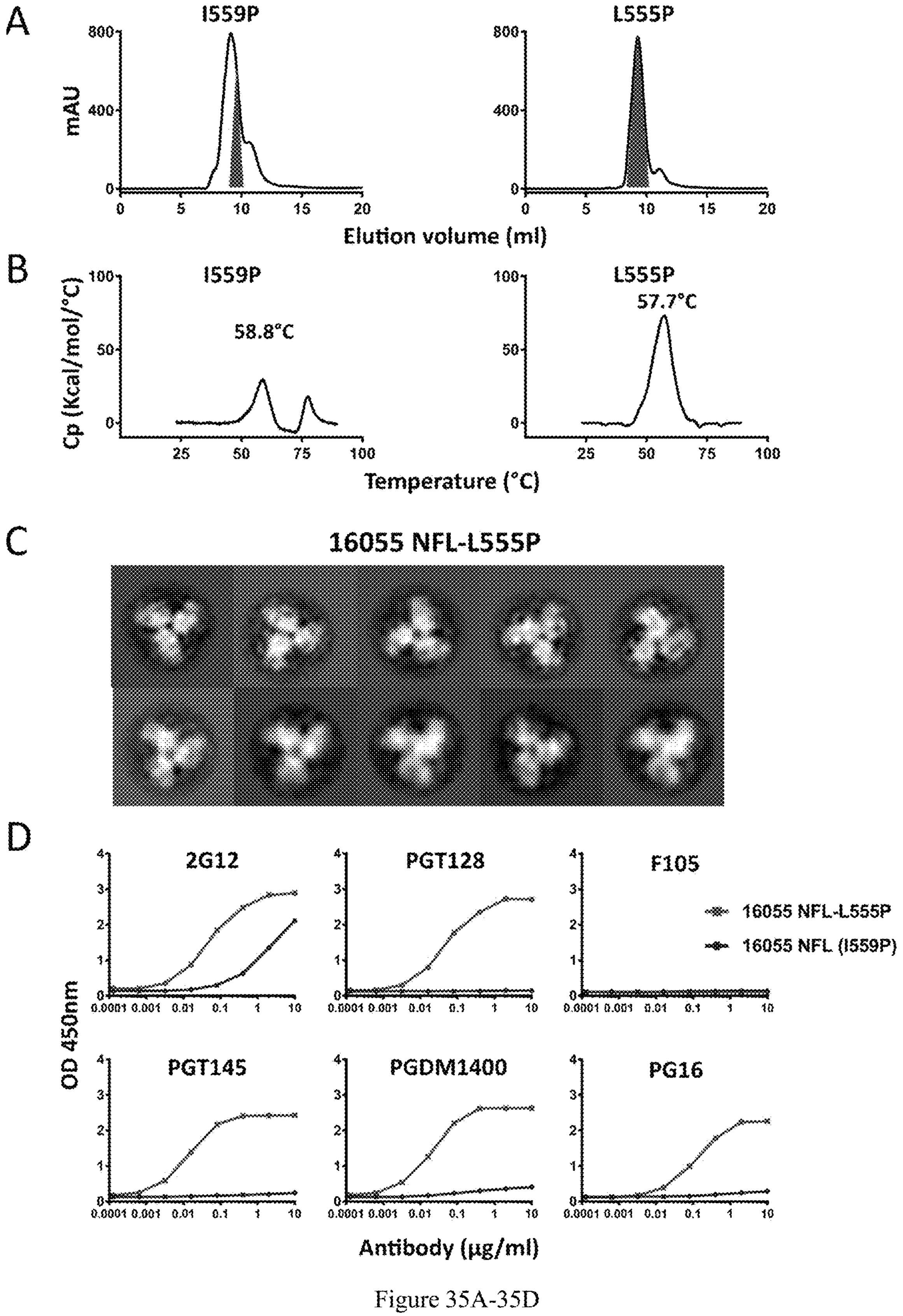
FIG. 35A-35D. Biochemical, biophysical and antigenic characterization of 16055 NFL trimers possessing the L555P substitution. (A) Comparison of the SEC profiles of the 16055 NFL trimers possessing the I559P and L555P substitutions following lectin affinity-purification. The shaded red area indicates the native-like trimer fractions. The yields are summarized in Table 1. (B) DSC measurements of 16055 NFL trimers possessing either I559P or L555P. The data for 16055 NFL (I559P) is adapted as previously reported (Guenaga et al. 2015. Structure-Guided Redesign Increases the Propensity of HIV Env To Generate Highly Stable Soluble Trimers. J Virol 90:2806-2817). The Tm values are shown on top of the peaks, and summarized in Table 1. (C) 2D class averages from negative-stain EM (NS-EM) of 16055 NFL-L555P trimers purified by negative selection using GE136. The data are summarized in Table 1. (D) ELISA binding of selected mAbs to the NFL trimers. The half-maximal binding concentrations (EC50, in μg/ml) are summarized in Table 2.
Figures 42A, 42B, 42C, 42D, 42E, 42F:
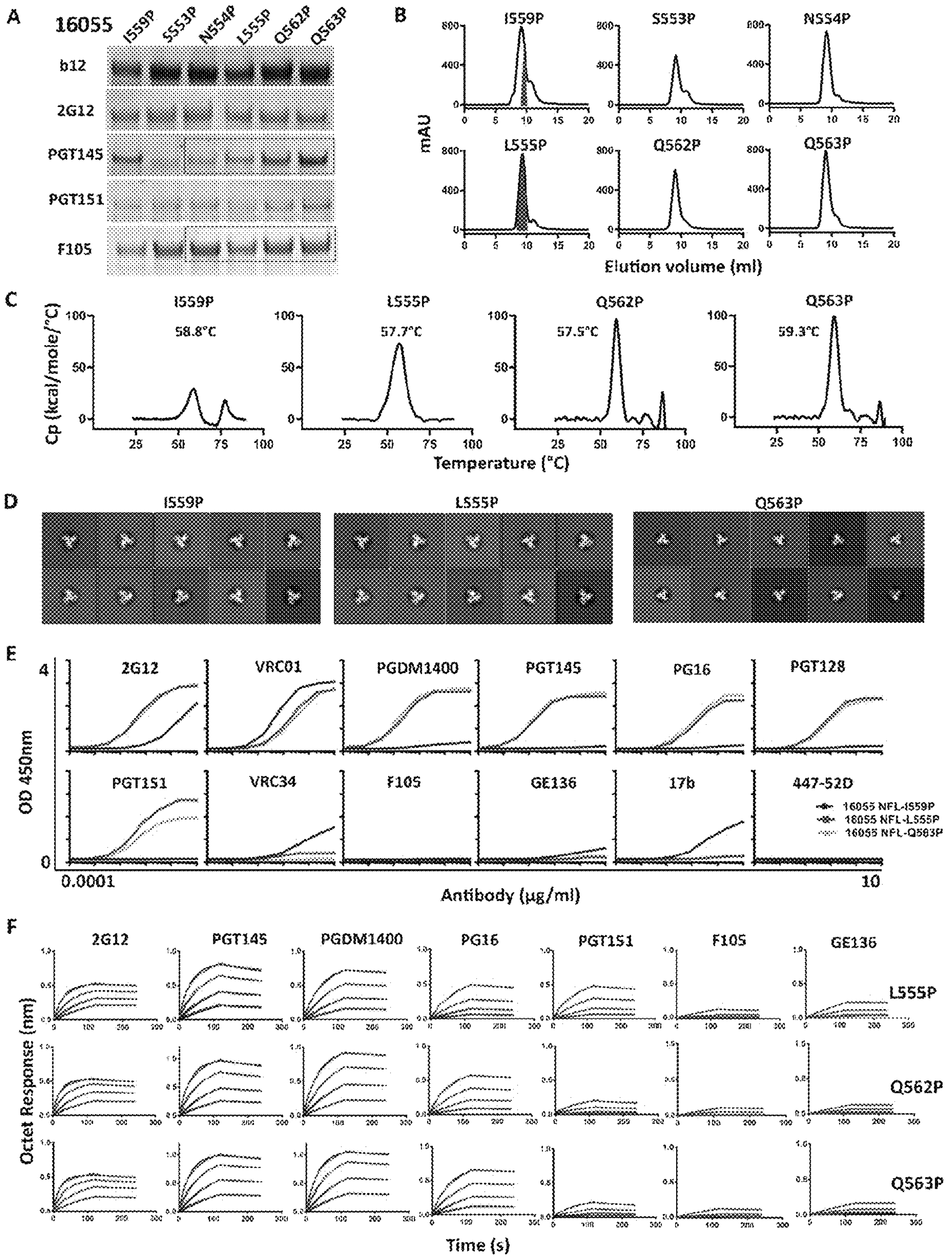
FIG. 42A-42F. Proline substitutions screening in 16055 NFL HR1 region. (A) IP analyses of 16055NFL trimer variants with selected proline substitutions. (B) SEC profiles of 16055 NFL trimer variants following lectin affinity-purification. The shaded red area indicates the native-like trimer fractions. (C) DSC measurements of 16055 NFL trimer variants. The Tm values are shown on top of the peaks. (D) 2D averages from NS-EM of NFL trimers purified by negative selection using GE136. (E) ELISA binding of selected mAbs to the NFL trimers. The EC50 values are summarized in Table 2. (F) BLI measuring trimer interaction with selected mAbs. The kinetic parameters are summarized in Table 3.

Because the HR1 region is fairly conserved among different clades, Applicants determined whether the proline substitutions that resulted in ordered trimers in the BG505 NFL context could be transferred to NFL Envs derived from other clades. Applicants examined the five proline substitutions in 16055 NFL, which is inefficient in its original I559P design in terms of yielding a high percentage of native-like trimers. The five proline substitutions (S553P, N554P, L555P, Q562P, Q563P) were compatible within the 16055 NFL backbone (FIG. 42A). All five trimer variants showed a single homogenous trimer peak by SEC, whereas the 16055 NFL-I559P SEC peak contains only small fractions of trimers (FIGS. 35A and 42B) as previously reported (Guenaga et al. 2015. Structure-Guided Redesign Increases the Propensity of HIV Env to Generate Highly Stable Soluble Trimers. J Virol 90:2806-2817). The trimer peak on SEC was slightly shifted "to the right" for 16055 NFL-L555P compared to 16055 NFL-I559P, corresponding with improved trimer formation and yield (Table 2). However, some trimer heterogeneity remained, so GE136 affinity negative selection was used to remove non-native trimers and other forms of Env. The yield of the 16055 NFL-L555P and -Q563P trimers were demonstrably increased compared to the original I559P variant (Table 2). DSC analysis revealed that L555P and Q563P substitution generated more homogenous 16055 NFL trimers with comparable or slightly better thermostability compared to I559P (FIGS. 35B and 42C; Table 2). NS-EM 2D average analysis showed that nearly 100% of the trimers are in closed native-like conformation (FIGS. 35C and 42D; Table 2). Antigenicity analysis by BLI and ELISA showed that L555P substitution improved the antigenic profile of the trimers with increased binding reactivity to trimer-specific V2-apex targeting bNAbs (PGT145, PGDM1400, PG16) and V3-targeting bNAb (PGT128), but little-to-no detectable binding by the non-NAbs (F105, GE136, 17b, 447-52D) (FIGS. 35D, 42E and 42F; Table 3 and 4).

TABLE 3

Antigenic characterization of stabilized trimers from 16055, BG505, JRFL isolates

| New Substitutions added to parental NFL | Broadly Neutralizing Antibodies 2G12 | PGDM1400 | PGT145 | PG16 | PGT151 | VRC01 | VRC34 | PGT128 | Non-neutralizing Antibodies 447-52D | F105 | GE136 | 17b |
|---|---|---|---|---|---|---|---|---|---|---|---|---|
| 16055 | | | | | | | | | | | | |
| 16055 NFL (I559P) parental | 2.339 | +/ND | +/ND | +/ND | 0 | 0.055 | 0.692 | +/ND | 0 | 0 | 0.913 | 0.438 |
| 16055 NFL-L555P | 0.051 | 0.019 | 0.014 | 0.121 | 0.048 | 0.178 | +/ND | 0.056 | 0 | 0 | +/ND | +/ND |
| 16056 NFL-Q563P | 0.066 | 0.016 | 0.013 | 0.102 | 0.047 | 0.294 | 0 | 0.068 | 0 | 0 | +/ND | +/ND |

TABLE 3-continued

Antigenic characterization of stabilized trimers from 16055, BG505, JRFL isolates

| New Substitutions added to parental NFL | Broadly Neutralizing Antibodies | | | | | | | | Non-neutralizing Antibodies | | | |
|---|---|---|---|---|---|---|---|---|---|---|---|---|
| | 2G12 | PGDM1400 | PGT145 | PG16 | PGT151 | VRC01 | VRC34 | PGT128 | 447-52D | F105 | GE136 | 17b |
| 16055 NFL-CC2 | 0.056 | 0.018 | 0.013 | 0.089 | 0 | 0.021 | 0.434 | 0.135 | 0 | 0 | 0 | 0 |
| 16055 NFL-TD + CC2-D4K_I559P | 0.043 | 0.025 | 0.015 | 0.123 | 0 | 0.059 | 0 | 0.055 | 0 | 0 | 0 | 0 |
| 16055 NFL-TD + CC2-D4K_I559P w/rEK | 0.105 | 0.030 | 0.019 | 0.190 | 0.041 | 0.208 | 0.034 | 0.080 | 0 | 0 | 0 | 0 |
| 16055 NFL-TD + CC2-D4K_L555P | 0.038 | 0.021 | 0.014 | 0.115 | 0 | 0.067 | 0 | 0.050 | 0 | 0 | 0 | 0 |
| 16055 NFL-TD + CC2-D4K_L555P w/rEK | 0.110 | 0.025 | 0.015 | 0.122 | 0.056 | 0.178 | 0.032 | 0.071 | 0 | 0 | 0 | 0 |
| BG505 | | | | | | | | | | | | |
| BG505 NFL (I559P) parental | 0.029 | 0.039 | 0.016 | 0.144 | 0.062 | 0.050 | 0.464 | 0.039 | 0 | +/ND | +/ND | +/ND |
| BG505 NFL-L555P | 0.022 | 0.020 | 0.018 | 0.101 | 0.058 | 0.070 | 0.017 | 0.021 | 0 | +/ND | +/ND | +/ND |
| BG505 NFL-CC2 | 0.025 | 0.018 | 0.011 | 0.143 | 0.059 | 0.059 | 0.457 | 0.035 | 0 | 0 | 0 | +/ND |
| BG505 NFL-TD + CC2-D4K_I559P | 0.024 | 0.038 | 0.013 | 0.206 | 0.065 | 0.042 | 0.072 | 0.036 | 0 | 0 | 0 | 0 |
| BG505 NFL-TD + CC2-D4K_I559P w/rEK | 0.031 | 0.038 | 0.016 | 0.336 | 0.091 | 0.066 | 0.037 | 0.036 | 0 | 0 | 0 | 0 |
| BG505 NFL-TD + CC2-D4K_L555P | 0.027 | 0.042 | 0.014 | 0.215 | 0.073 | 0.051 | 2.427 | 0.041 | 0 | 0 | 0 | 0 |
| BG505 NFL-TD + CC2-D4K_L555P w/rEK | 0.021 | 0.040 | 0.015 | 0.307 | 0.085 | 0.069 | 0.035 | 0.037 | 0 | 0 | 0 | 0 |
| JRFL | | | | | | | | | | | | |
| JRFL NFL-CC2 | 0.022 | 0.20 | 0.012 | 0.216 | 0.139 | 0.032 | 1.009 | 0.040 | 6.117 | 0 | 0 | 0 |

TABLE 4

Kinetic parameters of the NFL trimers with trimer-prefered V2-apex bNAbs and cleavage-sensitive bNAbs

| New Substitutions added to parental NFL | | PGDM1400 | PGT145 | PG16 | PGT151 | VRC34 |
|---|---|---|---|---|---|---|
| 16055 | | | | | | |
| 16055 NFL (I559P) parental | KD (nM) | NT | 1.9 | NT | NT | NT |
| 16055 NFL-L555P | KD (nM) | 2.3 | 3.3 | 6.9 | 5.7 | NT |
| | Kon (1/Ms) × $10^4$ | 20 | 31 | 13 | 15 | NT |
| | Koff (1/s) × $10^{-3}$ | 0.4 | 1.0 | 0.9 | 0.8 | NT |

TABLE 4-continued

Kinetic parameters of the NFL trimers with trimer-prefered V2-apex bNAbs and cleavage-sensitive bNAbs

| New Substitutions added to parental NFL | | PGDM1400 | PGT145 | PG16 | PGT151 | VRC34 |
|---|---|---|---|---|---|---|
| 16055 NFL-Q562P | KD (nM) | 1.4 | 2.9 | 2.8 | 9.2 | NT |
| | Kon (1/Ms) × $10^4$ | 23 | 30 | 17 | 18 | NT |
| | Koff (1/s) × $10^{-3}$ | 0.3 | 0.9 | 0.5 | 1.6 | NT |
| 16055 NFL-Q563P | KD (nM) | 1.3 | 1.6 | 1.7 | 8.9 | NT |
| | Kon (1/Ms) × $10^4$ | 30 | 32 | 19 | 18 | NT |
| | Koff (1/s) × $10^{-3}$ | 0.4 | 0.5 | 0.3 | 1.6 | NT |
| 16055 NFL-CC2 | KD (nM) | 14 | 16 | 15 | 21 | 63 |
| | Kon (1/Ms) × $10^4$ | 11 | 24 | 6.1 | 25 | 4.3 |
| | Koff (1/s) × $10^{-3}$ | 1.6 | 4.0 | 0.9 | 5.3 | 2.7 |
| 16055 NFL-TD + CC2-D4K_L555P | KD (nM) | 13 | 16 | 16 | 13 | 75 |
| | Kon (1/Ms) × $10^4$ | 12 | 22 | 4.3 | 4.5 | 5.0 |
| | Koff (1/s) × $10^{-3}$ | 1.6 | 3.5 | 0.7 | 5.5 | 3.8 |
| 16055 NFL-TD + CC2-D4K_I559P | KD (nM) | 21 | 25 | 23 | 8.7 | 92 |
| | Kon (1/Ms) × $10^4$ | 9.8 | 22 | 4.3 | 79 | 4.1 |
| | Koff (1/s) × $10^{-3}$ | 2.1 | 5.6 | 1.0 | 6.9 | 3.8 |
| BG505 | | | | | | |
| BG505 NFL (I559P) parental | KD (nM) | 11 | 6.2 | 15 | 5.5 | NT |
| BG505 NFL-L553P | KD (nM) | 11 | 5.0 | 7.2 | 3.3 | NT |
| BG505 NFL-N554P | KD (nM) | 2.5 | 4.3 | 14 | 1.4 | NT |
| BG505 NFL-L555P | KD (nM) | 5.1 | 2.9 | 7.8 | 1.4 | NT |
| BG505 NFL-Q562P | KD (nM) | 13 | 6.2 | 15 | 1.9 | NT |
| BG505 NFL-Q563P | KD (nM) | 5.0 | 3.6 | 12 | 1.7 | NT |
| BG505 NFL-CC2 | KD (nM) | 24 | 21 | 43 | 1.9 | 1.3 |
| | Kon (1/Ms) × $10^4$ | 7.6 | 16 | 7.8 | 29 | 2.7 |
| | Koff (1/s) × $10^{-3}$ | 1.8 | 3.4 | 3.3 | 0.6 | 0.04 |
| BG505 NFL-TD + CC2-D4K_I559P | KD (nM) | 18 | 16 | 59 | 2.3 | 12 |
| | Kon (1/Ms) × $10^4$ | 8.8 | 17 | 8.1 | 34 | 4.3 |
| | Koff (1/s) × $10^{-3}$ | 1.6 | 2.7 | 4.8 | 0.8 | 0.5 |
| BG505 NFL-TD + CC2-D4K_L555P | KD (nM) | 23 | 19 | 70 | 3.7 | 44 |
| | Kon (1/Ms) × $10^4$ | 8.8 | 17 | 8.1 | 37 | 4.4 |
| | Koff (1/s) × $10^{-3}$ | 2.0 | 3.1 | 5.7 | 1.4 | 2.0 |

Taken together, these data show that the new proline substitution L555P is comparable to or, often improved, compared to the original I559P substitution in regard to forming well-ordered, homogenous and stable NFL trimers.

Example 17: Inter-Protomer Disulfide Bond Improves the Stability and Antigenicity of Soluble Env Trimer To reduce the flexibility and increase the stability of the first generation of NFL (I559P) trimers, Applicants sought to identify additional internal disulfide pairs to stabilize NFL trimers. Accordingly, cysteine disulfide prediction software was used to identify potential intra or inter disulfide bond formation. Guided by the existing SOSIP and NFL structures, Applicants down-selected 15 potential cysteine pairs, predicted to be with 5 angstroms side chain distance in one of the most likely rotamers. Applicants first assessed these potential new disulfide linkages in the JRFL NFL (I559P) context (listed in Table 5). From the IP results of di-cysteine screening, three cysteine pairs (I201C-A433C, A501C-T605C, and A501C-L663C) showed favorable recognition by PGT145, VRC06 and PGT151, and low-level recognition by F105. The I201C-A433C stabilizes NFL and -SOSIP trimers as previously reported by us and others (Guenaga et al. 2015. Well-Ordered Trimeric HIV-1 Subtype B and C Soluble Spike Mimetics Generated by Negative Selection Display Native-like Properties. PLoS Pathog 11:e1004570; Guenaga et al. 2017. Glycine Substitution at Helix-to-Coil Transitions Facilitates the Structural Determination of a Stabilized Subtype C HIV Envelope Glycoprotein. Immunity 46:792-803 e793; Do Kwon et al. 2015. Crystal structure, conformational fixation and entry-related interactions of mature ligand-free HIV-1 Env. Nat Struct Mol Biol 22:522-531; Joyce et al. 2017. Soluble Prefusion Closed DS-SOSIP.664-Env Trimers of Diverse HIV-1 Strains. Cell Rep 21:2992-3002). The A501C-T605C intra-protomer linkage used to generate the original SOS and SOSIP trimers (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618'; Pancera et al. 2014. Structure and immune recognition of trimeric pre-fusion HIV-1 Env. Nature 514:455-461; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643. Georgiev et al. 2015. Single-Chain Soluble BG505.SOSIP gp140 Trimers as Structural and Antigenic Mimics of Mature Closed HIV-1 Env. J Virol 89:5318-5329) displayed higher binding reactivity to F105 compared to the newly identified A501C-L663C interprotomer disulfide linkage. Therefore, Applicants focused on further examining the A501C-L663C cysteine pair (designated here as "CC2") (schematically outlined in FIG. 34).

TABLE 5

Screen of engineered disulfide linkages to stabilize soluble JRFL NFL trimer.

| Name | Position #1 | Region | Sec Stuc | Position #2 | Region | Sec Stuc | CA-CA Distance | 2G12 | VRC06 | PGT145 | PGT151 | F105 | 19b |
|---|---|---|---|---|---|---|---|---|---|---|---|---|---|
| | L34C | C1 | S | W610C | CC-LOOP | L | 5.51 | +++ [a] | – | – | ND [b] | + | ND |
| | W35C | C1 | S | V608C | CC-LOOP | L | 5.62 | +++ | – | – | ND | + | ND |
| | W35C | C1 | S | P609C | CC-LOOP | L | 4.91 | ++ | – | – | ND | + | ND |
| | T37C | C1 | S | T605C | CC-LOOP | S | 4.68 | ++ | – | – | ND | ++ | ND |
| | Y39C | C1 | S | L602C | CC-LOOP | L | 5.62 | ++ | – | – | ND | ++ | ND |
| | Y39C | C1 | S | I603C | CC-LOOP | S | 4.99 | +++ | – | – | ND | ++ | ND |
| | Y40C | C1 | S | L602C | CC-LOOP | L | 4.55 | +++ | – | – | ND | ++ | ND |
| | P43C | C1 | L | A526C | FP | L | 5.06 | ++ | – | – | +/– | + | ++ |
| | N88C | C1 | L | G527C | FP | L | 4.62 | ++ | – | – | +/– | + | ++ |
| SOS | A501C | C5 | L | T605C | CC-LOOP | S | 6.26 | +++ | ++ | ++ | +/– | +/– | ++ |
| | V89C | C1 | L | G527C | FP | L | 4.77 | ++ | +/– | + | +/– | + | ++ |
| | T529C | FPPR | L | T627C | HR2 | L | 4.52 | +++ | – | – | – | ++ | ++ |
| | M626C | HR2 | L | T529C | HR2 | L | 5.17 | +/– | – | – | +/– | +/– | +/– |
| CC1 | I201C | C2 | S | A433C | C4 | S | 4.66 | +++ | ++ | + | + | + | + |
| CC2 | A501C | C5 | L | L663C | HR2 | H | 4.35 | ++ | ++ | ++ | +/– | + | ++ |

[a] Antibody binding is scaled from no binding reactivity (–) to strong binding (+++).
[b] ND: Not determined.

Figures 36A, 36B, 36C, 36D:
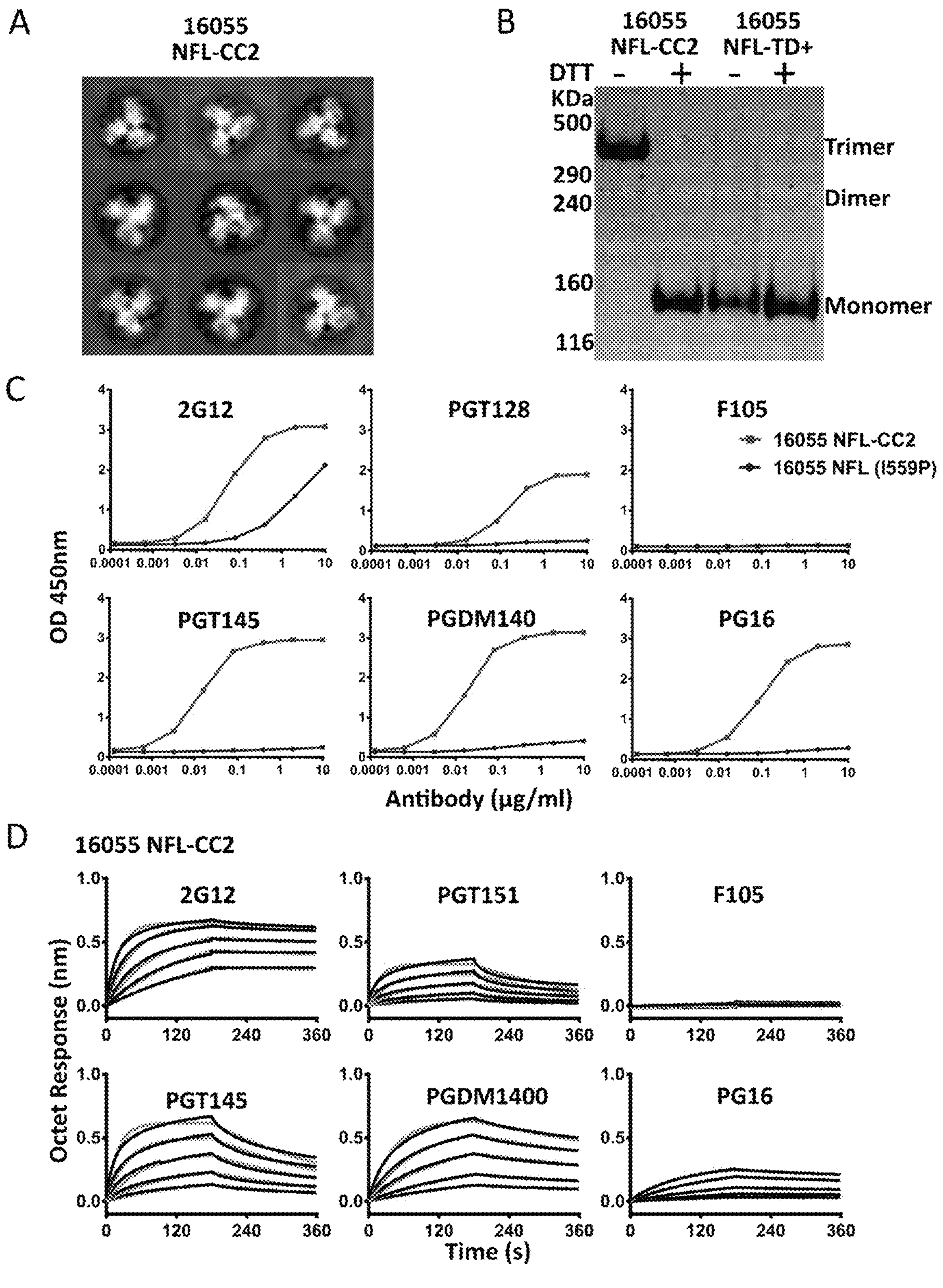
FIG. 36A-36D. Biochemical, biophysical and antigenic characterization of 16055 NFL-CC2 trimers. (A) 2D class averages from NS-EM of 16055 NFL-CC2 trimers. (B) Disulfide bond formation was determined by SDS-PAGE under reducing and non-reducing conditions, respectively. Under reducing conditions, all proteins displayed a gp140 species. Under non-reducing conditions, the CC2 proteins showed trimeric gp140s, migrating more slowly as determined by SDS-PAGE. (C) ELISA binding of selected mAbs to the 16055 NFL-CC2 trimers. The half-maximal binding concentrations are summarized in Table 2. (D) BLI measurements for 16055 NFL-CC2 trimers with selected mAbs. The fitting curves are shown in green color, and the kinetic parameters are summarized in Table 3.
Figures 43A, 43B, 43C, 43D, 43E, 43F, 43G:
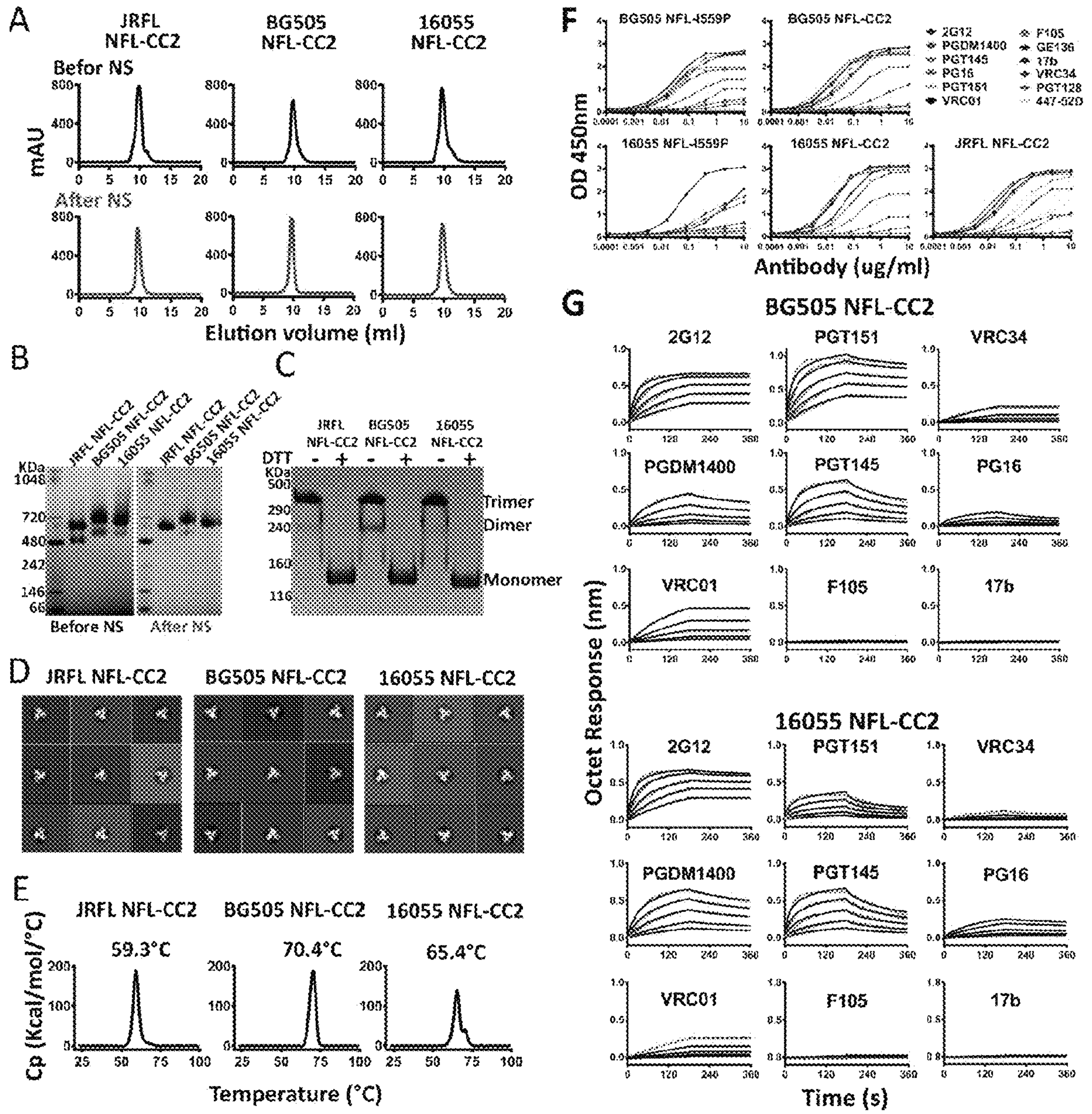
FIG. 43A-43G. Characterization of NFL-CC2 trimers from different clades. (A) SEC profile of JRFL (clade B), BG505 (clade A) and 16055 (clade C) NFL-CC2 trimers after lectin affinity-purification, and following by negative selection (NS). (B) BN-PAGE analyses of trimers before and after negative selection. (C) Disulfide bond formation was determined by SDS-PAGE under reducing and non-reducing conditions, respectively. (D) 2D class averages from NS-EM of JRFL, BG505 and 16055 NFL-CC2 trimers. (E) DSC measurements of NFL-CC2 trimers. The Tm values are shown on top of the peaks. (F) ELISA binding of selected mAbs to NFL-CC2 trimers. The EC50 values are summarized in Table 2. (G) BLI measurements for BG505 and 16055 NFL-CC2 trimers with selected mAbs. The fitting curves are shown in green color, and the kinetic parameters are summarized in Table 3.

Applicants analyzed the CC2 cysteine pair in Envs derived from different clades, JRFL (clade B), 16055 (clade C) and BG505 (clade A). All three NFL trimers with the new 501-663 cysteine substitutions form well-ordered trimers, revealing a single sharp trimer peak by SEC (FIG. 43A). The purified trimers were resolved on BN-PAGE, revealing a migration pattern consistent with predominantly trimeric Env. A low level of apparent dimer forms was detected for the new BG505 NFL-CC2 design (FIG. 43B). Homogeneous trimer formation was confirmed by EM 2D class average analysis as the A501C-663C trimers were highly ordered following negative staining (FIGS. 36A and 43D; Table 2). To better confirm efficient 501-663 disulfide bond formation, Applicants performed the following gel analysis. Under reducing and non-reducing conditions, by SDS-PAGE analysis, the NFL-TD+(without CC2) trimer proteins migrated as gp140 monomer. However, the NFL-CC2 proteins migrated as trimer under non-reducing conditions, whereas under reducing conditions they migrated as gp140 monomer (FIGS. 36B and 43C). The results were consistent with inter-protomer disulfide bond formation, linking adjacent protomers to form well-ordered trimers.

DSC analysis revealed that the new inter-protomer disulfide bond increased the thermostability of the NFL trimers. Substituting the new 501-663 CC2 in the NFL backbone increased the Tm by 6.6° C. for 16055 trimers and 4.1° C. for BG505 and 5.0° C. for JRFL trimers, respectively (FIG. 43E and Table 2). The antigenic profile of the NFL-CC2 trimers analyzed by BLI and ELISA showed that CC2 in 16055 NFL improved trimer recognition by the trimer-specific bNAbs (PGT145, PGDM1400 and PG16) and V3-targeting bNAb (PGT128) (FIGS. 36C and 36D; Tables 3 and 4). The improvement of CC2 on antigenicity was also evident for BG505 NFL, but to a lesser extent (FIGS. 43F and 43G).

Taken together, these data indicate that the new cysteine pair A501C-L663C (CC2) formed inter-protomer disulfide bonds, increasing the thermostability and antigenicity of NFL trimers derived from multiple Envs from different clades.

Example 18: Combinatorial Approaches to Improve NFL Trimer Design

As described above, the L555P substitution and the new CC2 inter-protomer disulfide bond improved the NFL trimer design, separately. In addition, Applicants recently reported that trimer-derived residue substitutions, glycine substitution at helix-to-coil transitions as well as targeted reduction of the inherent Env metastability facilitate the high-yield production of cross-clade stable soluble NFL-TD+ trimers. Therefore, Applicants combined these design strategies to the 16055 and BG505 NFL Env context, to generate NFL-TD+CC2 trimers. Applicants assessed whether these combined designs were cross-compatible to yield better well-ordered trimers. In addition, since the NFL trimers are cleavage-independent (un-cleaved), there is limited exposure of the N-terminus of the gp41 fusion peptide (FP) (FIGS. 42E, 43F and 43G). To restore exposure of the gp41 FP N-terminus, Applicants engineered an enterokinase (EK) cleavage site upstream of the FP. This modification would allow controlled post-expression cleavage of gp140, potentially exposing the VRC34-FP-directed binding site (outlined in FIG. 34). The FP was recently reported as a vulnerable site to the VRC34 and ACS202 bNAbs (Kong et al. 2016. Fusion peptide of HIV-1 as a site of vulnerability to neutralizing antibody. Science 352:828-833; van Gils et al. 2016. An HIV-1 antibody from an elite neutralizer implicates the fusion peptide as a site of vulnerability. Nat Microbiol 2:16199). The resulting trimers were designated as NFL-TD+CC2-D4K. For head-to-head comparison, two versions of NFL-TD+CC2-D4K trimers were generated in 16055 and BG505 backbone, one containing the original I559P substitution and the second possessing the L555P substitution.

Figures 37A, 37B, 37C, 37D, 37E:
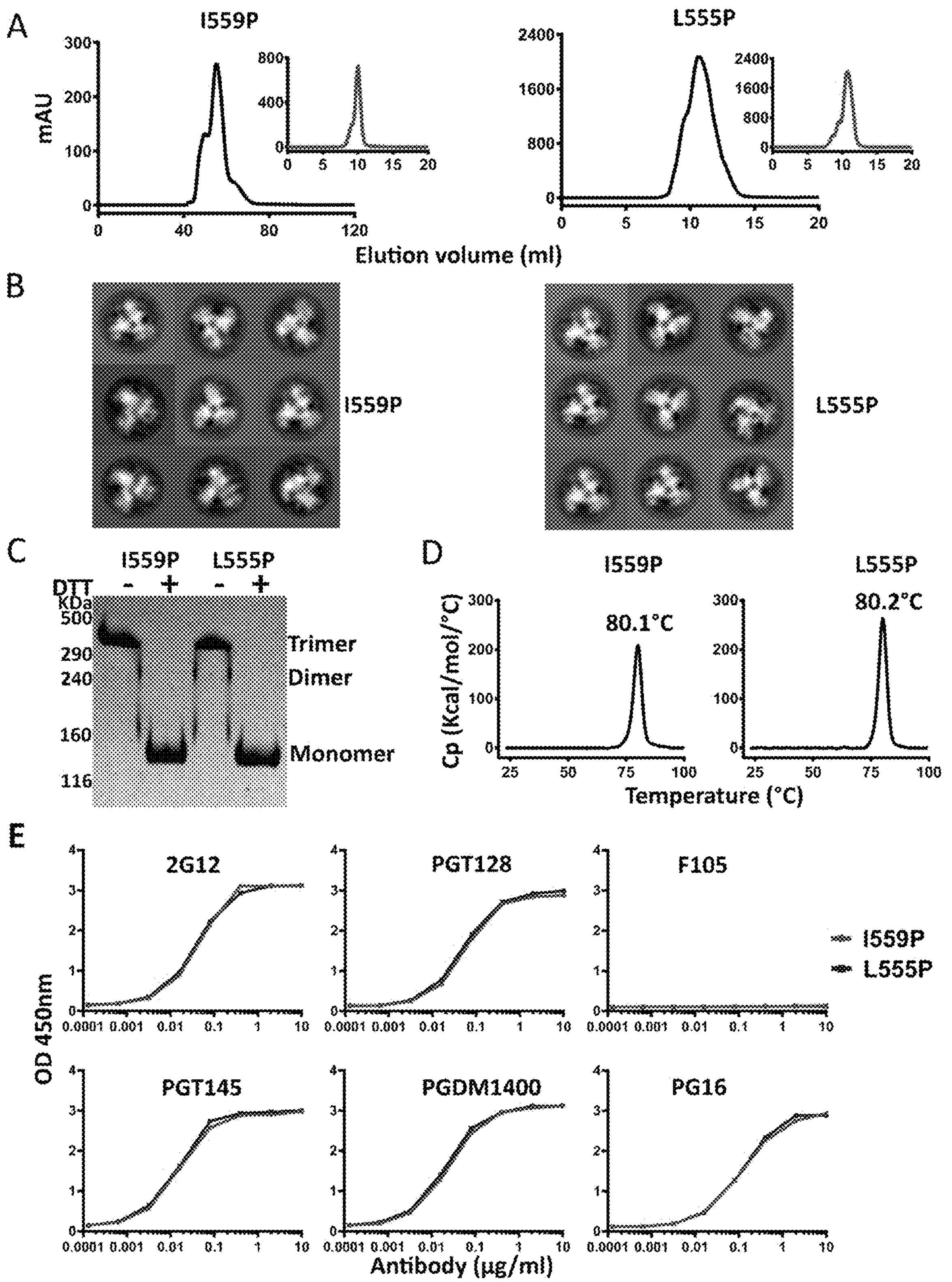
FIG. 37A-37E. Biochemical, biophysical and antigenic characterization of 16055 NFL-TD+CC2-D4K_I559P and _L555P trimers. (A) SEC profiles of 16055 NFL-TD+CC2-D4K_I559P and _L555P trimers following lectin affinity-purification. SEC profiles after GE136 negative selection are shown in the inset. (B) Comparison of 2D class averages from NS-EM of 16055 NFL-TD+CC2-D4K_I559P and _L555P trimers. (C) Disulfide bond formation was determined by SDS-PAGE under reducing and non-reducing conditions, respectively. (D) DSC measurements of 16055 NFL-TD+CC2-D4K_I559P and _L555P trimers. The Tm values are shown above the peak, and summarized in Table 1. (E) Comparison of ELISA binding properties of selected mAbs to 16055 NFL-TD+CC2-D4K_I559P and _L555P trimers. The half-maximal binding concentrations are summarized in Table 2.
Figures 44A, 44B, 44C:
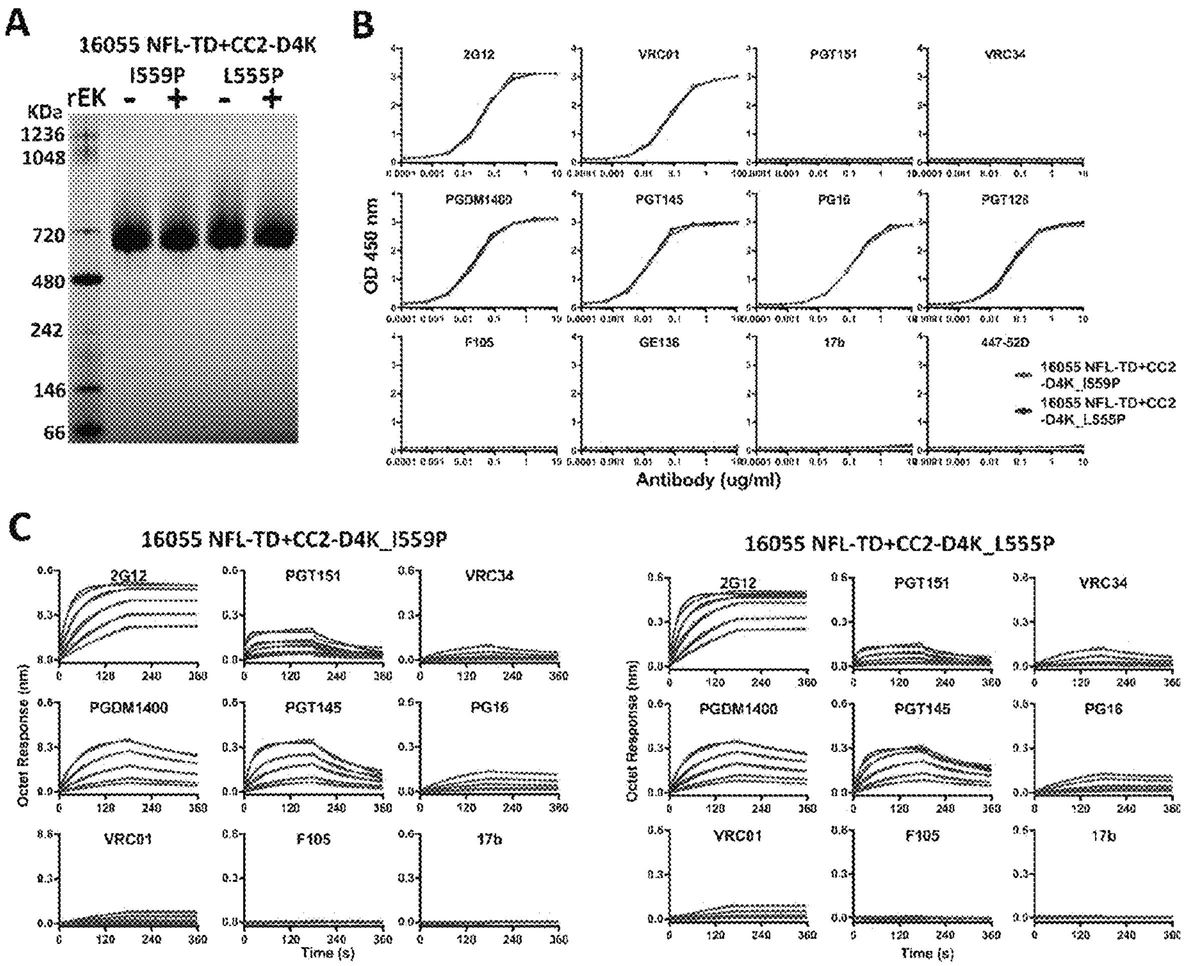
FIG. 44A-44C. Characterization of 16055 NFL-TD+CC2-D4K_I559P and _L555P trimers. (A) BN-PAGE analyses of 16055 NFL-TD+CC2-D4K trimers without or with rEK cleavage. (B) Comparison of ELISA binding properties of selected mAbs to 16055 NFL-TD+CC2-D4K_I559P and L555P trimers without rEK cleavage. The EC50 values are summarized in Table 2. (C) BLI measurements of 16055 NFL-TD+CC2-D4K_I559P and _L555P trimers without rEK cleavage. The fitting curves are shown in blue color, and the kinetic parameters are summarized in Table 3.
Figures 45A, 45B, 45C, 45D, 45E, 45F, 45G:
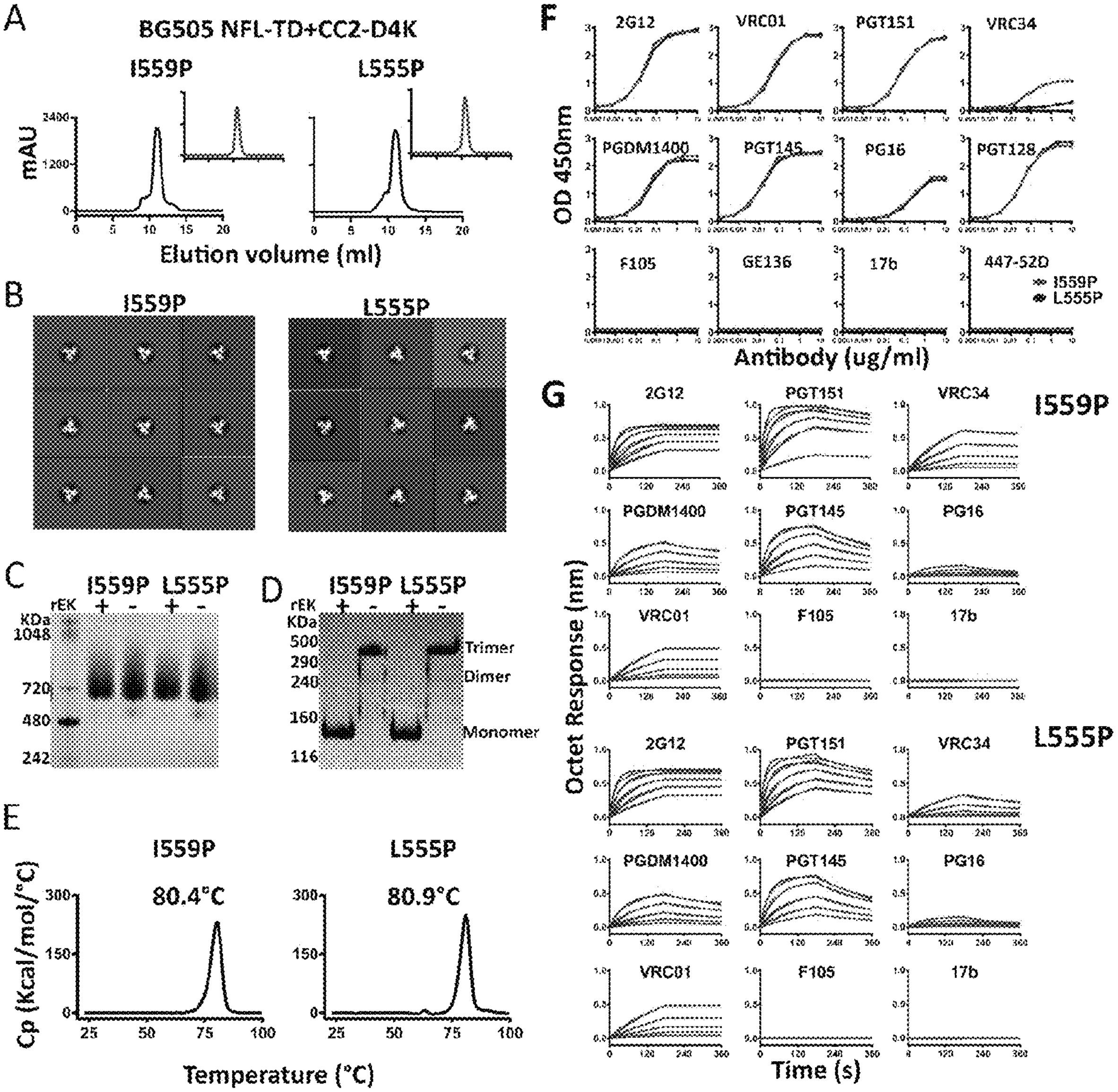
FIG. 45A-45G. Characterization of BG505 NFL-TD+CC2-D4K_I559P and _L555P trimers. (A) SEC profiles of BG505 NFL-TD+CC2-D4K_I559P and _L555P trimers following lectin affinity-purification. SEC profiles after F105 negative selection are shown in the inset. (B) 2D averages from NS-EM of BG505 NFL-TD+CC2-D4K_I559P and _L555P trimers. (C) BN-PAGE analyses of BG505 NFL-TD+CC2-D4K_I559P and _L555P trimers with or without rEK cleavage. (D) Disulfide bond formation was determined by SDS-PAGE under reducing and non-reducing conditions, respectively. (E) DSC measurements of BG505 NFL-TD+CC2-D4K_I559P and _L555P trimers without rEK cleavage. (F) Comparison of ELISA binding properties of selected mAbs to BG505 NFL-TD+CC2-D4K_I559P and _L555P trimers. The EC50 values are summarized in Table 2. (G) BLI measurements of BG505 NFL-TD+CC2-D4K_I559P and _L555P trimers without cleavage. The fitting curves are shown in blue color, and the kinetic parameters are summarized in Table 3.

The 16055 and BG505 NFL-TD+CC2-D4K_L555P and _I559P variants were purified via lectin-affinity chromatography, followed by SEC. The SEC trimer peak of 16055 NFL-TD+CC2-D4K_I559P was much sharper than that of NFL-TD+CC2-D4K_L555P, indicating the I559P substitution is more compatible with these modifications compared to L555P (FIG. 37A). As expected, the SEC profile revealed a single sharp trimer peak following negative selection. Similar SEC profiles were observed for BG505 NFL-TD+CC2-D4K_L555P and _I559P (FIG. 45A). Regardless of the P substitution used, the combinatorial design in 16055 dramatically increased the yield of well-ordered trimers by 20-fold compared to original 16055 NFL-I559P, and by over 1.6-fold compared to the latest 16055 NFL-TD+(Table 2). Trimer formation was confirmed by BN-PAGE (FIGS. 44A and 45C). In addition, negative stain-EM (NS-EM) analysis revealed that nearly 100% trimers in closed native-like conformation (FIGS. 4B and 45B; Table 2). Under non-reducing conditions, the NFL-TD+CC2-D4K proteins migrated as trimer on the SDS-PAGE, whereas under reducing conditions these proteins migrated as a gp140 monomer, consistent with the formation of inter-protomer disulfide bonds by CC2 substitutions. (FIGS. 37C and 45D).

DSC analysis revealed that the Tm of these trimers are over 80° C. for both NFL-TD+CC2-D4K_L555P and _I559P, with over a 21° C. increase for 16055 NFL-TD+CC2-D4K and over a 14° C. increase for BG505 NFL-TD+CC2-D4K, compared to the first generation of NFL I559P trimers (FIGS. 37D and 45E). There was no significant difference of thermostability between NFL-TD+CC2-D4K_L555P and _I559P, but there was over a 3° C. gain for 16055 and BG505 NFL-TD+CC2-D4K compared to their corresponding NFL-TD+ trimers, indicating the addition of CC2 increased trimer thermal stability (Table 2). The NFL-TD+CC2-D4K_L555P and _I559P trimers are highly stable in solution, displaying no detectable degradation at 37° C. for 30 h, not even with rEK at 37° C. for 30 h indicated by gel analysis. Assessment of 16055 NFL-TD+CC2-D4K_L555P and _I559P trimers with bNAbs and non-neutralizing Abs by ELISA and BLI revealed that both trimer variants were recognized comparably by the trimer-specific bNAbs with no detectable recognition by the non-neutralizing Abs tested (FIGS. 37E, 44; Tables 3 and 4). Comparable antigenicity profiles were similarly detected for BG505 NFL-TD+CC2-D4K_L555P and _I559P trimers (FIGS. 45F and 45G), consistent with trimer integrity.

Taken together, these analyses demonstrated that the combination of L555P, CC2 and TD+ mutations preserve the pre-fusion state of the NFL trimers with improve trimer formation, biophysical properties and antigenicity.

Figures 38A, 38B, 38C, 38D, 38E:
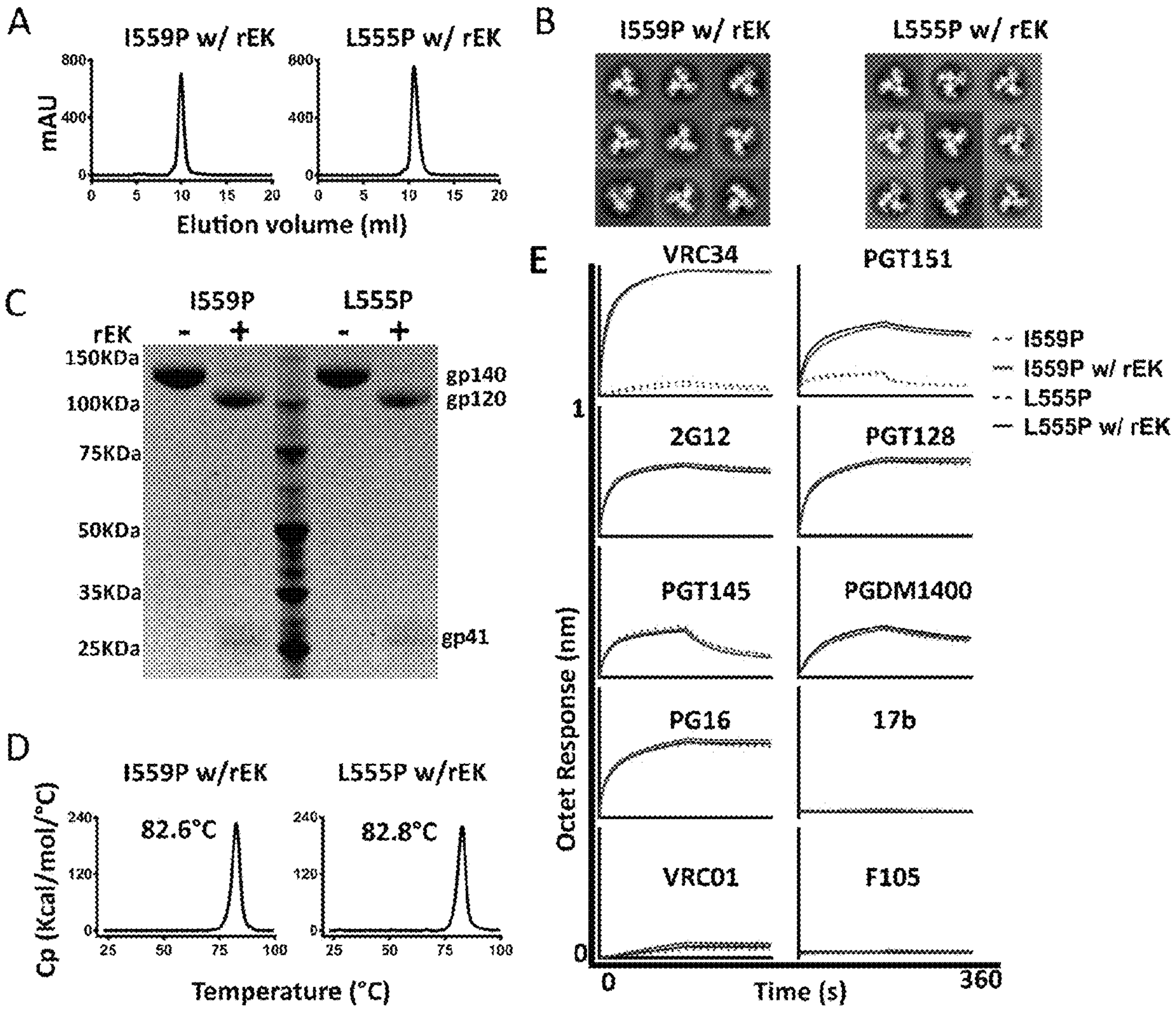
FIG. 38A-38E. Biochemical, biophysical and antigenic characterization of 16055 NFL-TD+CC2-D4K_I559P and _L555P trimers after rEK cleavage. (A) SEC profiles of 16055 NFL-TD+CC2-D4K_I559P and _L555P trimers after rEK cleavage (w/ rEK). (B) Comparison of 2D class averages from NS-EM of 16055 NFL-TD+CC2-D4K_I559P and _L555P trimers after rEK cleavage. (C) Cleavage efficiency was determined by SDS-PAGE under reducing conditions. (D) DSC measurements of 16055 NFL-TD+CC2-D4K_I559P and _L555P trimers after rEK cleavage. The Tm values are shown above the peak and are summarized in Table 1. (E) BLI measurements for the interaction of 16055 NFL-TD+CC2-D4K trimers (without and with rEK cleavage) with selected mAbs. The kinetic parameters are summarized in Table 3.

Example 19: Post-Expression Cleavage of NFL-TD+CC2-D4K Trimers Increases the Exposure of Cleavage-Sensitive Epitopes Next, Applicants assessed the impact of post-expression cleavage on the highly stable NFL-TD+CC2-D4K trimers regarding their structure, biochemical, biophysical properties and antigenicity. Following cleavage by rEK, 16055 NFL-TD+CC2-D4K_L555P and _I559P trimers showed single sharp trimer peaks on SEC (FIG. 38A) with nearly 100% of the trimers in a closed native-like conformation as resolved by NS-EM (FIG. 38B). Under native conditions, cleaved 16055 NFL-TD+CC2-D4K proteins migrated as trimer on BN-PAGE, similar to their un-cleaved counterparts (FIG. 44A). Similar results were observed for BG505 NFL-TD+CC2-D4K_L555P and _I559P trimers (FIGS. 46A, 46B and 45C).

To test the efficiency of post-expression cleavage, Applicants performed SDS-PAGE analysis. Under reducing conditions, cleaved 16055 NFL-TD+CC2-D4K_L555P and _I559P proteins migrated as two bands, gp120 and gp41, whereas the uncleaved proteins migrated as a single gp140 band (FIG. 38C), indicating the trimers were completely cleaved by rEK. Similar results were obtained for BG505 NFL-TD+CC2-D4K_L555P and _I559P trimers (FIG. 46C).

Figures 46A, 46B, 46C, 46D, 46E:
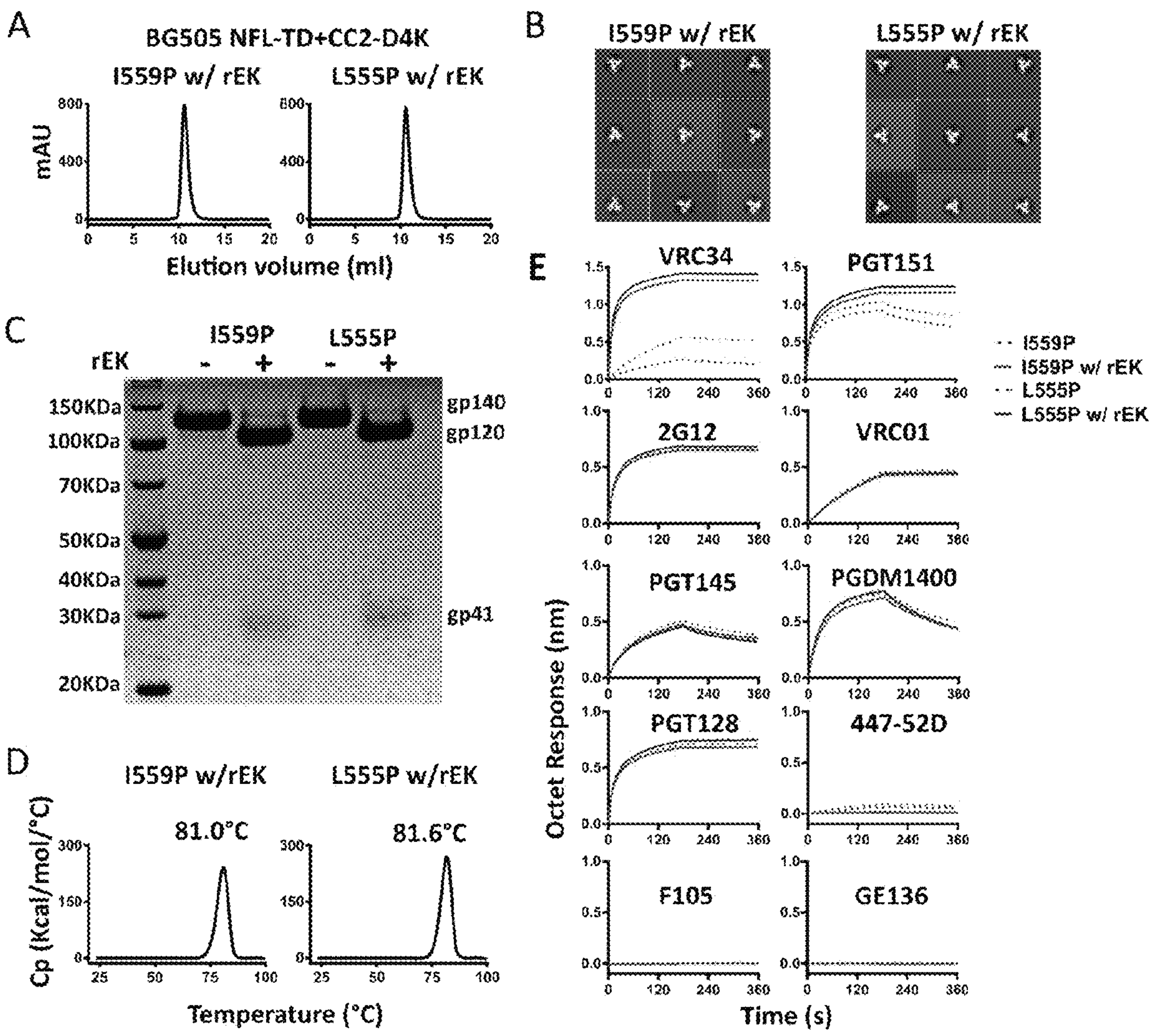
FIG. 46A-46E. Characterization of BG505 NFL-TD+CC2-D4K_I559P and _L555P trimers after rEK cleavage. (A) SEC profiles of BG505 NFL-TD+CC2-D4K_I559P and _L555P trimers after rEK cleavage (w/rEK). (B) Comparison of 2D averages from NS-EM of BG505 NFL-TD+CC2-D4K_I559P and _L555P trimers after rEK cleavage. (C) Cleavage efficiency was determined by SDS-PAGE under reducing conditions. (D) DSC measurements of BG505 NFL-TD+CC2-D4K_I559P and _L555P trimers after rEK cleavage. (E) BLI measurements for BG505 NFL-TD+CC2-D4K_I559P and _L555P trimers interaction with selected mAbs before and after rEK cleavage. The kinetic parameters are summarized in Table 3.

Following rEK-mediated cleavage, DSC analysis of putative trimers revealed single narrow symmetric thermal transition profiles, indicating that the trimers were homogeneous (FIGS. 38D and 46D). The Tms of the cleaved 16055 NFL-TD+CC2-D4K_L555P and _I559P trimers were 82.8° C. and 82.6° C., respectively, displaying 2.6° C. and 2.5° C. increases compared to their uncleaved counterparts. The Tms of cleaved BG505 NFL-TD+CC2-D4K_L555P and _I559P trimers were 81.6° C. and 81.0° C., respectively, with 0.7° C. and 0.6° C. increases over their uncleaved counterparts (Table 2).

Figures 47A, 47B:
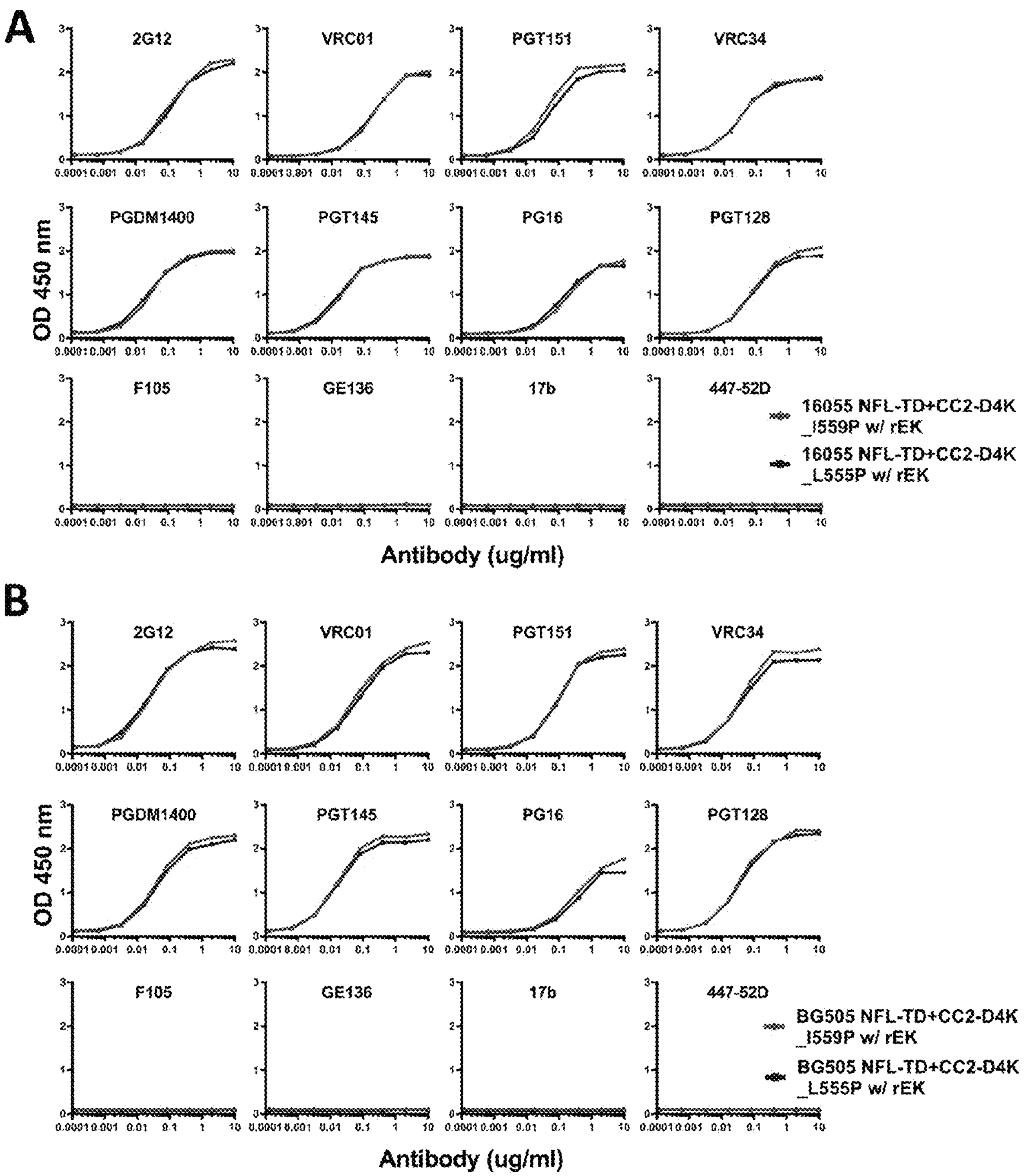
FIG. 47A-47B. Comparison of ELISA binding reactivities between NFL-TD+CC2-D4K 1559 and _L555P trimers after rEK cleavage. (A) Comparison of ELISA binding properties of selected mAbs to 16055 NFL-TD+CC2-D4K_I559 and _L555P trimers after rEK cleavage. (B) Comparison of ELISA binding properties of selected mAbs to BG505 NFL-TD+CC2-D4K_I559 and _L555P trimers after rEK cleavage. The EC50 values are summarized in Table 2.

Applicants used a panel of bNAbs and non-neutralizing Abs to assess the antigenicity changes of 16055 NFL-TD+CC2-D4K_L555P and _I559P trimers after cleavage by ELISA and BLI. Following rEK cleavage, the 16055 NFL-TD+CC2-D4K_L555P and _I559P trimers displayed increased recognition by the cleavage-sensitive bNAbs VRC34 and PGT151, while retaining similar levels of recognition by bNAbs targeting other epitopes (2G12, VRC01 and PGT128) (FIGS. 38E and 47A). In addition, there was no recognition by the non-neutralizing Abs (F105, GE136, 17b and 447-52D). Similar antigenic profile was observed for BG505 NFL-TD+CC2-D4K_L555P and _I559P trimers after cleavage (FIGS. 46E and 47B).

Overall, these data indicate that the CC2 covalently linked rEK-cleaved trimers to maintain native-like structure with enhanced stability and increased exposure of epitopes in the FP, gp120/gp41 interface.

The invention is further described by the following numbered paragraphs:

1. An engineered or non-naturally occurring trimer, wherein the trimer is a flexibly linked NFL2P trimer, wherein the trimer comprises one or more trimer-derived mutations ("TD mutations"), wherein said TD mutations comprise one or more mutations at residue 569.

2. The trimer of paragraph 1, wherein the mutation comprises G at residue 569.

3. The trimer of paragraph 1 or 2, wherein the trimer is derived from an Indian subtype C HIV-I Env sequence.

4. The trimer of any one of paragraphs paragraph 1-3, wherein the trimer further a disulfide linkage.

5. The trimer of paragraph 4, wherein the disulfide linkage is an engineered intra-protomer disulfide I201C-A433 C (CC).

6. The trimer of any one of paragraphs 1-5, further comprising a 10 residue (G45) flexible linker (SEQ ID NO: 34) between a REKR-deleted Env gp120 C-terminus ("REKR" disclosed as SEQ ID NO: 35) and the unmodified gp41 N-terminus.

7. The trimer of any one of paragraphs 1-6, further comprising substitutions E47D, K49E, V65K, E106T, 1165L, E429R, R432Q and/or A500R.

8. The trimer of any one of paragraphs 1-7, further comprising a T569G substitution.

9. An engineered or non-naturally occurring trimer, wherein the trimer is a flexibly linked NFL2P trimer or the trimer of any one of paragraphs 1-8, further comprising substitutions at residues 197, 276, 234, 262, 276, 301, 360, 463 or any combination thereof.

10. The trimer of paragraph 9 comprising substitutions N197Q, N276Q, N234Q, N262Q, N276Q, N301Q, N360Q, N463Q or any combination thereof.

11. The trimer of paragraph 9 or 10 comprising the substitutions at residues 276, 301, 360, 463 or any combination thereof.

12. The trimer of paragraph 10 comprising substitutions N276Q, N301Q, N360Q, N463Q or any combination thereof.

13. The trimer of any one of paragraphs 1-12, further comprising a potential N-linked glycans (PNGS) introduced at residue 332 by a K334S mutation ("+N332 PT"), wherein the italicized N refers to an N-glycan, not an asparagine residue.

14. An engineered or non-naturally occurring trimer, wherein the trimer is a flexibly linked NFL2P trimer, wherein the trimer comprises a N276Q/N463Q glycan-deleted variant with or without N332 restored, a +N332 N276Q/N360Q/N463Q triple N-glycan-deleted variant or a+N332 N276Q/N360Q/N463Q/N301Q quadruple N-glycan-deleted variant.

15. A method of eliciting an immune response in a mammal comprising administering the trimer of any one of paragraphs 1-14.

16. The method of paragraph 15, wherein the trimer is administered with an adjuvant.

17. The method of paragraph 16, wherein the adjuvant comprises a lecithin.

18. The method of paragraph 17, wherein the lecithin is (a) combined with an acrylic polymer, (b) in a coated oil droplet in an oil-in-water emulsion or (c) in an acrylic polymer in an oil-in-water emulsion.

19. The method of paragraph 17, wherein the adjuvant is ISCOMATRIX or Adjuplex.

20. The method of paragraph 16, wherein the adjuvant comprises alum.

21. The method of any one of paragraphs 15-21, wherein the trimer is administered in a liposome or in a nanoparticle.

22. The method of any one of paragraphs 15-22, wherein the trimer is fixed.

23. The method of paragraph 22, wherein the trimer is fixed in glutaraldehyde.

24. The method of any one of paragraphs 15-23, wherein the trimer is quenched with glycine.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An engineered or non-naturally occurring trimer, wherein the trimer is a flexibly linked NFL2P trimer, wherein the trimer comprises one or more trimer-derived mutations ("TD mutations"), wherein said TD mutations comprise one or more mutations at residue 569 wherein a numerical position of an amino acid residue of the trimer corresponds with a numerical position of an amino acid residue of a 16055 NFL Env protein upon direct alignment of the numerical positions of the amino acid residues of the trimer with the numerical positions of the amino acid residues of the 16055 NFL Env protein, whose sequence is based on a BG505 numbering system.

2. The trimer of claim 1, wherein the one or more mutations at residue 569 comprises G.

3. The trimer of claim 1, wherein the trimer is derived from an Indian subtype C HIV-I Env sequence.

4. The trimer of claim 1, wherein the trimer further comprises a disulfide linkage.

5. The trimer of claim 4, wherein the disulfide linkage is an engineered intra-protomer disulfide I201C-A433C (CC).

6. The trimer of claim 1, further comprising a 10 residue (G4S) flexible linker (SEQ ID NO: 34) between a REKR-deleted Env gp120 C-terminus ("REKR" disclosed as SEQ ID NO: 35) and the unmodified gp41 N-terminus.

7. The trimer of claim 1, further comprising substitutions E47D, K49E, V65K, E106T, 1165L, E429R, R432Q and/or A500R.

8. The trimer of claim 1, wherein the trimer further comprises, in addition to said mutations, a T569G substitution.

9. The trimer of claim 1, wherein the trimer further comprises substitutions at residues 197, 276, 234, 262, 301, 360, 463 or any combination thereof.

10. The trimer of claim 9, comprising substitutions N197Q, N276Q, N234Q, N262Q, N301Q, N360Q, N463Q or any combination thereof.

11. The trimer of claim 9, comprising the substitutions at residues 276, 301, 360, 463 or any combination thereof.

12. The trimer of claim 10, comprising substitutions N276Q, N301Q, N360Q, N463Q or any combination thereof.

13. The trimer of claim 1, further comprising a potential N-linked glycan (PNGS) introduced at residue 332 by a K334S mutation ("+N332 PT"), wherein an italicized N within the amino acid sequence refers to an N-glycan, not an asparagine residue.

14. An engineered or non-naturally occurring trimer, wherein the trimer is a flexibly linked NFL2P trimer, wherein the trimer comprises a N276Q/N463Q glycan-deleted variant with or without N332 restored, a +N332 N276Q/N360Q/N463Q triple N-glycan-deleted variant or a +N332 N276Q/N360Q/N463Q/N301Q quadruple N-glycan-deleted variant wherein a numerical position of an amino acid residue of the trimer corresponds with a numerical position of an amino acid residue of a 16055 NFL Env protein upon direct alignment of the numerical positions of the amino acid residues of the trimer with the numerical positions of the amino acid residues of the 16055 NFL Env protein, whose sequence is based on a BG505 numbering system.

* * * * *

SEQUENCE LISTING

```
<160> NUMBER OF SEQ ID NOS: 44

<210> SEQ ID NO 1
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
    50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
        115                 120                 125

Thr Thr Asn Ala Thr Ser Ser Val Asn Val Thr Asn Gly Glu Glu Ile
    130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175
```

-continued

```
Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Ala Lys Arg Arg Val
                485                 490                 495

Val Glu Gly Gly Gly Gly Ser Gly Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Ser Asn Pro Leu Lys Ala Ile Glu Ala Gln Gln
545                 550                 555                 560

His Leu Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590
```

```
Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Leu Asp Gly Gly Gly Gly Ser His His His His His His
            660                 665                 670

His His


<210> SEQ ID NO 2
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
    50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
        115                 120                 125

Thr Thr Asn Ala Thr Ser Ser Val Asn Val Thr Asn Gly Glu Glu Ile
    130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270
```

-continued

```
Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Ala Lys Arg Arg Val
                485                 490                 495

Val Glu Gly Gly Gly Gly Ser Gly Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Pro Asn Leu Leu Lys Ala Ile Glu Ala Gln Gln
545                 550                 555                 560

His Leu Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Leu Asp Gly Gly Gly Gly Ser His His His His His His
            660                 665                 670

His His
```

<210> SEQ ID NO 3

<211> LENGTH: 674
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

```
Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
    50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
        115                 120                 125

Thr Thr Asn Ala Thr Ser Ser Val Asn Val Thr Asn Gly Glu Glu Ile
    130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
```

```
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Ala Lys Arg Arg Val
                485                 490                 495

Val Glu Gly Gly Gly Gly Ser Gly Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Ser Pro Leu Leu Lys Ala Ile Glu Ala Gln Gln
545                 550                 555                 560

His Leu Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Leu Asp Gly Gly Gly Gly Ser His His His His His His
            660                 665                 670

His His


<210> SEQ ID NO 4
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
```

-continued

```
    50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
        115                 120                 125

Thr Thr Asn Ala Thr Ser Ser Val Asn Val Thr Asn Gly Glu Glu Ile
    130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480
```

Glu Ile Lys Pro Leu Gly Ile Ala Pro Thr Ala Ala Lys Arg Arg Val
485 490 495

Val Glu Gly Gly Gly Gly Ser Gly Gly Gly Gly Ser Ala Val Gly Leu
500 505 510

Gly Ala Val Ile Phe Gly Phe Leu Gly Ala Ala Gly Ser Thr Met Gly
515 520 525

Ala Ala Ser Ile Thr Leu Thr Val Gln Ala Arg Gln Leu Leu Ser Gly
530 535 540

Ile Val Gln Gln Gln Ser Asn Leu Leu Lys Ala Ile Glu Ala Pro Gln
545 550 555 560

His Leu Leu Gln Leu Thr Val Trp Gly Ile Lys Gln Leu Gln Thr Arg
565 570 575

Val Leu Ala Ile Glu Arg Tyr Leu Lys Asp Gln Gln Leu Leu Gly Ile
580 585 590

Trp Gly Cys Ser Gly Lys Leu Ile Cys Thr Thr Ala Val Pro Trp Asn
595 600 605

Ser Ser Trp Ser Asn Lys Ser His Asp Glu Ile Trp Gly Asn Met Thr
610 615 620

Trp Met Gln Trp Asp Arg Glu Ile Ser Asn Tyr Thr Asn Thr Ile Tyr
625 630 635 640

Arg Leu Leu Glu Asp Ser Gln Asn Gln Gln Glu Gln Asn Glu Lys Asp
645 650 655

Leu Leu Ala Leu Asp Gly Gly Gly Gly Ser His His His His His His
660 665 670

His His

<210> SEQ ID NO 5
<211> LENGTH: 674
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

Met Pro Met Gly Ser Leu Gln Pro Leu Ala Thr Leu Tyr Leu Leu Gly
1 5 10 15

Met Leu Val Ala Ser Val Leu Ala Gly Asn Leu Trp Val Thr Val Tyr
20 25 30

Tyr Gly Val Pro Val Trp Lys Glu Ala Lys Thr Thr Leu Phe Cys Ala
35 40 45

Ser Asp Ala Lys Ala Tyr Glu Lys Glu Val His Asn Val Trp Ala Thr
50 55 60

His Ala Cys Val Pro Thr Asp Pro Asn Pro Gln Glu Met Val Leu Glu
65 70 75 80

Asn Val Thr Glu Asn Phe Asn Met Trp Lys Asn Asp Met Val Glu Gln
85 90 95

Met His Glu Asp Val Ile Ser Leu Trp Asp Gln Ser Leu Lys Pro Cys
100 105 110

Val Lys Leu Thr Pro Leu Cys Val Thr Leu Glu Cys Arg Gln Val Asn
115 120 125

Thr Thr Asn Ala Thr Ser Ser Val Asn Val Thr Asn Gly Glu Glu Ile
130 135 140

Lys Asn Cys Ser Phe Asn Ala Thr Thr Glu Ile Arg Asp Lys Lys Gln
145 150 155 160

-continued

```
Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Ala Lys Arg Arg Val
                485                 490                 495

Val Glu Gly Gly Gly Gly Ser Gly Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Ser Asn Leu Leu Lys Ala Ile Glu Ala Gln Pro
545                 550                 555                 560

His Leu Leu Gln Leu Thr Val Trp Gly Ile Lys Gln Leu Gln Thr Arg
                565                 570                 575
```

-continued

```
Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Leu Asp Gly Gly Gly Gly Ser His His His His His His
            660                 665                 670

His His


<210> SEQ ID NO 6
<211> LENGTH: 674
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Pro Met Gly Ser Leu Gln Pro Leu Ala Thr Leu Tyr Leu Leu Gly
1               5                   10                  15

Met Leu Val Ala Ser Val Leu Ala Gly Asn Leu Trp Val Thr Val Tyr
            20                  25                  30

Tyr Gly Val Pro Val Trp Lys Glu Ala Lys Thr Thr Leu Phe Cys Ala
        35                  40                  45

Ser Asp Ala Lys Ala Tyr Glu Lys Glu Val His Asn Val Trp Ala Thr
    50                  55                  60

His Ala Cys Val Pro Thr Asp Pro Asn Pro Gln Glu Met Val Leu Glu
65                  70                  75                  80

Asn Val Thr Glu Asn Phe Asn Met Trp Lys Asn Asp Met Val Glu Gln
                85                  90                  95

Met His Glu Asp Val Ile Ser Leu Trp Asp Gln Ser Leu Lys Pro Cys
            100                 105                 110

Val Lys Leu Thr Pro Leu Cys Val Thr Leu Glu Cys Arg Gln Val Asn
        115                 120                 125

Thr Thr Asn Ala Thr Ser Ser Val Asn Val Thr Asn Gly Glu Glu Ile
    130                 135                 140

Lys Asn Cys Ser Phe Asn Ala Thr Thr Glu Ile Arg Asp Lys Lys Gln
145                 150                 155                 160

Lys Val Tyr Ala Leu Phe Tyr Arg Leu Asp Ile Val Pro Leu Glu Glu
                165                 170                 175

Glu Arg Lys Gly Asn Ser Ser Lys Tyr Arg Leu Ile Asn Cys Asn Thr
            180                 185                 190

Ser Ala Ile Thr Gln Ala Cys Pro Lys Val Thr Phe Asp Pro Ile Pro
        195                 200                 205

Ile His Tyr Cys Ala Pro Ala Gly Tyr Ala Ile Leu Lys Cys Asn Asn
    210                 215                 220

Lys Thr Phe Asn Gly Thr Gly Pro Cys Asn Asn Val Ser Thr Val Gln
225                 230                 235                 240

Cys Thr His Gly Ile Lys Pro Val Val Ser Thr Gln Leu Leu Leu Asn
                245                 250                 255
```

```
Gly Ser Leu Ala Glu Gly Glu Ile Ile Ile Arg Ser Glu Asn Leu Thr
            260                 265                 270

Asn Asn Val Lys Thr Ile Ile Val His Leu Asn Glu Ser Val Glu Ile
        275                 280                 285

Val Cys Thr Arg Pro Asn Asn Asn Thr Arg Lys Ser Ile Arg Ile Gly
    290                 295                 300

Pro Gly Gln Thr Phe Tyr Ala Thr Gly Asp Ile Ile Gly Asn Ile Arg
305                 310                 315                 320

Gln Ala Tyr Cys Asn Ile Lys Lys Asp Asp Trp Ile Arg Thr Leu Gln
                325                 330                 335

Arg Val Gly Lys Lys Leu Ala Glu His Phe Pro Arg Arg Ile Ile Asn
            340                 345                 350

Phe Thr Ser Pro Ala Gly Gly Asp Leu Glu Ile Thr Thr His Ser Phe
        355                 360                 365

Asn Cys Arg Gly Glu Phe Phe Tyr Cys Asn Thr Ser Ser Leu Phe Asn
    370                 375                 380

Ser Thr Tyr Asn Pro Asn Asp Thr Asn Ser Asn Ser Ser Ser Ser Asn
385                 390                 395                 400

Ser Ser Leu Asp Ile Thr Ile Pro Cys Arg Ile Lys Gln Ile Ile Asn
                405                 410                 415

Met Trp Gln Glu Val Gly Arg Ala Met Tyr Ala Pro Pro Ile Glu Gly
            420                 425                 430

Asn Ile Thr Cys Lys Ser Asn Ile Thr Gly Leu Leu Leu Val Arg Asp
        435                 440                 445

Gly Gly Val Glu Ser Asn Glu Thr Glu Ile Phe Arg Pro Gly Gly Gly
    450                 455                 460

Asp Met Arg Asn Asn Trp Arg Ser Glu Leu Tyr Lys Tyr Lys Val Val
465                 470                 475                 480

Glu Ile Lys Pro Leu Gly Ile Ala Pro Thr Ala Cys Lys Arg Arg Val
                485                 490                 495

Val Glu Gly Gly Gly Gly Ser Gly Gly Gly Gly Ser Ala Val Gly Leu
            500                 505                 510

Gly Ala Val Ile Phe Gly Phe Leu Gly Ala Ala Gly Ser Thr Met Gly
        515                 520                 525

Ala Ala Ser Ile Thr Leu Thr Val Gln Ala Arg Gln Leu Leu Ser Gly
    530                 535                 540

Ile Val Gln Gln Gln Ser Asn Leu Leu Lys Ala Pro Glu Ala Gln Gln
545                 550                 555                 560

His Leu Leu Gln Leu Thr Val Trp Gly Ile Lys Gln Leu Gln Thr Arg
                565                 570                 575

Val Leu Ala Ile Glu Arg Tyr Leu Lys Asp Gln Gln Leu Leu Gly Ile
            580                 585                 590

Trp Gly Cys Ser Gly Lys Leu Ile Cys Thr Thr Ala Val Pro Trp Asn
        595                 600                 605

Ser Ser Trp Ser Asn Lys Ser His Asp Glu Ile Trp Gly Asn Met Thr
    610                 615                 620

Trp Met Gln Trp Asp Arg Glu Ile Ser Asn Tyr Thr Asn Thr Ile Tyr
625                 630                 635                 640

Arg Leu Leu Glu Asp Ser Gln Asn Gln Gln Glu Gln Asn Glu Lys Asp
                645                 650                 655

Leu Leu Ala Cys Asp Gly Gly Gly Gly Ser His His His His His His
            660                 665                 670

His His
```

<210> SEQ ID NO 7
<211> LENGTH: 680
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 7

```
Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Tyr Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
```

```
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Arg Val Gly Gln Cys Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Arg Cys Lys Arg Arg
                485                 490                 495

Val Val Glu Gly Gly Gly Gly Ser Gly Gly Gly Gly Ser Asp Asp Asp
            500                 505                 510

Asp Lys Ala Val Gly Leu Gly Ala Val Arg Arg Gly Phe Leu Gly Ala
        515                 520                 525

Ala Gly Ser Thr Met Gly Ala Ala Ser Ile Thr Leu Thr Val Gln Ala
    530                 535                 540

Arg Gln Leu Leu Ser Gly Ile Val Gln Gln Gln Ser Asn Leu Leu Lys
545                 550                 555                 560

Ala Pro Glu Ala Gln Gln His Leu Leu Gln Leu Gly Val Trp Gly Ile
                565                 570                 575

Lys Gln Leu Gln Thr Arg Val Leu Ala Ile Glu Arg Tyr Leu Lys Asp
            580                 585                 590

Gln Gln Leu Leu Gly Ile Trp Gly Cys Ser Gly Lys Leu Ile Cys Thr
        595                 600                 605

Thr Ala Val Pro Trp Asn Ser Ser Trp Ser Asn Lys Ser His Asp Glu
    610                 615                 620

Ile Trp Gly Asn Met Thr Trp Met Gln Trp Asp Arg Glu Ile Gly Asn
625                 630                 635                 640

Tyr Thr Asn Thr Ile Tyr Arg Leu Leu Glu Asp Ser Gln Asn Gln Gln
                645                 650                 655

Glu Gln Asn Glu Lys Asp Leu Leu Ala Cys Asp Gly Gly Gly Gly Ser
            660                 665                 670

His His His His His His His His
        675                 680


<210> SEQ ID NO 8
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30
```

-continued

```
Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Tyr Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Arg Val Gly Gln Cys Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
```

-continued 450 455 460

Gly Asp Met Arg Asn Asn Trp Arg Ser Glu Leu Tyr Lys Tyr Lys Val
465 470 475 480

Val Glu Ile Lys Pro Leu Gly Ile Ala Pro Thr Arg Cys Lys Arg Arg
485 490 495

Val Val Glu Gly Gly Gly Gly Ser Gly Gly Gly Gly Ser Asp Asp Asp
500 505 510

Asp Lys Ala Val Gly Leu Gly Ala Val Arg Arg Gly Phe Leu Gly Ala
515 520 525

Ala Gly Ser Thr Met Gly Ala Ala Ser Ile Thr Leu Thr Val Gln Ala
530 535 540

Arg Gln Leu Leu Ser Gly Ile Val Gln Gln Gln Ser Asn Pro Leu Lys
545 550 555 560

Ala Ile Glu Ala Gln Gln His Leu Leu Gln Leu Gly Val Trp Gly Ile
565 570 575

Lys Gln Leu Gln Thr Arg Val Leu Ala Ile Glu Arg Tyr Leu Lys Asp
580 585 590

Gln Gln Leu Leu Gly Ile Trp Gly Cys Ser Gly Lys Leu Ile Cys Thr
595 600 605

Thr Ala Val Pro Trp Asn Ser Ser Trp Ser Asn Lys Ser His Asp Glu
610 615 620

Ile Trp Gly Asn Met Thr Trp Met Gln Trp Asp Arg Glu Ile Gly Asn
625 630 635 640

Tyr Thr Asn Thr Ile Tyr Arg Leu Leu Glu Asp Ser Gln Asn Gln Gln
645 650 655

Glu Gln Asn Glu Lys Asp Leu Leu Ala Cys Asp Gly Gly Gly Gly Ser
660 665 670

His His His His His His His His
675 680

<210> SEQ ID NO 9
<211> LENGTH: 675
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Met Pro Met Gly Ser Leu Gln Pro Leu Ala Thr Leu Tyr Leu Leu Gly
1 5 10 15

Met Leu Val Ala Ser Val Leu Ala Ala Glu Asn Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Glu Thr Glu Lys His Asn Val Trp Ala
50 55 60

Thr His Ala Cys Val Pro Thr Asp Pro Asn Pro Gln Glu Ile His Leu
65 70 75 80

Glu Asn Val Thr Glu Glu Phe Asn Met Trp Lys Asn Asn Met Val Glu
85 90 95

Gln Met His Thr Asp Ile Ile Ser Leu Trp Asp Gln Ser Leu Lys Pro
100 105 110

Cys Val Lys Leu Thr Pro Leu Cys Val Thr Leu Gln Cys Thr Asn Val
115 120 125

```
Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Pro Leu Arg Ala Ile Glu Ala Gln
```

545 550 555 560

Gln His Leu Leu Lys Leu Thr Val Trp Gly Ile Lys Gln Leu Gln Ala
565 570 575

Arg Val Leu Ala Val Glu Arg Tyr Leu Arg Asp Gln Gln Leu Leu Gly
580 585 590

Ile Trp Gly Cys Ser Gly Lys Leu Ile Cys Thr Thr Asn Val Pro Trp
595 600 605

Asn Ser Ser Trp Ser Asn Arg Asn Leu Ser Glu Ile Trp Asp Asn Met
610 615 620

Thr Trp Leu Gln Trp Asp Lys Glu Ile Ser Asn Tyr Thr Gln Ile Ile
625 630 635 640

Tyr Gly Leu Leu Glu Glu Ser Gln Asn Gln Gln Glu Lys Asn Glu Gln
645 650 655

Asp Leu Leu Ala Leu Asp Gly Gly Gly Gly Ser His His His His His
660 665 670

His His His
675

<210> SEQ ID NO 10
<211> LENGTH: 675
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Met Pro Met Gly Ser Leu Gln Pro Leu Ala Thr Leu Tyr Leu Leu Gly
1 5 10 15

Met Leu Val Ala Ser Val Leu Ala Ala Glu Asn Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Glu Thr Glu Lys His Asn Val Trp Ala
50 55 60

Thr His Ala Cys Val Pro Thr Asp Pro Asn Pro Gln Glu Ile His Leu
65 70 75 80

Glu Asn Val Thr Glu Glu Phe Asn Met Trp Lys Asn Asn Met Val Glu
85 90 95

Gln Met His Thr Asp Ile Ile Ser Leu Trp Asp Gln Ser Leu Lys Pro
100 105 110

Cys Val Lys Leu Thr Pro Leu Cys Val Thr Leu Gln Cys Thr Asn Val
115 120 125

Thr Asn Asn Ile Thr Asp Asp Met Arg Gly Glu Leu Lys Asn Cys Ser
130 135 140

Phe Asn Met Thr Thr Glu Leu Arg Asp Lys Lys Gln Lys Val Tyr Ser
145 150 155 160

Leu Phe Tyr Arg Leu Asp Val Val Gln Ile Asn Glu Asn Gln Gly Asn
165 170 175

Arg Ser Asn Asn Ser Asn Lys Glu Tyr Arg Leu Ile Asn Cys Asn Thr
180 185 190

Ser Ala Ile Thr Gln Ala Cys Pro Lys Val Ser Phe Glu Pro Ile Pro
195 200 205

Ile His Tyr Cys Ala Pro Ala Gly Phe Ala Ile Leu Lys Cys Lys Asp
210 215 220

-continued

Lys Lys Phe Asn Gly Thr Gly Pro Cys Pro Ser Val Ser Thr Val Gln
225 230 235 240

Cys Thr His Gly Ile Lys Pro Val Val Ser Thr Gln Leu Leu Leu Asn
245 250 255

Gly Ser Leu Ala Glu Glu Glu Val Met Ile Arg Ser Glu Asn Ile Thr
260 265 270

Asn Asn Ala Lys Asn Ile Leu Val Gln Phe Asn Thr Pro Val Gln Ile
275 280 285

Asn Cys Thr Arg Pro Asn Asn Asn Thr Arg Lys Ser Ile Arg Ile Gly
290 295 300

Pro Gly Gln Ala Phe Tyr Ala Thr Gly Asp Ile Ile Gly Asp Ile Arg
305 310 315 320

Gln Ala His Cys Asn Val Ser Lys Ala Thr Trp Asn Glu Thr Leu Gly
325 330 335

Lys Val Val Lys Gln Leu Arg Lys His Phe Gly Asn Asn Thr Ile Ile
340 345 350

Arg Phe Ala Asn Ser Ser Gly Gly Asp Leu Glu Val Thr Thr His Ser
355 360 365

Phe Asn Cys Gly Gly Glu Phe Phe Tyr Cys Asn Thr Ser Gly Leu Phe
370 375 380

Asn Ser Thr Trp Ile Ser Asn Thr Ser Val Gln Gly Ser Asn Ser Thr
385 390 395 400

Gly Ser Asn Asp Ser Ile Thr Leu Pro Cys Arg Ile Lys Gln Ile Ile
405 410 415

Asn Met Trp Gln Arg Ile Gly Gln Ala Met Tyr Ala Pro Pro Ile Gln
420 425 430

Gly Val Ile Arg Cys Val Ser Asn Ile Thr Gly Leu Ile Leu Thr Arg
435 440 445

Asp Gly Gly Ser Thr Asn Ser Thr Thr Glu Thr Phe Arg Pro Gly Gly
450 455 460

Gly Asp Met Arg Asp Asn Trp Arg Ser Glu Leu Tyr Lys Tyr Lys Val
465 470 475 480

Val Lys Ile Glu Pro Leu Gly Val Ala Pro Thr Arg Ala Lys Arg Arg
485 490 495

Val Val Gly Gly Gly Gly Gly Ser Gly Gly Gly Gly Ser Ala Val Gly
500 505 510

Ile Gly Ala Val Phe Leu Gly Phe Leu Gly Ala Ala Gly Ser Thr Met
515 520 525

Gly Ala Ala Ser Met Thr Leu Thr Val Gln Ala Arg Asn Leu Leu Ser
530 535 540

Gly Ile Val Gln Gln Gln Pro Asn Leu Leu Arg Ala Ile Glu Ala Gln
545 550 555 560

Gln His Leu Leu Lys Leu Thr Val Trp Gly Ile Lys Gln Leu Gln Ala
565 570 575

Arg Val Leu Ala Val Glu Arg Tyr Leu Arg Asp Gln Gln Leu Leu Gly
580 585 590

Ile Trp Gly Cys Ser Gly Lys Leu Ile Cys Thr Thr Asn Val Pro Trp
595 600 605

Asn Ser Ser Trp Ser Asn Arg Asn Leu Ser Glu Ile Trp Asp Asn Met
610 615 620

Thr Trp Leu Gln Trp Asp Lys Glu Ile Ser Asn Tyr Thr Gln Ile Ile
625 630 635 640

Tyr Gly Leu Leu Glu Glu Ser Gln Asn Gln Gln Glu Lys Asn Glu Gln

-continued 645 650 655

Asp Leu Leu Ala Leu Asp Gly Gly Gly Gly Ser His His His His His
660 665 670

His His His
675

<210> SEQ ID NO 11
<211> LENGTH: 675
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Met Pro Met Gly Ser Leu Gln Pro Leu Ala Thr Leu Tyr Leu Leu Gly
1 5 10 15

Met Leu Val Ala Ser Val Leu Ala Ala Glu Asn Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Glu Thr Glu Lys His Asn Val Trp Ala
50 55 60

Thr His Ala Cys Val Pro Thr Asp Pro Asn Pro Gln Glu Ile His Leu
65 70 75 80

Glu Asn Val Thr Glu Glu Phe Asn Met Trp Lys Asn Asn Met Val Glu
85 90 95

Gln Met His Thr Asp Ile Ile Ser Leu Trp Asp Gln Ser Leu Lys Pro
100 105 110

Cys Val Lys Leu Thr Pro Leu Cys Val Thr Leu Gln Cys Thr Asn Val
115 120 125

Thr Asn Asn Ile Thr Asp Asp Met Arg Gly Glu Leu Lys Asn Cys Ser
130 135 140

Phe Asn Met Thr Thr Glu Leu Arg Asp Lys Lys Gln Lys Val Tyr Ser
145 150 155 160

Leu Phe Tyr Arg Leu Asp Val Val Gln Ile Asn Glu Asn Gln Gly Asn
165 170 175

Arg Ser Asn Asn Ser Asn Lys Glu Tyr Arg Leu Ile Asn Cys Asn Thr
180 185 190

Ser Ala Ile Thr Gln Ala Cys Pro Lys Val Ser Phe Glu Pro Ile Pro
195 200 205

Ile His Tyr Cys Ala Pro Ala Gly Phe Ala Ile Leu Lys Cys Lys Asp
210 215 220

Lys Lys Phe Asn Gly Thr Gly Pro Cys Pro Ser Val Ser Thr Val Gln
225 230 235 240

Cys Thr His Gly Ile Lys Pro Val Val Ser Thr Gln Leu Leu Leu Asn
245 250 255

Gly Ser Leu Ala Glu Glu Glu Val Met Ile Arg Ser Glu Asn Ile Thr
260 265 270

Asn Asn Ala Lys Asn Ile Leu Val Gln Phe Asn Thr Pro Val Gln Ile
275 280 285

Asn Cys Thr Arg Pro Asn Asn Asn Thr Arg Lys Ser Ile Arg Ile Gly
290 295 300

Pro Gly Gln Ala Phe Tyr Ala Thr Gly Asp Ile Ile Gly Asp Ile Arg
305 310 315 320

-continued

```
Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Pro Leu Leu Arg Ala Ile Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675
```

<210> SEQ ID NO 12
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

-continued

```
Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415
```

-continued

```
Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Ile Glu Ala Pro
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675


<210> SEQ ID NO 13
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95
```

-continued

```
Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510
```

```
Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Ile Glu Ala Gln
545                 550                 555                 560

Pro His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675


<210> SEQ ID NO 14
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190
```

-continued

```
Ser Ala Ile Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Asn Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Ala Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Cys Lys Arg Arg
                485                 490                 495

Val Val Gly Gly Gly Gly Gly Ser Gly Gly Gly Gly Ser Ala Val Gly
            500                 505                 510

Ile Gly Ala Val Phe Leu Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605
```

-continued

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Cys Asp Gly Gly Gly Gly Ser His His His His His
            660                 665                 670

His His His
        675

<210> SEQ ID NO 15
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Cys Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

```
Asn Cys Thr Arg Pro Asn Asn Tyr Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Cys Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Cys Lys Arg Arg
                485                 490                 495

Val Val Gly Gly Gly Gly Gly Ser Gly Gly Gly Gly Ser Asp Asp Asp
            500                 505                 510

Asp Lys Ala Val Gly Ile Gly Ala Val Arg Arg Gly Phe Leu Gly Ala
        515                 520                 525

Ala Gly Ser Thr Met Gly Ala Ala Ser Met Thr Leu Thr Val Gln Ala
    530                 535                 540

Arg Asn Leu Leu Ser Gly Ile Val Gln Gln Gln Ser Asn Leu Leu Arg
545                 550                 555                 560

Ala Pro Glu Ala Gln Gln His Leu Leu Lys Leu Thr Val Trp Gly Ile
                565                 570                 575

Lys Gln Leu Gln Ala Arg Val Leu Ala Val Glu Arg Tyr Leu Arg Asp
            580                 585                 590

Gln Gln Leu Leu Gly Ile Trp Gly Cys Ser Gly Lys Leu Ile Cys Thr
        595                 600                 605

Thr Asn Val Pro Trp Asn Ser Ser Trp Ser Asn Arg Asn Leu Ser Glu
    610                 615                 620

Ile Trp Asp Asn Met Thr Trp Leu Gln Trp Asp Lys Glu Ile Ser Asn
625                 630                 635                 640

Tyr Thr Gln Ile Ile Tyr Gly Leu Leu Glu Glu Ser Gln Asn Gln Gln
                645                 650                 655

Glu Lys Asn Glu Gln Asp Leu Leu Ala Cys Asp Gly Gly Gly Gly Ser
            660                 665                 670

His His His His His His His His
        675                 680
```

<210> SEQ ID NO 16
<211> LENGTH: 680

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

Met Pro Met Gly Ser Leu Gln Pro Leu Ala Thr Leu Tyr Leu Leu Gly
1 5 10 15

Met Leu Val Ala Ser Val Leu Ala Ala Glu Asn Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Glu Thr Glu Lys His Asn Val Trp Ala
50 55 60

Thr His Ala Cys Val Pro Thr Asp Pro Asn Pro Gln Glu Ile His Leu
65 70 75 80

Glu Asn Val Thr Glu Glu Phe Asn Met Trp Lys Asn Asn Met Val Glu
85 90 95

Gln Met His Thr Asp Ile Ile Ser Leu Trp Asp Gln Ser Leu Lys Pro
100 105 110

Cys Val Lys Leu Thr Pro Leu Cys Val Thr Leu Gln Cys Thr Asn Val
115 120 125

Thr Asn Asn Ile Thr Asp Asp Met Arg Gly Glu Leu Lys Asn Cys Ser
130 135 140

Phe Asn Met Thr Thr Glu Leu Arg Asp Lys Lys Gln Lys Val Tyr Ser
145 150 155 160

Leu Phe Tyr Arg Leu Asp Val Val Gln Ile Asn Glu Asn Gln Gly Asn
165 170 175

Arg Ser Asn Asn Ser Asn Lys Glu Tyr Arg Leu Ile Asn Cys Asn Thr
180 185 190

Ser Ala Cys Thr Gln Ala Cys Pro Lys Val Ser Phe Glu Pro Ile Pro
195 200 205

Ile His Tyr Cys Ala Pro Ala Gly Phe Ala Ile Leu Lys Cys Lys Asp
210 215 220

Lys Lys Phe Asn Gly Thr Gly Pro Cys Pro Ser Val Ser Thr Val Gln
225 230 235 240

Cys Thr His Gly Ile Lys Pro Val Val Ser Thr Gln Leu Leu Leu Asn
245 250 255

Gly Ser Leu Ala Glu Glu Glu Val Met Ile Arg Ser Glu Asn Ile Thr
260 265 270

Asn Asn Ala Lys Asn Ile Leu Val Gln Phe Asn Thr Pro Val Gln Ile
275 280 285

Asn Cys Thr Arg Pro Asn Asn Tyr Thr Arg Lys Ser Ile Arg Ile Gly
290 295 300

Pro Gly Gln Ala Phe Tyr Ala Thr Gly Asp Ile Ile Gly Asp Ile Arg
305 310 315 320

Gln Ala His Cys Asn Val Ser Lys Ala Thr Trp Asn Glu Thr Leu Gly
325 330 335

Lys Val Val Lys Gln Leu Arg Lys His Phe Gly Asn Asn Thr Ile Ile
340 345 350

Arg Phe Ala Asn Ser Ser Gly Gly Asp Leu Glu Val Thr Thr His Ser
355 360 365

Phe Asn Cys Gly Gly Glu Phe Phe Tyr Cys Asn Thr Ser Gly Leu Phe
370 375 380

```
Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Cys Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Cys Lys Arg Arg
                485                 490                 495

Val Val Gly Gly Gly Gly Gly Ser Gly Gly Gly Gly Ser Asp Asp Asp
            500                 505                 510

Asp Lys Ala Val Gly Ile Gly Ala Val Arg Arg Gly Phe Leu Gly Ala
        515                 520                 525

Ala Gly Ser Thr Met Gly Ala Ala Ser Met Thr Leu Thr Val Gln Ala
    530                 535                 540

Arg Asn Leu Leu Ser Gly Ile Val Gln Gln Gln Ser Asn Pro Leu Arg
545                 550                 555                 560

Ala Ile Glu Ala Gln Gln His Leu Leu Lys Leu Thr Val Trp Gly Ile
                565                 570                 575

Lys Gln Leu Gln Ala Arg Val Leu Ala Val Glu Arg Tyr Leu Arg Asp
            580                 585                 590

Gln Gln Leu Leu Gly Ile Trp Gly Cys Ser Gly Lys Leu Ile Cys Thr
        595                 600                 605

Thr Asn Val Pro Trp Asn Ser Ser Trp Ser Asn Arg Asn Leu Ser Glu
    610                 615                 620

Ile Trp Asp Asn Met Thr Trp Leu Gln Trp Asp Lys Glu Ile Ser Asn
625                 630                 635                 640

Tyr Thr Gln Ile Ile Tyr Gly Leu Leu Glu Glu Ser Gln Asn Gln Gln
                645                 650                 655

Glu Lys Asn Glu Gln Asp Leu Leu Ala Cys Asp Gly Gly Gly Gly Ser
            660                 665                 670

His His His His His His His His
        675                 680
```

```
<210> SEQ ID NO 17
<211> LENGTH: 669
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
```

-continued

```
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Ser Ile Arg Asp Lys
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480
```

```
Gly Val Ala Pro Thr Lys Cys Lys Arg Arg Val Val Gln Gly Gly Gly
                485                 490                 495

Gly Ser Gly Gly Gly Gly Ser Ala Val Gly Ile Gly Ala Val Phe Leu
            500                 505                 510

Gly Phe Leu Gly Ala Ala Gly Ser Thr Met Gly Ala Ala Ser Met Thr
        515                 520                 525

Leu Thr Val Gln Ala Arg Leu Leu Leu Ser Gly Ile Val Gln Gln Gln
    530                 535                 540

Asn Asn Leu Leu Arg Ala Pro Glu Ala Gln Gln Arg Met Leu Gln Leu
545                 550                 555                 560

Thr Val Trp Gly Ile Lys Gln Leu Gln Ala Arg Val Leu Ala Val Glu
                565                 570                 575

Arg Tyr Leu Gly Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Glu Cys Asp
                645                 650                 655

Gly Gly Gly Gly Ser His His His His His His His His
            660                 665


<210> SEQ ID NO 18
<211> LENGTH: 1013
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Glu Leu Arg Asp Lys
145                 150                 155                 160

Val Gln Lys Val Tyr Ala Leu Phe Tyr Lys Leu Asp Val Val Pro Ile
```

-continued

```
                165                 170                 175

Asp Asn Asn Asn Thr Ser Tyr Arg Leu Ile Ser Cys Asp Thr Ser Val
            180                 185                 190

Cys Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Tyr Thr Arg Lys Ser Ile Arg Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Cys Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Arg Arg
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Pro Glu Ala Gln Gln Arg Met Leu Gln Leu
545                 550                 555                 560

Gly Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590
```

-continued

```
Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Ala Leu Asp
                645                 650                 655

Gly Ser Gly Gly Gly Gly Ser Gly Gly Gly Gly Ser Gly Ser Gly Gly
            660                 665                 670

Ser Gly Gly Gly Gly Ser Gly Gly Ser Gly Gly Ser Gly Ser Gly Gly
        675                 680                 685

Gly Gly Ser Gly Gly Gly Gly Ser Gly Ser Gly Gly Gly Gly Gly Gly
    690                 695                 700

Gly Ser Gly Gly Gly Gly Ser Gly Gly Gly Gly Ser Thr Pro Ala Gly
705                 710                 715                 720

Ser Gly Glu Gln His Met Ile Gly Met Thr Pro Thr Val Ile Ala Val
                725                 730                 735

His Tyr Leu Asp Gln Thr Glu Gln Trp Gly Lys Phe Gly Ile Glu Lys
            740                 745                 750

Arg Gln Glu Ala Leu Glu Leu Ile Lys Lys Gly Tyr Thr Gln Gln Leu
        755                 760                 765

Ala Phe Lys Gln Pro Ser Ser Ala Tyr Ala Ala Phe Asn Asn Arg Pro
    770                 775                 780

Pro Ser Thr Trp Leu Thr Ala Tyr Val Val Lys Val Phe Ser Leu Ala
785                 790                 795                 800

Ala Asn Leu Ile Ala Ile Asp Ser His Val Leu Cys Gly Ala Val Lys
                805                 810                 815

Trp Leu Ile Leu Glu Lys Gln Lys Pro Asp Gly Val Phe Gln Glu Asp
            820                 825                 830

Gly Pro Val Ile His Gln Glu Met Ile Gly Gly Phe Arg Asn Ala Lys
        835                 840                 845

Glu Ala Asp Val Ser Leu Thr Ala Phe Val Leu Ile Ala Leu Gln Glu
    850                 855                 860

Ala Arg Asp Ile Cys Glu Gly Gln Val Asn Ser Leu Pro Gly Ser Ile
865                 870                 875                 880

Asn Lys Ala Gly Glu Tyr Ile Glu Ala Ser Tyr Met Asn Leu Gln Arg
                885                 890                 895

Pro Tyr Thr Val Ala Ile Ala Gly Tyr Ala Leu Ala Leu Met Asn Lys
            900                 905                 910

Leu Glu Glu Pro Tyr Leu Gly Lys Phe Leu Asn Thr Ala Lys Asp Arg
        915                 920                 925

Asn Arg Trp Glu Glu Pro Asp Gln Gln Leu Tyr Asn Val Glu Ala Thr
    930                 935                 940

Ser Tyr Ala Leu Leu Ala Leu Leu Leu Leu Lys Asp Phe Asp Ser Val
945                 950                 955                 960

Pro Pro Val Val Arg Trp Leu Asn Glu Gln Arg Tyr Tyr Gly Gly Gly
                965                 970                 975

Tyr Gly Ser Thr Gln Ala Thr Phe Met Val Phe Gln Ala Leu Ala Gln
            980                 985                 990

Tyr Gln Thr Asp Val Pro Asp His  Lys Asp Leu Asn Met  Asp Val Ser
        995                 1000                1005
```

Phe His Leu Pro Ser
    1010

<210> SEQ ID NO 19
<211> LENGTH: 983
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Glu Leu Arg Asp Lys
145                 150                 155                 160

Val Gln Lys Val Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Cys Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Tyr Thr Arg Lys Ser Ile Arg Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350
```

-continued

```
His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Cys Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Arg Arg
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Pro Glu Ala Gln Gln Arg Met Leu Gln Leu
545                 550                 555                 560

Gly Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Ala Leu Asp
                645                 650                 655

Gly Ser Gly Gly Gly Gly Ser Gly Gly Gly Gly Ser Gly Ser Gly Gly
            660                 665                 670

Ser Gly Gly Gly Gly Ser Gly Gly Ser Gly Gly Ser Gly Ser Thr Pro
        675                 680                 685

Ala Gly Ser Gly Glu Gln His Met Ile Gly Met Thr Pro Thr Val Ile
    690                 695                 700

Ala Val His Tyr Leu Asp Gln Thr Glu Gln Trp Gly Lys Phe Gly Ile
705                 710                 715                 720

Glu Lys Arg Gln Glu Ala Leu Glu Leu Ile Lys Lys Gly Tyr Thr Gln
                725                 730                 735

Gln Leu Ala Phe Lys Gln Pro Ser Ser Ala Tyr Ala Ala Phe Asn Asn
            740                 745                 750

Arg Pro Pro Ser Thr Trp Leu Thr Ala Tyr Val Val Lys Val Phe Ser
        755                 760                 765
```

Leu Ala Ala Asn Leu Ile Ala Ile Asp Ser His Val Leu Cys Gly Ala
    770                 775                 780

Val Lys Trp Leu Ile Leu Glu Lys Gln Lys Pro Asp Gly Val Phe Gln
785                 790                 795                 800

Glu Asp Gly Pro Val Ile His Gln Glu Met Ile Gly Gly Phe Arg Asn
                805                 810                 815

Ala Lys Glu Ala Asp Val Ser Leu Thr Ala Phe Val Leu Ile Ala Leu
            820                 825                 830

Gln Glu Ala Arg Asp Ile Cys Glu Gly Gln Val Asn Ser Leu Pro Gly
        835                 840                 845

Ser Ile Asn Lys Ala Gly Glu Tyr Ile Glu Ala Ser Tyr Met Asn Leu
    850                 855                 860

Gln Arg Pro Tyr Thr Val Ala Ile Ala Gly Tyr Ala Leu Ala Leu Met
865                 870                 875                 880

Asn Lys Leu Glu Glu Pro Tyr Leu Gly Lys Phe Leu Asn Thr Ala Lys
                885                 890                 895

Asp Arg Asn Arg Trp Glu Glu Pro Asp Gln Gln Leu Tyr Asn Val Glu
            900                 905                 910

Ala Thr Ser Tyr Ala Leu Leu Ala Leu Leu Leu Leu Lys Asp Phe Asp
        915                 920                 925

Ser Val Pro Pro Val Val Arg Trp Leu Asn Glu Gln Arg Tyr Tyr Gly
    930                 935                 940

Gly Gly Tyr Gly Ser Thr Gln Ala Thr Phe Met Val Phe Gln Ala Leu
945                 950                 955                 960

Ala Gln Tyr Gln Thr Asp Val Pro Asp His Lys Asp Leu Asn Met Asp
                965                 970                 975

Val Ser Phe His Leu Pro Ser
            980

<210> SEQ ID NO 20
<211> LENGTH: 1011
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Pro Met Gly Ser Leu Gln Pro Leu Ala Thr Leu Tyr Leu Leu Gly
1               5                   10                  15

Met Leu Val Ala Ser Val Leu Ala Val Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu Asn Phe Asn Met Trp Lys Asn Asp Met Val Asp
                85                  90                  95

Gln Met Gln Thr Asp Val Ile Ser Ile Trp Asp Gln Ser Leu Lys Pro
            100                 105                 110

Cys Val Lys Leu Thr Pro Leu Cys Val Thr Leu Asn Cys Thr Asn Val
        115                 120                 125

Asn Val Thr Ser Asn Ser Thr Asn Val Asn Ser Ser Ser Thr Asp Asn
    130                 135                 140

-continued

```
Thr Thr Leu Gly Glu Ile Lys Asn Cys Ser Phe Asn Ile Thr Thr Glu
145                 150                 155                 160

Leu Arg Asp Lys Thr Arg Lys Val Tyr Ala Leu Phe Tyr Arg Leu Asp
                165                 170                 175

Ile Val Pro Leu Asp Asn Ser Ser Asn Pro Asn Ser Ser Asn Thr Tyr
            180                 185                 190

Arg Leu Ile Asn Cys Asn Thr Ser Thr Leu Thr Gln Ala Cys Pro Lys
        195                 200                 205

Val Thr Phe Asp Pro Ile Pro Ile His Tyr Cys Ala Pro Ala Gly Tyr
    210                 215                 220

Ala Ile Leu Lys Cys Asn Asn Lys Thr Phe Asn Gly Lys Gly Pro Cys
225                 230                 235                 240

Asn Asn Val Ser Thr Val Gln Cys Thr His Gly Ile Lys Pro Val Val
                245                 250                 255

Ser Thr Gln Leu Leu Leu Asn Gly Ser Leu Ala Glu Glu Glu Ile Val
            260                 265                 270

Ile Arg Ser Lys Asn Leu Arg Asp Asn Ala Lys Ile Ile Ile Val Gln
        275                 280                 285

Leu Asn Lys Ser Val Glu Ile Val Cys Thr Arg Pro Asn Asn Tyr Thr
    290                 295                 300

Arg Arg Ser Ile Arg Ile Gly Pro Gly Gln Thr Phe Tyr Ala Thr Asp
305                 310                 315                 320

Ile Ile Gly Asp Ile Arg Gln Ala Tyr Cys Asn Ile Ser Gly Arg Asn
                325                 330                 335

Trp Ser Glu Ala Val Asn Gln Val Lys Lys Lys Leu Lys Glu His Phe
            340                 345                 350

Pro His Lys Asn Ile Ser Phe Gln Ser Ser Ser Gly Gly Asp Leu Glu
        355                 360                 365

Ile Thr Thr His Ser Phe Asn Cys Gly Gly Glu Phe Phe Tyr Cys Asn
    370                 375                 380

Thr Ser Gly Leu Phe Asn Asp Thr Ile Ser Asn Ala Thr Ile Met Leu
385                 390                 395                 400

Pro Cys Arg Ile Lys Gln Ile Ile Asn Met Trp Gln Arg Val Gly Gln
                405                 410                 415

Ala Ile Tyr Ala Pro Pro Ile Lys Gly Asn Ile Thr Cys Lys Ser Asp
            420                 425                 430

Ile Thr Gly Leu Leu Leu Leu Arg Asp Gly Gly Asn Thr Ala Asn Asn
        435                 440                 445

Ala Glu Ile Phe Arg Pro Gly Gly Gly Asp Met Arg Asp Asn Trp Arg
    450                 455                 460

Ser Glu Leu Tyr Lys Tyr Lys Val Val Glu Ile Lys Pro Leu Gly Val
465                 470                 475                 480

Ala Pro Thr Arg Ala Lys Arg Arg Val Val Glu Gly Gly Gly Gly Ser
                485                 490                 495

Gly Gly Gly Gly Ser Ala Val Gly Ile Gly Ala Val Arg Arg Gly Phe
            500                 505                 510

Leu Gly Ala Ala Gly Ser Thr Met Gly Ala Ala Ser Ile Thr Leu Thr
        515                 520                 525

Val Gln Ala Arg Gln Gly Leu Ser Gly Ile Val Gln Gln Gln Ser Asn
    530                 535                 540

Leu Leu Arg Ala Pro Glu Ala Gln Gln His Met Leu Gln Leu Gly Val
545                 550                 555                 560
```

-continued

```
Trp Gly Ile Lys Gln Leu Gln Thr Arg Val Leu Ala Ile Glu Arg Tyr
                565                 570                 575

Leu Lys Asp Gln Gln Leu Leu Gly Leu Trp Gly Cys Ser Gly Lys Leu
            580                 585                 590

Ile Cys Thr Thr Ala Val Pro Trp Asn Ile Ser Trp Ser Asn Lys Ser
        595                 600                 605

Lys Glu Glu Ile Trp Glu Asn Met Thr Trp Met Gln Trp Asp Arg Glu
    610                 615                 620

Ile Gly Asn Tyr Thr Asn Thr Ile Tyr Arg Leu Leu Glu Glu Ser Gln
625                 630                 635                 640

Asn Gln Gln Glu Asn Asn Glu Lys Asp Leu Leu Ala Leu Asp Gly Ser
                645                 650                 655

Gly Gly Gly Gly Ser Gly Gly Gly Gly Ser Gly Ser Gly Gly Ser Gly
            660                 665                 670

Gly Gly Gly Ser Gly Gly Ser Gly Gly Ser Gly Ser Gly Gly Gly Gly
        675                 680                 685

Ser Gly Gly Gly Gly Ser Gly Ser Gly Gly Gly Gly Gly Gly Gly Ser
    690                 695                 700

Gly Gly Gly Gly Ser Gly Gly Gly Gly Ser Thr Pro Ala Gly Ser Gly
705                 710                 715                 720

Glu Gln His Met Ile Gly Met Thr Pro Thr Val Ile Ala Val His Tyr
                725                 730                 735

Leu Asp Gln Thr Glu Gln Trp Gly Lys Phe Gly Ile Glu Lys Arg Gln
            740                 745                 750

Glu Ala Leu Glu Leu Ile Lys Lys Gly Tyr Thr Gln Gln Leu Ala Phe
        755                 760                 765

Lys Gln Pro Ser Ser Ala Tyr Ala Ala Phe Asn Asn Arg Pro Pro Ser
    770                 775                 780

Thr Trp Leu Thr Ala Tyr Val Val Lys Val Phe Ser Leu Ala Ala Asn
785                 790                 795                 800

Leu Ile Ala Ile Asp Ser His Val Leu Cys Gly Ala Val Lys Trp Leu
                805                 810                 815

Ile Leu Glu Lys Gln Lys Pro Asp Gly Val Phe Gln Glu Asp Gly Pro
            820                 825                 830

Val Ile His Gln Glu Met Ile Gly Gly Phe Arg Asn Ala Lys Glu Ala
        835                 840                 845

Asp Val Ser Leu Thr Ala Phe Val Leu Ile Ala Leu Gln Glu Ala Arg
    850                 855                 860

Asp Ile Cys Glu Gly Gln Val Asn Ser Leu Pro Gly Ser Ile Asn Lys
865                 870                 875                 880

Ala Gly Glu Tyr Ile Glu Ala Ser Tyr Met Asn Leu Gln Arg Pro Tyr
                885                 890                 895

Thr Val Ala Ile Ala Gly Tyr Ala Leu Ala Leu Met Asn Lys Leu Glu
            900                 905                 910

Glu Pro Tyr Leu Gly Lys Phe Leu Asn Thr Ala Lys Asp Arg Asn Arg
        915                 920                 925

Trp Glu Glu Pro Asp Gln Gln Leu Tyr Asn Val Glu Ala Thr Ser Tyr
    930                 935                 940

Ala Leu Leu Ala Leu Leu Leu Leu Lys Asp Phe Asp Ser Val Pro Pro
945                 950                 955                 960

Val Val Arg Trp Leu Asn Glu Gln Arg Tyr Tyr Gly Gly Gly Tyr Gly
                965                 970                 975

Ser Thr Gln Ala Thr Phe Met Val Phe Gln Ala Leu Ala Gln Tyr Gln
```

980 985 990

Thr Asp Val Pro Asp His Lys Asp Leu Asn Met Asp Val Ser Phe His
995 1000 1005

Leu Pro Ser
1010

<210> SEQ ID NO 21
<211> LENGTH: 981
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Met Pro Met Gly Ser Leu Gln Pro Leu Ala Thr Leu Tyr Leu Leu Gly
1 5 10 15

Met Leu Val Ala Ser Val Leu Ala Val Gly Asn Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Glu Lys Glu Lys His Asn Val Trp Ala
50 55 60

Thr His Ala Cys Val Pro Thr Asp Pro Asn Pro Gln Glu Val Val Leu
65 70 75 80

Glu Asn Val Thr Glu Asn Phe Asn Met Trp Lys Asn Asp Met Val Asp
85 90 95

Gln Met Gln Thr Asp Val Ile Ser Ile Trp Asp Gln Ser Leu Lys Pro
100 105 110

Cys Val Lys Leu Thr Pro Leu Cys Val Thr Leu Asn Cys Thr Asn Val
115 120 125

Asn Val Thr Ser Asn Ser Thr Asn Val Asn Ser Ser Ser Thr Asp Asn
130 135 140

Thr Thr Leu Gly Glu Ile Lys Asn Cys Ser Phe Asn Ile Thr Thr Glu
145 150 155 160

Leu Arg Asp Lys Thr Arg Lys Val Tyr Ala Leu Phe Tyr Arg Leu Asp
165 170 175

Ile Val Pro Leu Asp Asn Ser Ser Asn Pro Asn Ser Ser Asn Thr Tyr
180 185 190

Arg Leu Ile Asn Cys Asn Thr Ser Thr Leu Thr Gln Ala Cys Pro Lys
195 200 205

Val Thr Phe Asp Pro Ile Pro Ile His Tyr Cys Ala Pro Ala Gly Tyr
210 215 220

Ala Ile Leu Lys Cys Asn Asn Lys Thr Phe Asn Gly Lys Gly Pro Cys
225 230 235 240

Asn Asn Val Ser Thr Val Gln Cys Thr His Gly Ile Lys Pro Val Val
245 250 255

Ser Thr Gln Leu Leu Leu Asn Gly Ser Leu Ala Glu Glu Glu Ile Val
260 265 270

Ile Arg Ser Lys Asn Leu Arg Asp Asn Ala Lys Ile Ile Ile Val Gln
275 280 285

Leu Asn Lys Ser Val Glu Ile Val Cys Thr Arg Pro Asn Asn Tyr Thr
290 295 300

Arg Arg Ser Ile Arg Ile Gly Pro Gly Gln Thr Phe Tyr Ala Thr Asp
305 310 315 320

-continued

```
Ile Ile Gly Asp Ile Arg Gln Ala Tyr Cys Asn Ile Ser Gly Arg Asn
                325                 330                 335

Trp Ser Glu Ala Val Asn Gln Val Lys Lys Lys Leu Lys Glu His Phe
            340                 345                 350

Pro His Lys Asn Ile Ser Phe Gln Ser Ser Ser Gly Gly Asp Leu Glu
        355                 360                 365

Ile Thr Thr His Ser Phe Asn Cys Gly Gly Glu Phe Phe Tyr Cys Asn
    370                 375                 380

Thr Ser Gly Leu Phe Asn Asp Thr Ile Ser Asn Ala Thr Ile Met Leu
385                 390                 395                 400

Pro Cys Arg Ile Lys Gln Ile Ile Asn Met Trp Gln Arg Val Gly Gln
                405                 410                 415

Ala Ile Tyr Ala Pro Pro Ile Lys Gly Asn Ile Thr Cys Lys Ser Asp
            420                 425                 430

Ile Thr Gly Leu Leu Leu Leu Arg Asp Gly Gly Asn Thr Ala Asn Asn
        435                 440                 445

Ala Glu Ile Phe Arg Pro Gly Gly Gly Asp Met Arg Asp Asn Trp Arg
    450                 455                 460

Ser Glu Leu Tyr Lys Tyr Lys Val Val Glu Ile Lys Pro Leu Gly Val
465                 470                 475                 480

Ala Pro Thr Arg Ala Lys Arg Arg Val Val Glu Gly Gly Gly Gly Ser
                485                 490                 495

Gly Gly Gly Gly Ser Ala Val Gly Ile Gly Ala Val Arg Arg Gly Phe
            500                 505                 510

Leu Gly Ala Ala Gly Ser Thr Met Gly Ala Ala Ser Ile Thr Leu Thr
        515                 520                 525

Val Gln Ala Arg Gln Gly Leu Ser Gly Ile Val Gln Gln Gln Ser Asn
    530                 535                 540

Leu Leu Arg Ala Pro Glu Ala Gln Gln His Met Leu Gln Leu Gly Val
545                 550                 555                 560

Trp Gly Ile Lys Gln Leu Gln Thr Arg Val Leu Ala Ile Glu Arg Tyr
                565                 570                 575

Leu Lys Asp Gln Gln Leu Leu Gly Leu Trp Gly Cys Ser Gly Lys Leu
            580                 585                 590

Ile Cys Thr Thr Ala Val Pro Trp Asn Ile Ser Trp Ser Asn Lys Ser
        595                 600                 605

Lys Glu Glu Ile Trp Glu Asn Met Thr Trp Met Gln Trp Asp Arg Glu
    610                 615                 620

Ile Gly Asn Tyr Thr Asn Thr Ile Tyr Arg Leu Leu Glu Glu Ser Gln
625                 630                 635                 640

Asn Gln Gln Glu Asn Asn Glu Lys Asp Leu Leu Ala Leu Asp Gly Ser
                645                 650                 655

Gly Gly Gly Gly Ser Gly Gly Gly Gly Ser Gly Ser Gly Gly Ser Gly
            660                 665                 670

Gly Gly Gly Ser Gly Gly Ser Gly Gly Ser Gly Ser Thr Pro Ala Gly
        675                 680                 685

Ser Gly Glu Gln His Met Ile Gly Met Thr Pro Thr Val Ile Ala Val
    690                 695                 700

His Tyr Leu Asp Gln Thr Glu Gln Trp Gly Lys Phe Gly Ile Glu Lys
705                 710                 715                 720

Arg Gln Glu Ala Leu Glu Leu Ile Lys Lys Gly Tyr Thr Gln Gln Leu
                725                 730                 735

Ala Phe Lys Gln Pro Ser Ser Ala Tyr Ala Ala Phe Asn Asn Arg Pro
```

```
            740                 745                 750

Pro Ser Thr Trp Leu Thr Ala Tyr Val Val Lys Val Phe Ser Leu Ala
        755                 760                 765

Ala Asn Leu Ile Ala Ile Asp Ser His Val Leu Cys Gly Ala Val Lys
    770                 775                 780

Trp Leu Ile Leu Glu Lys Gln Lys Pro Asp Gly Val Phe Gln Glu Asp
785                 790                 795                 800

Gly Pro Val Ile His Gln Glu Met Ile Gly Gly Phe Arg Asn Ala Lys
                805                 810                 815

Glu Ala Asp Val Ser Leu Thr Ala Phe Val Leu Ile Ala Leu Gln Glu
            820                 825                 830

Ala Arg Asp Ile Cys Glu Gly Gln Val Asn Ser Leu Pro Gly Ser Ile
        835                 840                 845

Asn Lys Ala Gly Glu Tyr Ile Glu Ala Ser Tyr Met Asn Leu Gln Arg
    850                 855                 860

Pro Tyr Thr Val Ala Ile Ala Gly Tyr Ala Leu Ala Leu Met Asn Lys
865                 870                 875                 880

Leu Glu Glu Pro Tyr Leu Gly Lys Phe Leu Asn Thr Ala Lys Asp Arg
                885                 890                 895

Asn Arg Trp Glu Glu Pro Asp Gln Gln Leu Tyr Asn Val Glu Ala Thr
            900                 905                 910

Ser Tyr Ala Leu Leu Ala Leu Leu Leu Leu Lys Asp Phe Asp Ser Val
        915                 920                 925

Pro Pro Val Val Arg Trp Leu Asn Glu Gln Arg Tyr Tyr Gly Gly Gly
    930                 935                 940

Tyr Gly Ser Thr Gln Ala Thr Phe Met Val Phe Gln Ala Leu Ala Gln
945                 950                 955                 960

Tyr Gln Thr Asp Val Pro Asp His Lys Asp Leu Asn Met Asp Val Ser
                965                 970                 975

Phe His Leu Pro Ser
            980


<210> SEQ ID NO 22
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110
```

-continued

```
Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Tyr Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Arg Val Gly Gln Cys Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Arg Ala Lys Arg Arg
                485                 490                 495

Val Val Glu Gly Gly Gly Gly Ser Gly Gly Gly Gly Ser Ala Val Gly
            500                 505                 510

Leu Gly Ala Val Arg Arg Gly Phe Leu Gly Ala Ala Gly Ser Thr Met
        515                 520                 525

Gly Ala Ala Ser Ile Thr Leu Thr Val Gln Ala Arg Gln Leu Leu Ser
```

```
    530                 535                 540

Gly Ile Val Gln Gln Gln Ser Asn Leu Leu Lys Ala Pro Glu Ala Gln
545                 550                 555                 560

Gln His Leu Leu Gln Leu Gly Val Trp Gly Ile Lys Gln Leu Gln Thr
                565                 570                 575

Arg Val Leu Ala Ile Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ser Ser Trp Ser Asn Lys Ser His Asp Glu Ile Trp Gly Asn Met
    610                 615                 620

Thr Trp Met Gln Trp Asp Arg Glu Ile Gly Asn Tyr Thr Asn Thr Ile
625                 630                 635                 640

Tyr Arg Leu Leu Glu Asp Ser Gln Asn Gln Gln Glu Gln Asn Glu Lys
                645                 650                 655

Asp Leu Leu Ala Leu Asp Gly Gly Gly Gly Ser His His His His His
            660                 665                 670

His His His
        675


<210> SEQ ID NO 23
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205
```

-continued

```
Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Gln Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Tyr Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Asn Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Arg Val Gly Gln Cys Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Asn Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Arg Ala Lys Arg Arg
                485                 490                 495

Val Val Glu Gly Gly Gly Gly Ser Gly Gly Gly Gly Ser Ala Val Gly
            500                 505                 510

Leu Gly Ala Val Arg Arg Gly Phe Leu Gly Ala Ala Gly Ser Thr Met
        515                 520                 525

Gly Ala Ala Ser Ile Thr Leu Thr Val Gln Ala Arg Gln Leu Leu Ser
    530                 535                 540

Gly Ile Val Gln Gln Gln Ser Asn Leu Leu Lys Ala Pro Glu Ala Gln
545                 550                 555                 560

Gln His Leu Leu Gln Leu Gly Val Trp Gly Ile Lys Gln Leu Gln Thr
                565                 570                 575

Arg Val Leu Ala Ile Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ser Ser Trp Ser Asn Lys Ser His Asp Glu Ile Trp Gly Asn Met
    610                 615                 620

Thr Trp Met Gln Trp Asp Arg Glu Ile Gly Asn Tyr Thr Asn Thr Ile
```

-continued

```
625                 630                 635                 640

Tyr Arg Leu Leu Glu Asp Ser Gln Asn Gln Gln Glu Gln Asn Glu Lys
                645                 650                 655

Asp Leu Leu Ala Leu Asp Gly Gly Gly Gly Ser His His His His His
            660                 665                 670

His His His
        675


<210> SEQ ID NO 24
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Gln Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Tyr Thr Arg Lys Ser Ile Arg Ile
    290                 295                 300
```

-continued

Gly Pro Gly Gln Thr Phe Tyr Ala Thr Gly Asp Ile Ile Gly Asn Ile
305 310 315 320

Arg Gln Ala Tyr Cys Asn Ile Ser Lys Asp Asp Trp Ile Arg Thr Leu
325 330 335

Gln Arg Val Gly Lys Lys Leu Ala Glu His Phe Pro Arg Arg Ile Ile
340 345 350

Asn Phe Thr Ser Pro Ala Gly Gly Asp Leu Glu Ile Thr Thr His Ser
355 360 365

Phe Asn Cys Arg Gly Glu Phe Phe Tyr Cys Asn Thr Ser Ser Leu Phe
370 375 380

Asn Ser Thr Tyr Asn Pro Asn Asp Thr Asn Ser Asn Ser Ser Ser Ser
385 390 395 400

Asn Ser Ser Leu Asp Ile Thr Ile Pro Cys Arg Ile Lys Gln Ile Ile
405 410 415

Asn Met Trp Gln Arg Val Gly Gln Cys Met Tyr Ala Pro Pro Ile Glu
420 425 430

Gly Asn Ile Thr Cys Lys Ser Asn Ile Thr Gly Leu Leu Leu Val Arg
435 440 445

Asp Gly Gly Val Glu Ser Gln Glu Thr Glu Ile Phe Arg Pro Gly Gly
450 455 460

Gly Asp Met Arg Asn Asn Trp Arg Ser Glu Leu Tyr Lys Tyr Lys Val
465 470 475 480

Val Glu Ile Lys Pro Leu Gly Ile Ala Pro Thr Arg Ala Lys Arg Arg
485 490 495

Val Val Glu Gly Gly Gly Gly Ser Gly Gly Gly Gly Ser Ala Val Gly
500 505 510

Leu Gly Ala Val Arg Arg Gly Phe Leu Gly Ala Ala Gly Ser Thr Met
515 520 525

Gly Ala Ala Ser Ile Thr Leu Thr Val Gln Ala Arg Gln Leu Leu Ser
530 535 540

Gly Ile Val Gln Gln Gln Ser Asn Leu Leu Lys Ala Pro Glu Ala Gln
545 550 555 560

Gln His Leu Leu Gln Leu Gly Val Trp Gly Ile Lys Gln Leu Gln Thr
565 570 575

Arg Val Leu Ala Ile Glu Arg Tyr Leu Lys Asp Gln Gln Leu Leu Gly
580 585 590

Ile Trp Gly Cys Ser Gly Lys Leu Ile Cys Thr Thr Ala Val Pro Trp
595 600 605

Asn Ser Ser Trp Ser Asn Lys Ser His Asp Glu Ile Trp Gly Asn Met
610 615 620

Thr Trp Met Gln Trp Asp Arg Glu Ile Gly Asn Tyr Thr Asn Thr Ile
625 630 635 640

Tyr Arg Leu Leu Glu Asp Ser Gln Asn Gln Gln Glu Gln Asn Glu Lys
645 650 655

Asp Leu Leu Ala Leu Asp Gly Gly Gly Gly Ser His His His His His
660 665 670

His His His
675

<210> SEQ ID NO 25
<211> LENGTH: 675
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Met Pro Met Gly Ser Leu Gln Pro Leu Ala Thr Leu Tyr Leu Leu Gly
1               5                   10                  15

Met Leu Val Ala Ser Val Leu Ala Asn Gly Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Thr Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Leu Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Cys Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Gln Leu
            260                 265                 270

Thr Asn Asn Val Lys Thr Ile Ile Val His Leu Asn Glu Ser Val Glu
        275                 280                 285

Ile Val Cys Thr Arg Pro Asn Gln Tyr Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Ser Lys Asp Asp Trp Ile Arg Thr Leu
                325                 330                 335

Gln Arg Val Gly Lys Lys Leu Ala Glu His Phe Pro Arg Arg Ile Ile
            340                 345                 350

Gln Phe Thr Ser Pro Ala Gly Gly Asp Leu Glu Ile Thr Thr His Ser
        355                 360                 365

Phe Asn Cys Arg Gly Glu Phe Phe Tyr Cys Asn Thr Ser Ser Leu Phe
    370                 375                 380

Asn Ser Thr Tyr Asn Pro Asn Asp Thr Asn Ser Asn Ser Ser Ser Ser
385                 390                 395                 400
```

-continued

```
Asn Ser Ser Leu Asp Ile Thr Ile Pro Cys Arg Ile Lys Gln Ile Ile
                405                 410                 415

Asn Met Trp Gln Arg Val Gly Gln Cys Met Tyr Ala Pro Pro Ile Glu
            420                 425                 430

Gly Asn Ile Thr Cys Lys Ser Asn Ile Thr Gly Leu Leu Leu Val Arg
        435                 440                 445

Asp Gly Gly Val Glu Ser Gln Glu Thr Glu Ile Phe Arg Pro Gly Gly
    450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Arg Ala Lys Arg Arg
                485                 490                 495

Val Val Glu Gly Gly Gly Gly Ser Gly Gly Gly Gly Ser Ala Val Gly
            500                 505                 510

Leu Gly Ala Val Arg Arg Gly Phe Leu Gly Ala Ala Gly Ser Thr Met
        515                 520                 525

Gly Ala Ala Ser Ile Thr Leu Thr Val Gln Ala Arg Gln Leu Leu Ser
    530                 535                 540

Gly Ile Val Gln Gln Gln Ser Asn Leu Leu Lys Ala Pro Glu Ala Gln
545                 550                 555                 560

Gln His Leu Leu Gln Leu Gly Val Trp Gly Ile Lys Gln Leu Gln Thr
                565                 570                 575

Arg Val Leu Ala Ile Glu Arg Tyr Leu Lys Asp Gln Gln Leu Leu Gly
            580                 585                 590

Ile Trp Gly Cys Ser Gly Lys Leu Ile Cys Thr Thr Ala Val Pro Trp
        595                 600                 605

Asn Ser Ser Trp Ser Asn Lys Ser His Asp Glu Ile Trp Gly Asn Met
    610                 615                 620

Thr Trp Met Gln Trp Asp Arg Glu Ile Gly Asn Tyr Thr Asn Thr Ile
625                 630                 635                 640

Tyr Arg Leu Leu Glu Asp Ser Gln Asn Gln Gln Glu Gln Asn Glu Lys
                645                 650                 655

Asp Leu Leu Ala Leu Asp Gly Gly Gly Gly Ser His His His His His
            660                 665                 670

His His His
        675


<210> SEQ ID NO 26
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80
```

-continued

```
Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Cys Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Asn Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Tyr Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Cys Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495
```

```
Val Val Gly Gly Gly Gly Gly Ser Gly Gly Gly Gly Ser Ala Val Gly
            500                 505                 510

Ile Gly Ala Val Arg Arg Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675


<210> SEQ ID NO 27
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175
```

-continued

```
Arg Ser Asn Asn Ser Asn Lys Glu Tyr Arg Leu Ile Asn Cys Asn Thr
            180                 185                 190

Ser Ala Cys Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Gln Ile Thr
            260                 265                 270

Asn Asn Ala Lys Asn Ile Leu Val Gln Phe Asn Thr Pro Val Gln Ile
        275                 280                 285

Asn Cys Thr Arg Pro Asn Asn Tyr Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Cys Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Asn Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510

Ile Gly Ala Val Arg Arg Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590
```

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675

<210> SEQ ID NO 28
<211> LENGTH: 675
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Ile His Leu
65                  70                  75                  80

Glu Asn Val Thr Glu Glu Phe Asn Met Trp Lys Asn Asn Met Val Glu
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Gln Cys Thr Asn Val
        115                 120                 125

Thr Asn Asn Ile Thr Asp Asp Met Arg Gly Glu Leu Lys Asn Cys Ser
    130                 135                 140

Phe Asn Met Thr Thr Glu Leu Arg Asp Lys Lys Gln Lys Val Tyr Ser
145                 150                 155                 160

Leu Phe Tyr Arg Leu Asp Val Val Gln Ile Asn Glu Asn Gln Gly Asn
                165                 170                 175

Arg Ser Asn Asn Ser Asn Lys Glu Tyr Arg Leu Ile Asn Cys Asn Thr
            180                 185                 190

Ser Ala Cys Thr Gln Ala Cys Pro Lys Val Ser Phe Glu Pro Ile Pro
        195                 200                 205

Ile His Tyr Cys Ala Pro Ala Gly Phe Ala Ile Leu Lys Cys Lys Asp
    210                 215                 220

Lys Lys Phe Asn Gly Thr Gly Pro Cys Pro Ser Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Glu Val Met Ile Arg Ser Glu Gln Ile Thr
            260                 265                 270

-continued

```
Asn Asn Ala Lys Asn Ile Leu Val Gln Phe Asn Thr Pro Val Gln Ile
        275                 280                 285

Asn Cys Thr Arg Pro Asn Asn Tyr Thr Arg Lys Ser Ile Arg Ile Gly
    290                 295                 300

Pro Gly Gln Ala Phe Tyr Ala Thr Gly Asp Ile Ile Gly Asp Ile Arg
305                 310                 315                 320

Gln Ala His Cys Asn Val Ser Lys Ala Thr Trp Asn Glu Thr Leu Gly
                325                 330                 335

Lys Val Val Lys Gln Leu Arg Lys His Phe Gly Asn Asn Thr Ile Ile
            340                 345                 350

Arg Phe Ala Asn Ser Ser Gly Gly Asp Leu Glu Val Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Ile Ser Asn Thr Ser Val Gln Gly Ser Asn Ser Thr
385                 390                 395                 400

Gly Ser Asn Asp Ser Ile Thr Leu Pro Cys Arg Ile Lys Gln Ile Ile
                405                 410                 415

Asn Met Trp Gln Arg Ile Gly Gln Cys Met Tyr Ala Pro Pro Ile Gln
            420                 425                 430

Gly Val Ile Arg Cys Val Ser Asn Ile Thr Gly Leu Ile Leu Thr Arg
        435                 440                 445

Asp Gly Gly Ser Thr Gln Ser Thr Thr Glu Thr Phe Arg Pro Gly Gly
    450                 455                 460

Gly Asp Met Arg Asp Asn Trp Arg Ser Glu Leu Tyr Lys Tyr Lys Val
465                 470                 475                 480

Val Lys Ile Glu Pro Leu Gly Val Ala Pro Thr Arg Ala Lys Arg Arg
                485                 490                 495

Val Val Gly Gly Gly Gly Gly Ser Gly Gly Gly Gly Ser Ala Val Gly
            500                 505                 510

Ile Gly Ala Val Arg Arg Gly Phe Leu Gly Ala Ala Gly Ser Thr Met
        515                 520                 525

Gly Ala Ala Ser Met Thr Leu Thr Val Gln Ala Arg Asn Leu Leu Ser
    530                 535                 540

Gly Ile Val Gln Gln Gln Ser Asn Leu Leu Arg Ala Pro Glu Ala Gln
545                 550                 555                 560

Gln His Leu Leu Lys Leu Thr Val Trp Gly Ile Lys Gln Leu Gln Ala
                565                 570                 575

Arg Val Leu Ala Val Glu Arg Tyr Leu Arg Asp Gln Gln Leu Leu Gly
            580                 585                 590

Ile Trp Gly Cys Ser Gly Lys Leu Ile Cys Thr Thr Asn Val Pro Trp
        595                 600                 605

Asn Ser Ser Trp Ser Asn Arg Asn Leu Ser Glu Ile Trp Asp Asn Met
    610                 615                 620

Thr Trp Leu Gln Trp Asp Lys Glu Ile Ser Asn Tyr Thr Gln Ile Ile
625                 630                 635                 640

Tyr Gly Leu Leu Glu Glu Ser Gln Asn Gln Gln Glu Lys Asn Glu Gln
                645                 650                 655

Asp Leu Leu Ala Leu Asp Gly Gly Gly Gly Ser His His His His His
            660                 665                 670

His His His
        675
```

<210> SEQ ID NO 29
<211> LENGTH: 668
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 29

Met Pro Met Gly Ser Leu Gln Pro Leu Ala Thr Leu Tyr Leu Leu Gly
1 5 10 15

Met Leu Val Ala Ser Val Leu Ala Val Glu Lys Leu Trp Val Thr Val
20 25 30

Tyr Tyr Gly Val Pro Val Trp Lys Asp Ala Glu Thr Thr Leu Phe Cys
35 40 45

Ala Ser Asp Ala Lys Ala Tyr Asp Thr Glu Lys His Asn Val Trp Ala
50 55 60

Thr His Ala Cys Val Pro Thr Asp Pro Asn Pro Gln Glu Val Val Leu
65 70 75 80

Glu Asn Val Thr Glu His Phe Asn Met Trp Lys Asn Asn Met Val Glu
85 90 95

Gln Met Gln Thr Asp Ile Ile Ser Leu Trp Asp Gln Ser Leu Lys Pro
100 105 110

Cys Val Lys Leu Thr Pro Leu Cys Val Thr Leu Asn Cys Lys Asp Val
115 120 125

Asn Ala Thr Asn Thr Thr Asn Asp Ser Glu Gly Thr Met Glu Arg Gly
130 135 140

Glu Ile Lys Asn Cys Ser Phe Asn Ile Thr Thr Glu Leu Arg Asp Lys
145 150 155 160

Val Gln Lys Val Tyr Ala Leu Phe Tyr Lys Leu Asp Val Val Pro Ile
165 170 175

Asp Asn Asn Asn Thr Ser Tyr Arg Leu Ile Ser Cys Asp Thr Ser Val
180 185 190

Cys Thr Gln Ala Cys Pro Lys Ile Ser Phe Glu Pro Ile Pro Ile His
195 200 205

Tyr Cys Ala Pro Ala Gly Phe Ala Ile Leu Lys Cys Asn Asp Lys Thr
210 215 220

Phe Asn Gly Lys Gly Pro Cys Lys Asn Val Ser Thr Val Gln Cys Thr
225 230 235 240

His Gly Ile Arg Pro Val Val Ser Thr Gln Leu Leu Leu Asn Gly Ser
245 250 255

Leu Ala Glu Glu Glu Val Val Ile Arg Ser Asp Asn Phe Thr Asn Asn
260 265 270

Ala Lys Thr Ile Ile Val Gln Leu Lys Glu Ser Val Glu Ile Asn Cys
275 280 285

Thr Arg Pro Asn Asn Tyr Thr Arg Lys Ser Ile Arg Ile Gly Pro Gly
290 295 300

Arg Ala Phe Tyr Thr Thr Gly Glu Ile Ile Gly Asp Ile Arg Gln Ala
305 310 315 320

His Cys Asn Ile Ser Arg Ala Lys Trp Asn Asp Thr Leu Lys Gln Ile
325 330 335

Val Ile Lys Leu Arg Glu Gln Phe Glu Asn Lys Thr Ile Val Phe Asn
340 345 350

His Ser Ser Gly Gly Asp Pro Glu Ile Val Met His Ser Phe Asn Cys
355 360 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Cys Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Arg Arg
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Pro Glu Ala Gln Gln Arg Met Leu Gln Leu
545                 550                 555                 560

Gly Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Ala Leu Asp
                645                 650                 655

Gly Gly Gly Gly Ser His His His His His His His
            660                 665

<210> SEQ ID NO 30
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala

-continued

```
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Glu Leu Arg Asp Lys
145                 150                 155                 160

Val Gln Lys Val Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Cys Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Gln Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Tyr Thr Arg Lys Ser Ile Arg Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Cys Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480
```

```
Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Arg Arg
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Pro Glu Ala Gln Gln Arg Met Leu Gln Leu
545                 550                 555                 560

Gly Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590

Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Ala Leu Asp
                645                 650                 655

Gly Gly Gly Gly Ser His His His His His His His
            660                 665


<210> SEQ ID NO 31
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Met Pro Met Gly Ser Leu Gln Pro Leu Ala Thr Leu Tyr Leu Leu Gly
1               5                   10                  15

Met Leu Val Ala Ser Val Leu Ala Val Glu Lys Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Asp Thr Glu Lys His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Thr Asp Ile Ile Ser Leu Trp Asp Gln Ser Leu Lys Pro
            100                 105                 110

Cys Val Lys Leu Thr Pro Leu Cys Val Thr Leu Asn Cys Lys Asp Val
        115                 120                 125

Asn Ala Thr Asn Thr Thr Asn Asp Ser Glu Gly Thr Met Glu Arg Gly
    130                 135                 140

Glu Ile Lys Asn Cys Ser Phe Asn Ile Thr Thr Glu Leu Arg Asp Lys
145                 150                 155                 160

Val Gln Lys Val Tyr Ala Leu Phe Tyr Lys Leu Asp Val Val Pro Ile
```

-continued

```
                165                 170                 175

Asp Asn Asn Asn Thr Ser Tyr Arg Leu Ile Ser Cys Asp Thr Ser Val
            180                 185                 190

Cys Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Gln Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Tyr Thr Arg Lys Ser Ile Arg Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Arg Val
                405                 410                 415

Gly Gln Cys Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Gln Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Arg Ala Lys Arg Arg Val Val Gln Gly Gly Gly
                485                 490                 495

Gly Ser Gly Gly Gly Gly Ser Ala Val Gly Ile Gly Ala Val Arg Arg
            500                 505                 510

Gly Phe Leu Gly Ala Ala Gly Ser Thr Met Gly Ala Ala Ser Met Thr
        515                 520                 525

Leu Thr Val Gln Ala Arg Asn Leu Leu Ser Gly Ile Val Gln Gln Gln
    530                 535                 540

Ser Asn Leu Leu Arg Ala Pro Glu Ala Gln Gln Arg Met Leu Gln Leu
545                 550                 555                 560

Gly Val Trp Gly Ile Lys Gln Leu Gln Ala Arg Val Leu Ala Val Glu
                565                 570                 575

Arg Tyr Leu Arg Asp Gln Gln Leu Leu Gly Ile Trp Gly Cys Ser Gly
            580                 585                 590
```

```
Lys Leu Ile Cys Thr Thr Ala Val Pro Trp Asn Ala Ser Trp Ser Asn
        595                 600                 605

Lys Ser Leu Asp Arg Ile Trp Asn Asn Met Thr Trp Met Glu Trp Glu
    610                 615                 620

Arg Glu Ile Asp Asn Tyr Thr Ser Glu Ile Tyr Thr Leu Ile Glu Glu
625                 630                 635                 640

Ser Gln Asn Gln Gln Glu Lys Asn Glu Gln Glu Leu Leu Ala Leu Asp
                645                 650                 655

Gly Gly Gly Gly Ser His His His His His His His
            660                 665


<210> SEQ ID NO 32
<211> LENGTH: 680
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Pro Met Gly Ser Leu Gln Pro Leu Ala Thr Leu Tyr Leu Leu Gly
1               5                   10                  15

Met Leu Val Ala Ser Val Leu Ala Ala Glu Asn Leu Trp Val Thr Val
            20                  25                  30

Tyr Tyr Gly Val Pro Val Trp Lys Asp Ala Glu Thr Thr Leu Phe Cys
        35                  40                  45

Ala Ser Asp Ala Lys Ala Tyr Glu Thr Glu Lys His Asn Val Trp Ala
    50                  55                  60

Thr His Ala Cys Val Pro Thr Asp Pro Asn Pro Gln Glu Met Val Leu
65                  70                  75                  80

Gly Asn Val Thr Glu Asn Phe Asn Met Trp Lys Asn Asp Met Val Asp
                85                  90                  95

Gln Met His Thr Asp Val Ile Ser Leu Trp Ala Gln Ser Leu Lys Pro
            100                 105                 110

Cys Val Lys Leu Thr Pro Leu Cys Val Thr Leu Glu Cys Thr Gln Val
        115                 120                 125

Asn Ala Thr Gln Gly Asn Thr Thr Gln Val Asn Val Thr Gln Val Asn
    130                 135                 140

Gly Asp Glu Met Lys Asn Cys Ser Phe Asn Thr Thr Thr Glu Leu Arg
145                 150                 155                 160

Asp Lys Lys Gln Lys Val Tyr Ala Leu Phe Tyr Arg Leu Asp Leu Val
                165                 170                 175

Pro Leu Glu Arg Glu Asn Arg Gly Asp Ser Asn Ser Ala Ser Lys Tyr
            180                 185                 190

Ile Leu Ile Asn Cys Asn Thr Ser Ala Ile Thr Gln Ala Cys Pro Lys
        195                 200                 205

Val Asn Phe Asp Pro Ile Pro Ile His Tyr Cys Thr Pro Ala Gly Tyr
    210                 215                 220

Ala Ile Leu Lys Cys Asn Asn Lys Thr Phe Asn Gly Thr Gly Ser Cys
225                 230                 235                 240

Asn Asn Val Ser Thr Val Gln Cys Thr His Gly Ile Lys Pro Val Val
                245                 250                 255

Ser Thr Gln Leu Leu Leu Asn Gly Ser Leu Ala Glu Glu Glu Ile Ile
            260                 265                 270

Ile Arg Ser Glu Asn Leu Thr Asp Asn Val Lys Thr Ile Ile Val His
```

```
        275                 280                 285

Leu Asp Gln Ser Val Glu Ile Val Cys Thr Arg Pro Asn Asn Tyr Thr
    290                 295                 300

Arg Lys Ser Ile Arg Ile Gly Pro Gly Gln Thr Phe Tyr Ala Thr Gly
305                 310                 315                 320

Asp Ile Ile Gly Asn Ile Arg Glu Ala His Cys Asn Ile Ser Glu Lys
                325                 330                 335

Lys Trp His Glu Met Leu Arg Arg Val Ser Glu Lys Leu Ala Glu His
            340                 345                 350

Phe Pro Asn Lys Thr Ile Lys Phe Thr Ser Ser Ser Gly Gly Asp Leu
        355                 360                 365

Glu Ile Thr Thr His Ser Phe Asn Cys Arg Gly Glu Phe Phe Tyr Cys
    370                 375                 380

Asn Thr Ser Gly Leu Phe Asn Ser Thr Tyr Met Pro Asn Gly Thr Tyr
385                 390                 395                 400

Met Pro Asn Gly Thr Asn Asn Ser Asn Ser Thr Ile Ile Leu Pro Cys
                405                 410                 415

Arg Ile Lys Gln Ile Ile Asn Met Trp Gln Arg Val Gly Gln Cys Met
            420                 425                 430

Tyr Ala Pro Pro Ile Ala Gly Asn Ile Thr Cys Asn Ser Asn Ile Thr
        435                 440                 445

Gly Leu Leu Leu Val Arg Asp Gly Gly Lys Asn Asn Asn Thr Glu Ile
    450                 455                 460

Phe Arg Pro Gly Gly Gly Asp Met Arg Asp Asn Trp Arg Ser Glu Leu
465                 470                 475                 480

Tyr Lys Tyr Lys Val Val Glu Ile Lys Pro Leu Gly Val Ala Pro Thr
                485                 490                 495

Arg Ala Lys Arg Arg Val Val Glu Gly Gly Gly Gly Ser Gly Gly Gly
            500                 505                 510

Gly Ser Ala Val Gly Leu Gly Ala Val Arg Arg Gly Phe Leu Gly Ala
        515                 520                 525

Ala Gly Ser Thr Met Gly Ala Ala Ser Ile Thr Leu Thr Val Gln Ala
    530                 535                 540

Arg Gln Leu Leu Ser Gly Ile Val Gln Gln Gln Ser Asn Leu Leu Gln
545                 550                 555                 560

Ala Pro Glu Ala Gln Gln His Leu Leu Gln Gly Thr Val Trp Gly Ile
                565                 570                 575

Lys Gln Leu Gln Thr Arg Val Leu Ala Ile Glu Arg Tyr Leu Lys Asp
            580                 585                 590

Gln Gln Leu Leu Gly Ile Trp Gly Cys Ser Gly Lys Leu Ile Cys Thr
        595                 600                 605

Thr Ala Val Pro Trp Asn Ser Ser Trp Ser Asn Lys Ser Leu Thr Asp
    610                 615                 620

Ile Trp Asp Asn Met Thr Trp Met Gln Trp Asp Arg Glu Val Gly Asn
625                 630                 635                 640

Tyr Thr Gly Ile Ile Tyr Arg Leu Leu Glu Asp Ser Gln Asn Gln Gln
                645                 650                 655

Glu Arg Asn Glu Gln Asp Leu Leu Ala Leu Asp Gly Gly Gly Gly Ser
            660                 665                 670

His His His His His His His His
        675                 680
```

<210> SEQ ID NO 33

<211> LENGTH: 690
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 33

```
Met Pro Met Gly Ser Leu Gln Pro Leu Ala Thr Leu Tyr Leu Leu Gly
1               5                   10                  15

Met Leu Val Ala Ser Val Leu Ala Met Glu Gln Leu Trp Val Thr Val
            20                  25                  30

Tyr Tyr Gly Val Pro Val Trp Lys Asp Ala Glu Ala Thr Leu Phe Cys
        35                  40                  45

Ala Ser Asp Ala Lys Ala Tyr Glu Lys Glu Lys His Asn Val Trp Ala
    50                  55                  60

Thr His Ala Cys Val Pro Thr Asp Pro Asn Pro Gln Glu Ile Pro Leu
65                  70                  75                  80

Gly Asn Val Thr Glu Asn Phe Asn Met Trp Lys Asn Asp Met Ala Asp
                85                  90                  95

Gln Met His Thr Asp Ile Ile Ser Leu Trp Asp Gln Ser Leu Lys Pro
            100                 105                 110

Cys Val Lys Leu Thr Pro Leu Cys Val Thr Leu Asn Cys Ser Asp Ala
        115                 120                 125

Thr Ser Asn Thr Thr Lys Asn Ala Thr Asn Thr Asn Thr Thr Ser Thr
    130                 135                 140

Asp Asn Arg Asn Ala Thr Ser Asn Asp Thr Glu Met Lys Gly Glu Ile
145                 150                 155                 160

Lys Asn Cys Thr Phe Asn Ile Thr Thr Glu Leu Arg Asp Arg Lys Thr
                165                 170                 175

Lys Val Arg Ala Leu Phe Tyr Lys Leu Asp Val Val Pro Leu Glu Glu
            180                 185                 190

Glu Lys Asn Ser Ser Ser Lys Asn Ser Ser Tyr Lys Glu Tyr Arg Leu
        195                 200                 205

Ile Ser Cys Asn Thr Ser Thr Cys Thr Gln Ala Cys Pro Lys Val Ser
    210                 215                 220

Phe Asp Pro Ile Pro Ile His Tyr Cys Ala Pro Ala Gly Tyr Ala Ile
225                 230                 235                 240

Leu Lys Cys Asn Asn Lys Thr Phe Asn Gly Thr Gly Pro Cys His Asn
                245                 250                 255

Val Ser Thr Val Gln Cys Thr His Gly Ile Lys Pro Val Val Ser Thr
            260                 265                 270

Gln Leu Leu Leu Asn Gly Ser Leu Ala Glu Glu Glu Ile Ile Ile Arg
        275                 280                 285

Ser Glu Asn Leu Thr Asp Asn Thr Lys Thr Ile Ile Val His Leu Asn
    290                 295                 300

Glu Ser Val Glu Ile Asn Cys Thr Arg Pro Asn Asn Tyr Thr Arg Lys
305                 310                 315                 320

Ser Val Arg Ile Gly Pro Gly Gln Thr Phe Phe Ala Thr Gly Glu Ile
                325                 330                 335

Ile Gly Asp Ile Arg Gln Ala His Cys Asn Leu Ser Lys Ser Asn Trp
            340                 345                 350

Thr Thr Thr Leu Lys Arg Ile Glu Lys Lys Leu Lys Glu His Phe Asn
        355                 360                 365

Asn Ala Thr Ile Lys Phe Glu Ser Ser Ala Gly Gly Asp Leu Glu Ile
```

```
    370                 375                 380

Thr Thr His Ser Phe Asn Cys Arg Gly Glu Phe Phe Tyr Cys Asn Thr
385                 390                 395                 400

Ser Gly Leu Phe Asn Ser Ser Leu Leu Asn Asp Thr Asp Gly Thr Ser
                405                 410                 415

Asn Ser Thr Ser Asn Ala Thr Ile Thr Leu Pro Cys Arg Ile Lys Gln
            420                 425                 430

Ile Ile Asn Met Trp Gln Arg Val Gly Gln Cys Met Tyr Ala Ser Pro
        435                 440                 445

Ile Ala Gly Ile Ile Thr Cys Lys Ser Asn Ile Thr Gly Leu Leu Leu
    450                 455                 460

Thr Arg Asp Gly Gly Asn Lys Ser Ala Gly Ile Glu Thr Phe Arg Pro
465                 470                 475                 480

Gly Gly Gly Asn Met Lys Asp Asn Trp Arg Ser Glu Leu Tyr Lys Tyr
                485                 490                 495

Lys Val Val Glu Ile Lys Pro Leu Gly Ile Ala Pro Thr Arg Ala Lys
            500                 505                 510

Arg Arg Val Val Glu Gly Gly Gly Gly Ser Gly Gly Gly Gly Ser Ala
        515                 520                 525

Ala Gly Ile Gly Ala Val Arg Arg Gly Phe Leu Gly Ala Ala Gly Ser
    530                 535                 540

Thr Met Gly Ala Ala Ser Val Met Leu Thr Val Gln Ala Arg Gln Leu
545                 550                 555                 560

Leu Ser Gly Ile Val Gln Gln Gln Ser Asn Leu Leu Arg Ala Pro Glu
                565                 570                 575

Ala Gln Gln His Met Leu Gln Gly Thr Val Trp Gly Ile Lys Gln Leu
            580                 585                 590

Gln Thr Arg Val Leu Ala Ile Glu Arg Tyr Leu Lys Asp Gln Gln Leu
        595                 600                 605

Leu Gly Leu Trp Gly Cys Ser Gly Lys Leu Ile Cys Thr Thr Ala Val
    610                 615                 620

Pro Trp Asn Thr Ser Trp Ser Asn Lys Ser Lys Asp Glu Ile Trp Asp
625                 630                 635                 640

Asn Met Thr Trp Met Gln Trp Asp Arg Glu Ile Gly Asn Tyr Thr Gln
                645                 650                 655

Val Ile Tyr Gln Leu Leu Glu Val Ser Gln Asn Gln Gln Glu Lys Asn
            660                 665                 670

Glu Asn Asp Leu Leu Ala Leu Asp Gly Gly Gly Gly His His His His
        675                 680                 685

His His
    690
```

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

```
Gly Gly Gly Gly Ser Gly Gly Gly Gly Ser
1               5                   10
```

<210> SEQ ID NO 35
<211> LENGTH: 4

<212> TYPE: PRT
<213> ORGANISM: Human immunodeficiency virus

<400> SEQUENCE: 35

Arg Glu Lys Arg
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Asp Asp Asp Asp Lys
1 5

<210> SEQ ID NO 37
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Ala Arg Gly Ala Val Thr Tyr Gly Leu Gly Gly Ala Tyr Leu Lys His
1 5 10 15

Phe Asn Leu

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Arg Phe Ala Gly Tyr Arg Tyr Ser Val Trp Ser Tyr Pro Asp Leu
1 5 10 15

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Leu Tyr Gly Tyr Ile Ser Ser Asp Arg Ile Asp
1 5 10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Gln Ser Ala Tyr Asn Gly Asp Gly Asp Asn Ala
1 5 10

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Gly Gly Gly Gly Ser
1 5

<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Gln Ser Leu Glu Glu Ser Gly Gly Asp Leu Val Lys Pro Gly Ala Ser
1 5 10 15

Leu Thr Leu Thr Cys Thr Ala Ser Gly Phe Ser Phe Gly Trp Asn Asp
20 25 30

Tyr Met Ser Trp Val Arg Gln Ala Pro Gly Lys Gly Leu Glu Trp Ile
35 40 45

Gly Cys Ile Tyr Ala Gly Ser Thr Arg Ser Thr Tyr Tyr Ala Asn Trp
50 55 60

Ala Lys Gly Arg Leu Thr Ile Ser Lys Thr Ser Ser Thr Ala Val Thr
65 70 75 80

Leu Gln Met Thr Ser Leu Thr Ala Ala Asp Thr Ala Thr Tyr Phe Cys
85 90 95

Ala Arg Gly Ala Val Thr Tyr Asp Gly Leu Gly Gly Ala Tyr Leu Lys
100 105 110

His Phe Asn Leu Trp Gly Pro Gly Thr Leu Val Thr Val Ser Ser
115 120 125

<210> SEQ ID NO 43
<211> LENGTH: 122
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

Gln Ser Leu Glu Glu Ser Gly Gly Gly Leu Val Lys Pro Gly Gly Thr
1 5 10 15

Leu Thr Leu Thr Cys Lys Ala Ser Gly Ile Asp Phe Thr Ser Gly Tyr
20 25 30

Asp Met Cys Trp Val Arg Gln Ala Pro Gly Lys Gly Leu Glu Trp Val
35 40 45

Ala Cys Ile Tyr Leu Gly Asp Gly Asn Thr Tyr Tyr Ala Ser Trp Ala
50 55 60

Lys Gly Gln Phe Thr Ile Ser Lys Thr Ser Ser Thr Thr Val Thr Leu
65 70 75 80

Gln Met Thr Ser Leu Thr Ala Ala Asp Thr Ala Thr Tyr Phe Cys Ala
85 90 95

-continued

```
Arg Phe Ala Gly Tyr Arg Tyr Ser Val Trp Ser Tyr Pro Asp Leu Trp
            100                 105                 110

Gly Pro Gly Thr Leu Val Thr Val Ser Ser
        115                 120


<210> SEQ ID NO 44
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Leu Val Gln Ser Gly Ala Glu Met Lys Asp Pro Gly Ala Ser Val
1               5                   10                  15

Lys Val Ser Cys Arg Ala Ser Gly Tyr Lys Phe Thr Asp Tyr Tyr Met
            20                  25                  30

His Trp Val Arg Gln Ala Pro Gly Gln Gly Leu Glu Trp Val Gly Trp
        35                  40                  45

Val Asn Thr Asn Gly Gly Phe Thr Lys Tyr Gly Ala Lys Phe Gln Gly
    50                  55                  60

Arg Val Thr Val Thr Arg Asp Thr Ser Thr Asn Thr Val Phe Leu Glu
65                  70                  75                  80

Leu Ser Arg Leu Thr Phe Gly Asp Thr Ala Met Tyr Phe Cys Ala Arg
                85                  90                  95

Pro Met Arg Pro Val Ser His Gly Ile Asp Tyr Ser Gly Leu Phe Val
            100                 105                 110

Phe Gln Phe Trp Gly Arg Gly Thr Met Val Thr Val Ser Ser
        115                 120                 125
```

UNITED STATES PATENT AND TRADEMARK OFFICE
CERTIFICATE OF CORRECTION

PATENT NO. : 10,870,683 B2
APPLICATION NO. : 16/130531
DATED : December 22, 2020
INVENTOR(S) : Viktoriya Dubrovskaya et al.

It is certified that error appears in the above-identified patent and that said Letters Patent is hereby corrected as shown below:

In the Claims

Please amend Claim 1, at Column 197, Line 42 as follows:
1. An engineered or non-naturally occurring trimer, wherein the trimer is a flexibly linked NFL2P trimer, wherein the trimer comprises one or more trimer-derived mutations ("TD mutations"), wherein said TD mutations comprise one or more mutations including at residue 569 wherein a numerical position of an amino acid residue of the trimer corresponds with a numerical position of an amino acid residue of a 16055 NFL Env protein upon direct alignment of the numerical positions of the amino acid residues of the trimer with the numerical positions of the amino acid residues of the 16055 NFL Env protein, whose sequence is based on a BG505 numbering system.

Please amend Claim 2, at Column 197, beginning at Line 50 as follows:
2. The trimer of claim 1, wherein the mutation at residue 569 comprises G.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*